(12) United States Patent
Kuang et al.

(10) Patent No.: US 10,472,347 B2
(45) Date of Patent: Nov. 12, 2019

(54) AMINOPYRAZINE COMPOUNDS WITH A2A ANTAGONIST PROPERTIES

(71) Applicant: Merck Sharp & Dohme Corp., Rahway, NJ (US)

(72) Inventors: Rongze Kuang, Green Brook, NJ (US); Pauline Ting, New Providence, NJ (US); Amjad Ali, Freehold, NJ (US); Heping Wu, Edison, NJ (US); Michael Berlin, Flemington, NJ (US); Andrew Stamford, Chatham, NJ (US); Hongwu Wang, Westfield, NJ (US); Gang Zhou, Rahway, NJ (US); David Kim, Rahway, NJ (US); Qiaolin Deng, Edison, NJ (US); Yeon-Hee Lim, Rahway, NJ (US); Younong Yu, Rahway, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 80 days.

(21) Appl. No.: 15/525,788

(22) PCT Filed: Nov. 13, 2015

(86) PCT No.: PCT/US2015/060509
§ 371 (c)(1),
(2) Date: May 10, 2017

(87) PCT Pub. No.: WO2016/081290
PCT Pub. Date: May 26, 2016

(65) Prior Publication Data
US 2018/0327385 A1 Nov. 15, 2018

Related U.S. Application Data

(60) Provisional application No. 62/081,262, filed on Nov. 18, 2014.

(51) Int. Cl.
*A61K 31/497* (2006.01)
*C07D 401/14* (2006.01)
(Continued)

(52) U.S. Cl.
CPC .......... *C07D 401/14* (2013.01); *A61K 31/497* (2013.01); *C07D 241/26* (2013.01); *C07D 401/12* (2013.01); *C07D 403/04* (2013.01); *C07D 403/14* (2013.01); *C07D 413/04* (2013.01); *C07D 413/14* (2013.01); *C07D 417/14* (2013.01); *C07D 471/04* (2013.01); *C07D 513/04* (2013.01); *A61P 25/16* (2018.01)

(58) Field of Classification Search
None
See application file for complete search history.

(56) References Cited

U.S. PATENT DOCUMENTS

| 7,407,961 B2 * | 8/2008 | Yonishi ................ C07D 401/04 514/255.05 |
|---|---|---|
| 2005/0113387 A1 | 5/2005 | Yonishi et al. |
| 2009/0233944 A1 | 9/2009 | Jaeschke et al. |
| 2010/0075989 A1 | 3/2010 | Berg et al. |
| 2012/0065205 A1 | 3/2012 | Mercer et al. |

FOREIGN PATENT DOCUMENTS

WO WO2004111033 A1 12/2004

OTHER PUBLICATIONS

International Search Report—dated Jan. 21, 2016.
Bonnefous, C., Dipyridyl amides: potent matebotropic glutamate subtype 5 (mGlu5) receptor antagonists, Bioorganic and Med Chem Letters, 2005, 1197-1200, 15-4.

* cited by examiner

*Primary Examiner* — Samantha L Shterengarts
(74) *Attorney, Agent, or Firm* — Keith D MacMillan; Catherine D Fitch

(57) ABSTRACT

Disclosed are compounds of Formula A and Formula A-1, or a salt thereof, and pharmaceutical formulations (pharmaceutical compositions) comprising those compounds, or a salt thereof; wherein "$R^1$", "$R^{4-1}$", "$R^2$", "$R^3$", and "Het" are defined herein above, which compounds are believed suitable for use in selectively antagonizing the A2a receptors, for example, those found in high density in the basal ganglia. Such compounds and pharmaceutical formulations are believed to be useful in treatment or management of neurodegenerative diseases, for example, Parkinson's disease, or movement disorders arising from use of certain medications used in the treatment or management of Parkinson's disease.

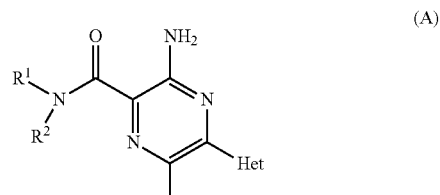

(A)

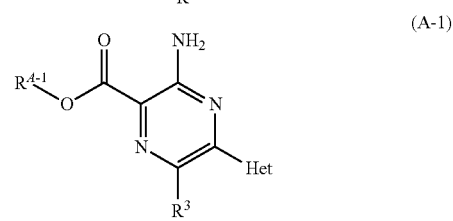

(A-1)

19 Claims, No Drawings

(51) Int. Cl.
*C07D 241/26* (2006.01)
*C07D 401/12* (2006.01)
*C07D 403/04* (2006.01)
*C07D 403/14* (2006.01)
*C07D 413/04* (2006.01)
*C07D 413/14* (2006.01)
*C07D 417/14* (2006.01)
*C07D 471/04* (2006.01)
*C07D 513/04* (2006.01)
*A61P 25/16* (2006.01)

1

AMINOPYRAZINE COMPOUNDS WITH A2A ANTAGONIST PROPERTIES

CROSS-REFERENCE TO RELATED APPLICATIONS

This application is the national stage entry of International Patent Application Serial No. PCT/US2015/060509, filed Nov. 13, 2015, which in turn claims the priority of U.S. provisional application Ser. No. 62/081,262 filed Nov. 18, 2015, which applications are incorporated herein in their entirety by reference thereto.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in PCT International Application Publication Nos. WO 95/01356; U.S. Pat. No. 5,565,460; WO 97/05138; and WO 98/52568.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-Dopa, directly through stimulation of the postsynaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-Dopa (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

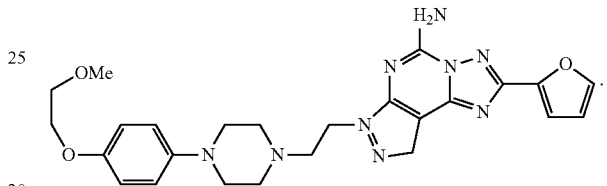

Formula PI

In the '475 patent example Schemes 1 to 5, along with preparative Schemes 1 to 4, show general methods of preparing compounds of Formula PI. The '475 patent describes also that the compound of Formula I can be prepared as a pharmaceutically acceptable salt which may be useful for treating Parkinson's disease.

The use of $A_{2A}$ receptor antagonists in the potential treatment of central nervous system diseases, in particular Parkinson's disease, and to pharmaceutical compositions comprising said compounds has elevated the need for potent, moderately lipophilic, brain penetrant inhibitors of the $A_{2A}$ receptor. Such compounds would provide an expansion of the arsenal of compounds which are believed to have value in the treatment of central nervous system disorders, in particular treating or managing the progression of such diseases, for example, but not limited to, Parkinson's disease.

SUMMARY OF THE INVENTION

In one aspect, the invention provides one or more compounds, or a pharmaceutically acceptable salt thereof, believed to have utility as an $A_{2A}$-receptor antagonist that have the structure of Formula A:

A compound of Formula A:

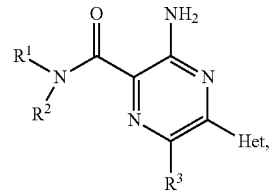

Formula A or a salt thereof, wherein:
"Het" is a moiety of the formula:

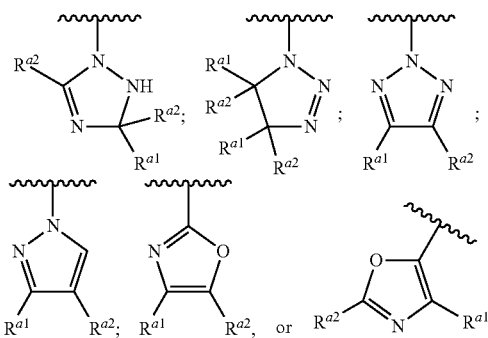

wherein "$R^{a1}$" and "$R^{a2}$" are, independently for each occurrence: (a) —H; or (b) lower alkyl which is optionally substituted with one or more moieties which are: (i) halogen, preferably —F; or (ii) lower alkoxy (A) one of $R^1$ or $R^2$ is lower alkyl or —H and the other is:
(a) a linear, branched, mono-cyclic, or bi-cyclic-alkyl moiety of up to 10 carbon atoms, which is optionally substituted with one or more substituents which are independently:
  (i) halogen, preferably —F;
  (ii) —NR$^{1g}$R$^{2g}$, wherein R$^{1g}$ and R$^{2g}$ are, independently: (aii) —H; or (bii) lower alkyl;
  (iii) —CN;
  (iv) —OH;
  (v) mono- or poly-cyclic heteroaryl comprising at least two carbon atoms and up to 3 heteroatoms which are, independently, N, O, or S and which is optionally substituted with:
    (ai) lower alkyl, which moiety is optionally substituted with one or more moieties which are independently;
      (aii) halogen, which in some embodiments is preferably —F;
      (bii) lower alkoxy;
      (cii) —OH
    (bi) —NR$^{1g}$R$^{2g}$, wherein R$^{1g}$ and R$^{2g}$ are, independently: (aii) —H; or (bii) lower alkyl;
    (ci) lower-alkoxy, which is optionally substituted in its alkyl portion with a halogen, and when unsubstituted, in some embodiments said lower alkoxy moiety is preferably methoxy; and when halogen-substituted, in some embodiments said halogen substituent is preferably —F;
    (di) halogen, which is some embodiments is preferably —F, or —Cl;
    (ei) —OH;
    (fi) heteroaryl;
    (gi) heterocycloalkyl which is optionally substituted with one or more halogen atoms, and when halogen-substituted, preferably the halogen is —F;
  and wherein, if said heteroaryl comprises a single nitrogen heteroatom in the ring, optionally said ring nitrogen is present in the N-oxide oxidized form;
  (vi) heteroarylone which is optionally substituted with one or more moieties which are, independently, a lower alkyl, which lower alkyl substituent is optionally fluorine substituted;
  (vii) heteroarylaryl fused moiety, which is optionally substituted with one or more lower alkyl moieties, which lower alkyl moieties are optionally substituted with fluorine;
  (viii) aryl, which is optionally substituted with one or more moieties which are independently:
    (ai) lower alkyl which is optionally substituted with a halogen, and in some embodiments where present, said optional halogen substituent is preferably —F;
    (bi) halogen, and in some embodiments where present, said halogen substituent is preferably —Cl or —F;
    (ci) —OH;
    (di) lower alkoxy which is optionally halogen substituted, and in some embodiments said lower alkoxy substituent is preferably H$_3$C—O— or F$_3$C—O—; or
    (ei) —N(R$^{a8}$)$_2$, wherein "R$^{a8}$" is independently —H or lower alkyl;
  (ix) arylheteroaryl fused moiety, which is optionally substituted with one or more moieties which are lower alkyl;
  (x) cycloalkylheteroaryl fused moiety;
  (xi) linear, branched, or cyclic alkyl of up to 6 carbon atoms which is optionally substituted with one or more moieties which are independently: (ai) —CN; (bi) lower alkoxy; or (ci) halogen;
  (xii) a moiety of the formula "—C(O)—R$^{a12}$", wherein "R$^{a12}$" is a moiety which is: (ai) lower alkyl; (bi) lower alkoxy; (ci) heteroaryl; or (di) aryl, and wherein said "R$^{a12}$" moiety is optionally substituted with one or more halogen moieties, and when one or more halogen moieties are present on said "R$^{a12}$" moiety in some embodiments said halogen is preferably —F;
  (xiii) a moiety of the formula "—O—R$^{a13}$", wherein "R$^{a13}$" is lower alkyl or aryl;
  (xiv) —OH;
  (xv) heteroaryl-heterocycloalkyl fused moiety;
(b) heteroarylcycloalkyl fused moiety which is optionally substituted with:
  (i) —OH; or (ii) halogen, and in some embodiments where present, said optional halogen substituent is preferably —F or —Cl;
(c) heterocycloalkyl, which is optionally substituted with one or more moieties which are independently: (i) —F; or (ii) heteroaryl;
(d) a compound of the Formula:

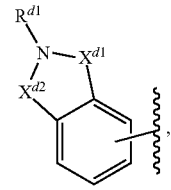

wherein "$R^{d1}$" is —H or lower alkyl, and wherein one of "$X^{d1}$" or "$X^{d2}$" is —CH$_2$— and the other is —C(=O)—;
(e) arylheterocycloalkyl fused moiety;
(f) heterocycloalkylaryl fused moiety which is optionally substituted with —OH or halogen;
(g) heteroarylheterocycloalkyl fused moiety which is optionally substituted with —OH or halogen;

(h) arylcycloalkyl fused moiety, which is optionally substituted with one or more moieties which are, independently:
   (i) —OH;
   (ii) —CN;
   (iii) halogen, and in some embodiments when a halogen substituent is present, preferably said halogen substituent is —Cl or —F; or
   (iv) lower alkoxy;
and in some embodiments, when said "$R^1$" or "$R^2$" moiety is a substituted linear, branched, monocyclic or bicyclic moiety, said alkyl moiety is preferably methylene or ethylene;
(B) $R^1$ and $R^2$ taken together are a moiety of the formula —[(CR$^{B1}$R$^{B2}$)$_2$)$_n$]—, wherein, "n" is an integer of 3 to 6, and "$R^{B1}$" and "$R^{B2}$" are independently for each occurrence: (a) lower alkyl; (b) hydrogen; (c) aryl; or (d) halogen, thereby forming with the nitrogen to which they are bonded a heterocycloalkyl moiety; or
(C) $R^1$ and $R^2$ taken together form an arylheterocycloalkyl fused moiety, which in some embodiments is preferably 6-N-bonded 6,7-dihydro-5H-pyrrolo[3,4-d]pyrimidine; and "$R^3$" is: (a) —CN; (b) halogen, preferably —Cl; (c) lower alkyl which is optionally substituted with one or more moieties which are: (i) —OH; or (ii) halogen, and when halogen-substituted the halogen substituent is preferably —F, and when unsubstituted said lower alkyl is preferably —CH$_3$.

In some embodiments it is preferred for compounds of the invention have the structure of Formula A-a:

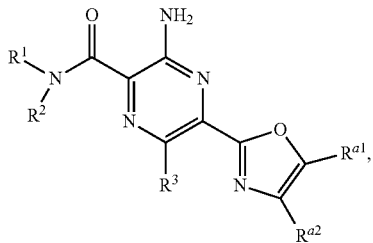

Formula A-a

Wherein $R^1$, $R^2$, $R^3$, $R^{a1}$, and $R^{a2}$ are as defined above.

In some embodiments it is preferred for compounds of the invention have the structure of Formula A-b:

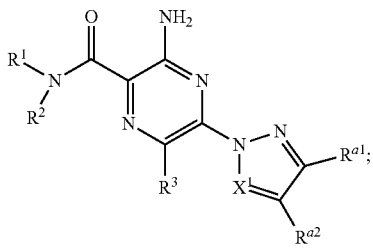

Formula A-b wherein: $R^1$, $R^2$, $R^3$, $R^{a1}$, and $R^{a2}$ are as defined above; and "X$^1$" is [—CH═] or [—N═].

In some embodiments, a compound of the invention is Ethyl-3-amino-6-methyl-5-(2H-1,2,3-triazol-2-yl)pyrazine-2-carboxylate.

In some embodiments, compounds of the invention have the structure of Formula A-1:

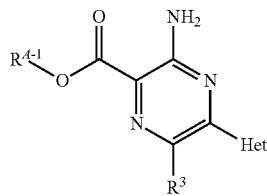

Formula A-1 wherein "$R^{A-1}$" is lower alkyl and "$R^3$" and "Het" have the definitions given above.

In some embodiments, a compound of the invention is Ethyl-3-amino-6-methyl-5-(2H-1,2,3-triazol-2-yl)pyrazine-2-carboxylate. In some embodiments, a compound of the invention is methyl-3-amino-6-chloro-5-(1H-pyrazol-1-yl)pyrazine-2-carboxylate.

In another aspect, the invention is a pharmaceutical formulation comprising at least one compound of Formula GI or a pharmaceutically acceptable salt thereof. In another aspect the invention is directed to the use of compounds, and pharmaceutical formulations thereof, in the potential treatment of movement disorders in which $A_{2A}$ receptors are involved.

In some aspects the present invention is the provision of a method of treating central nervous system disorders by administering to a subject in need thereof a therapeutic amount of at least one compound of Formula GI or a pharmaceutically acceptable salt thereof.

DETAILED DESCRIPTION OF THE INVENTION

As mentioned above, the invention provides compounds having the structure of Formula A, Formula A-1, or a salt thereof:

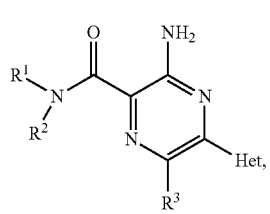

Formula A

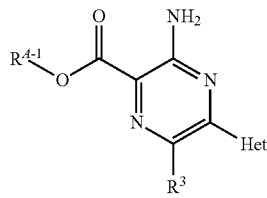

Formula A-1 wherein "$R^1$", "$R^{A-1}$", "$R^2$", "$R^3$", and "Het" are defined herein above, which compounds are believed to have activity as $A_{2A}$-receptor antagonist.

In some embodiments, it is preferred for compounds of the invention to be:
3-amino-6-methyl-N-[(3-methylpyridin-2-yl)methyl]-5-(1,3-oxazol-2-yl)pyrazine-2-carboxamide;
3-amino-N-[(3-cyclopropylpyridin-2-yl)methyl]-6-methyl-5-(1,3-oxazol-2-yl)pyrazine-2-carboxamide;
3-amino-N-(6,7-dihydro-5H-cyclopenta[b]pyridin-7-yl)-6-methyl-5-(1,3-oxazol-2-yl)pyrazine-2-carboxamide;

3-amino-N-(6,7-dihydro-5H-cyclopenta[b]pyridin-7-yl)-6-methyl-5-(1,3-oxazol-2-yl)pyrazine-2-carboxamide;

3-amino-6-methyl-5-(1,3-oxazol-2-yl)-N-(quinolin-8-ylmethyl)pyrazine-2-carboxamide;

3-amino-6-methyl-N-[(6-methylpyridin-2-yl)methyl]-5-(1,3-oxazol-2-yl)pyrazine-2-carboxamide;

3-amino-N-(2,6-difluorobenzyl)-6-methyl-5-(1,3-oxazol-2-yl)pyrazine-2-carboxamide;

3-amino-N-(isoxazol-5-ylmethyl)-6-methyl-5-(1,3-oxazol-2-yl)pyrazine-2-carboxamide;

3-amino-6-methyl-5-(1,3-oxazol-2-yl)-N-(1,3-oxazol-2-ylmethyl)pyrazine-2-carboxamide;

3-amino-6-methyl-N-[(4-methyl-1H-imidazol-2-yl)methyl]-5-(1,3-oxazol-2-yl)pyrazine-2-carboxamide;

3-amino-6-methyl-N-[(1-methyl-1H-imidazol-2-yl)methyl]-5-(1,3-oxazol-2-yl)pyrazine-2-carboxamide;

3-amino-N-(1H-imidazol-2-ylmethyl)-6-methyl-5-(1,3-oxazol-2-yl)pyrazine-2-carboxamide;

3-amino-6-methyl-5-(1,3-oxazol-2-yl)-N-(1,3-thiazol-5-ylmethyl)pyrazine-2-carboxamide;

3-amino-6-methyl-5-(1,3-oxazol-2-yl)-N-{[3-(trifluoromethyl)pyridin-2-yl]methyl}pyrazine-2-carboxamide;

3-amino-6-methyl-5-(1,3-oxazol-2-yl)-N-(pyrimidin-2-ylmethyl)pyrazine-2-carboxamide;

3-amino-N-[(3-fluoropyridin-2-yl)methyl]-6-methyl-5-(1,3-oxazol-2-yl)pyrazine-2-carboxamide;

3-amino-N-{[6-(dimethylamino)pyridin-2-yl]methyl}-6-methyl-5-(1,3-oxazol-2-yl)pyrazine-2-carboxamide;

3-amino-N-[(6-methoxypyridin-2-yl)methyl]-6-methyl-5-(1,3-oxazol-2-yl)pyrazine-2-carboxamide;

3-amino-N-(isoquinolin-8-ylmethyl)-6-methyl-5-(1,3-oxazol-2-yl)pyrazine-2-carboxamide;

3-(3,4-dihydroquinolin-1(2H)-ylcarbonyl)-5-methyl-6-(1,3-oxazol-2-yl)pyrazin-2-amine;

3-amino-6-methyl-5-(1,3-oxazol-2-yl)-N-(2-pyridin-2-ylethyl)pyrazine-2-carboxamide;

3-amino-6-methyl-N-[(1-methyl-1H-pyrazol-3-yl)methyl]-5-(1,3-oxazol-2-yl)pyrazine-2-carboxamide;

3-amino-6-methyl-5-(1,3-oxazol-2-yl)-N-(pyridin-4-ylmethyl)pyrazine-2-carboxamide;

3-amino-6-methyl-5-(1,3-oxazol-2-yl)-N-(pyridin-3-ylmethyl)pyrazine-2-carboxamide;

3-amino-N-(isoquinolin-3-ylmethyl)-6-methyl-5-(1,3-oxazol-2-yl)pyrazine-2-carboxamide;

3-amino-N-(2-fluorobenzyl)-6-methyl-5-(1,3-oxazol-2-yl)pyrazine-2-carboxamide;

3-amino-N-(3-fluorobenzyl)-6-methyl-5-(1,3-oxazol-2-yl)pyrazine-2-carboxamide;

3-amino-N-(4-fluorobenzyl)-6-methyl-5-(1,3-oxazol-2-yl)pyrazine-2-carboxamide;

3-amino-6-methyl-5-(1,3-oxazol-2-yl)-N-(quinolin-2-ylmethyl)pyrazine-2-carboxamide;

3-[(3,3-difluoropiperidin-1-yl)carbonyl]-5-methyl-6-(1,3-oxazol-2-yl)pyrazin-2-amine;

3-amino-N-[(4,6-dimethylpyridin-2-yl)methyl]-6-methyl-5-(1,3-oxazol-2-yl)pyrazine-2-carboxamide;

3-amino-N-{[1-(2,2-difluoroethyl)-1H-benzimidazol-4-yl]methyl}-6-methyl-5-(1,3-oxazol-2-yl)pyrazine-2-carboxamide;

3-amino-6-methyl-5-(1,3-oxazol-2-yl)-N-[(1,4,5-trimethyl-1H-imidazol-2-yl)methyl]pyrazine-2-carboxamide;

3-amino-6-methyl-N-{[5-methyl-1-(1-methylethyl)-1H-imidazol-4-yl]methyl}-5-(1,3-oxazol-2-yl)pyrazine-2-carboxamide;

3-amino-6-methyl-5-(1,3-oxazol-2-yl)-N-(1,3-oxazol-5-ylmethyl)pyrazine-2-carboxamide;

3-amino-N-(isothiazol-5-ylmethyl)-6-methyl-5-(1,3-oxazol-2-yl)pyrazine-2-carboxamide;

3-amino-N-[(3,6-dimethylpyridin-2-yl)methyl]-6-methyl-5-(1,3-oxazol-2-yl)pyrazine-2-carboxamide;

3-amino-6-methyl-5-(1,3-oxazol-2-yl)-N-{[4-(trifluoromethyl)pyridin-2-yl]methyl}pyrazine-2-carboxamide;

3-amino-N-[(3-methoxypyridin-2-yl)methyl]-6-methyl-5-(1,3-oxazol-2-yl)pyrazine-2-carboxamide;

3-amino-N-{[1-(2,2-difluoroethyl)-1H-imidazol-2-yl]methyl}-6-methyl-5-(1,3-oxazol-2-yl)pyrazine-2-carboxamide;

3-amino-N-[(4-chloropyridin-2-yl)methyl]-6-methyl-5-(1,3-oxazol-2-yl)pyrazine-2-carboxamide;

3-amino-N-[(3-chloropyridin-4-yl)methyl]-6-methyl-5-(1,3-oxazol-2-yl)pyrazine-2-carboxamide;

3-amino-N-[(3-chloro-5-fluoropyridin-2-yl)methyl]-6-methyl-5-(1,3-oxazol-2-yl)pyrazine-2-carboxamide;

3-amino-6-methyl-N-[(4-methylpyridazin-3-yl)methyl]-5-(1,3-oxazol-2-yl)pyrazine-2-carboxamide;

3-amino-N-[(5-chloropyridin-2-yl)methyl]-6-methyl-5-(1,3-oxazol-2-yl)pyrazine-2-carboxamide;

3-amino-6-methyl-N-[(1-methyl-2-oxo-1,2-dihydropyridin-3-yl)methyl]-5-(1,3-oxazol-2-yl)pyrazine-2-carboxamide;

3-amino-6-methyl-5-(1,3-oxazol-2-yl)-N-(pyridin-2-ylmethyl)pyrazine-2-carboxamide;

3-amino-6-methyl-5-(1,3-oxazol-2-yl)-N-[(1-oxidopyridin-2-yl)methyl]pyrazine-2-carboxamide;

3-amino-N-[(6-fluoropyridin-3-yl)methyl]-6-methyl-5-(1,3-oxazol-2-yl)pyrazine-2-carboxamide;

3-amino-N-{[6-chloro-4-(trifluoromethyl)pyridin-2-yl]methyl}-6-methyl-5-(1,3-oxazol-2-yl)pyrazine-2-carboxamide;

3-amino-N-{[5-methoxy-6-(trifluoromethyl)pyridin-2-yl]methyl}-6-methyl-5-(1,3-oxazol-2-yl)pyrazine-2-carboxamide;

3-amino-6-methyl-N-[(5-methylpyridazin-3-yl)methyl]-5-(1,3-oxazol-2-yl)pyrazine-2-carboxamide;

3-amino-N-[(5-fluoropyridin-2-yl)methyl]-6-methyl-5-(1,3-oxazol-2-yl)pyrazine-2-carboxamide;

3-amino-6-methyl-N-{[3-methyl-4-(2,2,2-trifluoroethoxy)pyridin-2-yl]methyl}-5-(1,3-oxazol-2-yl)pyrazine-2-carboxamide;

3-amino-6-methyl-5-(1,3-oxazol-2-yl)-N-{[5-(trifluoromethyl)pyridin-2-yl]methyl}pyrazine-2-carboxamide;

3-amino-6-methyl-N-(2-methyl-2-pyridin-4-ylpropyl)-5-(1,3-oxazol-2-yl)pyrazine-2-carboxamide;

3-amino-N-[(4-fluoropyridin-2-yl)methyl]-6-methyl-5-(1,3-oxazol-2-yl)pyrazine-2-carboxamide;

3-amino-N-[(3,5-difluoropyridin-2-yl)methyl]-6-methyl-5-(1,3-oxazol-2-yl)pyrazine-2-carboxamide;

3-amino-N-{[4,6-bis(difluoromethyl)pyridin-2-yl]methyl}-6-methyl-5-(1,3-oxazol-2-yl)pyrazine-2-carboxamide;

3-amino-N-[(2-hydroxypyridin-3-yl)methyl]-6-methyl-5-(1,3-oxazol-2-yl)pyrazine-2-carboxamide;

3-amino-N-[(2-chloropyridin-3-yl)methyl]-6-methyl-5-(1,3-oxazol-2-yl)pyrazine-2-carboxamide;

3-amino-6-methyl-5-(1,3-oxazol-2-yl)-N-(1-pyrimidin-2-ylpiperidin-4-yl)pyrazine-2-carboxamide;

3-amino-6-methyl-N-[(3-methylpyridin-4-yl)methyl]-5-(1,3-oxazol-2-yl)pyrazine-2-carboxamide;

3-amino-N-(2-azetidin-1-yl-2-oxoethyl)-6-methyl-5-(1,3-oxazol-2-yl)pyrazine-2-carboxamide;

3-amino-6-methyl-5-(1,3-oxazol-2-yl)-N-(pyrimidin-5-ylmethyl)pyrazine-2-carboxamide;

3-amino-N-[(2,6-dimethylpyridin-3-yl)methyl]-6-methyl-5-(1,3-oxazol-2-yl)pyrazine-2-carboxamide;

3-amino-N-[(2,4-dimethyl-1,3-thiazol-5-yl)methyl]-6-methyl-5-(1,3-oxazol-2-yl)pyrazine-2-carboxamide;
3-amino-N-[(3-chloropyridin-2-yl)methyl]-6-methyl-5-(1,3-oxazol-2-yl)pyrazine-2-carboxamide;
3-amino-N-[(2-fluoro-5-methylpyridin-3-yl)methyl]-6-methyl-5-(1,3-oxazol-2-yl)pyrazine-2-carboxamide;
3-amino-N-[(5-chloro-3-fluoropyridin-2-yl)methyl]-6-methyl-5-(1,3-oxazol-2-yl)pyrazine-2-carboxamide;
3-amino-N-{[2,6-bis(difluoromethyl)pyridin-4-yl]methyl}-6-methyl-5-(1,3-oxazol-2-yl)pyrazine-2-carboxamide;
3-amino-6-methyl-5-(1,3-oxazol-2-yl)-N-(pyrimidin-4-ylmethyl)pyrazine-2-carboxamide;
3-amino-N-[(1,4-dimethyl-1H-pyrazol-3-yl)methyl]-6-methyl-5-(1,3-oxazol-2-yl)pyrazine-2-carboxamide;
3-amino-N-[(1,5-dimethyl-1H-pyrazol-4-yl)methyl]-6-methyl-5-(1,3-oxazol-2-yl)pyrazine-2-carboxamide;
3-amino-N-[(1-ethyl-1H-imidazol-2-yl)methyl]-6-methyl-5-(1,3-oxazol-2-yl)pyrazine-2-carboxamide;
3-amino-N-[(6-methoxy-3-methylpyridin-2-yl)methyl]-6-methyl-5-(1,3-oxazol-2-yl)pyrazine-2-carboxamide;
3-amino-N-[(4,6-dimethylpyrimidin-2-yl)methyl]-6-methyl-5-(1,3-oxazol-2-yl)pyrazine-2-carboxamide;
3-amino-6-methyl-5-(1,3-oxazol-2-yl)-N-(1-pyridin-2-ylethyl)pyrazine-2-carboxamide;
3-amino-N-(4,4-difluorocyclohexyl)-6-methyl-5-(1,3-oxazol-2-yl)pyrazine-2-carboxamide;
3-amino-6-methyl-5-(1,3-oxazol-2-yl)-N-(5,6,7,8-tetrahydroisoquinolin-5-yl)pyrazine-2-carboxamide;
3-amino-6-methyl-N-{[6-(1-methylethyl)pyridin-2-yl]methyl}-5-(1,3-oxazol-2-yl)pyrazine-2-carboxamide;
3-amino-6-methyl-5-(1,3-oxazol-2-yl)-N-(1-pyridin-2-ylethyl)pyrazine-2-carboxamide;
3-amino-6-methyl-N-{[1-(1-methylethyl)-1H-imidazol-2-yl]methyl}-5-(1,3-oxazol-2-yl)pyrazine-2-carboxamide;
3-amino-6-methyl-N-[(3-methyl-2,2'-bipyridin-6-yl)methyl]-5-(1,3-oxazol-2-yl)pyrazine-2-carboxamide;
3-amino-6-methyl-N-{[3-methyl-6-(1-methylethyl)pyridin-2-yl]methyl}-5-(1,3-oxazol-2-yl)pyrazine-2-carboxamide;
3-amino-N-{[6-(2-ethoxyethyl)-3-methylpyridin-2-yl]methyl}-6-methyl-5-(1,3-oxazol-2-yl)pyrazine-2-carboxamide;
3-amino-N-{[1-(2,2-difluoroethyl)-2-oxo-1,2-dihydropyridin-3-yl]methyl}-6-methyl-5-(1,3-oxazol-2-yl)pyrazine-2-carboxamide;
3-amino-6-methyl-N-{[1-methyl-4-(trifluoromethyl)-1H-imidazol-2-yl]methyl}-5-(1,3-oxazol-2-yl)pyrazine-2-carboxamide;
3-amino-N-[(1-cyanocyclobutyl)methyl]-6-methyl-5-(1,3-oxazol-2-yl)pyrazine-2-carboxamide;
3-amino-6-methyl-5-(1,3-oxazol-2-yl)-N-(1-pyridin-2-ylpropyl)pyrazine-2-carboxamide;
3-amino-N-(1H-indol-7-ylmethyl)-6-methyl-5-(1,3-oxazol-2-yl)pyrazine-2-carboxamide;
3-amino-N-(imidazo-[1,2-a]pyridin-3-yl-methyl)-6-methyl-5-(1,3-oxazol-2-yl)-pyrazine-2-carboxamide;
3-amino-6-methyl-N-[(2-methylimidazo[1,2-a]pyridin-3-yl)methyl]-5-(1,3-oxazol-2-yl)pyrazine-2-carboxamide;
3-amino-6-methyl-5-(1,3-oxazol-2-yl)-N-(5,6,7,8-tetrahydro-1,8-naphthyridin-2-ylmethyl)pyrazine-2-carboxamide;
3-amino-6-methyl-5-(1,3-oxazol-2-yl)-N-[(1-oxidopyridin-3-yl)methyl]pyrazine-2-carboxamide;
3-amino-N-{[1-(cyclopropylmethyl)-5-methyl-1H-imidazol-4-yl]methyl}-6-methyl-5-(1,3-oxazol-2-yl)pyrazine-2-carboxamide;
3-amino-6-methyl-5-(1,3-oxazol-2-yl)-N-[cis-4-(trifluoromethyl)cyclohexyl]pyrazine-2-carboxamide;
3-amino-6-methyl-N-[(6-methylimidazo[1,2-a]pyridin-2-yl)methyl]-5-(1,3-oxazol-2-yl)pyrazine-2-carboxamide;
3-amino-6-methyl-5-(1,3-oxazol-2-yl)-N-(1,4,5,6-tetrahydrocyclopenta[c]pyrazol-3-ylmethyl)pyrazine-2-carboxamide;
3-amino-6-methyl-5-(1,3-oxazol-2-yl)-N-(5,6,7,8-tetrahydroisoquinolin-5-yl)pyrazine-2-carboxamide;
3-amino-6-methyl-5-(1,3-oxazol-2-yl)-N-(1-pyridin-2-ylpropyl)pyrazine-2-carboxamide;
3-amino-N,6-dimethyl-5-(1,3-oxazol-2-yl)-N-(1-pyridin-2-ylethyl)pyrazine-2-carboxamide;
3-amino-N-[(5-fluoro-3-methylpyridin-2-yl)methyl]-6-methyl-5-(1,3-oxazol-2-yl)pyrazine-2-carboxamide;
3-amino-6-methyl-5-(1,3-oxazol-2-yl)-N-{[4-(trifluoromethyl)pyrimidin-2-yl]methyl}pyrazine-2-carboxamide;
3-amino-N-[(5-fluoropyrimidin-2-yl)methyl]-6-methyl-5-(1,3-oxazol-2-yl)pyrazine-2-carboxamide;
3-amino-N-[(4-methoxypyrimidin-2-yl)methyl]-6-methyl-5-(1,3-oxazol-2-yl)pyrazine-2-carboxamide;
3-amino-6-methyl-N-[(7-methylimidazo[1,2-a]pyridin-2-yl)methyl]-5-(1,3-oxazol-2-yl)pyrazine-2-carboxamide;
3-amino-N-[2-(4-fluorophenyl)-2-oxoethyl]-6-methyl-5-(1,3-oxazol-2-yl)pyrazine-2-carboxamide;
3-amino-N-[3-(3,3-difluoropyrrolidin-1-yl)propyl]-6-methyl-5-(1,3-oxazol-2-yl)pyrazine-2-carboxamide;
3-amino-N-{[1-(cyclopropylmethyl)-1H-imidazol-4-yl]methyl}-6-methyl-5-(1,3-oxazol-2-yl)pyrazine-2-carboxamide;
3-amino-N-(3,3-difluorocyclopentyl)-6-methyl-5-(1,3-oxazol-2-yl)pyrazine-2-carboxamide;
3-amino-6-methyl-5-(1,3-oxazol-2-yl)-N-[1-(2,2,2-trifluoroethyl)piperidin-3-yl]pyrazine-2-carboxamide;
3-amino-6-methyl-5-(1,3-oxazol-2-yl)-N-piperidin-3-ylpyrazine-2-carboxamide;
3-amino-6-methyl-5-(1,3-oxazol-2-yl)-N-[trans-4-(trifluoromethyl)cyclohexyl]pyrazine-2-carboxamide;
3-amino-N-{[6-(1-hydroxy-1-methylethyl)pyridin-2-yl]methyl}-6-methyl-5-(1,3-oxazol-2-yl)pyrazine-2-carboxamide;
3-amino-N-[(1,4-dimethyl-1H-imidazol-2-yl)methyl]-6-methyl-5-(1,3-oxazol-2-yl)pyrazine-2-carboxamide;
3-amino-6-methyl-5-(1,3-oxazol-2-yl)-N-{[6-(trifluoromethyl)pyridin-2-yl]methyl}pyrazine-2-carboxamide;
3-amino-N-{[6-(methoxymethyl)pyridin-2-yl]methyl}-6-methyl-5-(1,3-oxazol-2-yl)pyrazine-2-carboxamide;
3-amino-N-(2-methoxyethyl)-6-methyl-5-(1,3-oxazol-2-yl)pyrazine-2-carboxamide;
3-amino-N-[(2-methoxypyridin-3-yl)methyl]-6-methyl-5-(1,3-oxazol-2-yl)pyrazine-2-carboxamide;
3-(5,8-dihydro-1,7-naphthyridin-7(6H)-ylcarbonyl)-5-methyl-6-(1,3-oxazol-2-yl)pyrazin-2-amine;
3-amino-6-methyl-5-(1,3-oxazol-2-yl)-N-{[5-(trifluoromethyl)pyrimidin-2-yl]methyl}pyrazine-2-carboxamide;
3-amino-N-[(1-cyclobutyl-1H-imidazol-2-yl)methyl]-6-methyl-5-(1,3-oxazol-2-yl)pyrazine-2-carboxamide;
3-amino-N-(cyclopropylmethyl)-6-methyl-5-(1,3-oxazol-2-yl)pyrazine-2-carboxamide;
3-amino-N-(5-fluoro-2-hydroxybenzyl)-6-methyl-5-(1,3-oxazol-2-yl)pyrazine-2-carboxamide;
3-amino-N-[(1S,2S)-2-hydroxy-2,3-dihydro-1H-inden-1-yl]-6-methyl-5-(1,3-oxazol-2-yl)pyrazine-2-carboxamide;
5-methyl-6-(1,3-oxazol-2-yl)-3-[(2-phenylazetidin-1-yl)carbonyl]pyrazin-2-amine;

3-amino-6-methyl-5-(1,3-oxazol-2-yl)-N-(thiophen-2-ylmethyl)pyrazine-2-carboxamide;
3-amino-6-methyl-N-[4-(1-methylethyl)benzyl]-5-(1,3-oxazol-2-yl)pyrazine-2-carboxamide;
3-amino-N-(4-cyclopropylbenzyl)-6-methyl-5-(1,3-oxazol-2-yl)pyrazine-2-carboxamide;
3-amino-N-(2-fluoro-3-methylbenzyl)-6-methyl-5-(1,3-oxazol-2-yl)pyrazine-2-carboxamide;
3-amino-6-methyl-5-(1,3-oxazol-2-yl)-N-(2,4,6-trimethylbenzyl)pyrazine-2-carboxamide;
3-amino-N-(4-fluoro-3-methylbenzyl)-6-methyl-5-(1,3-oxazol-2-yl)pyrazine-2-carboxamide;
3-amino-N-[(1S)-2,3-dihydro-1H-inden-1-yl]-6-methyl-5-(1,3-oxazol-2-yl)pyrazine-2-carboxamide;
3-amino-N-(4-ethylbenzyl)-6-methyl-5-(1,3-oxazol-2-yl)pyrazine-2-carboxamide;
3-amino-N-[(1R)-2,3-dihydro-1H-inden-1-yl]-6-methyl-5-(1,3-oxazol-2-yl)pyrazine-2-carboxamide;
3-amino-6-methyl-N-[(1-methyl-1H-pyrrol-2-yl)methyl]-5-(1,3-oxazol-2-yl)pyrazine-2-carboxamide;
3-amino-N-[(1,5-dimethyl-1H-pyrrol-2-yl)methyl]-6-methyl-5-(1,3-oxazol-2-yl)pyrazine-2-carboxamide;
3-amino-N-(3-methoxybenzyl)-6-methyl-5-(1,3-oxazol-2-yl)pyrazine-2-carboxamide;
3-amino-N-(2-methoxybenzyl)-6-methyl-5-(1,3-oxazol-2-yl)pyrazine-2-carboxamide;
3-amino-N-[(4R)-3,4-dihydro-2H-chromen-4-yl]-6-methyl-5-(1,3-oxazol-2-yl)pyrazine-2-carboxamide;
3-amino-N-[(4S)-3,4-dihydro-2H-chromen-4-yl]-6-methyl-5-(1,3-oxazol-2-yl)pyrazine-2-carboxamide;
3-amino-N-[(3R)-2,3-dihydro-1-benzofuran-3-yl]-6-methyl-5-(1,3-oxazol-2-yl)pyrazine-2-carboxamide;
3-amino-N-(4-methoxybenzyl)-6-methyl-5-(1,3-oxazol-2-yl)pyrazine-2-carboxamide;
3-amino-N-(1,3-benzothiazol-2-ylmethyl)-6-methyl-5-(1,3-oxazol-2-yl)pyrazine-2-carboxamide
3-amino-6-methyl-5-(1,3-oxazol-2-yl)-N-[(2-thiophen-2-yl-1,3-thiazol-4-yl)methyl]pyrazine-2-carboxamide;
3-(5,7-dihydro-6H-pyrrolo[3,4-d]pyrimidin-6-ylcarbonyl)-5-methyl-6-(1,3-oxazol-2-yl)pyrazin-2-amine;
3-(5,7-dihydro-6H-pyrrolo[3,4-d]pyrimidin-6-ylcarbonyl)-5-methyl-6-(1,3-oxazol-2-yl)pyrazin-2-amine;
3-amino-N-(2-hydroxybenzyl)-6-methyl-5-(1,3-oxazol-2-yl)pyrazine-2-carboxamide;
3-amino-N-(2-hydroxy-5-methylbenzyl)-6-methyl-5-(1,3-oxazol-2-yl)pyrazine-2-carboxamide;
3-amino-N-(4-hydroxybenzyl)-6-methyl-5-(1,3-oxazol-2-yl)pyrazine-2-carboxamide;
3-amino-N-[(1R,2S)-2-hydroxy-2,3-dihydro-1H-inden-1-yl]-6-methyl-5-(1,3-oxazol-2-yl)pyrazine-2-carboxamide;
3-amino-N-[(3S)-2,3-dihydro-1-benzofuran-3-yl]-6-methyl-5-(1,3-oxazol-2-yl)pyrazine-2-carboxamide;
3-amino-N-(3-hydroxybenzyl)-6-methyl-5-(1,3-oxazol-2-yl)pyrazine-2-carboxamide;
3-amino-N-[(1R,2R)-2-hydroxy-2,3-dihydro-1H-inden-1-yl]-6-methyl-5-(1,3-oxazol-2-yl)pyrazine-2-carboxamide;
3-amino-N-(6,7-dihydro-5H-pyrrolo[2,1-c][1,2,4]triazol-3-ylmethyl)-6-methyl-5-(1,3-oxazol-2-yl)pyrazine-2-carboxamide;
3-amino-N-(1,4,5,6,7,8-hexahydrocyclohepta[c]pyrazol-3-ylmethyl)-6-methyl-5-(1,3-oxazol-2-yl)pyrazine-2-carboxamide;
3-amino-N-[(4-fluoro-3-methylpyridin-2-yl)methyl]-6-methyl-5-(1,3-oxazol-2-yl)pyrazine-2-carboxamide;
3-amino-N-[(3-ethyl-4-fluoropyridin-2-yl)methyl]-6-methyl-5-(1,3-oxazol-2-yl)pyrazine-2-carboxamide;
3-amino-N-(1H-benzimidazol-2-ylmethyl)-6-methyl-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-[(1-ethyl-1H-1,2,4-triazol-5-yl)methyl]-6-methyl-5-(1,3-oxazol-2-yl)pyrazine-2-carboxamide;
3-amino-N-[(3-ethoxypyridin-2-yl)methyl]-6-methyl-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-[(3-cyclopropyl-5-fluoropyridin-2-yl)methyl]-6-methyl-5-(1,3-oxazol-2-yl)pyrazine-2-carboxamide;
3-amino-N-[(4-cyclopropyl-1-methyl-1H-pyrazol-3-yl)methyl]-6-methyl-5-(1,3-oxazol-2-yl)pyrazine-2-carboxamide;
3-amino-N-[(1R,2S)-2-(methoxymethyl)cyclopentyl]-6-methyl-5-(1,3-oxazol-2-yl)pyrazine-2-carboxamide;
3-amino-N-[(3-fluoropyrazin-2-yl)methyl]-6-methyl-5-(1,3-oxazol-2-yl)pyrazine-2-carboxamide;
3-amino-N-(2-ethoxy-6-fluorobenzyl)-6-methyl-5-(1,3-oxazol-2-yl)pyrazine-2-carboxamide;
3-amino-6-methyl-N-[(1-methyl-1,4,5,6-tetrahydrocyclopenta[c]pyrazol-3-yl)methyl]-5-(1,3-oxazol-2-yl)pyrazine-2-carboxamide;
3-amino-6-methyl-N-[(5-methylpyrimidin-4-yl)methyl]-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-(isoquinolin-1-ylmethyl)-6-methyl-5-(1,3-oxazol-2-yl)pyrazine-2-carboxamide;
3-amino-N-[(3-ethylpyridin-2-yl)methyl]-6-methyl-5-(1,3-oxazol-2-yl)pyrazine-2-carboxamide;
3-amino-N-[(3-cyclopropyl-4-fluoropyridin-2-yl)methyl]-6-methyl-5-(1,3-oxazol-2-yl)pyrazine-2-carboxamide;
3-amino-6-methyl-5-(1,3-oxazol-2-yl)-N-{[1-(2,2,2-trifluoroethyl)-1H-benzimidazol-4-yl]methyl}pyrazine-2-carboxamide;
3-amino-{[3-cyclopropyl-5-(trifluoromethyl)pyridin-2-yl]methyl}-6-methyl-5-(1,3-oxazol-2-yl)pyrazine-2-carboxamide;
3-amino-6-methyl-N-{[3-methyl-5-(trifluoromethyl)pyridin-2-yl]methyl}-5-(1,3-oxazol-2-yl)pyrazine-2-carboxamide;
3-amino-N-[(3-cyclopropyl-pyrazin-2-yl)methyl]-6-methyl-5-(1,3-oxazol-2-yl)pyrazine-2-carboxamide;
3-amino-6-methyl-N-[(5-methylpyrimidin-2-yl)methyl]-5-(1,3-oxazol-2-yl)pyrazine-2-carboxamide;
3-amino-N-(2-fluoro-6-methoxybenzyl)-6-methyl-5-(1,3-oxazol-2-yl)pyrazine-2-carboxamide;
3-amino-N-[(3-ethylpyrazin-2-yl)methyl]-6-methyl-5-(1,3-oxazol-2-yl)pyrazine-2-carboxamide;
3-amino-6-methyl-N-{[1-(1-methylethyl)-1H-1,2,4-triazol-5-yl]methyl}-5-(1,3-oxazol-2-yl)pyrazine-2-carboxamide;
3-amino-6-methyl-N-{[1-(1-methylethyl)-1H-benzimidazol-4-yl]methyl}-5-(1,3-oxazol-2-yl)pyrazine-2-carboxamide;
3-amino-6-methyl-N-[2-(2-methyl-6,7-dihydro[1,3]oxazolo[5,4-c]pyridin-5 (4H)-yl)ethyl]-5-(1,3-oxazol-2-yl)pyrazine-2-carboxamide;
3-amino-N-(2,2-difluorocyclopentyl)-6-methyl-5-(1,3-oxazol-2-yl)pyrazine-2-carboxamide;

3-amino-N-(2,2-difluorocyclopentyl)-6-methyl-5-(1,3-oxazol-2-yl)pyrazine-2-carboxamide;
3-amino-N-[(1-ethyl-1H-benzimidazol-4-yl)methyl]-6-methyl-5-(1,3-oxazol-2-yl)pyrazine-2-carboxamide;
3-amino-N-{[4-(difluoromethyl)-1-methyl-1H-pyrazol-3-yl]methyl}-6-methyl-5-(1,3-oxazol-2-yl)pyrazine-2-carboxamide;
3-amino-6-methyl-N-[(3-methylpyrazin-2-yl)methyl]-5-(1,3-oxazol-2-yl)pyrazine-2-carboxamide;
3-amino-N-{[3-ethyl-5-(trifluoromethyl)pyridin-2-yl]methyl}-6-methyl-5-(1,3-oxazol-2-yl)pyrazine-2-carboxamide;
3-amino-N-[(5-cyclopropylpyrimidin-2-yl)methyl]-6-methyl-5-(1,3-oxazol-2-yl)pyrazine-2-carboxamide;
3-amino-6-methyl-N-[(3-methyl-3H-imidazo[4,5-c]pyridin-4-yl)methyl]-5-(1,3-oxazol-2-yl)pyrazine-2-carboxamide;
3-amino-N-[(5-ethylpyrimidin-2-yl)methyl]-6-methyl-5-(1,3-oxazol-2-yl)pyrazine-2-carboxamide;
3-amino-N-[(1S)-5-fluoro-2,3-dihydro-1H-inden-1-yl]-6-methyl-5-(1,3-oxazol-2-yl)pyrazine-2-carboxamide;
3-amino-N-[(1S)-6-fluoro-2,3-dihydro-1H-inden-1-yl]-6-methyl-5-(1,3-oxazol-2-yl)pyrazine-2-carboxamide;
3-amino-N-[(1R,2R)-2-hydroxycyclopentyl]-6-methyl-5-(1,3-oxazol-2-yl)pyrazine-2-carboxamide;
3-amino-N-[(1S,2R)-2-fluorocyclopentyl]-6-methyl-5-(1,3-oxazol-2-yl)pyrazine-2-carboxamide;
3-amino-N-[(1R,2R)-2-(dimethylamino)cyclopentyl]-6-methyl-5-(1,3-oxazol-2-yl)pyrazine-2-carboxamide;
3-amino-N-[(1R,2R)-2-hydroxycyclopentyl]-N,6-dimethyl-5-(1,3-oxazol-2-yl)pyrazine-2-carboxamide;
3-amino-N-[(1R,2R)-2-fluorocyclopentyl]-6-methyl-5-(1,3-oxazol-2-yl)pyrazine-2-carboxamide;
3-amino-N-[(1S,2R,5R)-2-hydroxy-5-methylcyclopentyl]-6-methyl-5-(1,3-oxazol-2-yl)pyrazine-2-carboxamide;
3-amino-6-methyl-5-(1,3-oxazol-2-yl)-N-[(1R,2R)-2-prop-2-yn-1-ylcyclopentyl]pyrazine-2-carboxamide;
3-amino-N-[(1S,2R)-2-ethynylcyclopentyl]-6-methyl-5-(1,3-oxazol-2-yl)pyrazine-2-carboxamide;
3-amino-N-(2-fluorocyclopentyl)-6-methyl-5-(1,3-oxazol-2-yl)pyrazine-2-carboxamide;
3-amino-N-[(1S,2S)-2-hydroxycyclopentyl]-6-methyl-5-(1,3-oxazol-2-yl)pyrazine-2-carboxamide;
3-amino-N-[(1R,2S)-2-hydroxycyclopentyl]-6-methyl-5-(1,3-oxazol-2-yl)pyrazine-2-carboxamide;
3-amino-N-[(1R,2R,4S)-bicyclo[2.2.1]hept-2-yl]-6-methyl-5-(1,3-oxazol-2-yl)pyrazine-2-carboxamide;
3-amino-6-methyl-N-[(1-methyl-1H-pyrrolo[3,2-c]pyridin-4-yl)methyl]-5-(1,3-oxazol-2-yl)pyrazine-2-carboxamide;
3-amino-6-methyl-5-(1,3-oxazol-2-yl)-N-{[3-(trifluoromethyl)pyrazin-2-yl]methyl}pyrazine-2-carboxamide;
3-amino-N-[(2-ethyl-2H-indazol-7-yl)methyl]-6-methyl-5-(1,3-oxazol-2-yl)pyrazine-2-carboxamide;
3-amino-N-{[1-(2,2-difluoroethyl)-1H-indol-4-yl]methyl}-6-methyl-5-(1,3-oxazol-2-yl)pyrazine-2-carboxamide;
3-amino-6-methyl-N-[(1-methyl-1H-benzimidazol-4-yl)methyl]-5-(1,3-oxazol-2-yl)pyrazine-2-carboxamide;
3-amino-6-methyl-N-[(1-methyl-1H-benzimidazol-7-yl)methyl]-5-(1,3-oxazol-2-yl)pyrazine-2-carboxamide;
3-amino-N-(5-cyano-2,3-dihydro-1H-inden-1-yl)-6-methyl-5-(1,3-oxazol-2-yl)pyrazine-2-carboxamide;
3-amino-N-(5-cyano-2,3-dihydro-1H-inden-1-yl)-6-methyl-5-(1,3-oxazol-2-yl)pyrazine-2-carboxamide;
3-amino-N-[(1S)-5-chloro-2,3-dihydro-1H-inden-1-yl]-6-methyl-5-(1,3-oxazol-2-yl)pyrazine-2-carboxamide;
3-amino-N-(5-hydroxy-6,7-dihydro-5H-cyclopenta[b]pyridin-7-yl)-6-methyl-5-(1,3-oxazol-2-yl)pyrazine-2-carboxamide;
3-amino-N-{[3-(fluoromethyl)pyridin-2-yl]methyl}-6-methyl-5-(1,3-oxazol-2-yl)pyrazine-2-carboxamide;
3-amino-N-{[3-(hydroxymethyl)pyridin-2-yl]methyl}-6-methyl-5-(1,3-oxazol-2-yl)pyrazine-2-carboxamide;
3-amino-6-methyl-N-[1-(3-methylpyridin-2-yl)ethyl]-5-(1,3-oxazol-2-yl)pyrazine-2-carboxamide;
3-amino-6-methyl-N-[1-(3-methylpyridin-2-yl)ethyl]-5-(1,3-oxazol-2-yl)pyrazine-2-carboxamide;
3-amino-N-{[1-(2,2-difluoroethyl)-1H-indazol-4-yl]methyl}-6-methyl-5-(1,3-oxazol-2-yl)pyrazine-2-carboxamide;
3-amino-N-{[1-(cyclopropylmethyl)-1H-benzimidazol-4-yl]methyl}-6-methyl-5-(1,3-oxazol-2-yl)pyrazine-2-carboxamide;
3-amino-6-methyl-5-(1,3-oxazol-2-yl)-N-(5,6,7,8-tetrahydroquinolin-8-yl)pyrazine-2-carboxamide;
3-amino-N-(5-methoxy-2,3-dihydro-1H-inden-1-yl)-6-methyl-5-(1,3-oxazol-2-yl)pyrazine-2-carboxamide;
3-amino-N-(5-methoxy-2,3-dihydro-1H-inden-1-yl)-6-methyl-5-(1,3-oxazol-2-yl)pyrazine-2-carboxamide;
3-amino-6-methyl-5-(1,3-oxazol-2-yl)-N-(1,2,3,4-tetrahydronaphthalen-2-yl)pyrazine-2-carboxamide;
3-amino-6-methyl-5-(1,3-oxazol-2-yl)-N-(1,2,3,4-tetrahydronaphthalen-2-yl)pyrazine-2-carboxamide;
3-amino-N-(2,3-dihydro-1H-inden-2-yl)-6-methyl-5-(1,3-oxazol-2-yl)pyrazine-2-carboxamide;
3-amino-N-{[6-(1-hydroxy-1-methylethyl)-3-methylpyridin-2-yl]methyl}-6-methyl-5-(1,3-oxazol-2-yl)pyrazine-2-carboxamide;
3-amino-N-{[6-(1-hydroxy-1-methylethyl)-3-methoxypyridin-2-yl]methyl}-6-methyl-5-(1,3-oxazol-2-yl)pyrazine-2-carboxamide;
3-amino-N-(6-hydroxy-6,7-dihydro-5H-cyclopenta[b]pyridin-7-yl)-6-methyl-5-(1,3-oxazol-2-yl)pyrazine-2-carboxamide;
3-amino-N-(6-hydroxy-6,7-dihydro-5H-cyclopenta[b]pyridin-7-yl)-6-methyl-5-(1,3-oxazol-2-yl)pyrazine-2-carboxamide;
3-amino-N-(5-hydroxy-6,7-dihydro-5H-cyclopenta[b]pyridin-7-yl)-6-methyl-5-(1,3-oxazol-2-yl)pyrazine-2-carboxamide;
3-amino-N-(5-hydroxy-6,7-dihydro-5H-cyclopenta[b]pyridin-7-yl)-6-methyl-5-(1,3-oxazol-2-yl)pyrazine-2-carboxamide;
3-amino-N-[(1-ethyl-1H-indazol-4-yl)methyl]-6-methyl-5-(1,3-oxazol-2-yl)pyrazine-2-carboxamide;
3-amino-N-[(2-ethyl-2H-indazol-4-yl)methyl]-6-methyl-5-(1,3-oxazol-2-yl)pyrazine-2-carboxamide;
3-amino-N-(4-chloro-6,7-dihydro-5H-cyclopenta[b]pyridin-7-yl)-6-methyl-5-(1,3-oxazol-2-yl)pyrazine-2-carboxamide;
3-amino-N-(2-chloro-6,7-dihydro-5H-cyclopenta[b]pyridin-7-yl)-6-methyl-5-(1,3-oxazol-2-yl)pyrazine-2-carboxamide;
3-amino-6-methyl-5-(1,3-oxazol-2-yl)-N-(5,6,7,8-tetrahydroquinolin-8-yl)pyrazine-2-carboxamide;
3-amino-N-(4-chloro-6,7-dihydro-5H-cyclopenta[b]pyridin-7-yl)-6-methyl-5-(1,3-oxazol-2-yl)pyrazine-2-carboxamide;
3-amino-N-(2-chloro-6,7-dihydro-5H-cyclopenta[b]pyridin-7-yl)-6-methyl-5-(1,3-oxazol-2-yl)pyrazine-2-carboxamide;
3-amino-6-methyl-5-(1,3-oxazol-5-yl)-N-{[3-(trifluoromethyl)-pyridin-2-yl]-methyl}pyrazine-2-carboxamide;

3-amino-6-chloro-5-(1,3-oxazol-5-yl)-N-(quinolin-8-ylmethyl)pyrazine-2-carboxamide;
3-amino-N-(2,6-difluorobenzyl)-6-methyl-5-(1,3-oxazol-5-yl)pyrazine-2-carboxamide;
3-amino-6-methyl-N-[(3-methylpyridin-2-yl)methyl]-5-(1,3-oxazol-5-yl)pyrazine-2-carboxamide;
3-amino-N-(2,4-difluorobenzyl)-6-methyl-5-(1,3-oxazol-5-yl)pyrazine-2-carboxamide;
3-amino-N-(2-methoxybenzyl)-6-methyl-5-(1,3-oxazol-5-yl)pyrazine-2-carboxamide;
3-amino-N-(2,6-dichlorobenzyl)-6-methyl-5-(1,3-oxazol-5-yl)pyrazine-2-carboxamide;
3-amino-N-(2-chloro-6-methylbenzyl)-6-methyl-5-(1,3-oxazol-5-yl)pyrazine-2-carboxamide;
3-amino-6-methyl-5-(1,3-oxazol-5-yl)-N-{[3-(trifluoromethyl)pyridin-2-yl]methyl}pyrazine-2-carboxamide;
3-amino-N-(2,4-dichloro-6-methylbenzyl)-6-methyl-5-(1,3-oxazol-5-yl)pyrazine-2-carboxamide;
3-amino-6-methyl-N-(1-methyl-1-pyridin-2-ylethyl)-5-(1,3-oxazol-5-yl)pyrazine-2-carboxamide;
3-amino-N-[1-(3,4-difluorophenyl)-1-methylethyl]-6-methyl-5-(1,3-oxazol-5-yl)pyrazine-2-carboxamide;
3-amino-6-methyl-N-(1-methyl-1-pyridin-4-ylethyl)-5-(1,3-oxazol-5-yl)pyrazine-2-carboxamide;
3-amino-N-(2,2-difluoropropyl)-6-methyl-5-(1,3-oxazol-5-yl)pyrazine-2-carboxamide;
3-amino-6-methyl-N-[(6-methylpyridin-2-yl)methyl]-5-(1,3-oxazol-5-yl)pyrazine-2-carboxamide;
3-amino-N-(6,7-dihydro-5H-cyclopenta[b]pyridin-7-yl)-6-methyl-5-(1,3-oxazol-5-yl)pyrazine-2-carboxamide;
3-amino-N-(6,7-dihydro-5H-cyclopenta[b]pyridin-7-yl)-6-methyl-5-(1,3-oxazol-5-yl)pyrazine-2-carboxamide;
3-amino-6-chloro-5-(1H-1,2,3-triazol-1-yl)-N-[2-(trifluoromethyl)benzyl]pyrazine-2-carboxamide;
3-amino-6-chloro-5-(2H-1,2,3-triazol-2-yl)-N-[2-(trifluoromethyl)benzyl]pyrazine-2-carboxamide;
3-amino-6-chloro-N-(2,4-difluorobenzyl)-5-(1H-1,2,3-triazol-1-yl)pyrazine-2-carboxamide;
3-amino-6-chloro-N-(2,4-difluorobenzyl)-5-(2H-1,2,3-triazol-2-yl)pyrazine-2-carboxamide;
3-amino-6-chloro-N-(quinolin-8-ylmethyl)-5-(1H-1,2,3-triazol-1-yl)pyrazine-2-carboxamide;
3-amino-6-chloro-N-(quinolin-8-ylmethyl)-5-(2H-1,2,3-triazol-2-yl)pyrazine-2-carboxamide;
3-amino-N-(2,6-difluorobenzyl)-6-methyl-5-(2H-1,2,3-triazol-2-yl)pyrazine-2-carboxamide;
3-amino-6-methyl-N-(quinolin-8-ylmethyl)-5-(2H-1,2,3-triazol-2-yl)pyrazine-2-carboxamide;
ethyl 3-amino-6-methyl-5-(2H-1,2,3-triazol-2-yl)pyrazine-2-carboxylate;
3-amino-6-methyl-N-[(3-methylpyridin-2-yl)methyl]-5-(2H-1,2,3-triazol-2-yl)pyrazine-2-carboxamide;
3-amino-6-methyl-N-[(3-methylpyridin-2-yl)methyl]-5-(1H-1,2,3-triazol-1-yl)pyrazine-2-carboxamide;
3-amino-N-(2,4-dichlorobenzyl)-6-methyl-5-(2H-1,2,3-triazol-2-yl)pyrazine-2-carboxamide;
3-amino-6-methyl-N-(1,2,3,4-tetrahydroquinolin-4-yl)-5-(2H-1,2,3-triazol-2-yl)pyrazine-2-carboxamide;
3-amino-6-chloro-N-[(1R)-2,3-dihydro-1H-inden-1-yl]-5-(2H-1,2,3-triazol-2-yl)pyrazine-2-carboxamide;
3-amino-6-chloro-N-[(3-methylpyridin-2-yl)methyl]-5-(2H-1,2,3-triazol-2-yl)pyrazine-2-carboxamide;
3-amino-6-chloro-N-(2-methoxybenzyl)-5-(2H-1,2,3-triazol-2-yl)pyrazine-2-carboxamide;
3-amino-6-chloro-5-(2H-1,2,3-triazol-2-yl)-N-[2-(trifluoromethoxy)benzyl]pyrazine-2-carboxamide;
3-amino-6-chloro-5-(2H-1,2,3-triazol-2-yl)-N-[(1R)-2,2,2-trifluoro-1-phenylethyl]pyrazine-2-carboxamide;
3-amino-6-chloro-5-(2H-1,2,3-triazol-2-yl)-N-[(1S)-2,2,2-trifluoro-1-phenylethyl]pyrazine-2-carboxamide;
3-amino-6-chloro-N-[(1R)-1-quinolin-2-ylethyl]-5-(2H-1,2,3-triazol-2-yl)pyrazine-2-carboxamide;
3-amino-N-(2-bromobenzyl)-6-chloro-5-(2H-1,2,3-triazol-2-yl)pyrazine-2-carboxamide;
3-amino-N-[2-(2-bromophenyl)ethyl]-6-chloro-5-(2H-1,2,3-triazol-2-yl)pyrazine-2-carboxamide;
3-amino-6-chloro-N-methyl-N-(quinolin-8-ylmethyl)-5-(2H-1,2,3-triazol-2-yl)pyrazine-2-carboxamide;
3-amino-6-chloro-N-(1-pyridin-3-ylcyclopropyl)-5-(2H-1,2,3-triazol-2-yl)pyrazine-2-carboxamide;
3-[(8-bromo-3,4-dihydroisoquinolin-2(1H)-yl)carbonyl]-5-chloro-6-(2H-1,2,3-triazol-2-yl)pyrazin-2-amine;
3-amino-6-chloro-N-(1,2,3,4-tetrahydroquinolin-4-yl)-5-(2H-1,2,3-triazol-2-yl)pyrazine-2-carboxamide;
3-amino-6-chloro-N-[2-(3,4-dimethoxyphenyl)ethyl]-5-(2H-1,2,3-triazol-2-yl)pyrazine-2-carboxamide;
3-amino-6-chloro-N-(pyrazolo[1,5-a]pyridin-3-ylmethyl)-5-(2H-1,2,3-triazol-2-yl)pyrazine-2-carboxamide;
3-amino-6-chloro-N-(isoquinolin-5-ylmethyl)-5-(2H-1,2,3-triazol-2-yl)pyrazine-2-carboxamide;
3-amino-6-chloro-N-(isoquinolin-8-ylmethyl)-5-(2H-1,2,3-triazol-2-yl)pyrazine-2-carboxamide;
3-amino-N-(1,3-benzothiazol-2-ylmethyl)-6-chloro-5-(2H-1,2,3-triazol-2-yl)pyrazine-2-carboxamide;
3-amino-N-(1,3-benzoxazol-2-ylmethyl)-6-chloro-5-(2H-1,2,3-triazol-2-yl)pyrazine-2-carboxamide;
3-amino-6-chloro-N-(quinoxalin-5-ylmethyl)-5-(2H-1,2,3-triazol-2-yl)pyrazine-2-carboxamide;
3-amino-6-chloro-N-(quinolin-4-ylmethyl)-5-(2H-1,2,3-triazol-2-yl)pyrazine-2-carboxamide;
3-amino-N-(1H-benzimidazol-2-ylmethyl)-6-chloro-5-(2H-1,2,3-triazol-2-yl)pyrazine-2-carboxamide;
3-amino-N-(2-aminobenzyl)-6-chloro-5-(2H-1,2,3-triazol-2-yl)pyrazine-2-carboxamide;
3-amino-N-(2-amino-6-fluorobenzyl)-6-chloro-5-(2H-1,2,3-triazol-2-yl)pyrazine-2-carboxamide;
3-amino-6-chloro-N-(imidazo[1,2-a]pyridin-3-ylmethyl)-5-(2H-1,2,3-triazol-2-yl)pyrazine-2-carboxamide;
3-amino-6-chloro-N-(quinolin-2-ylmethyl)-5-(2H-1,2,3-triazol-2-yl)pyrazine-2-carboxamide;
3-amino-6-chloro-N-(isoquinolin-3-ylmethyl)-5-(2H-1,2,3-triazol-2-yl)pyrazine-2-carboxamide;
3-amino-6-chloro-N-(1H-indol-2-ylmethyl)-5-(2H-1,2,3-triazol-2-yl)pyrazine-2-carboxamide;
3-amino-6-chloro-N-(quinolin-5-ylmethyl)-5-(2H-1,2,3-triazol-2-yl)pyrazine-2-carboxamide;
3-amino-6-chloro-N-(imidazo[2,1-b][1,3]thiazol-6-ylmethyl)-5-(2H-1,2,3-triazol-2-yl)pyrazine-2-carboxamide;
3-amino-6-chloro-N-(2-pyrazin-2-ylethyl)-5-(2H-1,2,3-triazol-2-yl)pyrazine-2-carboxamide;
3-amino-6-chloro-N-[(1R)-2-hydroxy-1-phenylethyl]-5-(2H-1,2,3-triazol-2-yl)pyrazine-2-carboxamide;
3-amino-6-chloro-N-[(1S)-2-hydroxy-1-phenylethyl]-5-(2H-1,2,3-triazol-2-yl)pyrazine-2-carboxamide;
3-amino-6-chloro-N-[(3-oxo-2,3-dihydro-1H-isoindol-4-yl)methyl]-5-(2H-1,2,3-triazol-2-yl)pyrazine-2-carboxamide;
3-amino-6-chloro-N-(2-phenoxyethyl)-5-(2H-1,2,3-triazol-2-yl)pyrazine-2-carboxamide;
3-amino-6-chloro-N-[(1R,2R)-2-fluoro-2-phenyl cyclopropyl]-5-(2H-1,2,3-triazol-2-yl)pyrazine-2-carboxamide;
3-amino-6-chloro-N-[(1S,2R)-2-fluoro-2-phenylcyclopropyl]-5-(2H-1,2,3-triazol-2-yl)pyrazine-2-carboxamide;

methyl N-{[3-amino-6-chloro-5-(2H-1,2,3-triazol-2-yl)pyrazin-2-yl]carbonyl}-D-serinate;
3-amino-6-chloro-N-(5,6,7,8-tetrahydroquinolin-8-ylmethyl)-5-(2H-1,2,3-triazol-2-yl)pyrazine-2-carboxamide;
3-amino-N-[(1S)-1-benzyl-2-hydroxyethyl]-6-chloro-5-(2H-1,2,3-triazol-2-yl)pyrazine-2-carboxamide;
3-amino-6-chloro-N-(1H-imidazol-2-ylmethyl)-5-(2H-1,2,3-triazol-2-yl)pyrazine-2-carboxamide;
3-amino-6-chloro-N-(1-methyl-1,2,3,4-tetrahydroquinolin-4-yl)-5-(2H-1,2,3-triazol-2-yl)pyrazine-2-carboxamide;
methyl (2S)-({[3-amino-6-chloro-5-(2H-1,2,3-triazol-2-yl)pyrazin-2-yl]carbonyl}amino)(phenyl)ethanoate;
3-amino-6-chloro-N-[(1S)-2-hydroxy-1-pyridin-2-ylethyl]-5-(2H-1,2,3-triazol-2-yl)pyrazine-2-carboxamide;
3-amino-6-chloro-N-[(1S)-2-hydroxy-1-(1H-indol-3-ylmethyl)ethyl]-5-(2H-1,2,3-triazol-2-yl)pyrazine-2-carboxamide;
3-amino-6-chloro-N-[(6-methylpyridin-2-yl)methyl]-5-(2H-1,2,3-triazol-2-yl)pyrazine-2-carboxamide;
3-amino-6-chloro-5-(1H-1,2,4-triazol-1-yl)-N-[2-(trifluoromethyl)benzyl]pyrazine-2-carboxamide;
3-amino-6-chloro-N-(2,4-difluorobenzyl)-5-(1H-1,2,4-triazol-1-yl)pyrazine-2-carboxamide
methyl 3-amino-6-chloro-5-(1H-pyrazol-1-yl)pyrazine-2-carboxylate;
3-amino-6-chloro-5-(1H-pyrazol-1-yl)-N-[2-(trifluoromethyl)benzyl]pyrazine-2-carboxamide;
3-amino-6-chloro-N-(4-fluorobenzyl)-5-(1H-pyrazol-1-yl)pyrazine-2-carboxamide;
3-amino-6-chloro-N-(2,4-difluorobenzyl)-5-(1H-pyrazol-1-yl)pyrazine-2-carboxamide;
3-amino-6-chloro-5-(1H-pyrazol-1-yl)-N-(quinolin-8-ylmethyl)pyrazine-2-carboxamide;
3-amino-6-chloro-N-[(1R)-2,3-dihydro-1H-inden-1-yl]-5-(1H-pyrazol-1-yl)pyrazine-2-carboxamide;
3-amino-6-chloro-N-[(3-methylpyridin-2-yl)methyl]-5-(1H-pyrazol-1-yl)pyrazine-2-carboxamide;
3-amino-6-chloro-5-(4-methyl-1H-pyrazol-1-yl)-N-[2-(trifluoromethyl)benzyl]pyrazine-2-carboxamide;
3-amino-6-chloro-N-[(1R)-2,3-dihydro-1H-inden-1-yl]-5-(4-methyl-1H-pyrazol-1-yl)pyrazine-2-carboxamide;
3-amino-6-chloro-5-(4-methyl-1H-pyrazol-1-yl)-N-[(3-methylpyridin-2-yl)methyl]pyrazine-2-carboxamide;
3-amino-6-chloro-5-(3-methyl-1H-pyrazol-1-yl)-N-[2-(trifluoromethyl)benzyl]pyrazine-2-carboxamide;
3-amino-6-chloro-N-[(1R)-2,3-dihydro-1H-inden-1-yl]-5-(3-methyl-1H-pyrazol-1-yl)pyrazine-2-carboxamide;
3-amino-6-chloro-5-(4-methyl-1H-pyrazol-1-yl)-N-(quinolin-8-ylmethyl)pyrazine-2-carboxamide;
3-amino-6-methyl-5-(4-methyl-1H-pyrazol-1-yl)-N-[(3-methylpyridin-2-yl)methyl]pyrazine-2-carboxamide;
3-amino-N-(isoquinolin-1-ylmethyl)-6-methyl-5-(4-methyl-1H-pyrazol-1-yl)pyrazine-2-carboxamide;
3-amino-6-chloro-5-(4-methyl-1H-pyrazol-1-yl)-N-{[3-(trifluoromethyl)pyridin-2-yl]methyl}pyrazine-2-carboxamide;
3-amino-6-chloro-N-(2,4-difluorobenzyl)-5-(4-methyl-2H-1,2,3-triazol-2-yl)pyrazine-2-carboxamide;
3-amino-6-chloro-N-[(3-methylpyridin-2-yl)methyl]-5-(4-methyl-2H-1,2,3-triazol-2-yl)pyrazine-2-carboxamide;
3-amino-6-chloro-5-(4-methyl-2H-1,2,3-triazol-2-yl)-N-(1,2,3,4-tetrahydroquinolin-4-yl)pyrazine-2-carboxamide;
3-amino-6-methyl-5-(1H-pyrazol-1-yl)-N-(quinolin-8-ylmethyl)pyrazine-2-carboxamide;
3-amino-6-chloro-5-(4-methyl-2H-1,2,3-triazol-2-yl)-N-(quinolin-8-ylmethyl)pyrazine-2-carboxamide;
3-amino-6-chloro-N-[(1S)-2-hydroxy-1-phenylethyl]-5-(4-methyl-1H-pyrazol-1-yl)pyrazine-2-carboxamide;
3-amino-6-chloro-N-(1H-indol-5-ylmethyl)-5-(4-methyl-1H-pyrazol-1-yl)pyrazine-2-carboxamide;
3-amino-6-chloro-N-[(1-methyl-1H-benzimidazol-2-yl)methyl]-5-(4-methyl-1H-pyrazol-1-yl)pyrazine-2-carboxamide;
3-amino-6-chloro-N-(1H-indol-7-ylmethyl)-5-(4-methyl-1H-pyrazol-1-yl)pyrazine-2-carboxamide;
3-amino-6-chloro-N-(1H-indol-4-ylmethyl)-5-(4-methyl-1H-pyrazol-1-yl)pyrazine-2-carboxamide;
3-amino-6-chloro-N-(1H-indol-6-ylmethyl)-5-(4-methyl-1H-pyrazol-1-yl)pyrazine-2-carboxamide;
3-amino-N-(1,3-benzothiazol-2-ylmethyl)-6-chloro-5-(4-methyl-1H-pyrazol-1-yl)pyrazine-2-carboxamide;
3-amino-N-(1,3-benzoxazol-2-ylmethyl)-6-chloro-5-(4-methyl-1H-pyrazol-1-yl)pyrazine-2-carboxamide;
3-amino-6-chloro-5-(4-methyl-1H-pyrazol-1-yl)-N-(quinoxalin-5-ylmethyl)pyrazine-2-carboxamide;
3-amino-N-benzyl-6-chloro-5-(4-methyl-1H-pyrazol-1-yl)pyrazine-2-carboxamide;
3-amino-6-chloro-N-(imidazo[2,1-b][1,3]thiazol-6-ylmethyl)-5-(4-methyl-1H-pyrazol-1-yl)pyrazine-2-carboxamide;
3-amino-6-chloro-N-(imidazo[1,2-a]pyridin-3-ylmethyl)-5-(4-methyl-1H-pyrazol-1-yl)pyrazine-2-carboxamide;
3-amino-6-chloro-N-(isoquinolin-4-ylmethyl)-5-(4-methyl-1H-pyrazol-1-yl)pyrazine-2-carboxamide
3-amino-6-chloro-5-(4-methyl-1H-pyrazol-1-yl)-N-(pyrazolo[1,5-a]pyridin-3-ylmethyl)pyrazine-2-carboxamide;
3-amino-6-chloro-5-(4-methyl-1H-pyrazol-1-yl)-N-[(3-oxo-2,3-dihydro-1H-isoindol-4-yl)methyl]pyrazine-2-carboxamide;
3-amino-6-methyl-N-((3-methylpyridin-2-yl)methyl)-5-(4-(trifluoromethyl) oxazol-2-yl) pyrazine-2-carboxamide;
3-amino-5-(4,5-dimethyloxazol-2-yl)-6-methyl-N-((3-methylpyridin-2-yl)methyl)pyrazine-2-carboxamide;
3-amino-5-(4-methyl-1H-pyrazol-1-yl)-N-(quinolin-8-ylmethyl)-6-vinylpyrazine-2-carboxamide;
3-amino-6-(1,2-dihydroxyethyl)-5-(4-methyl-1H-pyrazol-1-yl)-N-(quinolin-8-ylmethyl)pyrazine-2-carboxamide;
3-amino-6-formyl-5-(4-methyl-1H-pyrazol-1-yl)-N-(quinolin-8-ylmethyl)pyrazine-2-carboxamide
3-amino-6-(difluoromethyl)-5-(4-methyl-1H-pyrazol-1-yl)-N-(quinolin-8-ylmethyl)pyrazine-2-carboxamide;
3-amino-6-(hydroxymethyl)-N-(quinolin-8-ylmethyl)-5-(2H-1,2,3-triazol-2-yl)pyrazine-2-carboxamide;
3-amino-6-cyano-5-(1H-pyrazol-1-yl)-N-(quinolin-8-ylmethyl)pyrazine-2-carboxamide;
3-amino-6-cyano-5-(oxazol-2-yl)-N-((3-(trifluoromethyl)pyridin-2-yl)methyl)pyrazine-2-carboxamide;
1-(3-amino-6-methyl-5-(oxazol-2-yl)pyrazin-2-yl)-3-(4,6-dimethylpyridin-2-yl)propan-1-one;
3-amino-6-methyl-N-((5-methylpyrimidin-4-yl)methyl)-5-(oxazol-2-yl)pyrazine-2-carboxamide;
3-amino-6-methyl-5-(5-methyloxazol-2-yl)-N-((3-methylpyridin-2-yl)methyl)pyrazine-2-carboxamide;
3-amino-N-((5R,7S)-5-fluoro-6,7-dihydro-5H-cyclopenta[b]pyridin-7-yl)-6-methyl-5-(oxazol-2-yl)pyrazine-2-carboxamide;
3-amino-N-((5R,7R)-5-fluoro-6,7-dihydro-5H-cyclopenta[b]pyridin-7-yl)-6-methyl-5-(oxazol-2-yl)pyrazine-2-carboxamide;
3-amino-N-((5S,7S)-5-fluoro-6,7-dihydro-5H-cyclopenta[b]pyridin-7-yl)-6-methyl-5-(oxazol-2-yl)pyrazine-2-carboxamide;

3-amino-N-((5S,7R)-5-fluoro-6,7-dihydro-5H-cyclopenta[b]pyridin-7-yl)-6-methyl-5-(oxazol-2-yl)pyrazine-2-carboxamide;
3-Amino-N-(6-fluoro-6,7-dihydro-5H-cyclopenta[b]pyridin-7-yl)-6-methyl-5-(oxazol-2-yl)pyrazine-2-carboxamide;
3-amino-N-(7H-cyclopenta[b]pyridin-7-yl)-6-methyl-5-(oxazol-2-yl)pyrazine-2-carboxamide;
3-amino-6-methyl-N-[(3-methylpyridin-2-yl)methyl]-5-[4-(trifluoromethyl)-1,3-oxazol-2-yl]pyrazine-2-carboxamide;
3-amino-6-methyl-5-(4-methyl-1,3-oxazol-2-yl)-N-[(3-methylpyridin-2-yl)methyl]pyrazine-2-carboxamide;
3-amino-5-(4,5-dimethyl-1,3-oxazol-2-yl)-6-methyl-N-[(3-methylpyridin-2-yl)methyl]pyrazine-2-carboxamide;
3-amino-5-[4-(methoxymethyl)-1,3-oxazol-2-yl]-6-methyl-N-[(3-methylpyridin-2-yl)methyl]pyrazine-2-carboxamide;
3-amino-6-methyl-5-(5-methyl-1,3-oxazol-2-yl)-N-[(3-methylpyridin-2-yl)methyl]pyrazine-2-carboxamide;
3-amino-6-methyl-N-[(3-methylpyridin-2-yl)methyl]-5-[5-(trifluoromethyl)-1,3-oxazol-2-yl]pyrazine-2-carboxamide;
3-amino-6-cyano-5-(1H-pyrazol-1-yl)-N-(quinolin-8-ylmethyl)pyrazine-2-carboxamide;
3-amino-6-cyano-5-(1,3-oxazol-2-yl)-N-{[3-(trifluoromethyl)pyridin-2-yl]methyl}pyrazine-2-carboxamide;
3-amino-6-(difluoromethyl)-5-(4-methyl-1H-pyrazol-1-yl)-N-(quinolin-8-ylmethyl)pyrazine-2-carboxamide;
3-amino-6-(hydroxymethyl)-N-(quinolin-8-ylmethyl)-5-(2H-1,2,3-triazol-2-yl)pyrazine-2-carboxamide;
3-amino-N-(5-fluoro-6,7-dihydro-5H-cyclopenta[b]pyridin-7-yl)-6-methyl-5-(1,3-oxazol-2-yl)pyrazine-2-carboxamide;
3-amino-N-(5-fluoro-6,7-dihydro-5H-cyclopenta[b]pyridin-7-yl)-6-methyl-5-(1,3-oxazol-2-yl)pyrazine-2-carboxamide;
3-amino-N-(5-fluoro-6,7-dihydro-5H-cyclopenta[b]pyridin-7-yl)-6-methyl-5-(1,3-oxazol-2-yl)pyrazine-2-carboxamide;
3-amino-N-(5-fluoro-6,7-dihydro-5H-cyclopenta[b]pyridin-7-yl)-6-methyl-5-(1,3-oxazol-2-yl)pyrazine-2-carboxamide; or
3-amino-N-(6-fluoro-6,7-dihydro-5H-cyclopenta[b]pyridin-7-yl)-6-methyl-5-(1,3-oxazol-2-yl)pyrazine-2-carboxamide,
or a pharmaceutically acceptable salt thereof.
In some embodiments, it is preferred for compounds of the invention to be:
3-amino-6-methyl-N-[(3-methylpyridin-2-yl)methyl]-5-(1,3-oxazol-2-yl)pyrazine-2-carboxamide;
3-amino-6-methyl-5-(1,3-oxazol-2-yl)-N-{[3-(trifluoromethyl)pyridin-2-yl]methyl}pyrazine-2-carboxamide;
3-amino-6-methyl-5-(1,3-oxazol-2-yl)-N-(pyrimidin-2-ylmethyl)pyrazine-2-carboxamide;
3-amino-N-[(3-cyclopropylpyridin-2-yl)methyl]-6-methyl-5-(1,3-oxazol-2-yl)pyrazine-2-carboxamide;
3-amino-6-methyl-N-[(4-methylpyridazin-3-yl)methyl]-5-(1,3-oxazol-2-yl)pyrazine-2-carboxamide;
3-amino-6-methyl-N-{[1-(1-methylethyl)-1H-imidazol-2-yl]methyl}-oxazol-2-yl)pyrazine-2-carboxamide;
3-amino-N-(6,7-dihydro-5H-cyclopenta[b]pyridin-7-yl)-6-methyl-5-(1,3-oxazol-2-yl)pyrazine-2-carboxamide;
3-amino-N-[(3-ethyl-4-fluoropyridin-2-yl)methyl]-6-methyl-5-(1,3-oxazol-2-yl)pyrazine-2-carboxamide;
3-amino-N-[(1-ethyl-1H-1,2,4-triazol-5-yl)methyl]-6-methyl-5-(1,3-oxazol-2-yl)pyrazine-2-carboxamide;
3-amino-N-[(3-ethylpyridin-2-yl)methyl]-6-methyl-5-(1,3-oxazol-2-yl)pyrazine-2-carboxamide;
3-amino-N-[(3-cyclopropyl-4-fluoropyridin-2-yl)methyl]-6-methyl-5-(1,3-oxazol-2-yl)pyrazine-2-carboxamide;
3-amino-N-[(3-cyclopropylpyrazin-2-yl)methyl]-6-methyl-5-(1,3-oxazol-2-yl)pyrazine-2-carboxamide;
3-amino-6-methyl-N-{[1-(1-methylethyl)-1H-1,2,4-triazol-5-yl]methyl}-5-(1,3-oxazol-2-yl)pyrazine-2-carboxamide;
3-amino-N-[(1-ethyl-1H-benzimidazol-4-yl)methyl]-6-methyl-5-(1,3-oxazol-2-yl)pyrazine-2-carboxamide;
3-amino-6-methyl-N-[(3-methylpyrazin-2-yl)methyl]-5-(1,3-oxazol-2-yl)pyrazine-2-carboxamide;
3-amino-6-cyano-5-(1,3-oxazol-2-yl)-N-{[3-(trifluoromethyl)pyridin-2-yl]methyl}pyrazine-2-carboxamide;
3-amino-N-{[3-(fluoromethyl)pyridin-2-yl]methyl}-6-methyl-5-(1,3-oxazol-2-yl)pyrazine-2-carboxamide;
3-amino-N-{[3-(hydroxymethyl)pyridin-2-yl]methyl}-6-methyl-5-(1,3-oxazol-2-yl)pyrazine-2-carboxamide;
3-amino-6-methyl-N-[1-(3-methylpyridin-2-yl)ethyl]-5-(1,3-oxazol-2-yl)pyrazine-2-carboxamide;
3-amino-N-(6-hydroxy-6,7-dihydro-5H-cyclopenta[b]pyridin-7-yl)-6-methyl-5-(1,3-oxazol-2-yl)pyrazine-2-carboxamide;

As used herein, unless otherwise specified, the term "A2a receptor antagonist" (equivalently, A2a antagonist) means a compound exhibiting a potency ($IC_{50}$) of less than about 1 µM when assayed in accordance with the procedure described herein. Preferred compounds exhibit at least 10-fold selectivity for antagonizing the A2a receptor over any other andenosine receptor (e.g., A1, A2b, or A3).

Compounds of the invention and formulations comprising compounds of the invention are believed to be useful in providing potential treatment, management, alleviation or amelioration of conditions or disease states which can be treated, managed, alleviated or ameliorated by specific antagonism of A2a receptors. Conditions for which such therapy may be provided include, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential, or are believed to have the potential, for use in preventing or lessening the effect of drugs that cause movement disorders As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

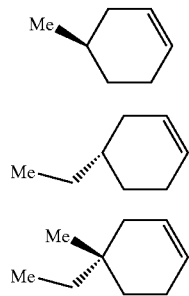

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated (or default substituents for the specified substrate, for example, hydrogen on an alkyl or aromatic moiety) can be present on the substrate in a bonding position normally occupied by the default substituent, for example, a hydrogen atom, in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

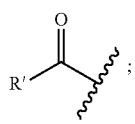

"alkoxy" means a moiety of the structure: alkyl-O— (i.e., the bond to the substrate moiety is through the oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxycarbonyl" means a moiety of the structure alkyl-O—C(O)—, equivalently represented as [alkyl-O—(C=O)—] and also as R—O(C=O)—, where "R" is a defined alkyl moiety, i.e., the bond to the parent moiety is through the carbonyl carbon; non-limiting examples of suitable alkoxycarbonyl groups include methoxycarbonyl and ethoxycarbonyl;

"alkoxy-aryl" means a moiety of the structure alkyl-O-aryl-, where the substituent is bonded to a substrate through the aryl portion of the moiety and the terms "alkyl" and "aryl" have the meaning presented herein;

"alkoxy-aryl" means a moiety of the structure alkyl-O-aryl-, where the substituent is bonded to a substrate through the aryl portion of the moiety and the terms "alkyl" and "aryl" have the meaning presented herein;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a cyclic aliphatic moiety comprising at least 3 carbon atoms (the minimum number necessary to provide a cyclic moiety) up to the maximum number of specified carbon atoms. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to about 20 carbon atoms which may optionally be substituted as defined herein for "alkyl" generally. Suitable multicyclic cycloalkyls are, for example, but are not limited to: 1-decalin; norbornyl; adamantly; and the like;

any of the afore-mentioned linear-, branched-, or cyclic-alkyl moieties which are defined to be "optionally substituted" means that one or more of the carbon atoms in the structure can have one or more of the C—H bonds associated therewith substituted with a moiety selected from the list of possible substituents called out in the definition of the moiety, and in like manner where the phrase "substituted" appears in the definition of the moiety, it means that at least 1 hydrogen atom has been replaced where a C—H bond would be with at least one of the enumerated substituents in the list of substituents called out in the definition of the alkyl moiety;

"lower alkyl" means a linear, branched, or cycloalkyl moiety comprising up to about 6 carbon atoms; non-limiting examples of suitable lower alkyl groups include methyl, ethyl, n-propyl, isopropyl, cyclopropyl, n-butyl, t-butyl, cyclobutyl, n-pentyl, isopentyl, neopentyl, cyclopentyl, n-hexyl, cyclohexyl and the like;

"lower alkoxy" means [R—O—] where "R" is a linear, branched, or cycloalkyl moiety comprising up to about 6 carbon atoms; examples of suitable lower alkoxy groups include, but are not limited to, methoxy, ethoxy, n-propoxy, isopropoxy, cyclopropoxy, n-butoxy, t-butoxy, cyclobutoxy, n-pentoxy, isopentoxy, neopentoxy, cyclopentoxy, methoxy-cyclopentane, and the like "alkylaryl-" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

in general, as exemplified by the term "alkyl-aryl" defined above, a substituent which is the called out by the combination of terms used to define two other substituent fragments indicates that the substituent called out by the last term used is bonded to the substrate whilst the preceding term called out is bonded in turn to the substituent fragment it precedes, proceeding right to left to understand the order in which the various fragments are bonded to the substrate;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group can be optionally substituted with one or more independently selected "ring system substituents" (defined below). Non-limiting examples of suitable aryl groups include phenyl

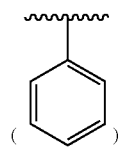

and naphthyl

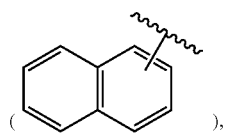

wherein bonding can be through any of the carbons in the aromatic ring, and wherein any ring carbon atoms not participating in a bond to the substrate may have bonded to it a substituent other than —H, independently selected in each instance from the list of substituents called out in an enumerated list of substituents presented in defining the moiety;

"arylcycloalkyl" means a moiety having an aryl-portion fused to two carbon atoms of a cycloalkyl portion, wherein either portion may be optionally substituted with one or more substituents called out in an enumerated list of substituents presented in defining the moiety, and wherein the aryl portion and the cycloalkyl portion comprises up to 10 carbon atoms in the ring, and in some embodiments the cycloalkyl portion preferably comprises 6 carbon atoms. Examples of arylcycloalkyl moieties include, but are not limited to, tetrahydroanthracene, tetrahydronaphthalene, dihydroindene, and the like. Unless specified otherwise, bonding of an arylcycloalkyl moiety to a substrate may be through any aryl or cycloalkyl ring carbon atom. When the term is used with "spiro", e.g. "arylspirocycloalkyl" it means that the alkyl portion of the moiety contains one carbon in common with a substrate to which it is attached forming a spirocylo structure, for example, the structure:

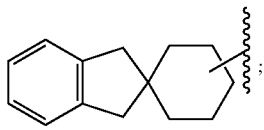

wherein the structure is bonded to a substrate through the cycloalkyl portion with which the arylcycloalkyl moiety forms a spirocyloalkyl structure;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —CF$_3$;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-,

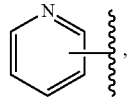

thiopenyl-

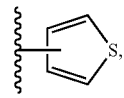

furanyl-,

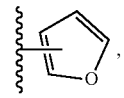

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure:

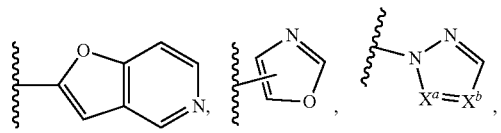

where one of $X^a$ or $X^b$ is —CH= or —N= and the other is —CH=;

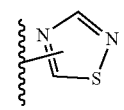

and the like (wherein, unless otherwise noted, bonded to the substrate through any available ring atom that results in a stable bonding arrangement);

"heteroarylone" means a heteroaryl moiety having one of the ring carbons bonded to an "oxo" moiety, for example, a 1-methyl-1,6-dihydropyridine-6-one moiety of the formula:

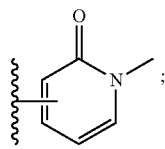

"heteroarylcycloalkyl" means a moiety having a heteroaryl-portion fused to two carbon atoms of a cycloalkyl portion, wherein ring carbon atoms in either portion may be optionally substituted with one or more substituents called out in an enumerated list of substituents presented in defining the moiety, and wherein the heteroaryl portion comprises up to 8 carbon atoms and up to three hetero atoms which are independently nitrogen, oxygen or sulfur, and the cycloalkyl portion comprises up to 10 carbon atoms. In the same manner, "heteroarylheterocycloalkyl" means a moiety in which the fused cycloalkyl portion has, in addition to saturated carbon, one or more heteroatoms comprising the ring. In some embodiments it is preferred for the cycloalkyl portion to comprise up to 6 carbon atoms. Examples of heteroarylcycloalkyl moieties include, but are not limited to: 6,7-dihydro-5H-cyclopenta[b]pyrazine and 5,6,7,8-tetrahydroquinoline. When the term is used with "spiro", e.g. "heteroarylspirocycloalkyl" it means that the alkyl portion of the moiety contains one carbon in common with a substrate to which it is attached forming a spirocyloalkyl structure, for example, the structure:

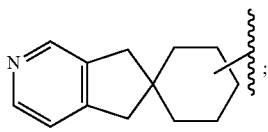

wherein the structure is bonded to a substrate through the cycloalkyl portion with which the heteroarylcycloalkyl moiety forms the spirocyloalkyl structure.

"arylheterocycloalkyl" or "heterocycloalkylaryl" means a moiety having an aryl portion, as aryl is defined herein, wherein two adjacent carbon atoms in the ring are fused to a heterocycloalkyl portion comprising at least one carbon atom and up to 3 heteroatoms. Examples of arylheterocycloalkyl moieties include, but are not limited to, tetrahydroquinoxaline, tetrahydroquinoline, dihydrocyclopentapyridine, and the like. Unless specified otherwise, bonding of an arylheterocycloalkyl or heteroarylcycloalkyl moiety to a substrate may be through any aryl, heteroaryl, heterocycloalkyl or cycloalkyl ring atom present in the moiety.

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system; preferred heterocyclyl moieties contain about 5 to about 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide ($SO_2$); non-limiting examples of suitable monocyclic heterocyclyl rings include piperidyl, pyrrolidinyl, piperazinyl, morpholinyl—

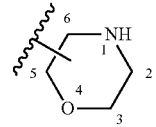

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

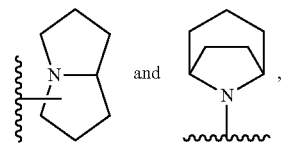

and the like.

"tetrahydropyranyl" moiety means a 6-member cyclic ether of the formula:

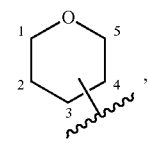

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" means:

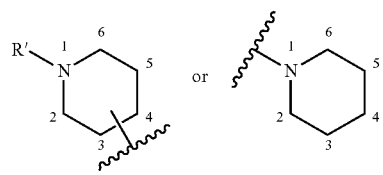

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either —H or another specified substituent;

"pyridinyl" means:

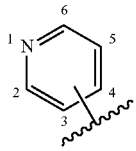

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"quinoline" means:

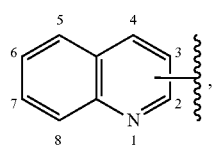

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

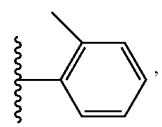

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

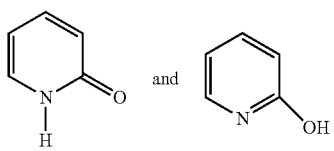

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^3H$, $^{11}C$ and $^{14}C$) are recognized as being particularly useful in compound and/or substrate tissue distribution assays using a variety of known techniques. Tritiated (i.e., $^3H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

In one aspect, as mentioned above, the present invention provides pharmaceutical formulations (pharmaceutical compositions) for use in antagonizing $A_{2A}$ receptors, believed to be useful in treating central nervous system (CNS) disorders, for example, movement disorders associated with Parkinson's disease or the treatment thereof, wherein the compositions comprising at least one compound, or pharmaceutically acceptable salt thereof, of Formula A or Formula A-1, as defined herein.

As mentioned above, in one aspect the invention provides pharmaceutical formulations (pharmaceutical compositions) suitable for use in blocking adenosine A2a receptors found in the basal ganglia, comprising at least one compound of Formula A presented above, or a pharmaceutically acceptable salt thereof, and at least one pharmaceutically acceptable carrier (described below). It will be appreciated that pharmaceutically formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more other compounds which also have pharmacological activity, for example, as described herein below.

As mentioned above, in one aspect the invention provides pharmaceutical formulations (pharmaceutical compositions) suitable for use in selectively antagonizing the A2a receptors, for example, those found in high density in the basal ganglia, comprising at least one compound of Formula A, Formula A-1, or a salt thereof:

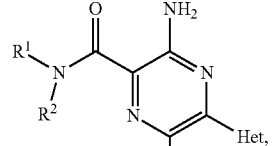

Formula A

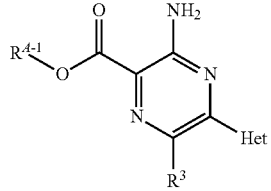

Formula A-1 wherein "$R^1$", "$R^{A-1}$", "$R^2$", "$R^3$", and "Het" are defined herein above, which compounds are believed to have activity as $A_{2A}$-receptor antagonist. Such compounds are believed to be useful in treatment or management of neurodegenerative diseases, for example, Parkinson's disease.

In some embodiments the formulation preferably comprises one or more compounds of Formula A or Formula A-1, as defined herein, and at least one pharmaceutically acceptable carrier (described below). It will be appreciated that pharmaceutically formulations of the invention may comprise more than one compound of the invention, for example, the combination of two or three compounds of Formula A or Formula A-1, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula A. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for injection, for example, an injectable solution or suspension adapted for subcutaneous injection (Sub-Q) or intramuscular administration (IM), for example, where the injectable solution or suspension may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for use of the compounds described herein for the potential treatment, management, alleviation or amelioration of conditions or disease states which can be, or are believed to be, treated, managed, alleviated or ameliorated by specific antagonism of adenosine A2a receptors, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential for use in preventing or lessening the effect of drugs that cause movement disorders.

In accordance with the present invention, antagonism of adenosine A2a receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, for example, a compound of Formula A or Formula A-1, or a salt of either thereof, and at least one pharmaceutically acceptable carrier (described below). It will be appreciated that pharmaceutically formulations of the invention may comprise more than one compound of the invention, or a salt thereof, for example, the combination of two or three compounds of the invention, each present by adding to the formulation the desired amount of the compound or a salt thereof which has been isolated in a pharmaceutically acceptably pure form.

As mentioned above, administration of a compound of the invention to effect antagonism of A2a receptor sites, which is believed to be beneficial in the treatment of central nervous system diseases is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As mentioned above, administration of a compound of the invention is preferably accomplished by incorporating the compound into a pharmaceutical formulation incorporated into a dosage form, for example, one of the above-described dosage forms comprising an effective amount of at least one compound of the invention (for example, 1, 2 or 3, or 1 or 2, or 1, and usually 1 compound of the invention), or a pharmaceutically acceptable salt thereof. Methods for determining safe and effective administration of compounds which are pharmaceutically active, for example, a compound, or a pharmaceutically acceptable salt thereof, of Formula A or of Formula A-1, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in what ever form administered, the dosage form administered will contain an amount of at least one compound of the invention, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include compounds with dopaminergic activity, for example, but not limited to: i) L-DOPA; ii) DOPA decarboxylase inghibitors; and iii) COMT inhibitors.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In the examples that follow certain of the exemplified compounds are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

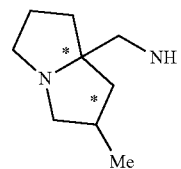

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

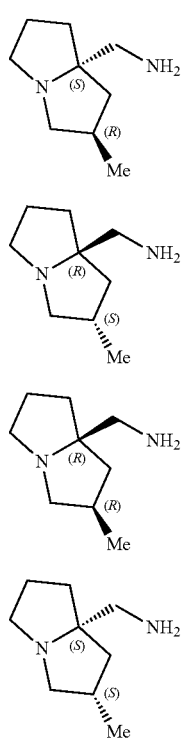

ABC-1

ABC-2

ABC-3

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine, In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds.

EXAMPLES

In general, compounds of the invention (Ex-GP-1) may be prepared by amine acylation using an appropriate acid and an appropriately-substituted amine in the presence of Hunig's base and HATU, as indicated in General Scheme GS-1 below:

Scheme GS-1

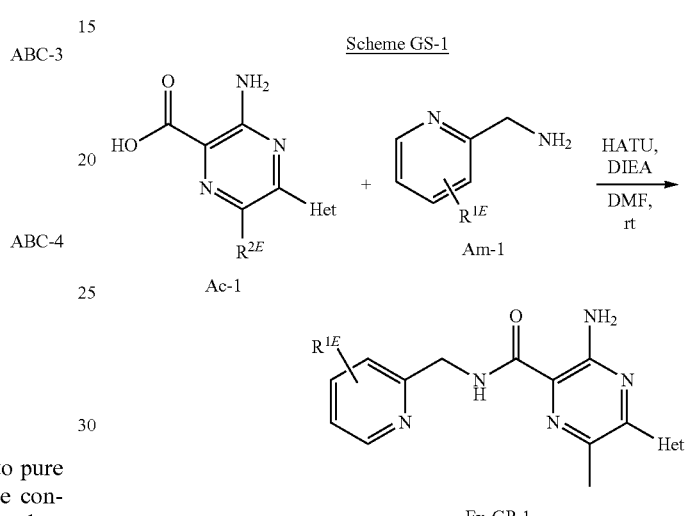

This is further illustrated in the preparation of Example compounds Ex-1A and Ex-1B, below.

Example 1

Preparation of (S)-3-amino-N-(6,7-dihydro-5H-cyclopenta[b]pyridin-7-yl)-6-methyl-5-(oxazol-2-yl)pyrazine-2-carboxamide, and (R)-3-amino-N-(6,7-dihydro-5H-cyclopenta[b]pyridin-7-yl)-6-methyl-5-(oxazol-2-yl)pyrazine-2-carboxamide (Ex-1A and Ex-1B)

SCHEME ES-1

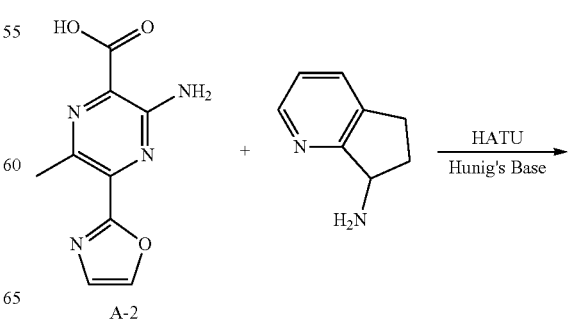

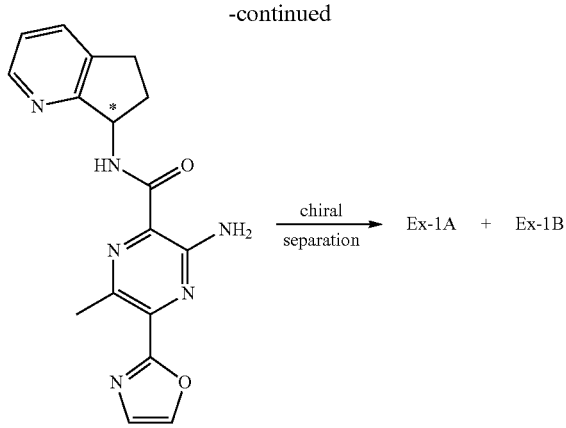

3-Amino-6-methyl-5-(oxazol-2-yl)pyrazine-2-carboxylic acid (A-2, 200 mg, 0.91 mmol) in DMF (4 ml) was mixed with 6,7-dihydro-5H-cyclopenta[b]pyridin-7-amine, 2HCl (245 mg, 1.2 mmol), Hunig's base (0.64 ml, 3.6 mmol) and 2-(3H-[1,2,3]triazolo[4,5-b]pyridin-3-yl)-1,1,3,3-tetramethylisouronium hexafluorophosphate(V) (450 mg, 1.2 mmol). Mixture was stirred under at room temperature for 2 hours. Mixture was poured into 100 mL of water. Precipitate was collected by filtration, the aqueous was extracted with EtOAc. The solution was concentrated to give a small amount of crude product. The combined crude product was purified The residue was purified by column chromatography on a 50 g prepacked silica gel, eluting with gradient 20~100% EtOAc/hexane to give the product as a solid after concentrated. The two enantiomers were separated by chiral separation according to the following conditions: chiral OD-H (3×15 cm) column, eluting with 25% methanol (0.1% DEA)/$CO_2$, 100 bar, 60 mL/min.

Both enantiomers were characterized by LC/MS. Stereochemistry was assigned by VCD (vibrational circular dichroism spectroscopy). The faster-eluting isomer, Ex-1A was assigned as the (R)-enantiomer: LCMS: 337 [M+1]), and the slower-eluting enantiomer, Ex-1B, was assigned as the (S)-enantiomer: LCMS: 337 [M+1]).

In the same manner illustrated above, 3-amino-6-methyl-N-((3-methylpyridin-2-yl)methyl)-5-(oxazol-2-yl)pyrazine-2-carboxamide (Compound Ex-3) was prepared from an appropriate amine and the same A-2 carboxylic acid precursor:

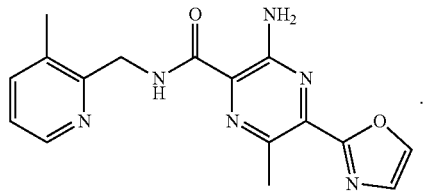

Accordingly, to a mixture of (3-methylpyridin-2-yl)methanamine (17 mg, 0.14 mmol) and 3-amino-6-methyl-5-(oxazol-2-yl)pyrazine-2-carboxylic acid (30 mg, 0.14 mmol), DMF (0.55 mL) was added, followed by Hunig's Base (24 µl, 0.14 mmol) and HATU (52 mg, 0.14 mmol) at room temperature. The mixture was allowed to stir at room temperature for overnight, and then directly chromatographed on the prep Gilson HPLC, eluting with gradient acetonitrile/water (containing 0.05% TFA) to afford the TFA salt of 3-amino-6-methyl-N-((3-methylpyridin-2-yl)methyl)-5-(oxazol-2-yl)pyrazine-2-carboxamide as a solid (Ex-3). Ex-3 was characterized by LC/MS. LC/MS=325 [M+1].

In the same manner as for preparation of compounds Ex-1A and Ex-1B, 3-amino-N-((3-cyclopropylpyridin-2-yl)methyl)-6-methyl-5-(oxazol-2-yl)pyrazine-2-carboxamide (compound Ex-4) was prepared in accordance with Scheme ES-2:

Scheme ES-2

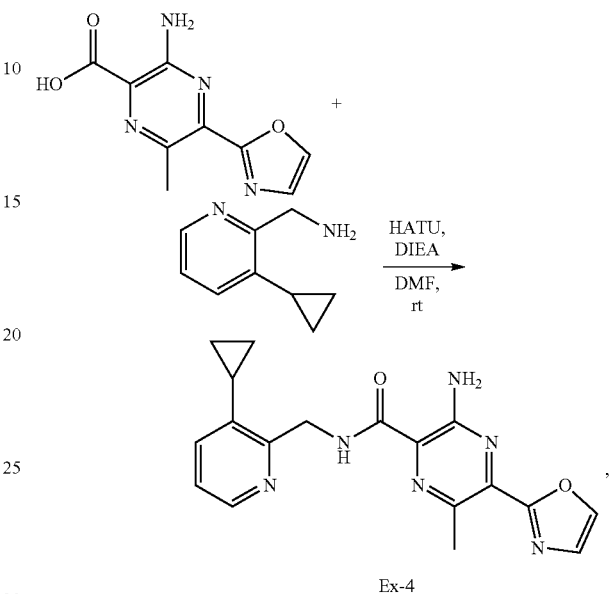

Compound Ex-4 was characterized with the following results: LC/MS=351 [M+1]. $^1$H NMR (DMSO-d6, 400 MHz) δ9.42 (s, 1H), 7.49 (d, 1H), 7.88 (s, 1H), 7.42-7.37 (m, 2H), 7.22-7.17 (m, 1H), 4.94 (d, 2H), 2.92 (s, 3H). 1.99 (t, 1H), 1.07 (m, 2H), 0.72 (m, 2H).

Table I presents additional compounds of the invention prepared using this same procedure from an appropriate amine and precursor acid A2. All compounds were characterized using LC/MS data (shown in the table). Where indicated in the table, enantiomeric forms present were separated via chiral HPLC. Absolute stereochemistry was not determined in all instances. In the examples noted in Table I, absolute stereochemistry was determined using using super critical $CO_2$-chromatography (SCF chromatography). Isomers separated are labelled in Table 1 as "First", "Second", etc. as their order of elution from the column. The following conditions were employed (noted in Table 1 as "Conditions 1" or "Conditions 2" in Table 1, in the column identifying the example:

Conditions 1: SCF/$CO_2$ with 25% methanol (1% DEA) running OD-H column;

Conditions 2: SCF/$CO_2$ with n-hexane/ethanol (1% DEA) running AY-H column;

Conditions 3: SCF/$CO_2$ with n-hexane/ethanol (1% DEA) running OZ-H column;

Conditions 4: SCF/$CO_2$ with 15% methanol (2% DEA) running OD column;

Conditions 5: SCF/$CO_2$ with 30% methanol (1% DEA) running AD-H column;

Conditions 6: SCF/$CO_2$ with 50% methanol running AD-H column;

Conditions 7: SCF/$CO_2$ with 20% methanol (1% DEA) running OJ-H column;

Conditions 8: SCF/$CO_2$ with 35% isopropanol running OD-H column.

TABLE I

| Exp. No. | Structure | IUPAC Name | MS [M + H]+ |
|---|---|---|---|
| Ex-5 | 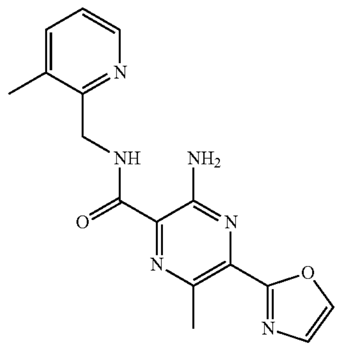 [SMILES: Cc1cccnc1CNC(=O)c1nc(C)c(-c2ncco2)nc1N] | 3-amino-6-methyl-N-[(3-methylpyridin-2-yl)methyl]-5-(1,3-oxazol-2-yl)pyrazine-2-carboxamide | 325 |
| Ex-6 | 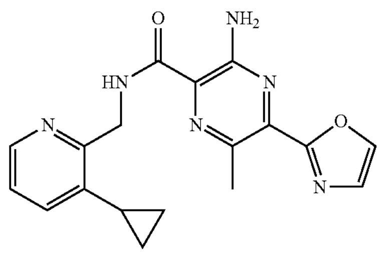 [SMILES: Cc1nc(C(=O)NCc2ncccc2C2CC2)c(N)nc1-c1ncco1] | 3-amino-N-[(3-cyclopropylpyridin-2-yl)methyl]-6-methyl-5-(1,3-oxazol-2-yl)pyrazine-2-carboxamide | 351 |
| Ex-7A Cond. 1 First | 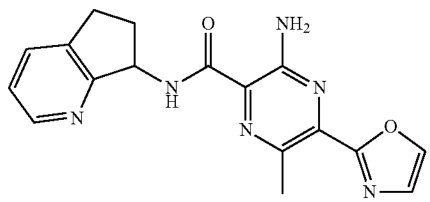 [SMILES: Cc1nc(C(=O)NC2CCc3cccnc32)c(N)nc1-c1ncco1] | (R)-3-amino-N-(6,7-dihydro-5H-cyclopenta[b]pyridin-7-yl)-6-methyl-5-(1,3-oxazol-2-yl)pyrazine-2-carboxamide | 337 |
| Ex-7B Cond. 1 Second | 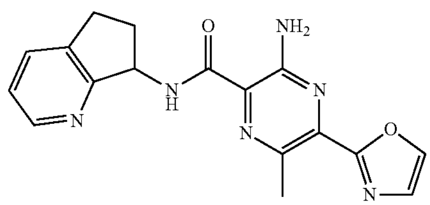 [SMILES: Cc1nc(C(=O)NC2CCc3cccnc32)c(N)nc1-c1ncco1] | (S)-3-amino-N-(6,7-dihydro-5H-cyclopenta[b]pyridin-7-yl)-6-methyl-5-(1,3-oxazol-2-yl)pyrazine-2-carboxamide | 337 |
| Ex-9 | 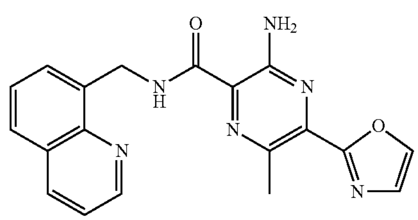 [SMILES: Cc1nc(C(=O)NCc2cccc3cccnc23)c(N)nc1-c1ncco1] | 3-amino-6-methyl-5-(1,3-oxazol-2-yl)-N-(quinolin-8-ylmethyl)pyrazine-2-carboxamide | 361 |
| Ex-10 | 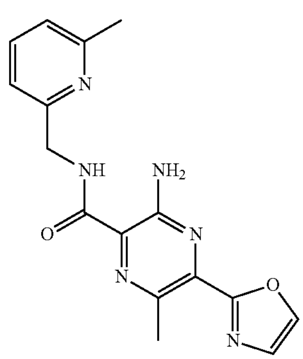 [SMILES: Cc1cccc(CNC(=O)c2nc(C)c(-c3ncco3)nc2N)n1] | 3-amino-6-methyl-N-[(6-methylpyridin-2-yl)methyl]-5-(1,3-oxazol-2-yl)pyrazine-2-carboxamide | 325 |

TABLE I-continued

| Exp. No. | Structure | IUPAC Name | MS [M + H]+ |
|---|---|---|---|
| Ex-11 | 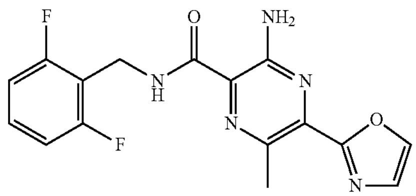 [SMILES: Cc1nc(C(=O)NCc2c(F)cccc2F)c(N)nc1-c1ncco1] | 3-amino-N-(2,6-difluorobenzyl)-6-methyl-5-(1,3-oxazol-2-yl)pyrazine-2-carboxamide | 346 |
| Ex-12 | 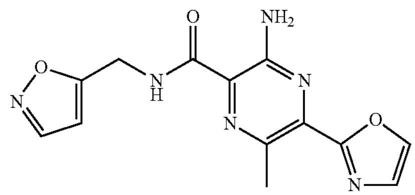 [SMILES: Cc1nc(C(=O)NCc2ccno2)c(N)nc1-c1ncco1] | 3-amino-N-(isoxazol-5-ylmethyl)-6-methyl-5-(1,3-oxazol-2-yl)pyrazine-2-carboxamide | 301 |
| Ex-13 | 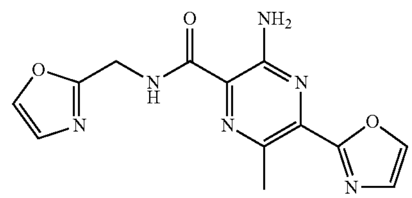 [SMILES: Cc1nc(C(=O)NCc2ncco2)c(N)nc1-c1ncco1] | 3-amino-6-methyl-5-(1,3-oxazol-2-yl)-N-(1,3-oxazol-2-ylmethyl)pyrazine-2-carboxamide | 301 |
| Ex-14 | 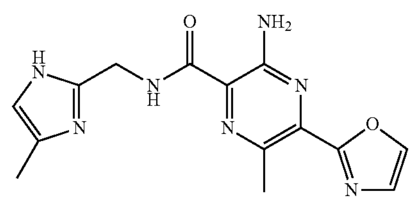 [SMILES: Cc1c[nH]c(CNC(=O)c2nc(C)c(-c3ncco3)nc2N)n1] | 3-amino-6-methyl-N-[(4-methyl-1H-imidazol-2-yl)methyl]-5-(1,3-oxazol-2-yl)pyrazine-2-carboxamide | 314 |
| Ex-15 | 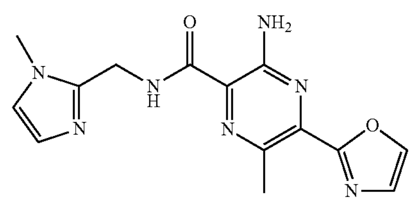 [SMILES: Cc1nc(C(=O)NCc2nccn2C)c(N)nc1-c1ncco1] | 3-amino-6-methyl-N-[(1-methyl-1H-imidazol-2-yl)methyl]-5-(1,3-oxazol-2-yl)pyrazine-2-carboxamide | 314 |
| Ex-16 | 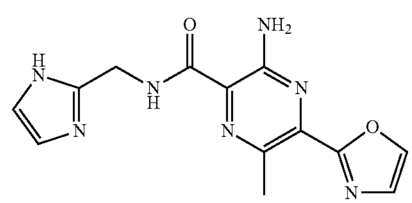 [SMILES: Cc1nc(C(=O)NCc2ncc[nH]2)c(N)nc1-c1ncco1] | 3-amino-N-(1H-imidazol-2-ylmethyl)-6-methyl-5-(1,3-oxazol-2-yl)pyrazine-2-carboxamide | 300 |
| Ex-17 | 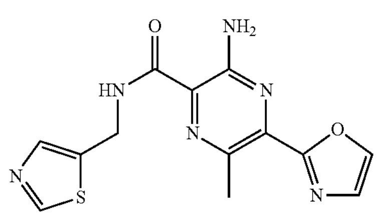 [SMILES: Cc1nc(C(=O)NCc2cncs2)c(N)nc1-c1ncco1] | 3-amino-6-methyl-5-(1,3-oxazol-2-yl)-N-(1,3-thiazol-5-ylmethyl)pyrazine-2-carboxamide | 317 |

TABLE I-continued

| Exp. No. | Structure | IUPAC Name | MS [M + H]+ |
|---|---|---|---|
| Ex-18 | 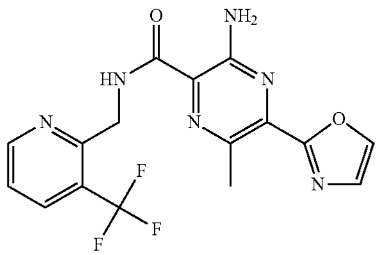 [SMILES: Cc1nc(C(=O)NCc2ncccc2C(F)(F)F)c(N)nc1-c1ncco1] | 3-amino-6-methyl-5-(1,3-oxazol-2-yl)-N-{[3-(trifluoromethyl)pyridin-2-yl]methyl}pyrazin-2-carboxamide | 379 |
| Ex-19 | 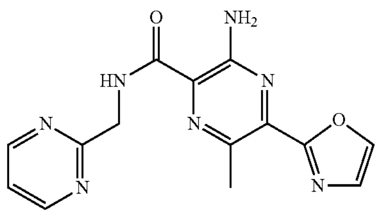 [SMILES: Cc1nc(C(=O)NCc2ncccn2)c(N)nc1-c1ncco1] | 3-amino-6-methyl-5-(1,3-oxazol-2-yl)-N-(pyrimidin-2-ylmethyl)pyrazine-2-carboxamide | 312 |
| Ex-20 | 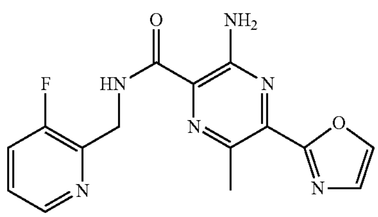 [SMILES: Cc1nc(C(=O)NCc2ncccc2F)c(N)nc1-c1ncco1] | 3-amino-N-[(3-fluoropyridin-2-yl)methyl]-6-methyl-5-(1,3-oxazol-2-yl)pyrazine-2-carboxamide | 329 |
| Ex-21 | 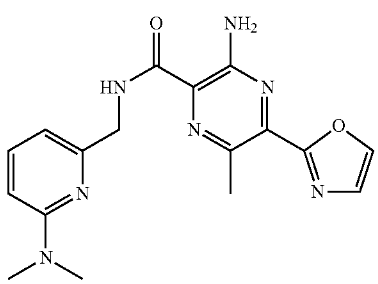 [SMILES: Cc1nc(C(=O)NCc2cccc(N(C)C)n2)c(N)nc1-c1ncco1] | 3-amino-N-{[6-(dimethylamino)pyridin-2-yl]methyl}-6-methyl-5-(1,3-oxazol-2-yl)pyrazine-2-carboxamide | 354 |
| Ex-22 | 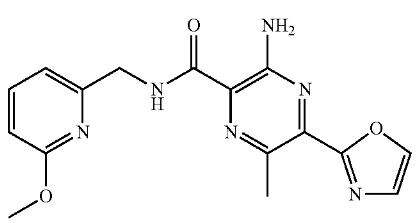 [SMILES: COc1cccc(CNC(=O)c2nc(C)c(-c3ncco3)nc2N)n1] | 3-amino-N-[(6-methoxypyridin-2-yl)methyl]-6-methyl-5-(1,3-oxazol-2-yl)pyrazine-2-carboxamide | 341 |
| Ex-23 | 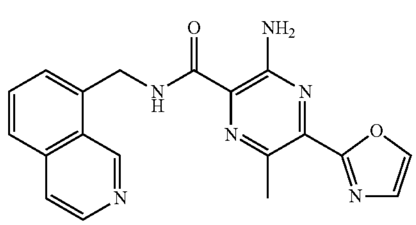 [SMILES: Cc1nc(C(=O)NCc2cccc3ccncc23)c(N)nc1-c1ncco1] | 3-amino-N-(isoquinolin-8-ylmethyl)-6-methyl-5-(1,3-oxazol-2-yl)pyrazine-2-carboxamide | 361 |

TABLE I-continued

| Exp. No. | Structure | IUPAC Name | MS [M + H]+ |
|---|---|---|---|
| Ex-24 | 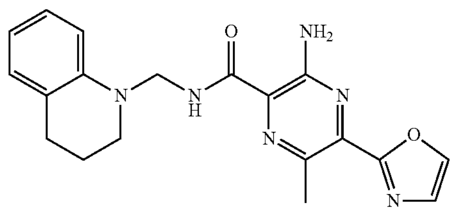 [SMILES: Cc1nc(C(=O)NCN2CCCc3ccccc32)c(N)nc1-c1ncco1] | 3-(3,4-dihydroquinolin-1(2H-ylcarbonyl)-5-methyl-6-(1,3-oxazol-2-yl)pyrazin-2-amine | 336 |
| Ex-25 | 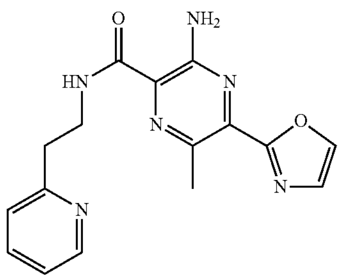 [SMILES: Cc1nc(C(=O)NCCc2ccccn2)c(N)nc1-c1ncco1] | 3-amino-6-methyl-5-(1,3-oxazol-2-yl)-N-(2-pyridin-2-ylethyl)pyrazine-2-carboxamide | 325 |
| Ex-26 | 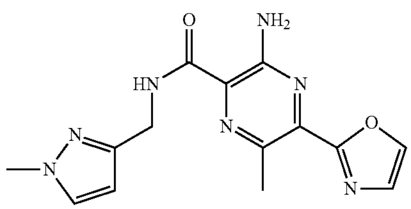 [SMILES: Cc1nc(C(=O)NCc2ccn(C)n2)c(N)nc1-c1ncco1] | 3-amino-6-methyl-N-[(1-methyl-1H-pyrazol-3-yl)methyl]-5-(1,3-oxazol-2-yl)pyrazine-2-carboxamide | 314 |
| Ex-27 | 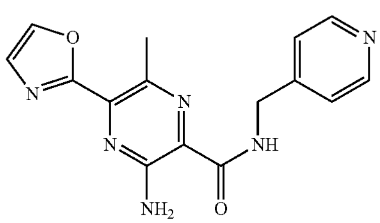 [SMILES: Cc1nc(C(=O)NCc2ccncc2)c(N)nc1-c1ncco1] | 3-amino-6-methyl-5-(1,3-oxazol-2-yl)-N-(pyridin-4-ylmethyl)pyrazine-2-carboxamide | 311 |
| Ex-28 | 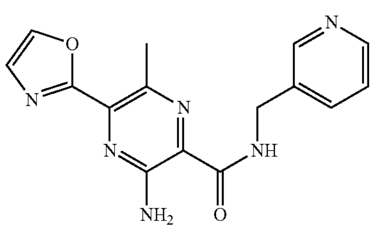 [SMILES: Cc1nc(C(=O)NCc2cccnc2)c(N)nc1-c1ncco1] | 3-amino-6-methyl-5-(1,3-oxazol-2-yl)-N-(pyridin-3-ylmethyl)pyrazine-2-carboxamide | 311 |
| Ex-29 | 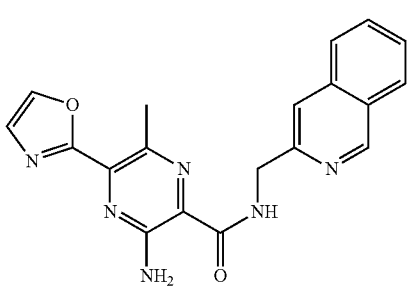 [SMILES: Cc1nc(C(=O)NCc2cc3ccccc3cn2)c(N)nc1-c1ncco1] | 3-amino-N-(isoquinolin-3-ylmethyl)-6-methyl-5-(1,3-oxazol-2-yl)pyrazine-2-carboxamide | 361 |

TABLE I-continued

| Exp. No. | Structure | IUPAC Name | MS [M + H]+ |
|---|---|---|---|
| Ex-30 | 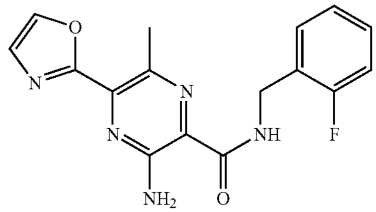 [SMILES: Cc1nc(C(=O)NCc2ccccc2F)c(N)nc1-c1ncco1] | 3-amino-N-(2-fluorobenzyl)-6-methyl-5-(1,3-oxazol-2-yl)pyrazine-2-carboxamide | 328 |
| Ex-31 | 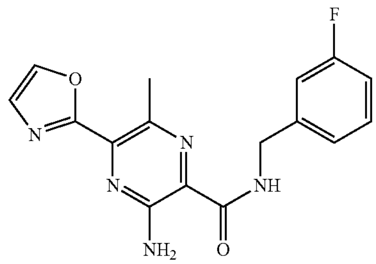 [SMILES: Cc1nc(C(=O)NCc2cccc(F)c2)c(N)nc1-c1ncco1] | 3-amino-N-(3-fluorobenzyl)-6-methyl-5-(1,3-oxazol-2-yl)pyrazine-2-carboxamide | 328 |
| Ex-32 | 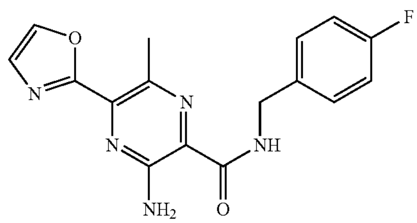 [SMILES: Cc1nc(C(=O)NCc2ccc(F)cc2)c(N)nc1-c1ncco1] | 3-amino-N-(4-fluorobenzyl)-6-methyl-5-(1,3-oxazol-2-yl)pyrazine-2-carboxamide | 328 |
| Ex-33 | 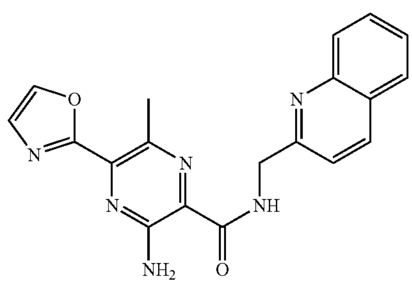 [SMILES: Cc1nc(C(=O)NCc2ccc3ccccc3n2)c(N)nc1-c1ncco1] | 3-amino-6-methyl-5-(1,3-oxazol-2-yl)-N-(quinolin-2-ylmethyl)pyrazine-2-carboxamide | 361 |
| Ex-34 | 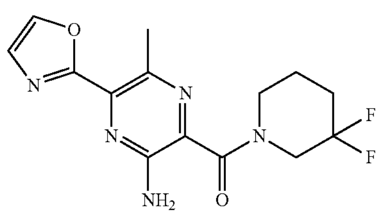 [SMILES: Cc1nc(C(=O)N2CCCC(F)(F)C2)c(N)nc1-c1ncco1] | 3-[(3,3-difluoropiperidin-1-yl)carbonyl]-5-methyl-6-(1,3-oxazol-2-yl)pyrazin-2-amine | 324 |
| Ex-35 | 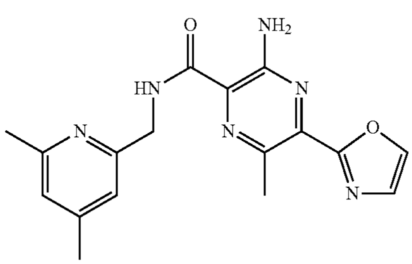 [SMILES: Cc1cc(C)nc(CNC(=O)c2nc(C)c(-c3ncco3)nc2N)c1] | 3-amino-N-[(4,6-dimethylpyridin-2-yl)methyl]-6-methyl-5-(1,3-oxazol-2-yl)pyrazine-2-carboxamide | 339 |

TABLE I-continued

| Exp. No. | Structure | IUPAC Name | MS [M + H]+ |
|---|---|---|---|
| Ex-36 | 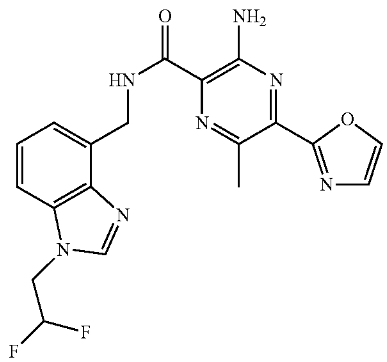 [SMILES: Cc1nc(C(=O)NCc2cccc3c2ncn3CC(F)F)c(N)nc1-c1ncco1] | 3-amino-N-{[1-(2,2-difluoroethyl)-1H-benzimidazol-4-yl]methyl}-6-methyl-5-(1,3-oxazol-2-yl)pyrazine-2-carboxamide | 414 |
| Ex-37 | 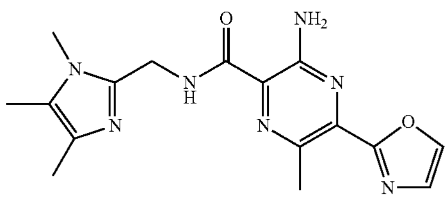 [SMILES: Cc1nc(C(=O)NCc2nc(C)c(C)n2C)c(N)nc1-c1ncco1] | 3-amino-6-methyl-5-(1,3-oxazol-2-yl)-N-[(1,4,5-trimethyl-1H-imidazol-2-yl)methyl]pyrazine-2-carboxamide | 342 |
| Ex-38 | 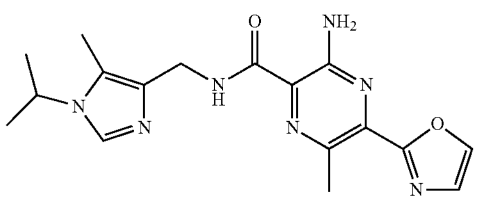 [SMILES: Cc1nc(C(=O)NCc2ncn(C(C)C)c2C)c(N)nc1-c1ncco1] | 3-amino-6-methyl-N-{[5-methyl-1-(1-methylethyl)-1H-imidazol-4-yl]methyl}-5-(1,3-oxazol-2-yl)pyrazine-2-carboxamide | 356 |
| Ex-39 | 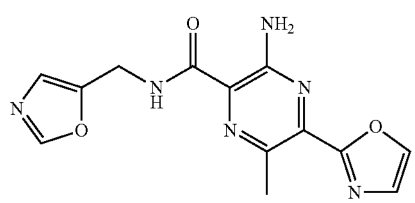 [SMILES: Cc1nc(C(=O)NCc2cnco2)c(N)nc1-c1ncco1] | 3-amino-6-methyl-5-(1,3-oxazol-2-yl)-N-(1,3-oxazol-5-ylmethyl)pyrazine-2-carboxamide | 301 |
| Ex-40 | 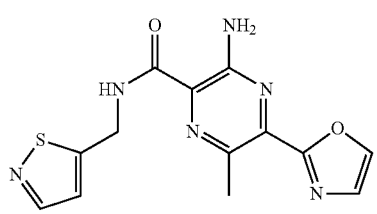 [SMILES: Cc1nc(C(=O)NCc2ccns2)c(N)nc1-c1ncco1] | 3-amino-N-(isothiazol-5-ylmethyl)-6-methyl-5-(1,3-oxazol-2-yl)pyrazine-2-carboxamide | 317 |
| Ex-41 | 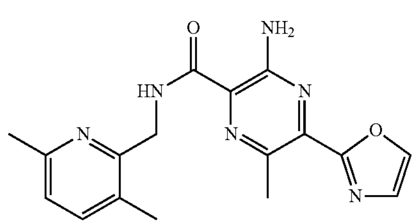 [SMILES: Cc1ccc(C)c(CNC(=O)c2nc(C)c(-c3ncco3)nc2N)n1] | 3-amino-N-[(3,6-dimethylpyridin-2-yl)methyl]-6-methyl-5-(1,3-oxazol-2-yl)pyrazine-2-carboxamide | 339 |

TABLE I-continued

| Exp. No. | Structure | IUPAC Name | MS [M + H]+ |
|---|---|---|---|
| Ex-42 | 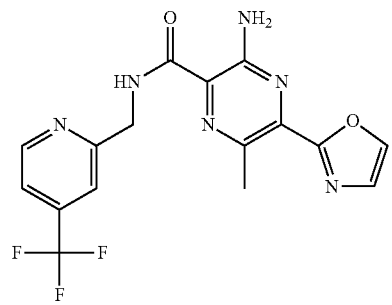 [SMILES: Cc1nc(C(=O)NCc2cc(C(F)(F)F)ccn2)c(N)nc1-c1ncco1] | 3-amino-6-methyl-5-(1,3-oxazol-2-yl)-N-{[4-(trifluoromethyl)pyridin-2-yl]methyl}pyrazine-2-carboxamide | 379 |
| Ex-43 | 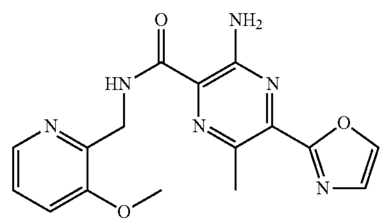 [SMILES: COc1cccnc1CNC(=O)c1nc(C)c(-c2ncco2)nc1N] | 3-amino-N-[(3-methoxypyridin-2-yl)methyl]-6-methyl-5-(1,3-oxazol-2-yl)pyrazine-2-carboxamide | 341 |
| Ex-44 | 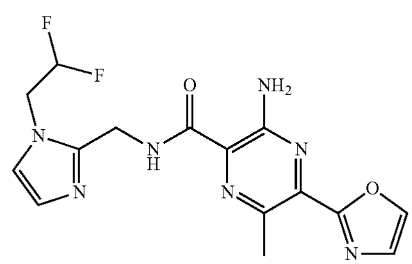 [SMILES: Cc1nc(C(=O)NCc2nccn2CC(F)F)c(N)nc1-c1ncco1] | 3-amino-N-{[1-(2,2-difluoroethyl)-1H-imidazol-2-yl]methyl}-6-methyl-5-(1,3-oxazol-2-yl)pyrazine-2-carboxamide | 364 |
| Ex-45 | 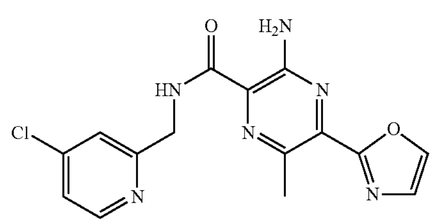 [SMILES: Cc1nc(C(=O)NCc2cc(Cl)ccn2)c(N)nc1-c1ncco1] | 3-amino-N-[(4-chloropyridin-2-yl)methyl]-6-methyl-5-(1,3-oxazol-2-yl)pyrazine-2-carboxamide | 345 |
| Ex-46 | 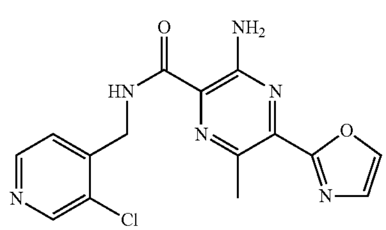 [SMILES: Cc1nc(C(=O)NCc2ccncc2Cl)c(N)nc1-c1ncco1] | 3-amino-N-[(3-chloropyridin-4-yl)methyl]-6-methyl-5-(1,3-oxazol-2-yl)pyrazine-2-carboxamide | 345 |
| Ex-47 | 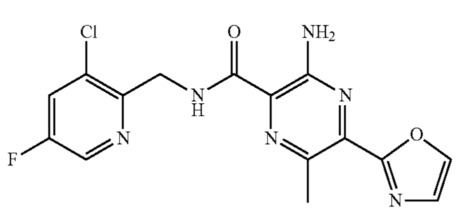 [SMILES: Cc1nc(C(=O)NCc2ncc(F)cc2Cl)c(N)nc1-c1ncco1] | 3-amino-N-[(3-chloro-5-fluoropyridin-2-yl)methyl]-6-methyl-5-(1,3-oxazol-2-yl)pyrazine-2-carboxamide | 363 |

TABLE I-continued

| Exp. No. | Structure | IUPAC Name | MS [M + H]+ |
|---|---|---|---|
| Ex-48 | 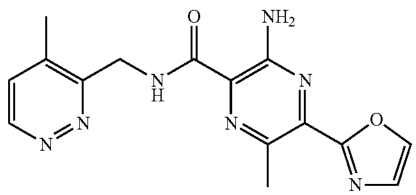 [SMILES: Cc1ccnnc1CNC(=O)c1nc(C)c(-c2ncco2)nc1N] | 3-amino-6-methyl-N-[(4-methylpyridazin-3-yl)methyl]-5-(1,3-oxazol-2-yl)pyrazine-2-carboxamide | 326 |
| Ex-49 | 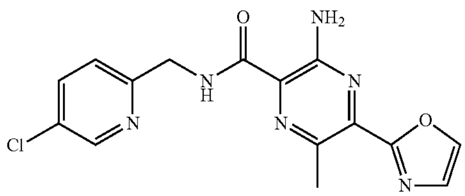 [SMILES: Cc1nc(C(=O)NCc2ccc(Cl)cn2)c(N)nc1-c1ncco1] | 3-amino-N-[(5-chloropyridin-2-yl)methyl]-6-methyl-5-(1,3-oxazol-2-yl)pyrazine-2-carboxamide | 345 |
| Ex-50 | 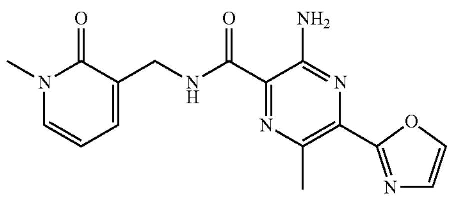 [SMILES: Cc1nc(C(=O)NCc2cccn(C)c2=O)c(N)nc1-c1ncco1] | 3-amino-6-methyl-N-[(1-methyl-2-oxo-1,2-dihydropyridin-3-yl)methyl]-5-(1,3-oxazol-2-yl)pyrazine-2-carboxamide | 341 |
| Ex-51 | 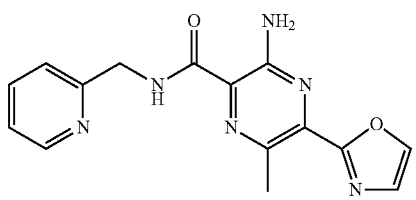 [SMILES: Cc1nc(C(=O)NCc2ccccn2)c(N)nc1-c1ncco1] | 3-amino-6-methyl-5-(1,3-oxazol-2-yl)-N-(pyridin-2-ylmethyl)pyrazine-2-carboxamide | 311 |
| Ex-52 | 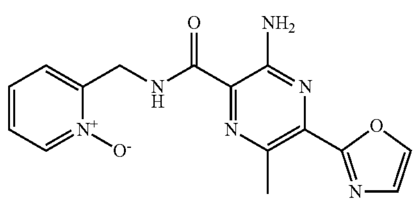 [SMILES: Cc1nc(C(=O)NCc2cccc[n+]2[O-])c(N)nc1-c1ncco1] | 3-amino-6-methyl-5-(1,3-oxazol-2-yl)-N-[(1-oxidopyridin-2-yl)methyl]pyrazine-2-carboxamide | 327 |
| Ex-53 | 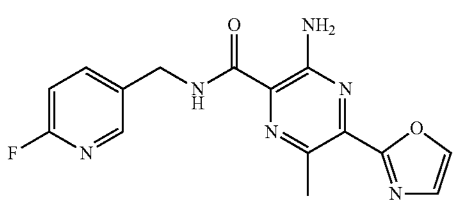 [SMILES: Cc1nc(C(=O)NCc2ccc(F)nc2)c(N)nc1-c1ncco1] | 3-amino-N-[(6-fluoropyridin-3-yl)methyl]-6-methyl-5-(1,3-oxazol-2-yl)pyrazine-2-carboxamide | 329 |
| Ex-54 | 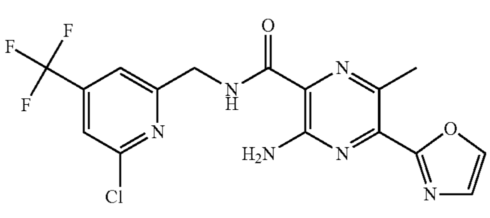 [SMILES: Cc1nc(C(=O)NCc2cc(C(F)(F)F)cc(Cl)n2)c(N)nc1-c1ncco1] | 3-amino-N-{[6-chloro-4-(trifluoromethyl)pyridin-2-yl]methyl}-6-methyl-5-(1,3-oxazol-2-yl)pyrazine-2-carboxamide | 413 |

TABLE I-continued

| Exp. No. | IUPAC Name | MS [M + H]+ |
|---|---|---|
| Ex-55 | 3-amino-N-{[5-methoxy-6-(trifluoromethyl)pyridin-2-yl]methyl}-6-methyl-5-(1,3-oxazol-2-yl)pyrazine-2-carboxamide | 409 |
| Ex-56 | 3-amino-6-methyl-N-[(5-methylpyridazin-3-yl)methyl]-5-(1,3-oxazol-2-yl)pyrazine-2-carboxamide | 326 |
| Ex-57 | 3-amino-N-[(5-fluoropyridin-2-yl)methyl]-6-methyl-5-(1,3-oxazol-2-yl)pyrazine-2-carboxamide | 329 |
| Ex-58 | 3-amino-6-methyl-N-{[3-methyl-4-(2,2,2-trifluoroethoxy)pyridin-2-yl]methyl}-5-(1,3-oxazol-2-yl)pyrazine-2-carboxamide | 423 |
| Ex-59 | 3-amino-6-methyl-5-(1,3-oxazol-2-yl)-N-{[5-(trifluoromethyl)pyridin-2-yl]methyl}pyrazine-2-carboxamide | 379 |
| Ex-60 | 3-amino-6-methyl-N-(2-methyl-2-pyridin-4-ylpropyl)-5-(1,3-oxazol-2-yl)pyrazine-2-carboxamide | 353 |
| Ex-61 | 3-amino-N-[(4-fluoropyridin-2-yl)methyl]-6-methyl-5-(1,3-oxazol-2-yl)pyrazine-2-carboxamide | 329 |

TABLE I-continued

| Exp. No. | Structure | IUPAC Name | MS [M + H]+ |
|---|---|---|---|
| Ex-62 | 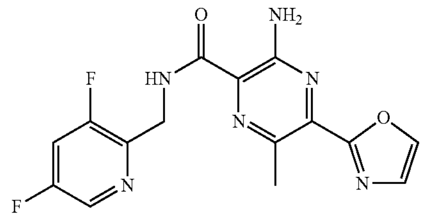 [SMILES: Cc1nc(C(=O)NCc2ncc(F)cc2F)c(N)nc1-c1ncco1] | 3-amino-N-[(3,5-difluoropyridin-2-yl)methyl]-6-methyl-5-(1,3-oxazol-2-yl)pyrazine-2-carboxamide | 347 |
| Ex-63 | 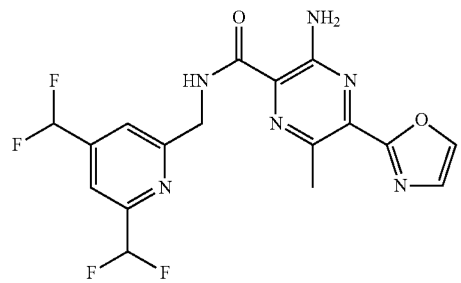 [SMILES: Cc1nc(C(=O)NCc2cc(C(F)F)cc(C(F)F)n2)c(N)nc1-c1ncco1] | 3-amino-N-{[4,6-bis(difluoromethyl)pyridin-2-yl]methyl}-6-methyl-5-(1,3-oxazol-2-yl)pyrazine-2-carboxamide | 411 |
| Ex-64 | 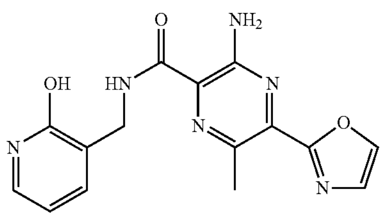 [SMILES: Cc1nc(C(=O)NCc2cccnc2O)c(N)nc1-c1ncco1] | 3-amino-N-[(2-hydroxypyridin-3-yl)methyl]-6-methyl-5-(1,3-oxazol-2-yl)pyrazine-2-carboxamide | 327 |
| Ex-65 | 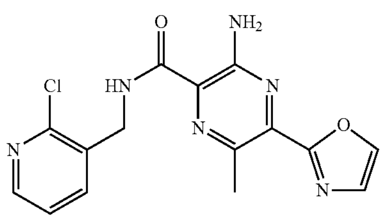 [SMILES: Cc1nc(C(=O)NCc2cccnc2Cl)c(N)nc1-c1ncco1] | 3-amino-N-[(2-chloropyridin-3-yl)methyl]-6-methyl-5-(1,3-oxazol-2-yl)pyrazine-2-carboxamide | 345 |
| Ex-66 | 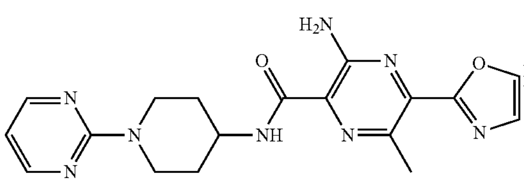 [SMILES: Cc1nc(C(=O)NC2CCN(c3ncccn3)CC2)c(N)nc1-c1ncco1] | 3-amino-6-methyl-5-(1,3-oxaol-2-yl)-N-(1-pyrimidin-2-ylpiperidin-4-yl)pyrazine-2-carboxamide | 381 |
| Ex-67 | 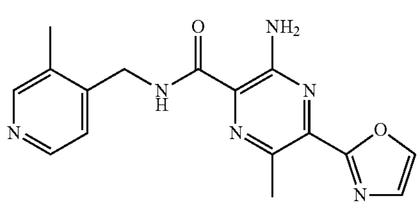 [SMILES: Cc1cnccc1CNC(=O)c1nc(C)c(-c2ncco2)nc1N] | 3-amino-6-methyl-N-[(3-methylpyridin-4-yl)methyl]-5-(1,3-oxazol-2-yl)pyrazine-2-carboxamide | 325 |

TABLE I-continued

| Exp. No. | Structure | IUPAC Name | MS [M + H]+ |
|---|---|---|---|
| Ex-68 | 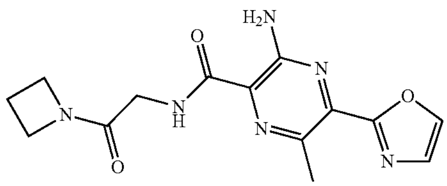 [SMILES: Cc1nc(C(=O)NCC(=O)N2CCC2)c(N)nc1-c1ncco1] | 3-amino-N-(2-azetidin-1-yl-2-oxoethyl)-6-methyl-5-(1,3-oxazol-2-yl)pyrazine-2-carboxamide | 317 |
| Ex-69 | 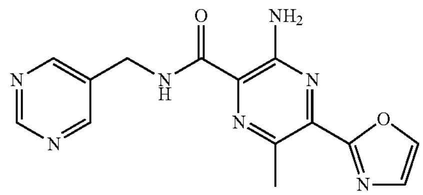 [SMILES: Cc1nc(C(=O)NCc2cncnc2)c(N)nc1-c1ncco1] | 3-amino-6-methyl-5-(1,3-oxazol-2-yl)-N-(pyrimidin-5-ylmethyl)pyrazine-2-carboxamide | 312 |
| Ex-70 | 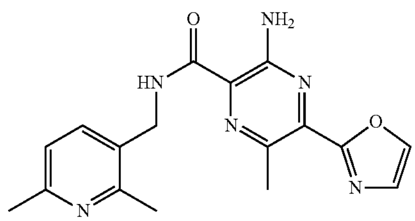 [SMILES: Cc1ccc(CNC(=O)c2nc(C)c(-c3ncco3)nc2N)c(C)n1] | 3-amino-N-[(2,6-dimethylpyridin-3-yl)methyl]-6-methyl-5-(1,3-oxazol-2-yl)pyrazine-2-carboxamide | 339 |
| Ex-71 | 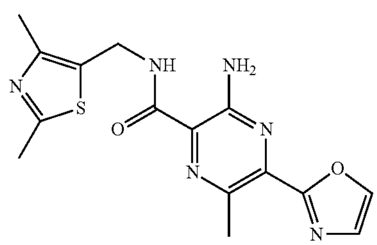 [SMILES: Cc1nc(C)c(CNC(=O)c2nc(C)c(-c3ncco3)nc2N)s1] | 3-amino-N-[(2,4-dimethyl-1,3-thiazol-5-yl)methyl]-6-methyl-5-(1,3-oxazol-2-yl)pyrazine-2-carboxamide | 345 |
| Ex-72 | 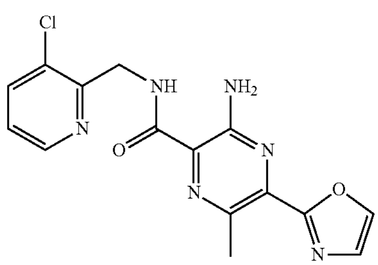 [SMILES: Cc1nc(C(=O)NCc2ncccc2Cl)c(N)nc1-c1ncco1] | 3-amino-N-[(3-chloropyridin-2-yl)methyl]-6-methyl-5-(1,3-oxazol-2-yl)pyrazine-2-carboxamide | 345 |
| Ex-73 | 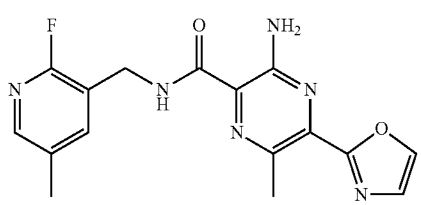 [SMILES: Cc1cnc(F)c(CNC(=O)c2nc(C)c(-c3ncco3)nc2N)c1] | 3-amino-N-[(2-fluoro-5-methylpyridin-3-yl)methyl]-6-methyl-5-(1,3-oxazol-2-yl)pyrazine-2-carboxamide | 343 |
| Ex-74 | 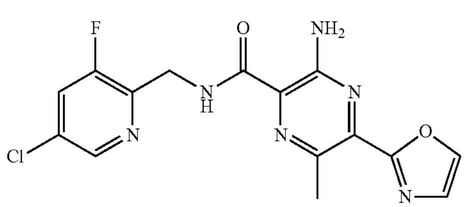 [SMILES: Cc1nc(C(=O)NCc2ncc(Cl)cc2F)c(N)nc1-c1ncco1] | 3-amino-N-[(5-chloro-3-fluoropyridin-2-yl)methyl]-6-methyl-5-(1,3-oxazol-2-yl)pyrazine-2-carboxamide | 363 |

TABLE I-continued

| Exp. No. | Structure | IUPAC Name | MS [M + H]+ |
|---|---|---|---|
| Ex-75 | 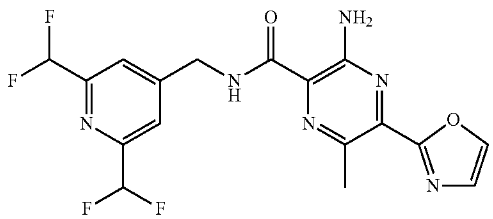 [SMILES: Cc1nc(C(=O)NCc2cc(C(F)F)nc(C(F)F)c2)c(N)nc1-c1ncco1] | 3-amino-N-{[2,6-bis(difluoromethyl)pyridin-4-yl]methyl}-6-methyl-5-(1,3-oxazol-2-yl)pyrazine-2-carboxamide | 411 |
| Ex-76 | 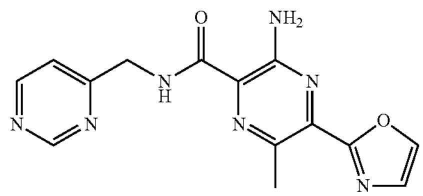 [SMILES: Cc1nc(C(=O)NCc2ccncn2)c(N)nc1-c1ncco1] | 3-amino-6-methyl-5-(1,3-oxazol-2-yl)-N-(pyrimidin-4-ylmethyl)pyrazine-2-carboxamide | 312 |
| Ex-77 | 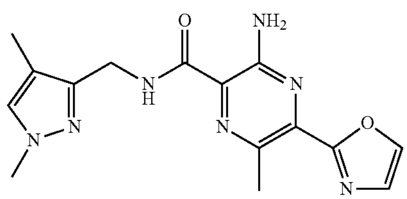 [SMILES: Cc1cn(C)nc1CNC(=O)c1nc(C)c(-c2ncco2)nc1N] | 3-amino-N-[(1,4-dimethyl-1H-pyrazol-3-yl)methyl]-6-methyl-5-(1,3-oxazol-2-yl)pyrazine-2-carboxamide | 328 |
| Ex-78 | 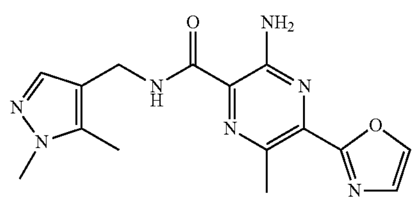 [SMILES: Cc1nc(C(=O)NCc2cnn(C)c2C)c(N)nc1-c1ncco1] | 3-amino-N-[(1,5-dimethyl-1H-pyrazol-4-yl)methyl]-6-methyl-5-(1,3-oxazol-2-yl)pyrazine-2-carboxamide | 328 |
| Ex-79 | 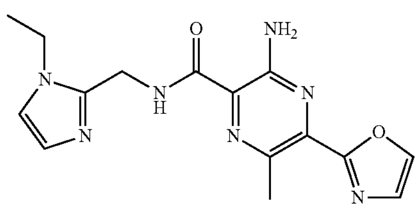 [SMILES: CCn1ccnc1CNC(=O)c1nc(C)c(-c2ncco2)nc1N] | 3-amino-N-[(1-ethyl-1H-imidazol-2-yl)methyl]-6-methyl-5-(1,3-oxazol-2-yl)pyrazine-2-carboxamide | 328 |
| Ex-80 | 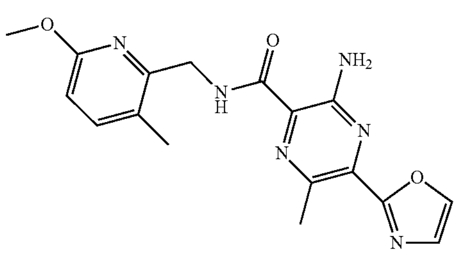 [SMILES: COc1ccc(C)c(CNC(=O)c2nc(C)c(-c3ncco3)nc2N)n1] | 3-amino-N-[(6-methoxy-3-methylpyridin-2-yl)methyl]-6-methyl-5-(1,3-oxazol-2-yl)pyrazine-2-carboxamide | 355 |
| Ex-81 | 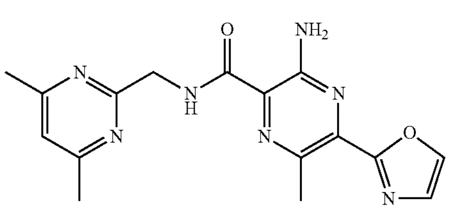 [SMILES: Cc1cc(C)nc(CNC(=O)c2nc(C)c(-c3ncco3)nc2N)n1] | 3-amino-N-[(4,6-dimethylpyrimidin-2-yl)methyl]-6-methyl-5-(1,3-oxazol-2-yl)pyrazine-2-carboxamide | 340 |

TABLE I-continued

| Exp. No. | Structure | IUPAC Name | MS [M + H]+ |
|---|---|---|---|
| Ex-82A Cond. 1 First | 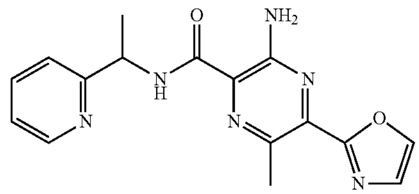 [SMILES: Cc1nc(C(=O)NC(C)c2ccccn2)c(N)nc1-c1ncco1] | 3-amino-6-methyl-5-(1,3-oxazol-2-yl)-N-(1-pyridin-2-ylethyl)pyrazine-2-carboxamide | 325 |
| Ex-82B Cond. 1 Second | 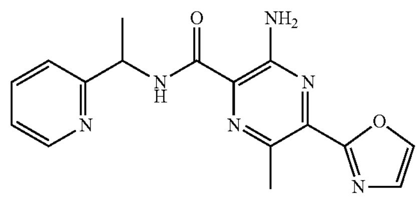 [SMILES: Cc1nc(C(=O)NC(C)c2ccccn2)c(N)nc1-c1ncco1] | 3-amino-6-methyl-5-(1,3-oxazol-2-yl)-N-(1-pyridin-2-ylethyl)pyrazine-2-carboxamide | 325 |
| Ex-83 | 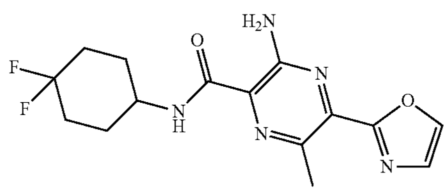 [SMILES: Cc1nc(C(=O)NC2CCC(F)(F)CC2)c(N)nc1-c1ncco1] | 3-amino-N-(4,4-difluorocyclohexyl)-6-methyl-5-(1,3-oxazol-2-yl)pyrazine-2-carboxamide | 338 |
| Ex-84A Cond. 1 First | 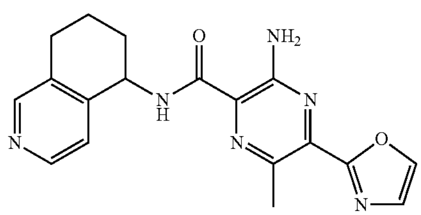 [SMILES: Cc1nc(C(=O)NC2CCCc3cnccc32)c(N)nc1-c1ncco1] | 3-amino-6-methyl-5-(1,3-oxazol-2-yl)-N-(5,6,7,8-tetrahydroisoquinolin-5-yl)pyrazine-2-carboxamide | 351 |
| Ex-84B Cond. 1 Second | 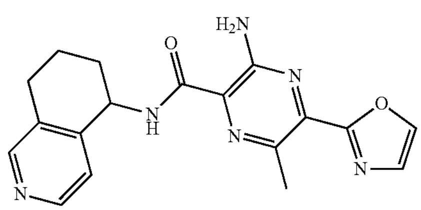 [SMILES: Cc1nc(C(=O)NC2CCCc3cnccc32)c(N)nc1-c1ncco1] | 3-amino-6-methyl-5-(1,3-oxazol-2-yl)-N-(5,6,7,8-tetrahydroisoquinolin-5-yl)pyrazine-2-carboxamide | 351 |
| Ex-85 | 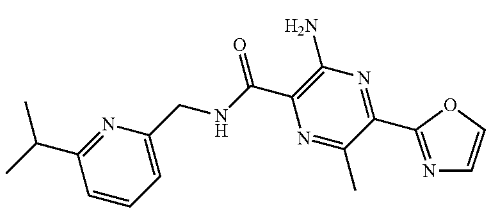 [SMILES: Cc1nc(C(=O)NCc2cccc(C(C)C)n2)c(N)nc1-c1ncco1] | 3-amino-6-methyl-N-{[6-(1-methylethyl)pyridin-2-yl]methyl}-5-(1,3-oxazol-2-yl)pyrazine-2-carboxamide | 353 |
| Ex-87 | 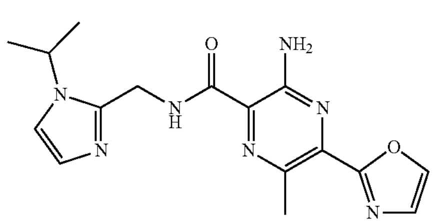 [SMILES: Cc1nc(C(=O)NCc2nccn2C(C)C)c(N)nc1-c1ncco1] | 3-amino-6-methyl-N-{[1-(1-methylethyl)-1H-imidazol-2-yl]methyl}-5-(1,3-oxazol-2-yl)pyrazine-2-carboxamide | 342 |

TABLE I-continued

| Exp. No. | Structure | IUPAC Name | MS [M + H]+ |
|---|---|---|---|
| Ex-88 | 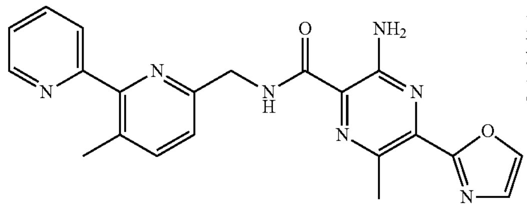 [SMILES: Cc1ccc(CNC(=O)c2nc(C)c(-c3ncco3)nc2N)nc1-c1ccccn1] | 3-amino-6-methyl-N-[(3-methyl-2,2'-bipyridin-6-yl)methyl]-5-(1,3-oxazol-2-yl)pyrazine-2-carboxamide | 402 |
| Ex-89 | 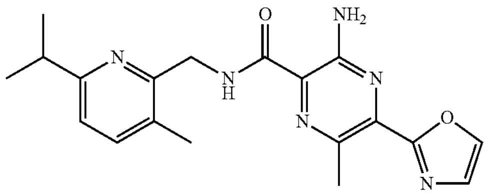 [SMILES: Cc1ccc(C(C)C)nc1CNC(=O)c1nc(C)c(-c2ncco2)nc1N] | 3-amino-6-methyl-N-{[3-methyl-6-(1-methylethyl)pyridin-2-yl]methyl}-5-(1,3-oxazol-2-yl)pyrazine-2-carboxamide | 367 |
| Ex-90 | 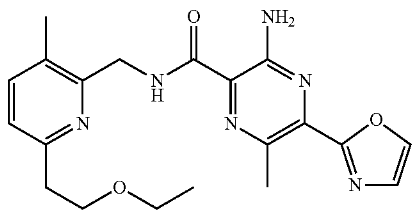 [SMILES: CCOCCc1ccc(C)c(CNC(=O)c2nc(C)c(-c3ncco3)nc2N)n1] | 3-amino-N-{[6-(2-ethoxyethyl)-3-methylpyridin-2-yl]methyl}-6-methyl-5-(1,3-oxazol-2-yl)pyrazine-2-carboxamide | 397 |
| Ex-91 | 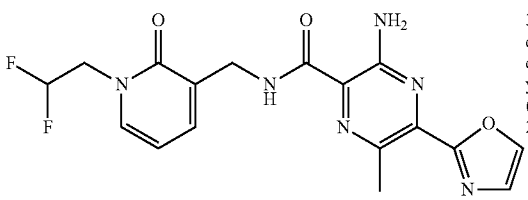 | 3-amino-N-{[1-(2,2-difluoroethyl)-2-oxo-1,2-dihydropyridin-3-yl]methyl}-6-methyl-5-(1,3-oxazol-2-yl)pyrazine-2-carboxamide | 391 |
| Ex-92 | 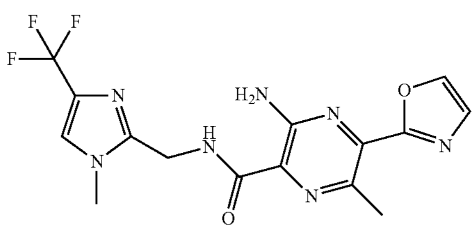 [SMILES: Cc1nc(C(=O)NCc2nc(C(F)(F)F)cn2C)c(N)nc1-c1ncco1] | 3-amino-6-methyl-N-{[1-methyl-4-(trifluoromethyl)-1H-imidazol-2-yl]methyl}-5-(1,3-oxazol-2-yl)pyrazine-2-carboxamide | 382 |
| Ex-93 | 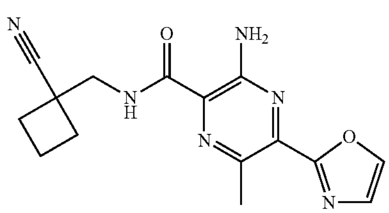 [SMILES: Cc1nc(C(=O)NCC2(C#N)CCC2)c(N)nc1-c1ncco1] | 3-amino-N-[(1-cyanocyclobutyl)methyl]-6-methyl-5-(1,3-oxazol-2-yl)pyrazine-2-carboxamide | 313 |
| Ex-94A Cond 1 First | 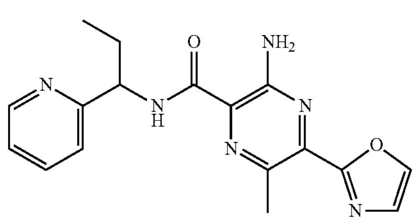 [SMILES: CCC(NC(=O)c1nc(C)c(-c2ncco2)nc1N)c1ccccn1] | 3-amino-6-methyl-5-(1,3-oxazol-2-yl)-N-(1-pyridin-2-ylpropyl)pyrazine-2-carboxamide | 339 |

TABLE I-continued

| Exp. No. | Structure | IUPAC Name | MS [M + H]+ |
|---|---|---|---|
| Ex-94B Cond 1 Second | 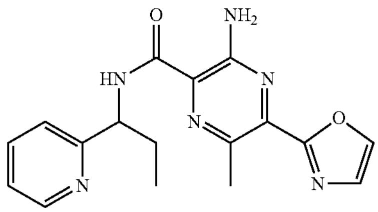 [SMILES: CCC(NC(=O)c1nc(C)c(-c2ncco2)nc1N)c1ccccn1] | 3-amino-6-methyl-5-(1,3-oxazol-2-yl)-N-(1-pyridin-2-ylpropyl)pyrazine-2-carboxamide | 339 |
| Ex-95 | 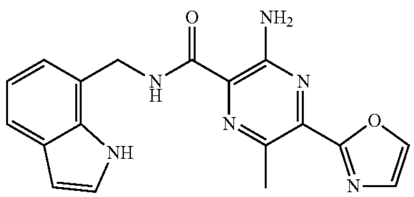 [SMILES: Cc1nc(C(=O)NCc2cccc3cc[nH]c23)c(N)nc1-c1ncco1] | 3-amino-N-(1H-indol-7-ylmethyl)-6-methyl-5-(1,3-oxazol-2-yl)pyrazine-2-carboxamide | 349 |
| Ex-96 | 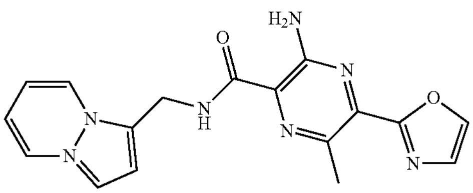 | 3-amino-N-(imidazo-[1,2-a]pyridin-3-yl-methyl)-6-methyl-5-(1,3-oxazol-2-yl)-pyrazine-2-carboxamide | 350 |
| Ex-97 | 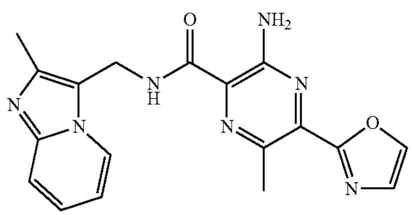 [SMILES: Cc1nc(C(=O)NCc2c(C)nc3ccccn23)c(N)nc1-c1ncco1] | 3-amino-6-methyl-N-[(2-methylimidazo[1,2-a]pyridin-3-yl)methyl]-5-(1,3-oxazol-2-yl)pyrazine-2-carboxamide | 364 |
| Ex-98 | 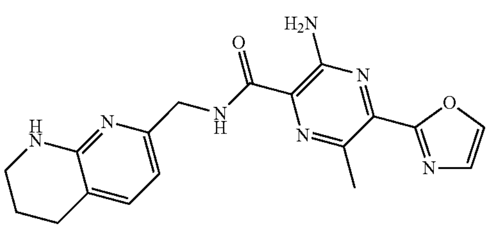 [SMILES: Cc1nc(C(=O)NCc2ccc3c(n2)NCCC3)c(N)nc1-c1ncco1] | 3-amino-6-methyl-5-(1,3-oxazol-2-yl)-N-(5,6,7,8-tetrahydro-1,8-naphthyridin-2-ylmethyl)pyrazine-2-carboxamide | 366 |
| Ex-99 | 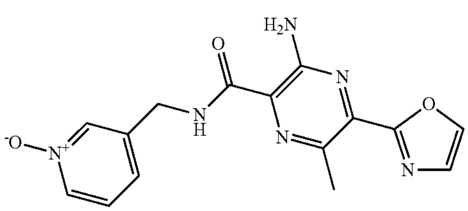 | 3-amino-6-methyl-5-(1,3-oxazol-2-yl)-N-[(1-oxidopyridin-3-yl)methyl]pyrazine-2-carboxamide | 327 |
| Ex-100 | 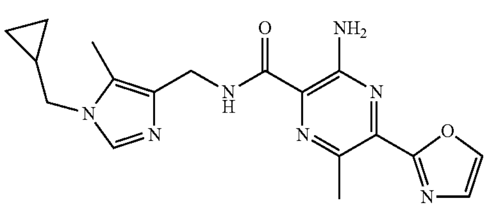 [SMILES: Cc1nc(C(=O)NCc2ncn(CC3CC3)c2C)c(N)nc1-c1ncco1] | 3-amino-N-{[1-(cyclopropylmethyl)-5-methyl-1H-imidazol-4-yl]methyl}-6-methyl-5-(1,3-oxazol-2-yl)pyrazine-2-carboxamide | 368 |

TABLE I-continued

| Exp. No. | IUPAC Name | MS [M + H]+ |
|---|---|---|
| Ex-101 | 3-amino-6-methyl-5-(1,3-oxazol-2-yl)-N-[cis-4-(trifluoromethyl)cyclohexyl]pyrazine-2-carboxamide | 370 |
| Ex-102 | 3-amino-6-methyl-N-[(6-methylimidazo[1,2-a]pyridin-2-yl)methyl]-5-(1,3-oxazol-2-yl)pyrazine-2-carboxamide | 364 |
| Ex-103 | 3-amino-6-methyl-5-(1,3-oxazol-2-yl)-N-(1,4,5,6-tetrahydrocyclopenta[c]pyrazol-3-ylmethyl)pyrazine-2-carboxamide | 340 |
| Ex-106 | 3-amino-N,6-dimethyl-5-(1,3-oxazol-2-yl)-N-(1-pyridin-2-ylethyl)pyrazine-2-carboxamide | 339 |
| Ex-107 | 3-amino-N-[(5-fluoro-3-methylpyridin-2-yl)methyl]-6-methyl-5-(1,3-oxazol-2-yl)pyrazine-2-carboxamide | 343 |
| Ex-108 | 3-amino-6-methyl-5-(1,3-oxazol-2-yl)-N-{[4-(trifluoromethyl)pyrimidin-2-yl]methyl}pyrazine-2-carboxamide | 380 |
| Ex-109 | 3-amino-N-[(5-fluoropyrimidin-2-yl)methyl]-6-methyl-5-(1,3-oxazol-2-yl)pyrazine-2-carboxamide | 330 |

TABLE I-continued

| Exp. No. | Structure | IUPAC Name | MS [M + H]+ |
|---|---|---|---|
| Ex-110 | 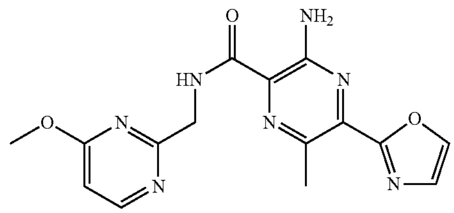 [SMILES: COc1ccnc(CNC(=O)c2nc(C)c(-c3ncco3)nc2N)n1] | 3-amino-N-[(4-methoxypyrimidin-2-yl)methyl]-6-methyl-5-(1,3-oxazol-2-yl)pyrazine-2-carboxamide | 342 |
| Ex-111 | 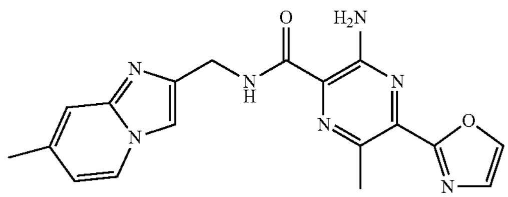 [SMILES: Cc1ccn2cc(CNC(=O)c3nc(C)c(-c4ncco4)nc3N)nc2c1] | 3-amino-6-methyl-N-[(7-methylimidazo[1,2-a]pyridin-2-yl)methyl]-5-(1,3-oxazol-2-yl)pyrazine-2-carboxamide | 364 |
| Ex-112 | 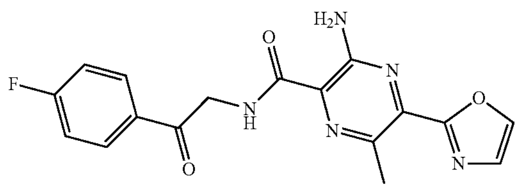 [SMILES: Cc1nc(C(=O)NCC(=O)c2ccc(F)cc2)c(N)nc1-c1ncco1] | 3-amino-N-[2-(4-fluorophenyl)-2-oxoethyl]-6-methyl-5-(1,3-oxazol-2-yl)pyrazine-2-carboxamide | 356 |
| Ex-113 | 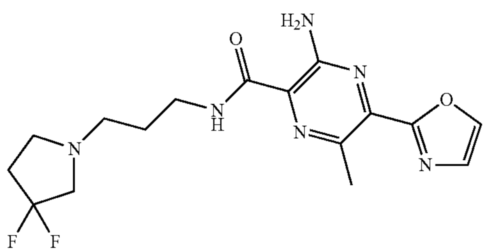 [SMILES: Cc1nc(C(=O)NCCCN2CCC(F)(F)C2)c(N)nc1-c1ncco1] | 3-amino-N-[3-(3,3-difluoropyrrolidin-1-yl)propyl]-6-methyl-5-(1,3-oxazol-2-yl)pyrazine-2-carboxamide | 367 |
| Ex-114 | 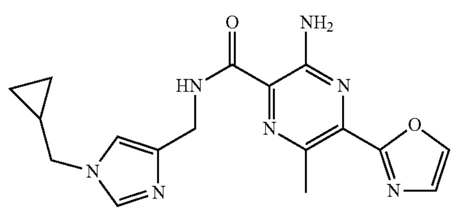 [SMILES: Cc1nc(C(=O)NCc2cn(CC3CC3)cn2)c(N)nc1-c1ncco1] | 3-amino-N-{[1-(cyclopropylmethyl)-1H-imidazol-4-yl]methyl}-6-methyl-5-(1,3-oxazol-2-yl)pyrazine-2-carboxamide | 354 |
| Ex-115 | 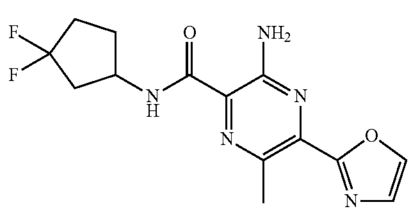 [SMILES: Cc1nc(C(=O)NC2CCC(F)(F)C2)c(N)nc1-c1ncco1] | 3-amino-N-(3,3-difluorocyclopentyl)-6-methyl-5-(1,3-oxazol-2-yl)pyrazine-2-carboxamide | 324 |
| Ex-116 | 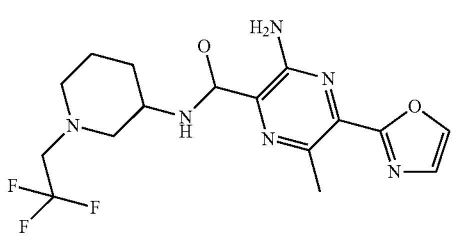 [SMILES: Cc1nc(C(O)NC2CCCN(CC(F)(F)F)C2)c(N)nc1-c1ncco1] | 3-amino-6-methyl-5-(1,3-oxazol-2-yl)-N-[1-(2,2,2-trifluoroethyl)piperidin-3-yl]pyrazine-2-carboxamide | 385 |

TABLE I-continued

| Exp. No. | Structure | IUPAC Name | MS [M + H]+ |
|---|---|---|---|
| Ex-117 | 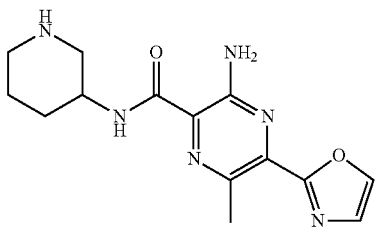 [SMILES: Cc1nc(C(=O)NC2CCCNC2)c(N)nc1-c1ncco1] | 3-amino-6-methyl-5-(1,3-oxazol-2-yl)-N-piperidin-3-ylpyrazine-2-carboxamide | 303 |
| Ex-118 | 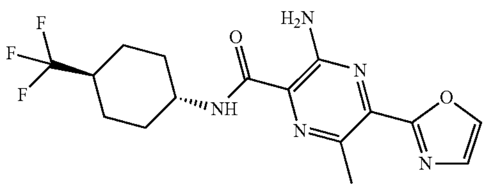 [SMILES: Cc1nc(C(=O)N[C@H]2CC[C@H](C(F)(F)F)CC2)c(N)nc1-c1ncco1] | 3-amino-6-methyl-5-(1,3-oxaozl-2-yl)-N-[trans-4-(trifluoromethyl)cyclohexyl]pyrazine-2-carboxamide | 370 |
| Ex-119 | 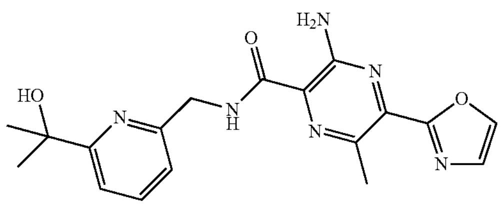 [SMILES: Cc1nc(C(=O)NCc2cccc(C(C)(C)O)n2)c(N)nc1-c1ncco1] | 3-amino[N-{[6-(1-hydroxy-1-methylethyl)pyridin-2-yl]methyl}-6-methyl-5-(1,3-oxazol-2-yl)pyrazine-2-carboxmaide | 369 |
| Ex-120 | 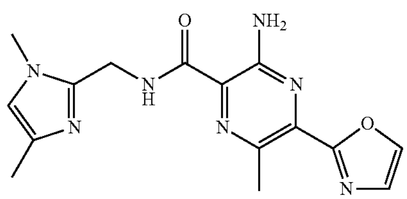 [SMILES: Cc1cn(C)c(CNC(=O)c2nc(C)c(-c3ncco3)nc2N)n1] | 3-amino-N-[(1,4-dimethyl-1H-imidazol-2-yl)methyl]-6-methyl-5-(1,3-oxazol-2-yl)pyrazine-2-carboxamide | 328 |
| Ex-121 | 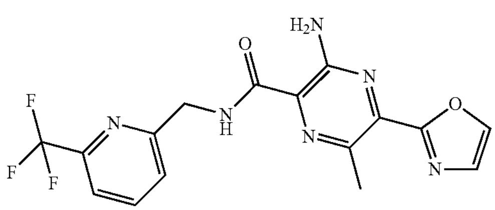 [SMILES: Cc1nc(C(=O)NCc2cccc(C(F)(F)F)n2)c(N)nc1-c1ncco1] | 3-amino-6-methyl-5-(1,3-oxazol-2-yl)-N-{[6-(trifluoromethyl)pyridin-2-yl]methyl}pyrazine-2-carboxamide | 379 |
| Ex-122 | 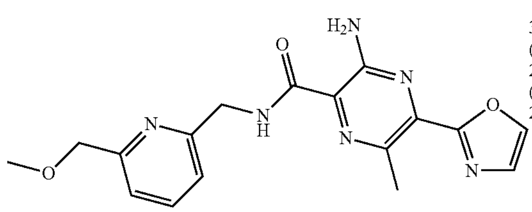 [SMILES: COCc1cccc(CNC(=O)c2nc(C)c(-c3ncco3)nc2N)n1] | 3-amino-N-{[6-(methoxymethyl)pyridin-2-yl]methyl}-6-methyl-5-(1,3-oxazol-2-yl)pyrazine-2-carboxamide | 355 |
| Ex-123 | 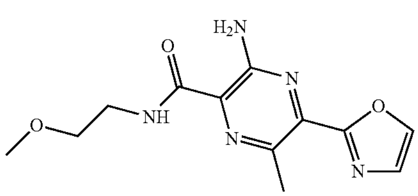 [SMILES: COCCNC(=O)c1nc(C)c(-c2ncco2)nc1N] | 3-amino-N-(2-methoxyethyl)-6-methyl-5-(1,3-oxazol-2-yl)pyrazine-2-carboxamide | 278 |

TABLE I-continued

| Exp. No. | Structure | IUPAC Name | MS [M + H]+ |
|---|---|---|---|
| Ex-124 | 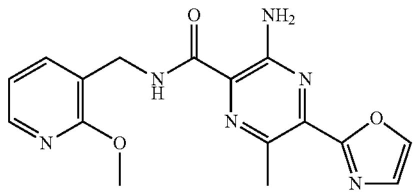 [SMILES: COc1ncccc1CNC(=O)c1nc(C)c(-c2ncco2)nc1N] | 3-amino-N-[(2-methoxypyridin-3-yl)methyl]-6-methyl-5-(1,3-oxazol-2-yl)pyrazine-2-carboxamide | 341 |
| Ex-125 | 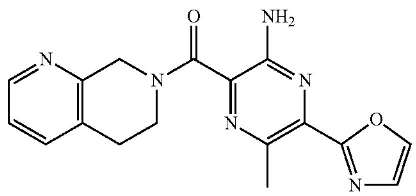 [SMILES: Cc1nc(C(=O)N2CCc3cccnc3C2)c(N)nc1-c1ncco1] | 3-(5,8-dihydro-1,7-naphthyridin-7(6H)-ylcarbonyl)-5-methyl-6-(1,3-oxazol-2-yl)pyrazin-2-amine | 337 |
| Ex-126 | 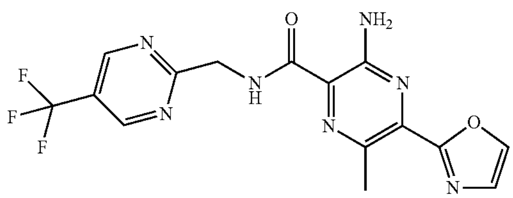 [SMILES: Cc1nc(C(=O)NCc2ncc(C(F)(F)F)cn2)c(N)nc1-c1ncco1] | 3-amino-6-methyl-5-(1,3-oxazol-2-yl)-N-{[5-(trifluoromethyl)pyrimidin-2-yl]methyl}pyrazine-2-carboxamide | 380 |
| Ex-127 | 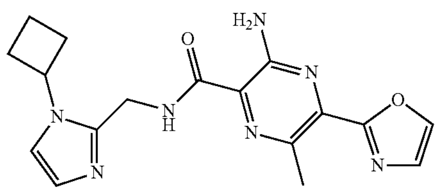 [SMILES: Cc1nc(C(=O)NCc2nccn2C2CCC2)c(N)nc1-c1ncco1] | 3-amino-N-[(1-cyclobutyl-1H-imidazol-2-yl)methyl]-6-methyl-5-(1,3-oxazol-2-yl)pyrazine-2-carboxamide | 354 |
| Ex-128 | 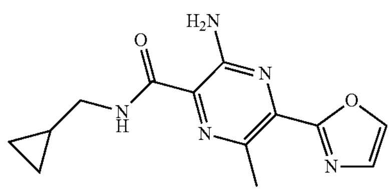 [SMILES: Cc1nc(C(=O)NCC2CC2)c(N)nc1-c1ncco1] | 3-amino-N-(cyclopropylmethyl)-6-methyl-5-(1,3,-oxazol-2-yl)pyrazine-2-carboxamide | 274 |
| Ex-129 | 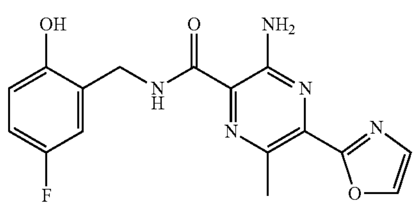 [SMILES: Cc1nc(C(=O)NCc2cc(F)ccc2O)c(N)nc1-c1ncco1] | 3-amino-N-(5-fluoro-2-hydroxybenzyl)-6-methyl-5-(1,3-oxazol-2-yl)pyrazine-2-carboxamide | 344 |
| Ex-130 | 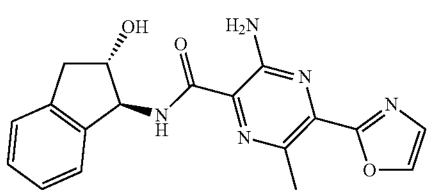 [SMILES: Cc1nc(C(=O)N[C@H]2c3ccccc3C[C@@H]2O)c(N)nc1-c1ncco1] | 3-amino-N-[(1S,2S)-2-hydroxy-2,3-dihydro-1H-inden-1-yl]-6-methyl-5-(1,3-oxazol-2-yl)pyrazine-2-carboxamide | 352 |
| Ex-131 | 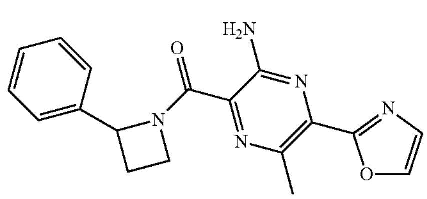 [SMILES: Cc1nc(C(=O)N2CCC2c2ccccc2)c(N)nc1-c1ncco1] | 5-methyl-6-(1,3-oxazol-2-yl)-3-[(2-phenylazetidin-1-yl)carbonyl]pyrazin-2-amine | 336 |

TABLE I-continued

| Exp. No. | Structure | IUPAC Name | MS [M + H]+ |
|---|---|---|---|
| Ex-132 | 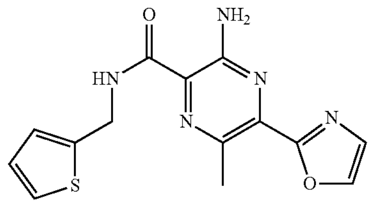 [SMILES: Cc1nc(C(=O)NCc2cccs2)c(N)nc1-c1ncco1] | 3-amino-6-methyl-5-(1,3-oxazol-2-yl)-N-(thiophen-2-ylmethyl)pyrazine-2-carboxamide | 316 |
| Ex-133 | 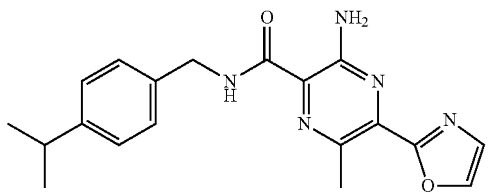 [SMILES: Cc1nc(C(=O)NCc2ccc(C(C)C)cc2)c(N)nc1-c1ncco1] | 3-amino-6-methyl-N-[4-(1-methylethyl)benzyl]-5-(1,3-oxazol-2-yl)pyrazine-2-carboxamide | 352 |
| Ex-134 | 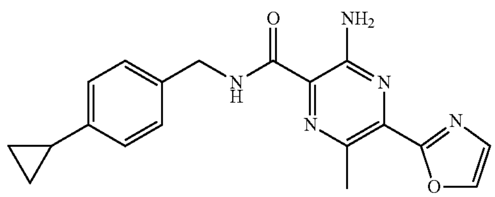 [SMILES: Cc1nc(C(=O)NCc2ccc(C3CC3)cc2)c(N)nc1-c1ncco1] | 3-amino-N-(4-cyclopropylbenzyl)-6-methyl-5-(1,3-oxazol-2-yl)pyrazine-2-carboxamide | 350 |
| Ex-135 | 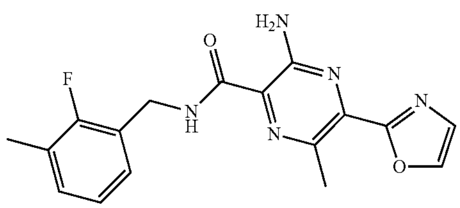 [SMILES: Cc1cccc(CNC(=O)c2nc(C)c(-c3ncco3)nc2N)c1F] | 3-amino-N-(2-fluoro-3-methylbenzyl)-6-methyl-5-(1,3-oxazol-2-yl)pyrazine-2-carboxamide | 342 |
| Ex-136 | 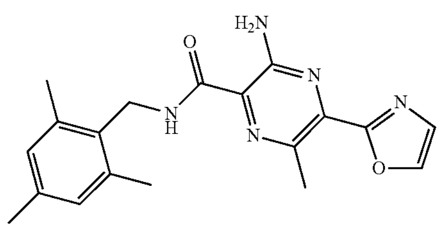 [SMILES: Cc1cc(C)c(CNC(=O)c2nc(C)c(-c3ncco3)nc2N)c(C)c1] | 3-amino-6-methyl-5-(1,3-oxazol-2-yl)-N-(2,4,6-trimethylbenzyl)pyrazine-2-carboxamide | 352 |
| Ex-137 | 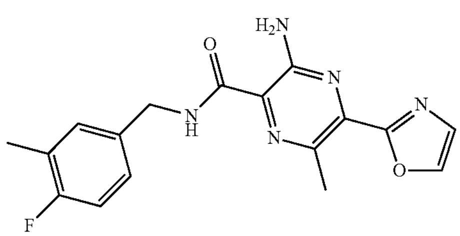 [SMILES: Cc1cc(CNC(=O)c2nc(C)c(-c3ncco3)nc2N)ccc1F] | 3-amino-N-(4-fluoro-3-methylbenzyl)-6-methyl-5-(1,3-oxazol-2-yl)pyrazine-2-carboxamide | 342 |
| Ex-138 | 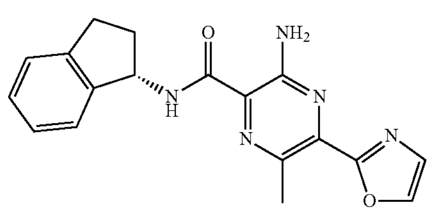 [SMILES: Cc1nc(C(=O)N[C@H]2CCc3ccccc32)c(N)nc1-c1ncco1] | 3-amino-N-[(1S)-2,3-dihydro-1H-inden-1-yl]-6-methyl-5-(1,3-oxazol-2-yl)pyrazine-2-carboxamide | 336 |

TABLE I-continued

| Exp. No. | Structure | IUPAC Name | MS [M + H]+ |
|---|---|---|---|
| Ex-139 | 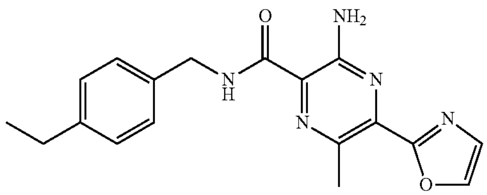 [SMILES: CCc1ccc(CNC(=O)c2nc(C)c(-c3ncco3)nc2N)cc1] | 3-amino-N-(4-ethylbenzyl)-6-methyl-5-(1,3-oxazol-2-yl)pyrazine-2-carboxamide | 338 |
| Ex-140 | 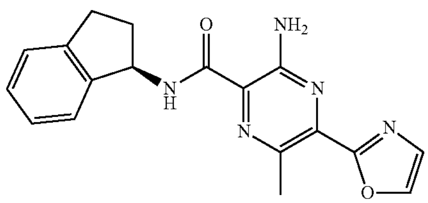 [SMILES: Cc1nc(C(=O)N[C@@H]2CCc3ccccc32)c(N)nc1-c1ncco1] | 3-amino-N-[(1R)-2,3-dihydro-1H-inden-1-yl]-6-methyl-5-(1,3-oxazol-2-yl)pyrazine-2-carboxamide | 336 |
| Ex-141 | 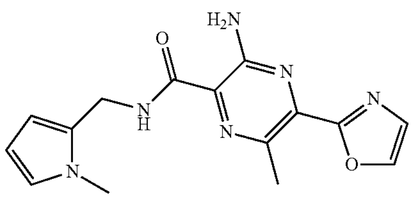 [SMILES: Cc1nc(C(=O)NCc2cccn2C)c(N)nc1-c1ncco1] | 3-amino-6-methyl-N-[(1-methyl-1H-pyrrol-2-yl)methyl]-5-(1,3-oxazol-2-yl)pyrazine-2-carboxamide | 313 |
| Ex-142 | 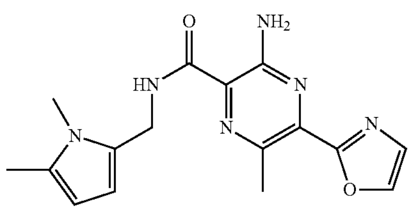 [SMILES: Cc1nc(C(=O)NCc2ccc(C)n2C)c(N)nc1-c1ncco1] | 3-amino-N-[(1,5-dimethyl-1H-pyrrol-2-yl)methyl]-6-methyl-5-(1,3-oxazol-2-yl)pyrazine-2-carboxamide | 327 |
| Ex-143 | 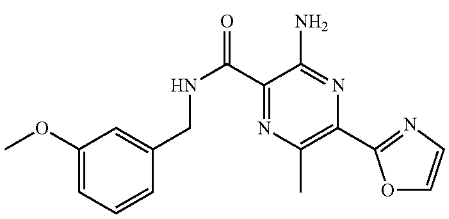 [SMILES: COc1cccc(CNC(=O)c2nc(C)c(-c3ncco3)nc2N)c1] | 3-amino-N-(3-methoxybenzyl)-6-methyl-5-(1,3-oxazol-2-yl)pyrazine-2-carboxamide | 340 |
| Ex-144 | 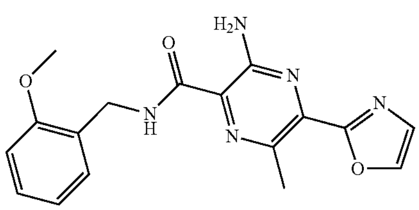 [SMILES: COc1ccccc1CNC(=O)c1nc(C)c(-c2ncco2)nc1N] | 3-amino-N-(2-methoxybenzyl)-6-methyl-5-(1,3-oxazol-2-yl)pyrazine-2-carboxamide | 340 |
| Ex-145 | 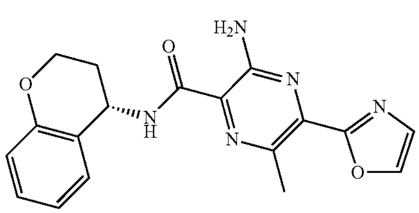 [SMILES: Cc1nc(C(=O)N[C@H]2CCOc3ccccc32)c(N)nc1-c1ncco1] | 3-amino-N-[(4R)-3,4-dihydro-2H-chromen-44-yl]-6-methyl-5-(1,3-oxazol-2-yl)pyrazine-2-carboxamide | 352 |

TABLE I-continued

| Exp. No. | Structure | IUPAC Name | MS [M + H]+ |
|---|---|---|---|
| Ex-146 | 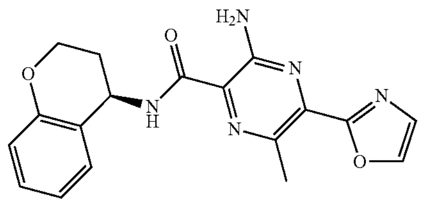 [SMILES: Cc1nc(C(=O)N[C@@H]2CCOc3ccccc32)c(N)nc1-c1ncco1] | 3-amino-N-[(4S)-3,4-dihydro-2H-chromen-4-yl]-6-methyl-5-(1,3-oxazol-2-yl)pyrazine-2-carboxamide | 352 |
| Ex-147 | 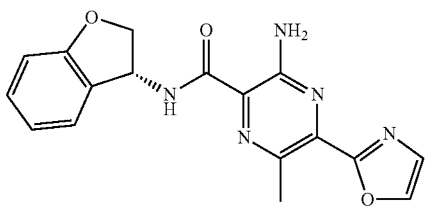 [SMILES: Cc1nc(C(=O)N[C@H]2COc3ccccc32)c(N)nc1-c1ncco1] | 3-amino-N-[(3R)-2,3-dihydro-1-benzofuran-3-yl]-6-methyl-5-(1,3-oxazol-2-yl)pyrazine-2-carboxamide | 338 |
| Ex-148 | 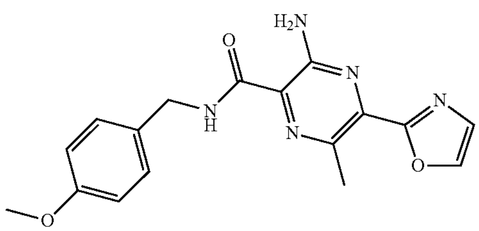 [SMILES: COc1ccc(CNC(=O)c2nc(C)c(-c3ncco3)nc2N)cc1] | 3-amino-N-(4-methoxybenzyl)-6-methyl-5-(1,3-oxazol-2-yl)pyrazine-2-carboxamide | 340 |
| Ex-149 | 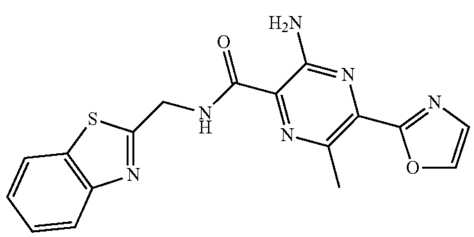 [SMILES: Cc1nc(C(=O)NCc2nc3ccccc3s2)c(N)nc1-c1ncco1] | 3-amino-N-(1,3-benzothiazol-2-ylmethyl)-6-methyl-5-(1,3-oxazol-2-yl)pyrazine-2-carboxamide | 367 |
| Ex-150 | 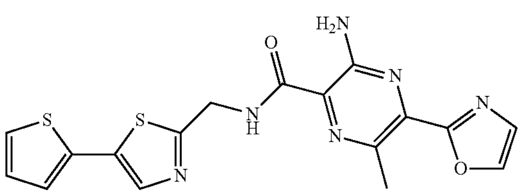 [SMILES: Cc1nc(C(=O)NCc2ncc(-c3cccs3)s2)c(N)nc1-c1ncco1] | 3-amino-6-methyl-5-(1,3-oxazol-2-yl)-N-[(2-thiophen-2-yl-1,3-thiazol-4-yl)methyl]pyrazine-2-carboxamide | 399 |
| Ex-151 | 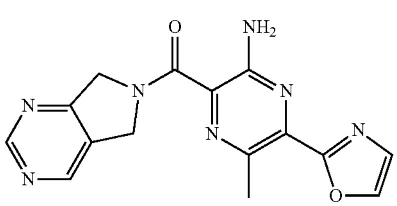 [SMILES: Cc1nc(C(=O)N2Cc3cncnc3C2)c(N)nc1-c1ncco1] | 3-(5,7-dihydro-6H-pyrrolo[3,4-d]pyrimidin-6-ylcarbonyl)-5-methyl-6-(1,3-oxazol-2-yl)pyrazin-2-amine | 324 |
| Ex-153 | 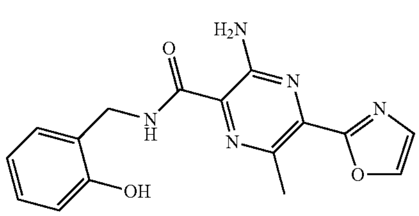 [SMILES: Cc1nc(C(=O)NCc2ccccc2O)c(N)nc1-c1ncco1] | 3-amino-N-(2-hydroxybenzyl)-6-methyl-5-(1,3-oxazol-2-yl)pyrazine-2-carboxamide | 326 |

TABLE I-continued

| Exp. No. | Structure | IUPAC Name | MS [M + H]+ |
|---|---|---|---|
| Ex-154 | 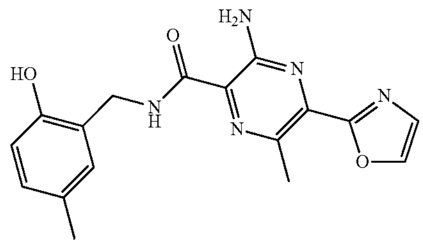 [SMILES: Cc1ccc(O)c(CNC(=O)c2nc(C)c(-c3ncco3)nc2N)c1] | 3-amino-N-(2-hydroxy-5-methylbenzyl)-6-methyl-5-(1,3-oxazol-2-yl)pyrazine-2-carboxamide | 340 |
| Ex-155 | 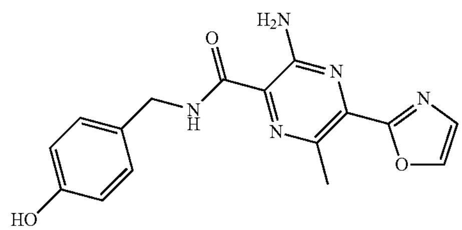 [SMILES: Cc1nc(C(=O)NCc2ccc(O)cc2)c(N)nc1-c1ncco1] | 3-amino-N-(4-hydroxybenzyl)-6-methyl-5-(1,3-oxazol-2-yl)pyrazine-2-carboxamide | 326 |
| Ex-156 | 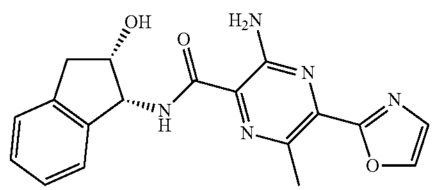 [SMILES: Cc1nc(C(=O)N[C@@H]2c3ccccc3C[C@@H]2O)c(N)nc1-c1ncco1] | 3-amino-N-[(1R,2S)-2-hydroxy-2,3-dihydro-1H-inden-1-yl]-6-methyl-5-(1,3-oxazol-2-yl)pyrazine-2-carboxamide | 352 |
| Ex-157 | 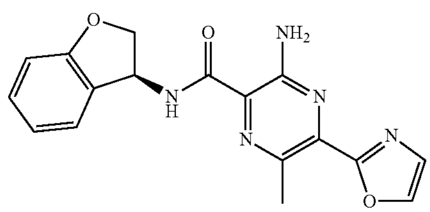 [SMILES: Cc1nc(C(=O)N[C@@H]2COc3ccccc32)c(N)nc1-c1ncco1] | 3-amino-N-[(3S)-2,3-dihydro-1-benzofuran-3-yl]-6-methyl-5-(1,3-oxazol-2-yl)pyrazine-2-carboxamide | 338 |
| Ex-158 | 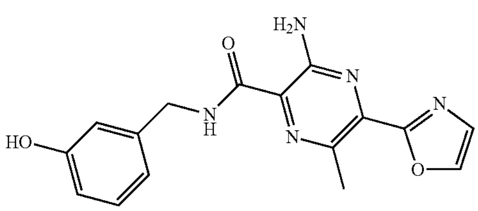 [SMILES: Cc1nc(C(=O)NCc2cccc(O)c2)c(N)nc1-c1ncco1] | 3-amino-N-(3-hydroxybenzyl)-6-methyl-5-(1,3-oxazol-2-yl)pyrazine-2-carboxamide | 326 |
| Ex-159 | 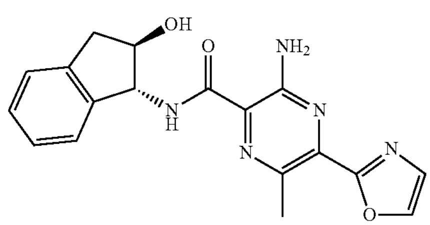 [SMILES: Cc1nc(C(=O)N[C@@H]2c3ccccc3C[C@H]2O)c(N)nc1-c1ncco1] | 3-amino-N-[(1R,2R)-2-hydroxy-2,3-dihydro-1H-inden-1-yl]-6-methyl-5-(1,3-oxazol-2-yl)pyrazine-2-carboxamide | 352 |
| Ex-160 | 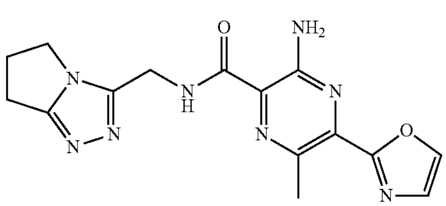 [SMILES: Cc1nc(C(=O)NCc2nnc3n2CCC3)c(N)nc1-c1ncco1] | 3-amino-N-(6,7-dihydro-5H-pyrrolo[2,1-c][1,2,4]triazol-3-ylmethyl)-6-methyl-5-(1,3-oxazol-2-yl)pyrazine-2-carboxamide | 341 |

TABLE I-continued

| Exp. No. | Structure | IUPAC Name | MS [M + H]+ |
|---|---|---|---|
| Ex-161 | 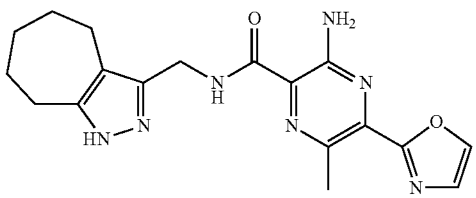 [SMILES: Cc1nc(C(=O)NCc2n[nH]c3c2CCCCC3)c(N)nc1-c1ncco1] | 3-amino-N-(1,4,5,6,7,8-hexahydrocyclohepta[c]pyrazol-3-ylmethyl)-6-methyl-5-(1,3-oxazol-2-yl)pyrazine-2-carboxamide | 368 |
| Ex-162 | 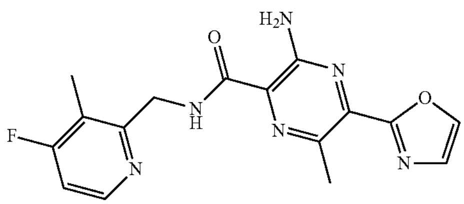 [SMILES: Cc1nc(C(=O)NCc2nccc(F)c2C)c(N)nc1-c1ncco1] | 3-amino-N-[(4-fluoro-3-methylpyridin-2-yl)methyl]-6-methyl-5-(1,3-oxazol-2-yl)pyrazine-2-carboxamide | 343 |
| Ex-163 | 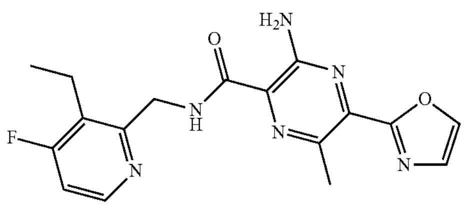 [SMILES: CCc1c(F)ccnc1CNC(=O)c1nc(C)c(-c2ncco2)nc1N] | 3-amino-N-[(3-ethyl-4-fluoropyridin-2-yl)methyl]-6-methyl-5-(1,3-oxazol-2-yl)pyrazine-2-carboxamide | 357 |
| Ex-164 | 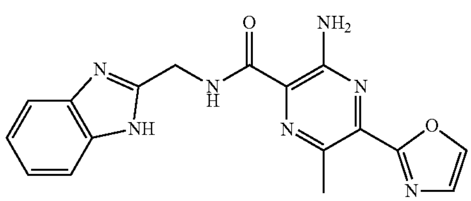 [SMILES: Cc1nc(C(=O)NCc2nc3ccccc3[nH]2)c(N)nc1-c1ncco1] | 3-amino-N-(1H-benzimidazol-2-ylmethyl)-6-methyl-5-(1,3-oxazol-2-yl)pyrazine-2-carboxamide | 350 |
| Ex-165A Cond. 2 First | 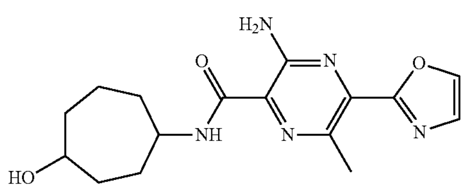 [SMILES: Cc1nc(C(=O)NC2CCCC(O)CC2)c(N)nc1-c1ncco1] | 3-amino-N-(4-hydroxycycloheptyl)-6-methyl-5-(1,3-oxazol-2-yl)pyrazine-2-carboxamide | 332 |
| Ex-165B Cond. 2 Second | 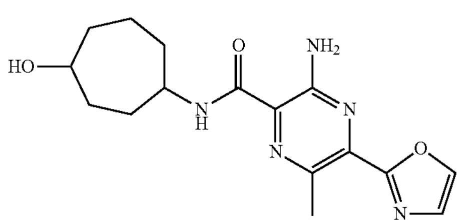 [SMILES: Cc1nc(C(=O)NC2CCCC(O)CC2)c(N)nc1-c1ncco1] | 3-amino-N-(4-hydroxycycloheptyl)-6-methyl-5-(1,3-oxazol-2-yl)pyrazine-2-carboxamide | 332 |
| Ex-165C Cond. 3 First | 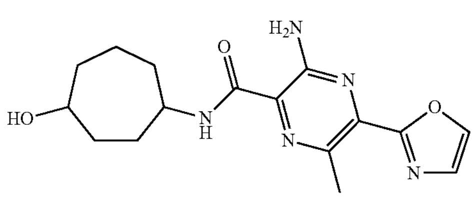 [SMILES: Cc1nc(C(=O)NC2CCCC(O)CC2)c(N)nc1-c1ncco1] | 3-amino-N-(4-hydroxycycloheptyl)-6-methyl-5-(1,3-oxazol-2-yl)pyrazine-2-carboxamide | 332 |

TABLE I-continued

| Exp. No. | Structure | IUPAC Name | MS [M + H]+ |
|---|---|---|---|
| Ex-165D Cond. 3 Second | 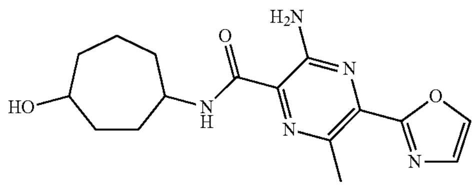 [SMILES: Cc1nc(C(=O)NC2CCCC(O)CC2)c(N)nc1-c1ncco1] | 3-amino-N-(4-hydroxycycloheptyl)-6-methyl-5-(1,3-oxazol-2-yl)pyrazine-2-carboxamide | 332 |
| Ex-166 | 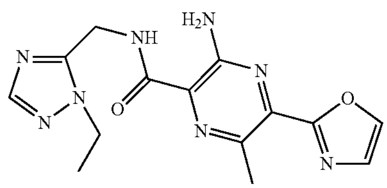 [SMILES: CCn1ncnc1CNC(=O)c1nc(C)c(-c2ncco2)nc1N] | 3-amino-N-[(1-ethyl-1H-1,2,4-triazol-5-yl)methyl]-6-methyl-5-(1,3-oxazol-2-yl)pyrazine-2-carboxamide | 329 |
| Ex-167 | 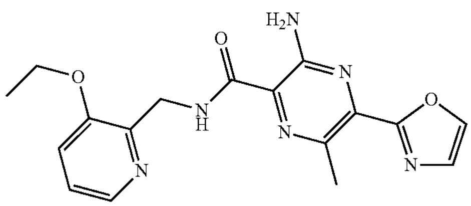 [SMILES: CCOc1cccnc1CNC(=O)c1nc(C)c(-c2ncco2)nc1N] | 3-amino-N-[(3-ethoxypyridin-2-yl)methyl]-6-methyl-5-(1,3-oxazol-2-yl)pyrazine-2-carboxamide | 355 |
| Ex-169 | 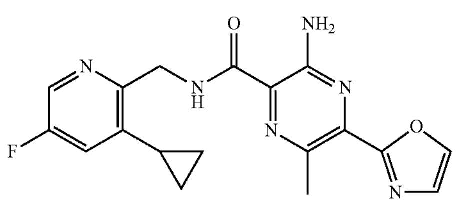 [SMILES: Cc1nc(C(=O)NCc2ncc(F)cc2C2CC2)c(N)nc1-c1ncco1] | 3-amino-N-[(3-cyclopropyl-5-fluoropyridin-2-yl)methyl]-6-methyl-5-(1,3-oxazol-2-yl)pyrazine-2-carboxamide | 369 |
| Ex-170 | 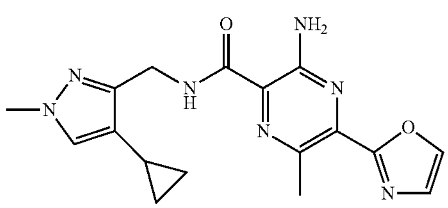 [SMILES: Cc1nc(C(=O)NCc2nn(C)cc2C2CC2)c(N)nc1-c1ncco1] | 3-amino-N-[(4-cyclopropyl-1-methyl-1H-pyrazol-3-yl)methyl]-6-methyl-5-(1,3-oxazol-2-yl)pyrazine-2-carboxmamide | 354 |
| Ex-171 | 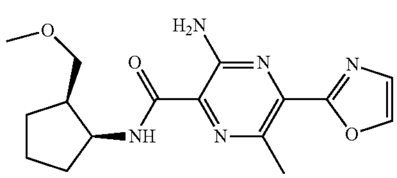 [SMILES: COC[C@@H]1CCC[C@@H]1NC(=O)c1nc(C)c(-c2ncco2)nc1N] | 3-amino-N-[(1R,2S)-2-(methoxymethyl)cyclopentyl]-6-methyl-5-(1,3-oxazol-2-yl)pyrazine-2-carboxamide | 332 |
| Ex-172 | 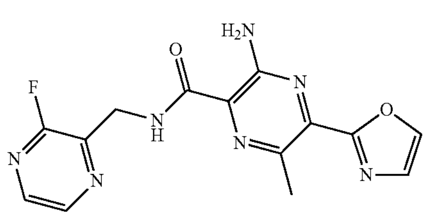 [SMILES: Cc1nc(C(=O)NCc2nccnc2F)c(N)nc1-c1ncco1] | 3-amino-N-[(3-fluoropyrazin-2-yl)methyl]-6-methyl-5-(1,3-oxazol-2-yl)pyrazine-2-carboxamide | 330 |

TABLE I-continued

| Exp. No. | Structure | IUPAC Name | MS [M + H]+ |
|---|---|---|---|
| Ex-173 | 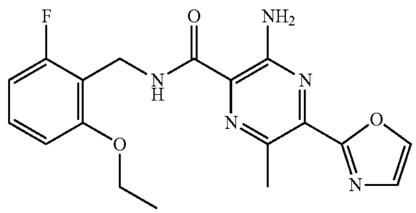 [SMILES: CCOc1cccc(F)c1CNC(=O)c1nc(C)c(-c2ncco2)nc1N] | 3-amino-N-(2-ethoxy-6-fluorobenzyl)-6-methyl-5-(1,3-oxazol-2-yl)pyrazine-2-carboxamide | 372 |
| Ex-174 | 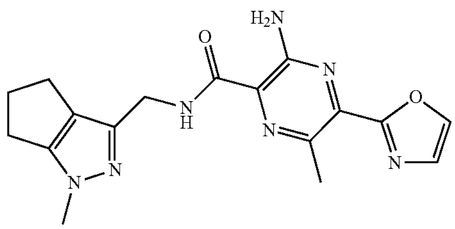 [SMILES: Cc1nc(C(=O)NCc2nn(C)c3c2CCC3)c(N)nc1-c1ncco1] | 3-amino-6-methyl-N-[(1-methyl-1,4,5,6-tetrahydrocyclopenta[c]pyrazol-3-yl)methyl]-5-(1,3-oxazol-2-yl)pyrazine-2-carboxamide | 354 |
| Ex-175 | 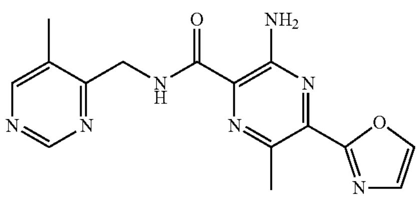 [SMILES: Cc1cncnc1CNC(=O)c1nc(C)c(-c2ncco2)nc1N] | 3-amino-6-methyl-N-[(5-methylpyrimidin-4-yl)methyl]-5-(1,3-oxazol-2-yl)pyrazine-2-carboxamide | 326 |
| Ex-178 | 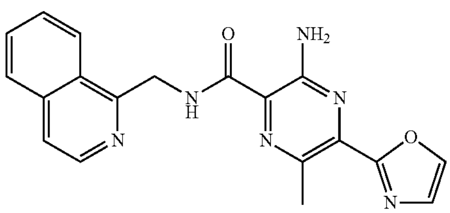 [SMILES: Cc1nc(C(=O)NCc2nccc3ccccc23)c(N)nc1-c1ncco1] | 3-amino-N-(isoquinolin-1-ylmethyl)-6-methyl-5-(1,3-oxazol-2-yl)pyrazine-2-carboxamide | 361 |
| Ex-179 | 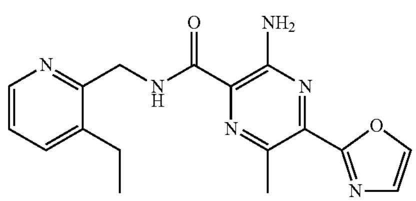 [SMILES: CCc1cccnc1CNC(=O)c1nc(C)c(-c2ncco2)nc1N] | 3-amino-N-[(3-ethylpyridin-2-yl)methyl]-6-methyl-5-(1,3-oxazol-2-yl)pyrazine-2-carboxamide | 339 |
| Ex-180 | 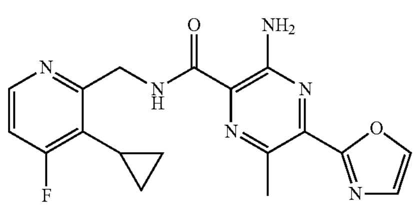 [SMILES: Cc1nc(C(=O)NCc2nccc(F)c2C2CC2)c(N)nc1-c1ncco1] | 3-amino-N-[(3-cyclopropyl-4-fluoropyridin-2-yl)methyl]-6-methyl-5-(1,3-oxazol-2-yl)pyrazine-2-carboxamide | 369 |
| Ex-181 | 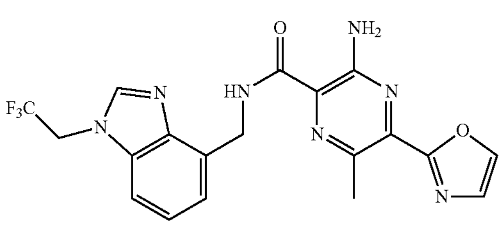 [SMILES: Cc1nc(C(=O)NCc2cccc3c2ncn3CC(F)(F)F)c(N)nc1-c1ncco1] | 3-amino-6-methyl-5-(1,3-oxazol-2-yl)-N-{[1-(2,2,2-trifluoroethyl)-1H-benzimidazol-4-yl]methyl}pyrazine-2-carboxamide | 432 |

TABLE I-continued

| Exp. No. | Structure | IUPAC Name | MS [M + H]+ |
|---|---|---|---|
| Ex-182 | 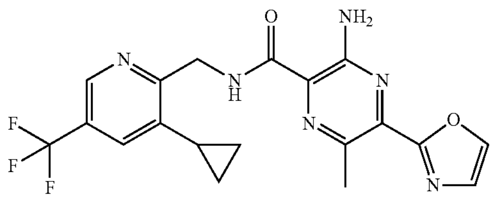 [SMILES: Cc1nc(C(=O)NCc2ncc(C(F)(F)F)cc2C2CC2)c(N)nc1-c1ncco1] | 3-amino-N-{[3-cyclopropyl-5-(trifluoromethyl)pyridin-2-yl]methyl}-6-methyl-5-(1,3-oxazol-2-yl)pyrazine-2-carboxamide | 419 |
| Ex-183 | 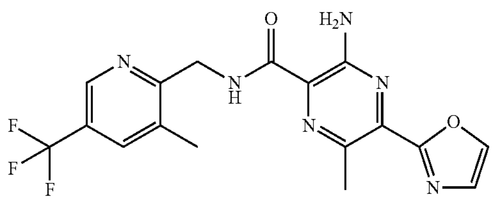 [SMILES: Cc1cc(C(F)(F)F)cnc1CNC(=O)c1nc(C)c(-c2ncco2)nc1N] | 3-amino-6-methyl-N-{[3-methyl-5-(trifluoromethyl)pyridin-2-yl]methyl}-5-(1,3-oxazol-2-yl)pyrazine-2-carboxamide | 393 |
| Ex-184 | 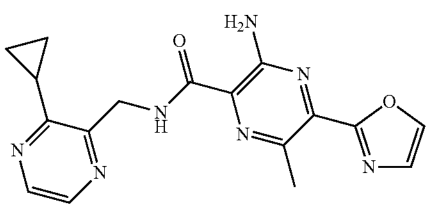 [SMILES: Cc1nc(C(=O)NCc2nccnc2C2CC2)c(N)nc1-c1ncco1] | 3-amino-N-[(3-cyclopropyl-pyrazin-2-yl)methyl]-6-methyl-5-(1,3-oxazol-2-yl)pyrazine-2-carboxamide | 352 |
| Ex-185 | 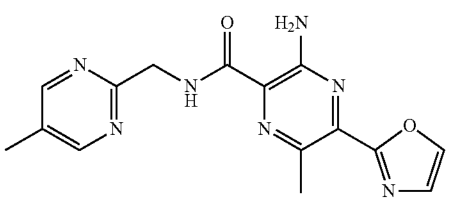 [SMILES: Cc1cnc(CNC(=O)c2nc(C)c(-c3ncco3)nc2N)nc1] | 3-amino-6-methyl-N-[(5-methylpyrimidin-2-yl)methyl]-5-(1,3-oxazol-2-yl)pyrazine-2-carboxamide | 326 |
| Ex-186 | 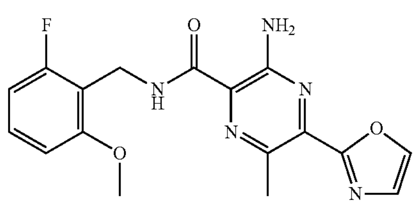 [SMILES: COc1cccc(F)c1CNC(=O)c1nc(C)c(-c2ncco2)nc1N] | 3-amino-N-(2-fluoro-6-methoxybenzyl)-6-methyl-5-(1,3-oxazol-2-yl)pyrazine-2-carboxamide | 358 |
| Ex-187 | 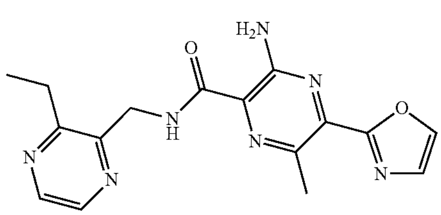 [SMILES: CCc1nccnc1CNC(=O)c1nc(C)c(-c2ncco2)nc1N] | 3-amino-N-[(3-ethylpyrazin-2-yl)methyl]-6-methyl-5-(1,3-oxazol-2-yl)pyrazine-2-carboxamide | 340 |
| Ex-188 | 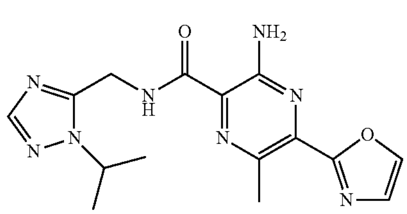 [SMILES: Cc1nc(C(=O)NCc2ncnn2C(C)C)c(N)nc1-c1ncco1] | 3-amino-6-methyl-N-{[1-(1-methylethyl)-1H-1,2,4-triazol-5-yl]methyl}-5-(1,3-oxazol-2-yl)pyrazine-2-carboxamide | 343 |

TABLE I-continued

| Exp. No. | Structure | IUPAC Name | MS [M + H]+ |
|---|---|---|---|
| Ex-189 | 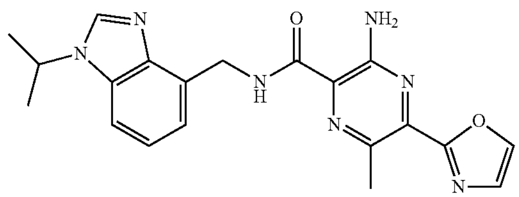 [SMILES: Cc1nc(C(=O)NCc2cccc3c2ncn3C(C)C)c(N)nc1-c1ncco1] | 3-amino-6-methyl-N-{[1-(1-methylethyl-1H-benzimidazol-4-yl]methyl}-5-(1,3-oxazol-2-yl)pyrazine-2-carboxamide | 392 |
| Ex-190 | 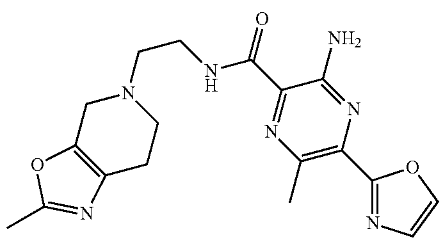 [SMILES: Cc1nc2c(o1)CN(CCNC(=O)c1nc(C)c(-c3ncco3)nc1N)CC2] | 3-amino-6-methyl-N-[2-(2-methyl-6,7-dihydro[1,3]oxazolo[5,4-c]pyridin-5-(4H)-yl)ethyl]-5-(1,3-oxazol-2-yl)pyrazine-2-carboxamide | 384 |
| Ex-191A Cond. 4 First | 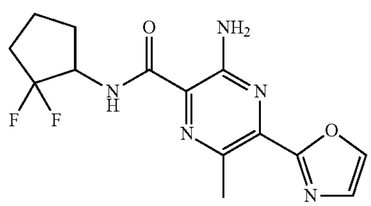 [SMILES: Cc1nc(C(=O)NC2CCCC2(F)F)c(N)nc1-c1ncco1] | 3-amino-N-(2,2-difluorocyclopentyl)-6-methyl-5-(1,3-oxazol-2-yl)pyrazine-2-carboxamide | 324 |
| Ex-191B Cond. 4 First | 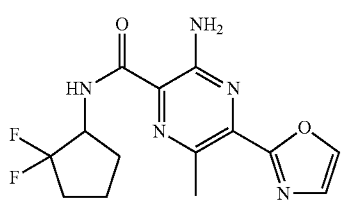 [SMILES: Cc1nc(C(=O)NC2CCCC2(F)F)c(N)nc1-c1ncco1] | 3-amino-N-(2,2-difluorocyclopentyl)-6-methyl-5-(1,3-oxazol-2-yl)pyrazine-2-carboxamide | 324 |
| Ex-193 | 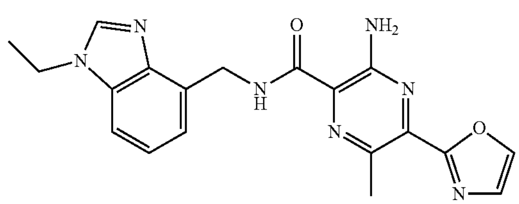 [SMILES: CCn1cnc2c(CNC(=O)c3nc(C)c(-c4ncco4)nc3N)cccc21] | 3-amino-N-[(1-ethyl-1H-benzimidazol-4-yl)methyl]-6-methyl-5-(1,3-oxazol-2-yl)pyrazine-2-carboxamide | 378 |
| Ex-194 | 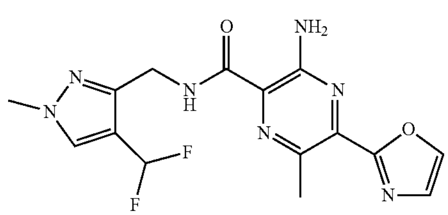 [SMILES: Cc1nc(C(=O)NCc2nn(C)cc2C(F)F)c(N)nc1-c1ncco1] | 3-amino-N-{[4-(difluoromethyl)-1-methyl-1H-pyrazol-3-yl]methyl}-6-methyl-5-(1,3-oxazol-2-yl)pyrazine-2-carboxamide | 364 |
| Ex-195 | 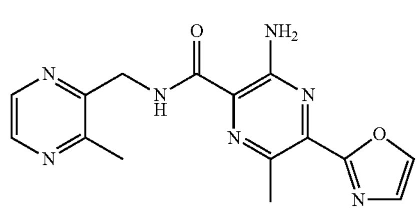 [SMILES: Cc1nccnc1CNC(=O)c1nc(C)c(-c2ncco2)nc1N] | 3-amino-6-methyl-N-[(3-methylpyrazin-2-yl)methyl]-5-(1,3-oxazol-2-yl)pyrazine-2-carboxamide | 326 |

TABLE I-continued

| Exp. No. | Structure | IUPAC Name | MS [M + H]+ |
|---|---|---|---|
| Ex-196 | 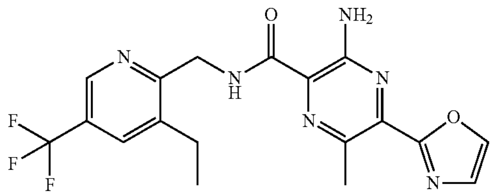 [SMILES: CCc1cc(C(F)(F)F)cnc1CNC(=O)c1nc(C)c(-c2ncco2)nc1N] | 3-amino-N-{[3-ethyl-5-(trifluoromethyl)pyridin-2-yl]methyl}-6-methyl-5-(1,3-oxazol-2-yl)pyrazine-2-carboxamide | 407 |
| Ex-197 | 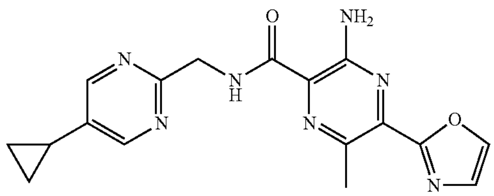 [SMILES: Cc1nc(C(=O)NCc2ncc(C3CC3)cn2)c(N)nc1-c1ncco1] | 3-amino-N-[(5-cyclopropylpyrimidin-2-yl)methyl]-6-methyl-5-(1,3-oxazol-2-yl)pyrazine-2-carboxamide | 352 |
| Ex-198 | 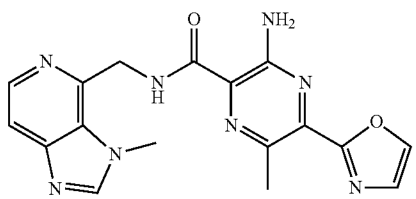 [SMILES: Cc1nc(C(=O)NCc2nccc3ncn(C)c23)c(N)nc1-c1ncco1] | 3-amino-6-methyl-N-[(3-methyl-3H-imidazo[4,5-c]pyridin-4-yl)methyl]-5-(1,3-oxazol-2-yl)pyrazine-2-carboxamide | 365 |
| Ex-199 | 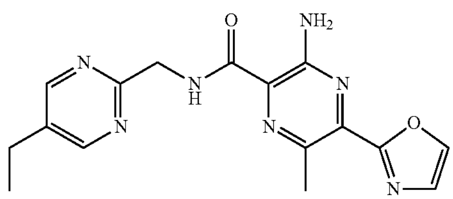 [SMILES: CCc1cnc(CNC(=O)c2nc(C)c(-c3ncco3)nc2N)nc1] | 3-amino-N-[(5-ethylpyrimidin-2-yl)methyl]-6-methyl-5-(1,3-oxazol-2-yl)pyrazine-2-carboxamide | 340 |
| Ex-200 | 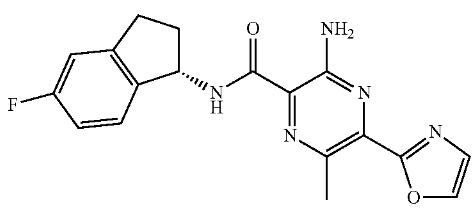 [SMILES: Cc1nc(C(=O)N[C@H]2CCc3cc(F)ccc32)c(N)nc1-c1ncco1] | 3-amino-N-[(1S)-5-fluoro-2,3-dihydro-1H-inden-1-yl]-6-methyl-5-(1,3-oxazol-2-yl)pyrazine-2-carboxamide | 354 |
| Ex-201 | 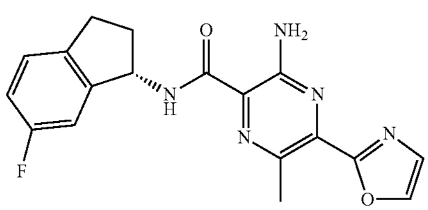 [SMILES: Cc1nc(C(=O)N[C@H]2CCc3ccc(F)cc32)c(N)nc1-c1ncco1] | 3-amino-N-[(1S)-6-fluoro-2,3-dihydro-1H-inden-1-yl]-6-methyl-5-(1,3-oxazol-2-yl)pyrazine-2-carboxamide | 354 |
| Ex-202 | 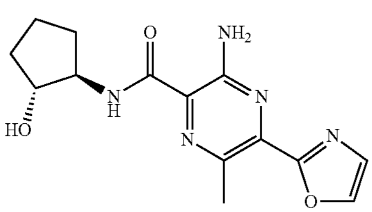 [SMILES: Cc1nc(C(=O)N[C@@H]2CCC[C@H]2O)c(N)nc1-c1ncco1] | 3-amino-N-[(1R,2R)-2-hydroxycyclopentyl]-6-methyl-5-(1,3-oxazol-2-yl)pyrazine-2-carboxamide | 304 |

TABLE I-continued

| Exp. No. | Structure | IUPAC Name | MS [M + H]+ |
|---|---|---|---|
| Ex-203 | 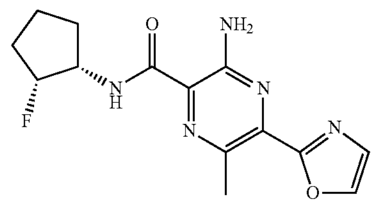 [SMILES: Cc1nc(C(=O)N[C@H]2CCC[C@H]2F)c(N)nc1-c1ncco1] | 3-amino-N-[(1S,2R)-2-fluorocyclopentyl]-6-methyl-5-(1,3-oxazol-2-yl)pyrazine-2-carboxamide | 306 |
| Ex-204 | 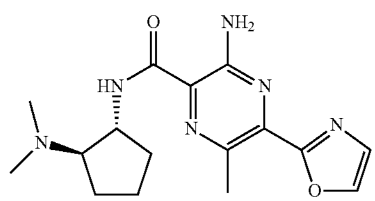 [SMILES: Cc1nc(C(=O)N[C@@H]2CCC[C@H]2N(C)C)c(N)nc1-c1ncco1] | 3-amino-N-[(1R,2R)-2-(dimethylamino)cyclopentyl]-6-methyl-5-(1,3-oxazol-2-yl)pyrazine-2-carboxamide | 331 |
| Ex-205 | 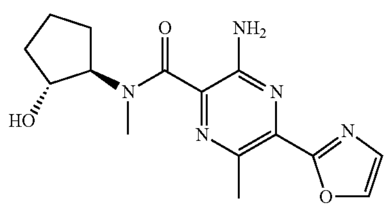 [SMILES: Cc1nc(C(=O)N(C)[C@@H]2CCC[C@H]2O)c(N)nc1-c1ncco1] | 3-amino-N-[(1R,2R)-2-hydroxycyclopentyl]-N,6-dimethyl-5-(1,3-oxazol-2-yl)pyrazine-2-carboxamide | 318 |
| Ex-206 | 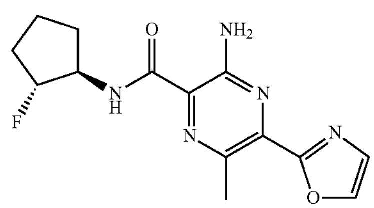 [SMILES: Cc1nc(C(=O)N[C@@H]2CCC[C@H]2F)c(N)nc1-c1ncco1] | 3-amino-N-[(1R,2R)-2-fluorocyclopentyl]-6-methyl-5-(1,3-oxazol-2-yl)pyrazine-2-carboxamide | 306 |
| Ex-207 | 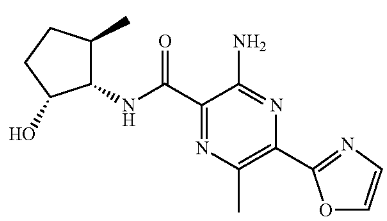 [SMILES: Cc1nc(C(=O)N[C@H]2[C@H](C)CC[C@H]2O)c(N)nc1-c1ncco1] | 3-amino-N-[(1S,2R,5R)-2-hydroxy-5-methylcyclopentyl]-6-methyl-5-(1,3-oxazol-2-yl)pyrazine-2-carboxamide | 318 |
| Ex-208 | 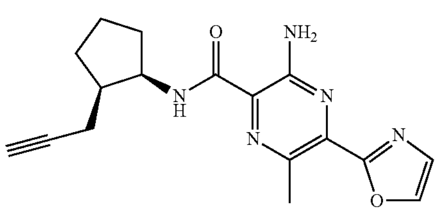 [SMILES: C#CC[C@H]1CCC[C@H]1NC(=O)c1nc(C)c(-c2ncco2)nc1N] | 3-amino-6-methyl-5-(1,3-oxazol-2-yl)-N-[(1R,2R)-2-prop-2-yl-1-ylcyclopentyl]pyrazine-2-carboxamide | 326 |
| Ex-209 | 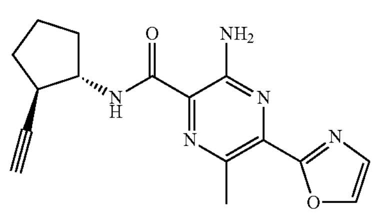 [SMILES: C#C[C@H]1CCC[C@@H]1NC(=O)c1nc(C)c(-c2ncco2)nc1N] | 3-amino-N-[(1S,2R)-2-ethynylcyclopentyl]-6-methyl-5-(1,3-oxazol-2-yl)pyrazine-2-carboxamide | 312 |

TABLE I-continued

| Exp. No. | Structure | IUPAC Name | MS [M + H]+ |
| --- | --- | --- | --- |
| Ex-210 | 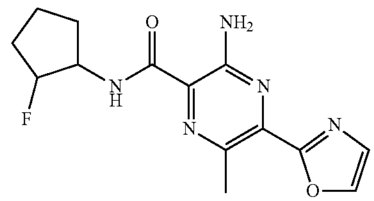 [SMILES: Cc1nc(C(=O)NC2CCCC2F)c(N)nc1-c1ncco1] | 3-amino-N-(2-fluorocyclopentyl)-6-methyl-5-(1,3-oxazol-2-yl)pyrazine-2-carboxamide | 306 |
| Ex-211 | 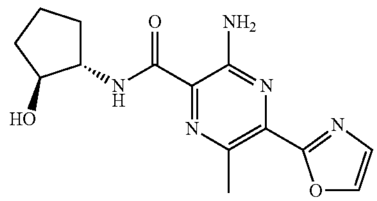 [SMILES: Cc1nc(C(=O)N[C@H]2CCC[C@@H]2O)c(N)nc1-c1ncco1] | 3-amino-N-[(1S,2S)-2-hydroxycyclopentyl]-6-methyl-5-(1,3-oxazol-2-yl)pyrazine-2-carboxamide | 304 |
| Ex-212 | 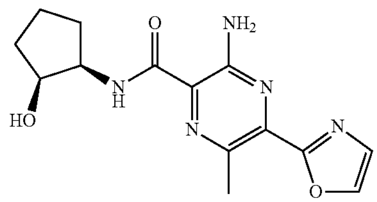 [SMILES: Cc1nc(C(=O)N[C@@H]2CCC[C@@H]2O)c(N)nc1-c1ncco1] | 3-amino-N-[(1R,2S)-2-hydroxycyclopentyl]-6-methyl-5-(1,3-oxazol-2-yl)pyrazine-2-carboxamide | 304 |
| Ex-213 | 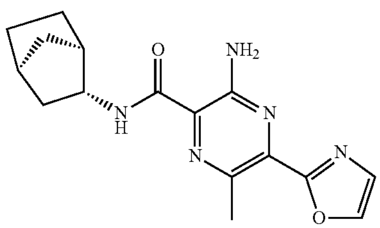 [SMILES: Cc1nc(C(=O)N[C@@H]2C[C@H]3CC[C@@H]2C3)c(N)nc1-c1ncco1] | 3-amino-N-[(1R,2R,4S)-bicyclo[2.2.1]hept-2-yl]-6-methyl-5-(1,3-oxazol-2-yl)pyrazine-2-carboxamide | 314 |
| Ex-214 | 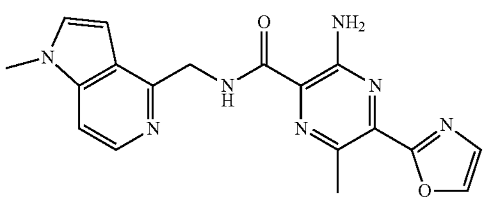 [SMILES: Cc1nc(C(=O)NCc2nccc3c2ccn3C)c(N)nc1-c1ncco1] | 3-amino-6-methyl-N-[(1-methyl-1H-pyrrolo[3,2-c]pyridin-4-yl)methyl]-5-(1,3-oxazol-2-yl)pyrazine-2-carboxamide | 364 |
| Ex-215 | 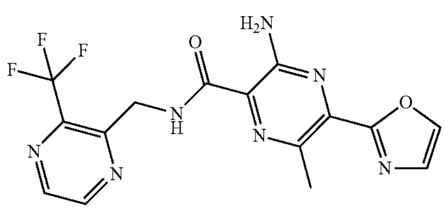 [SMILES: Cc1nc(C(=O)NCc2nccnc2C(F)(F)F)c(N)nc1-c1ncco1] | 3-amino-6-methyl-5-(1,3-oxazol-2-yl)-N-{[3-(trifluoromethyl)pyrazin-2-yl]methyl}pyrazine-2-carboxamide | 380 |
| Ex-216 | 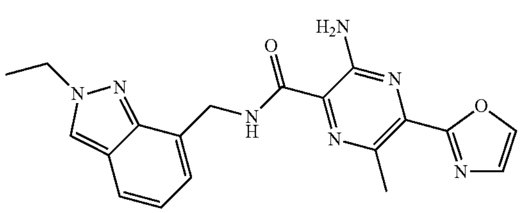 [SMILES: CCn1cc2cccc(CNC(=O)c3nc(C)c(-c4ncco4)nc3N)c2n1] | 3-amino-N-[(2-ethyl-2H-indazol-7-yl)methyl]-6-methyl-5-(1,3-oxazol-2-yl)pyrazine-2-carboxamide | 378 |

TABLE I-continued

| Exp. No. | Structure | IUPAC Name | MS [M + H]+ |
|---|---|---|---|
| Ex-217 | 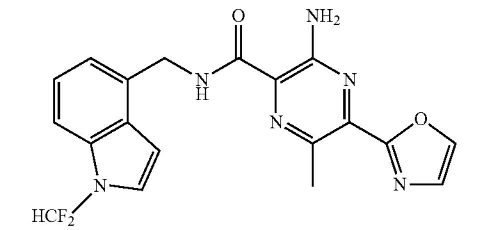 | 3-amino-N-{[1-(2,2-difluoroethyl)-1H-indol-4-yl]methyl}-6-methyl-5-(1,3-oxazol-2-yl)pyrazine-2-carboxamide | 413 |
| Ex-218 | 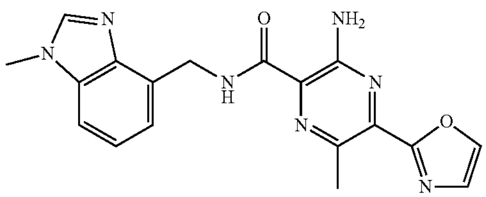 [SMILES: Cc1nc(C(=O)NCc2cccc3c2ncn3C)c(N)nc1-c1ncco1] | 3-amino-6-methyl-N-[(1-methyl-1H-benzimidazol-4-yl)methyl]-5-(1,3-oxazol-2-yl)pyrazine-2-carboxamide | 364 |
| Ex-219 | 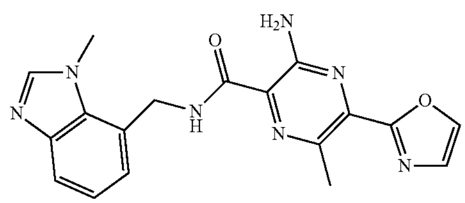 [SMILES: Cc1nc(C(=O)NCc2cccc3ncn(C)c23)c(N)nc1-c1ncco1] | 3-amino-6-methyl-N-[(1-methyl-1H-benzimidazol-7-yl)methyl]-5-(1,3-oxazol-2-yl)pyrazine-2-carboxamide | 364 |
| Ex-222 | 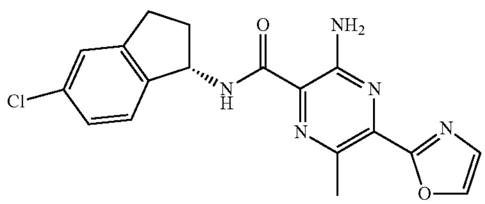 [SMILES: Cc1nc(C(=O)N[C@H]2CCc3cc(Cl)ccc32)c(N)nc1-c1ncco1] | 3-amino-N-[[(1S)-5-chloro-2,3-dihydro-1H-inden-1-yl]-6-methyl-5-(1,3-oxazol-2-yl)pyrazine-2-carboxamide | 370 |
| Ex-223 | 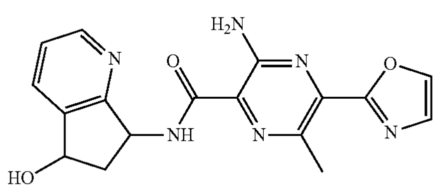 [SMILES: Cc1nc(C(=O)NC2CC(O)c3cccnc32)c(N)nc1-c1ncco1] | 3-amino-N-(5-hydroxy-6,7-dihydro-5H-cyclopenta[b]pyridin-7-yl)-6-methyl-5-(1,3-oxazol-2-yl)pyrazine-2-carboxamide | 353 |
| Ex-224 | 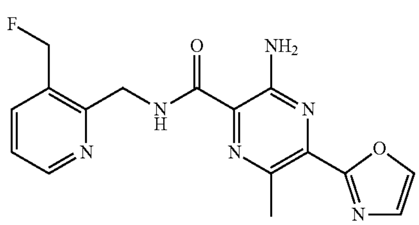 [SMILES: Cc1nc(C(=O)NCc2ncccc2CF)c(N)nc1-c1ncco1] | 3-amino-N-{[3-(fluoromethyl)pyridin-2-yl]methyl}-6-methyl-5-(1,3-oxazol-2-yl)pyrazine-2-carboxamide | 343 |
| Ex-225 | 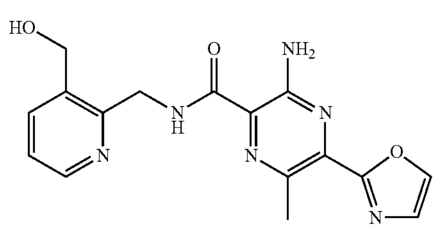 [SMILES: Cc1nc(C(=O)NCc2ncccc2CO)c(N)nc1-c1ncco1] | 3-amino-N-{[3-(hydroxymethyl)pyridin-2-yl]methyl}-6-methyl-5-(1,3-oxazol-2-yl)pyrazine-2-carboxamide | 341 |

TABLE I-continued

| Exp. No. | Structure | IUPAC Name | MS [M + H]+ |
|---|---|---|---|
| Ex-226A Cond. 5 First | 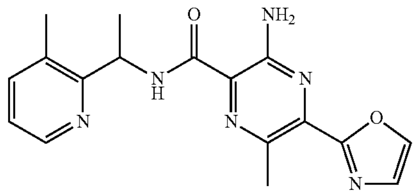 [SMILES: Cc1cccnc1C(C)NC(=O)c1nc(C)c(-c2ncco2)nc1N] | 3-amino-6-methyl-N-[1-(3-methylpyridin-2-yl)ethyl]-5-(1,3-oxazol-2-yl)pyrazine-2-carboxamide | 339 |
| Ex-226B Cond. 5 Second | 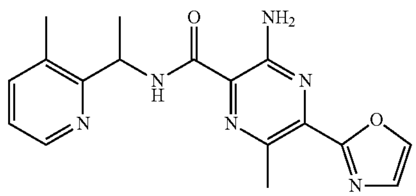 [SMILES: Cc1cccnc1C(C)NC(=O)c1nc(C)c(-c2ncco2)nc1N] | 3-amino-6-methyl-N-[1-(3-methylpyridin-2-yl)ethyl]-5-(1,3-oxazol-2-yl)pyrazine-2-carboxamide | 339 |
| Ex-228 | 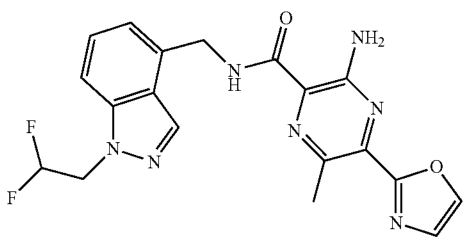 [SMILES: Cc1nc(C(=O)NCc2cccc3c2cnn3CC(F)F)c(N)nc1-c1ncco1] | 3-amino-N-{[1-(2,2-difluoroethyl)-1H-indazol-4-yl]methyl}-6-methyl-5-(1,3-oxazol-2-yl)pyrazine-2-carboxamide | 414 |
| Ex-229 | 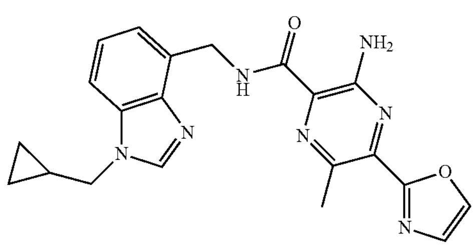 [SMILES: Cc1nc(C(=O)NCc2cccc3c2ncn3CC2CC2)c(N)nc1-c1ncco1] | 3-amino-N-{[1-(cyclopropylmethyl)-1H-benzimidazol-4-yl]methyl}-6-methyl-5-(1,3-oxazol-2-yl)pyrazine-2-carboxamide | 404 |
| Ex-230A Cond. 5 First | 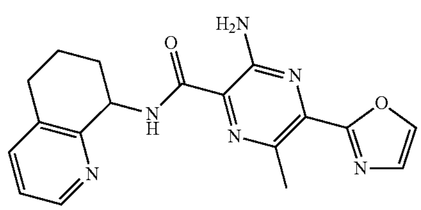 [SMILES: Cc1nc(C(=O)NC2CCCc3cccnc32)c(N)nc1-c1ncco1] | 3-amino-6-methyl-5-(1,3-oxazol-2-yl)-N-(5,6,7,8-tetrahydroquinolin-8-yl)pyrazine-2-carboxamide | 351 |
| Ex-230B Cond. 5 Second | 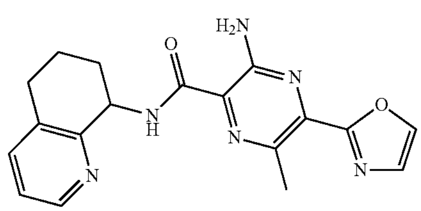 [SMILES: Cc1nc(C(=O)NC2CCCc3cccnc32)c(N)nc1-c1ncco1] | 3-amino-6-methyl-5-(1,3-oxazol-2-yl)-N-(5,6,7,8-tetrahydroquinolin-8-yl)pyrazine-2-carboxamide | 351 |
| Ex-231A Cond. 5 First | 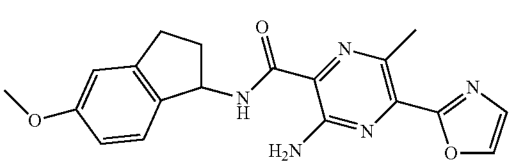 [SMILES: COc1ccc2c(c1)CCC2NC(=O)c1nc(C)c(-c2ncco2)nc1N] | 3-amino-N-(5-methoxy-2,3-dihydro-1H-inden-1-yl)-6-methyl-5-(1,3-oxazol-2-yl)pyrazine-2-carrboxamide | 366 |

TABLE I-continued

| Exp. No. | Structure | IUPAC Name | MS [M + H]+ |
|---|---|---|---|
| Ex-231B Cond. 5 Second | 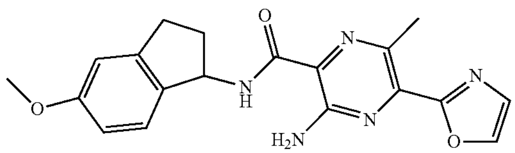 [SMILES: COc1ccc2c(c1)CCC2NC(=O)c1nc(C)c(-c2ncco2)nc1N] | 3-amino-N-(5-methoxy-2,3-dihydro-1H-inden-1-yl)-6-methyl-5-(1,3-oxazol-2-yl)pyrazine-2-carboxamide | 366 |
| Ex-233A Cond. 5 First | 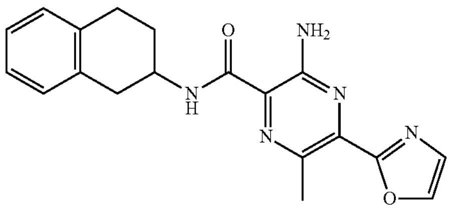 [SMILES: Cc1nc(C(=O)NC2CCc3ccccc3C2)c(N)nc1-c1ncco1] | 3-amino-6-methyl-5-(1,3-oxazol-2-yl)-N-(1,2,3,4-tetrahydronaphthalen-2-yl)pyrazine-2-carboxamide | 350 |
| Ex-233B Cond. 5 Second | 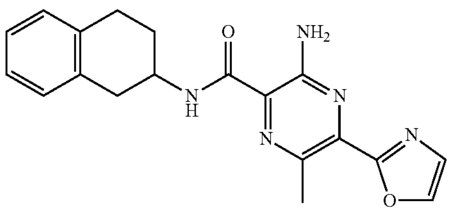 [SMILES: Cc1nc(C(=O)NC2CCc3ccccc3C2)c(N)nc1-c1ncco1] | 3-amino-6-methyl-5-(1,3-oxazol-2-yl)-N-(1,2,3,4-tetrahydronaphthalen-2-yl)pyrazine-2-carboxamide | 350 |
| Ex-235 | 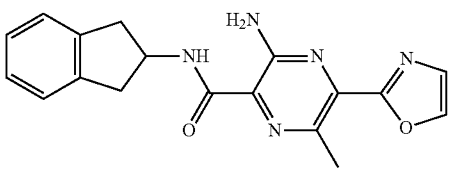 [SMILES: Cc1nc(C(=O)NC2Cc3ccccc3C2)c(N)nc1-c1ncco1] | 3-amino-N-(2,3-dihydro-1H-inden-2-yl)-6-methyl-5-(1,3-oxazol-2-yl)pyrazine-2-carboxamide | 336 |
| Ex-236 | 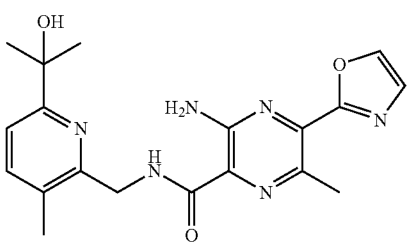 [SMILES: Cc1ccc(C(C)(C)O)nc1CNC(=O)c1nc(C)c(-c2ncco2)nc1N] | 3-amino-N-{[6-(1-hydroxy-1-methylethyl)-3-methylpyridin-2-yl]methyl}-6-methyl-5-(1,3-oxazol-2-yl)pyrazine-2-carboxamide | 383 |
| Ex-237 | 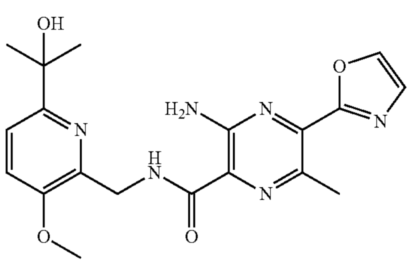 [SMILES: COc1ccc(C(C)(C)O)nc1CNC(=O)c1nc(C)c(-c2ncco2)nc1N] | 3-amino-N-{[6-(1-hydroxy-1-methylethyl)-3-methoxypyridin-2-yl]methyl}-6-methyl-5-(1,3-oxazol-2-yl)pyrazine-2-carboxamide | 399 |
| Ex-238A trans-isomer | 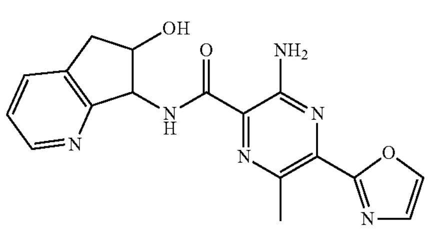 [SMILES: Cc1nc(C(=O)NC2c3ncccc3CC2O)c(N)nc1-c1ncco1] | 3-amino-N-(6-hydroxy-6,7-dihydro-5H-cyclopenta[b]pyridin-7-yl)-6-methyl-5-(1,3-oxazol-2-yl)pyrazine-2-carboxamide | 353 |

TABLE I-continued

| Exp. No. | Structure | IUPAC Name | MS [M + H]+ |
|---|---|---|---|
| Ex-238B cis-isomer | 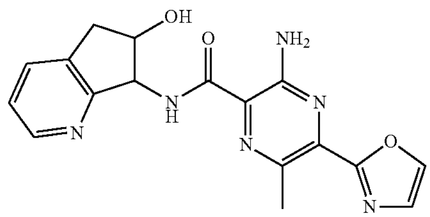 [SMILES: Cc1nc(C(=O)NC2c3ncccc3CC2O)c(N)nc1-c1ncco1] | 3-amino-N-(6-hydroxy-6,7-dihydro-5H-cyclopenta[b]pyridin-7-yl)-6-methyl-5-(1,3-oxazol-2-yl)pyrazine-2-carboxamide | 353 |
| Ex-240A Cond. 6 First | 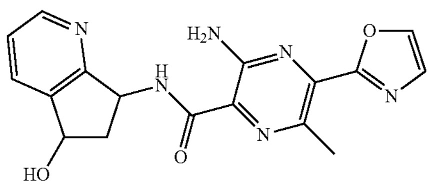 [SMILES: Cc1nc(C(=O)NC2CC(O)c3cccnc32)c(N)nc1-c1ncco1] | 3-amino-N-(5-hydroxy-6,7-dihydro-5H-cyclopenta[b]pyridin-7-yl)-6-methyl-5-(1,3-oxazol-2-yl)pyrazine-2-carboxamide | 353 |
| Ex-240B Cond. 6 Second | 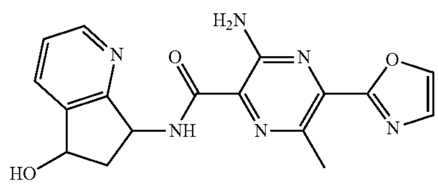 [SMILES: Cc1nc(C(=O)NC2CC(O)c3cccnc32)c(N)nc1-c1ncco1] | 3-amino-N-(5-hydroxy-6,7-dihydro-5H-cyclopenta[b]pyridin-7-yl)-6-methyl-5-(1,3-oxazol-2-yl)pyrazine-2-carboxamide | 353 |
| Ex-242 | 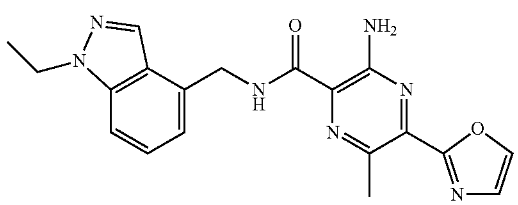 [SMILES: CCn1ncc2c(CNC(=O)c3nc(C)c(-c4ncco4)nc3N)cccc21] | 3-amino-N-[(1-ethyl-1H-indazol-4-yl)methyl]-6-methyl-5-(1,3-oxazol-2-yl)pyrazine-2-carboxamide | 378 |
| Ex-243 | 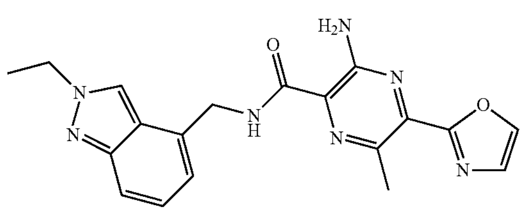 [SMILES: CCn1cc2c(CNC(=O)c3nc(C)c(-c4ncco4)nc3N)cccc2n1] | 3-amino-N-[(2-ethyl-2H-indazol-4-yl)methyl]-6-methyl-5-(1,3-oxazol-2-yl)pyrazine-2-carboxamide | 378 |
| Ex-244A Cond. 3 First | 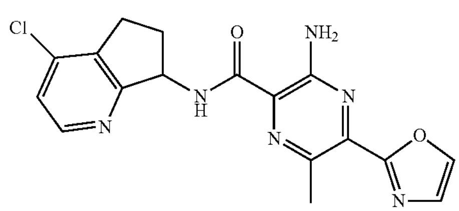 [SMILES: Cc1nc(C(=O)NC2CCc3c(Cl)ccnc32)c(N)nc1-c1ncco1] | 3-amino-N-(4-chloro-6,7-dihydro-5H-cyclopenta[b]pyridin-7-yl)-6-methyl-5-(1,3-oxazol-2-yl)pyrazine-2-carboxamide | 371 |
| Ex-244B Cond. 3 Second | 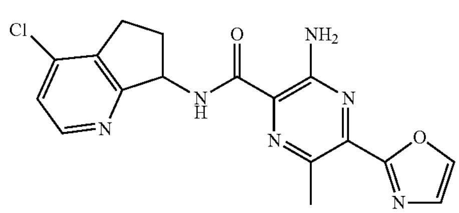 [SMILES: Cc1nc(C(=O)NC2CCc3c(Cl)ccnc32)c(N)nc1-c1ncco1] | 3-amino-N-(4-chloro-6,7-dihydro-5H-cyclopenta[b]pyridin-7-yl)-6-methyl-5-(1,3-oxazol-2-yl)pyrazine-2-carboxamide | 371 |

TABLE I-continued

| Exp. No. | Structure | IUPAC Name | MS [M + H]+ |
|---|---|---|---|
| Ex-245A Cond. 7 First | 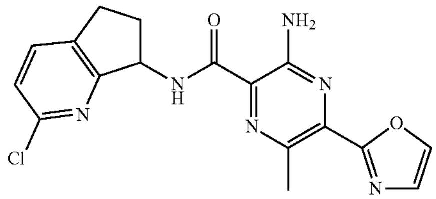 [SMILES: Cc1nc(C(=O)NC2CCc3ccc(Cl)nc32)c(N)nc1-c1ncco1] | 3-amino-N-(2-chloro-6,7-dihydro-5H-cyclopenta[b]pyridin-7-yl)-6-methyl-5-(1,3-oxazol-2-yl)pyrazine-2-carboxamide | 371 |
| Ex-245B Cond. 7 Second | 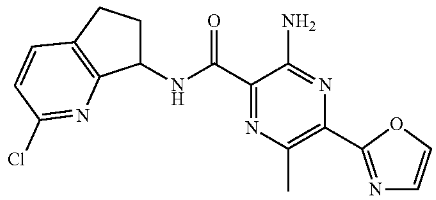 [SMILES: Cc1nc(C(=O)NC2CCc3ccc(Cl)nc32)c(N)nc1-c1ncco1] | 3-amino-N-(2-chloro-6,7-dihydro-5H-cyclopenta[b]pyridin-7-yl)-6-methyl-5-(1,3-oxazol-2-yl)pyrazine-2-carboxamide | 371 |

Preparation of 3-Amino-6-methyl-5-(oxazol-5-yl)-N-(2-(trifluoromethyl)benzyl) pyrazine-2-carboxamide (Ex-249)

SCHEME ES-3

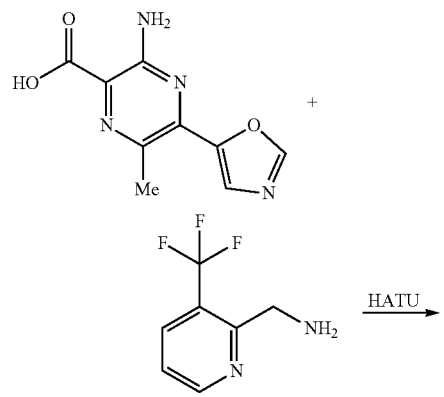

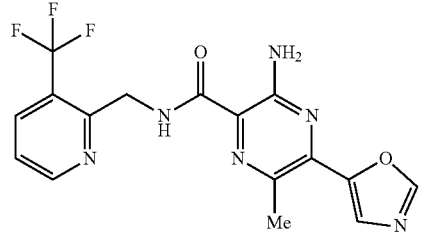

Ex-249

Hunig's base (0.052 ml, 0.30 mmol) was added to a stirred mixture of 3-amino-6-methyl-5-(oxazol-5-yl)pyrazine-2-carboxylic acid (0.022 g, 0.10 mmol), (2-(trifluoromethyl)-phenyl)methanamine (0.019 g, 0.110 mmol) and HATU (0.042 g, 0.110 mmol) in DMF, followed by stirring at RT for 3 h. The solution was purified by HPLC Gilson with acetonitrile/water (each of them with 01.% TFA) as eluants to give the compound Ex-249 as a solid. LC/MS=379 [M+1].

Using the above-described chemistries and appropriately-substituted precursors, compounds of the invention listed in Table II were prepared.

TABLE II

| Exp. No. | Structure | IUPAC Name | Exact Mass [M + H]+ |
|---|---|---|---|
| Ex-249 | 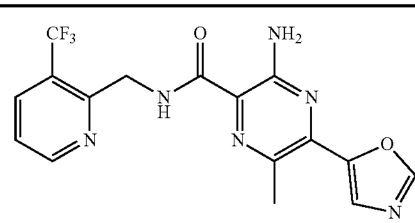 | 3-amino-6-methyl-5-(1,3-oxaol-5-yl)-N-{[3-(trifluoromethyl)-pyridin-2-yl]-methyl}pyrazine-2-carboxamide | 379 |

TABLE II-continued

| Exp. No. | IUPAC Name | Exact Mass [M + H]+ |
|---|---|---|
| Ex-250 | 3-amino-6-chloro-5-(1,3-oxazol-5-yl)-N-(quinolin-8-ylmethyl)pyrazine-2-carboxamide | 381 |
| Ex-251 | 3-amino-N-(2,6-difluorobenzyl)-6-methyl-5-(1,3-oxazol-5-yl)pyrazine-2-carboxamide | 346 |
| Ex-252 | 3-amino-6-methyl-N-[(3-methylpyridin-2-yl)methyl]-5-(1,3-oxazol-5-yl)pyrazine-2-carboxamide | 325 |
| Ex-253 | 3-amino-N-(2,4-difluorobenzyl)-6-methyl-5-(1,3-oxazol-5-yl)pyrazine-2-carboxamide | 346 |
| Ex-254 | 3-amino-N-(2-methoxybenzyl)-6-methyl-5-(1,3-oxazol-5-yl)pyrazine-2-carboxamide | 340 |
| Ex-255 | 3-amino-N-(2,6-dichlorobenzyl)-6-methyl-5-(1,3-oxazol-5-yl)pyrazine-2-carboxamide | 378 |
| Ex-256 | 3-amino-N-(2-chloro-6-methylbenzyl)-6-methyl-5-(1,3-oxazol-5-yl)pyrazine-2-carboxamide | 358 |

TABLE II-continued

| Exp. No. | Structure | IUPAC Name | Exact Mass [M + H]+ |
|---|---|---|---|
| Ex-257 | 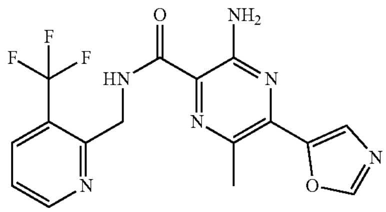 [SMILES: Cc1nc(C(=O)NCc2ncccc2C(F)(F)F)c(N)nc1-c1cnco1] | 3-amino-6-methyl-5-(1,3-oxazol-5-yl)-N-{[3-(trifluoromethyl)pyridin-2-yl]methyl}pyrazine-2-carboxamide | 379 |
| Ex-258 | 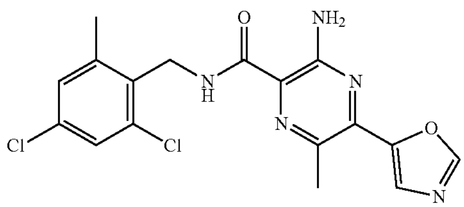 [SMILES: Cc1cc(Cl)cc(Cl)c1CNC(=O)c1nc(C)c(-c2cnco2)nc1N] | 3-amino-N-(2,4-dichloro-6-methylbenzyl)-6-methyl-5-(1,3-oxazol-5-yl)pyrazine-2-carboxamide | 392 |
| Ex-259 | 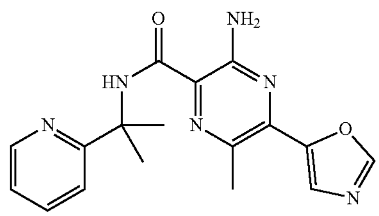 [SMILES: Cc1nc(C(=O)NC(C)(C)c2ccccn2)c(N)nc1-c1cnco1] | 3-amino-6-methyl-N-(1-methyl-1-pyridin-2-ylethyl)-5-(1,3-oxazol-5-yl)pyrazine-2-carboxamide | 339 |
| Ex-260 | 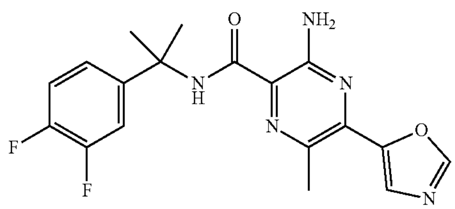 [SMILES: Cc1nc(C(=O)NC(C)(C)c2ccc(F)c(F)c2)c(N)nc1-c1cnco1] | 3-amino-N-[1-(3,4-difluorophenyl)-1-methylethyl]-6-methyl-5-(1,3-oxazol-5-yl)pyrazine-2-carboxamide | 374 |
| Ex-261 | 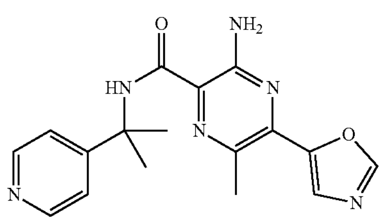 [SMILES: Cc1nc(C(=O)NC(C)(C)c2ccncc2)c(N)nc1-c1cnco1] | 3-amino-6-methyl-N-(1-methyl-1-pyridin-4-ylethyl)-5-(1,3-oxazol-5-yl)pyrazine-2-carboxamide | 339 |
| Ex-262 | 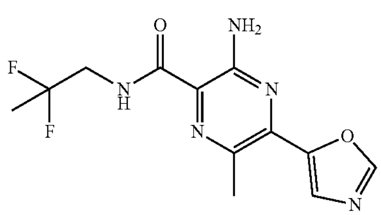 [SMILES: Cc1nc(C(=O)NCC(C)(F)F)c(N)nc1-c1cnco1] | 3-amino-N-(2,2-difluoropropyl)-6-methyl-5-(1,3-oxazol-5-yl)pyrazine-2-carboxamide | 298 |
| Ex-263 | 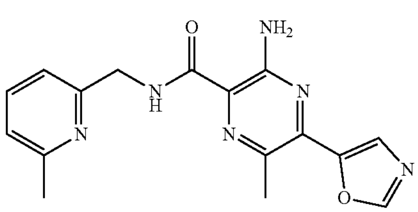 [SMILES: Cc1cccc(CNC(=O)c2nc(C)c(-c3cnco3)nc2N)n1] | 3-amino-6-methyl-N-[(6-methylpyridin-2-yl)methyl]-5-(1,3-oxazol-5-yl)pyrazine-2-carboxamide | 325 |

TABLE II-continued

| Exp. No. | Structure | IUPAC Name | Exact Mass [M + H]+ |
|---|---|---|---|
| Ex-264A Cond. 8 First | 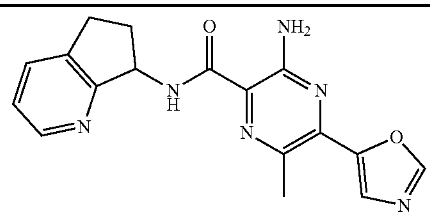 | 3-amino-N-(6,7-dihydro-5H-cyclopenta[b]pyridin-7-yl)-6-methyl-5-(1,3-oxazol-5-yl)pyrazine-2-carboxamide | 337 |
| Ex-264B Cond. 8 Second | 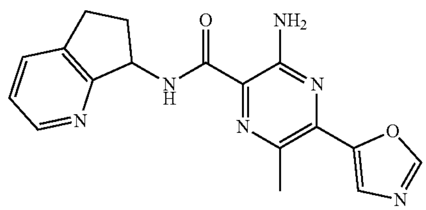 [SMILES: Cc1nc(C(=O)NC2CCc3cccnc32)c(N)nc1-c1cnco1] | 3-amino-N-(6,7-dihydro-5H-cyclopenta[b]pyridin-7-yl)-6-methyl-5-(1,3-oxazol-5-yl)pyrazine-2-carboxamide | 337 |

Preparation of 3-Amino-6-methyl-5-(4-methyl-1H-pyrazol-1-yl)-N-((3-methylpyridin-2-yl)methyl)pyrazine-2-carboxamide (Ex-267)

The compound of Ex-267 was prepared in accordance with Scheme ES-4.

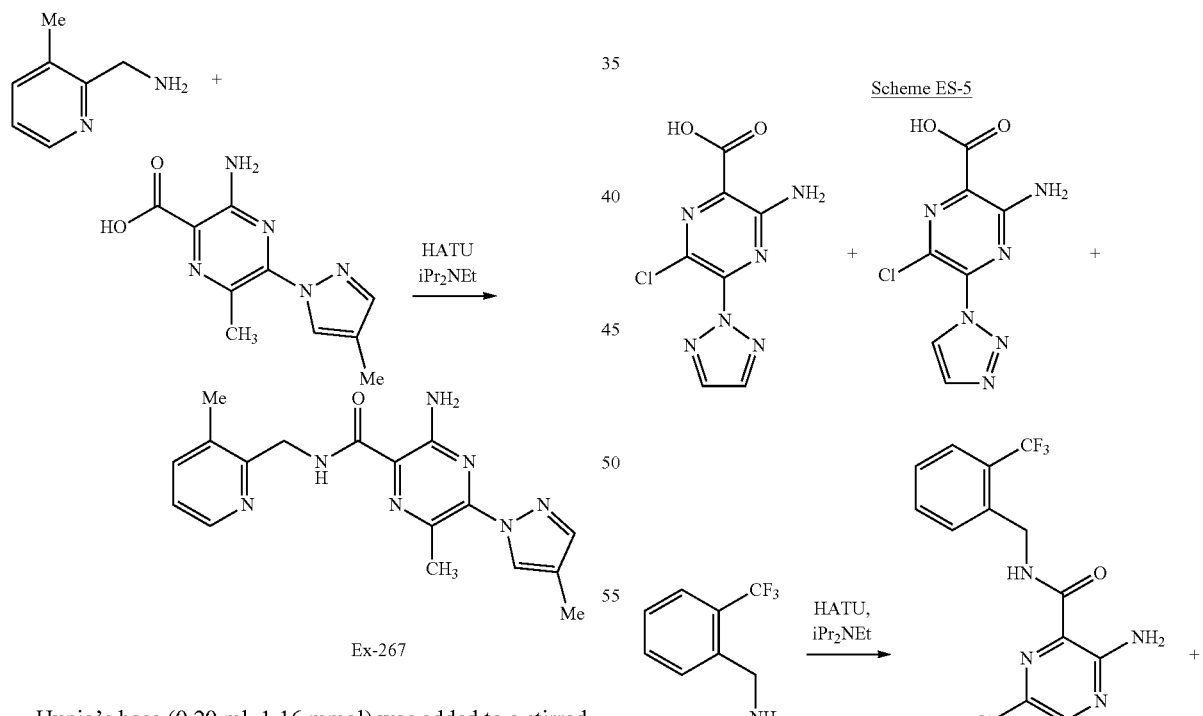

Hunig's base (0.20 ml, 1.16 mmol) was added to a stirred mixture of 3-amino-6-methyl-5-(4-methyl-1H-pyrazol-1-yl) pyrazine-2-carboxylic acid (0.090 g, 0.39 mmol), 3-methyl-2-aminomethyl-pyridine (0.052 g, 0.42 mmol) and HATU (0.161 g, 0.42 mmol) in DMF (2 ml) and the mixture was stirred at RT for 3 h. The solution was purified by HPLC Gilson with acetonitrile/water with 0.01% TFA as eluants to give the title compound as a solid. LC/MS=338 [M+1].

Preparation of Example Compounds Ex-268 and Ex-269

3-Amino-6-chloro-5-(2H-1,2,3-triazol-2-yl)-N-(2-(trifluoromethyl)benzyl)pyrazine-2-carboxamide (Ex-269) and 3-amino-6-chloro-5-(1H-1,2,3-triazol-1-yl)-N-(2-(trifluoromethyl)-benzyl)pyrazine-2-carboxamide (Ex-268) were prepared in accordance with Reaction Scheme ES-5:

-continued

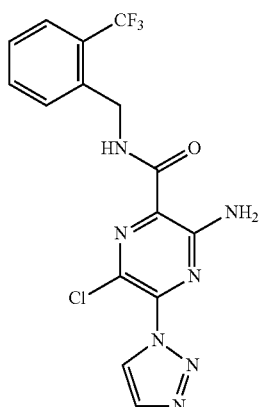
Ex-269

Into a reaction vessel was placed a mixture of 3-amino-6-chloro-5-(2H-1,2,3-triazol-2-yl)pyrazine-2-carboxylic acid and 3-amino-6-chloro-5-(1H-1,2,3-triazol-1-yl)pyrazine-2-carboxylic acid (36 mg, 0.15 mmol) in 1.5 mL of DMF and it was mixed with diisopropylethylamine (0.07 mL, 0.39 mmol), (2-(trifluoromethyl)phenyl)methanamine (39 mg, 0.22 mmol), and HATU (95 mg, 0.25 mmol). The mixture was stirred at room temperature overnight then diluted with DMF, and purified by prep Gilson HPLC, eluting with acetonitrile/water containing 0.1% TFA. The eluent was collected separately, concentrated and the concentrate dried in vacuum oven overnight to provide 3-amino-6-chloro-5-(2H-1,2,3-triazol-2-yl)-N-(2-(trifluoromethyl)benzyl)pyrazine-2-carboxamide, LC/MS=398 [M+1], and 3-amino-6-chloro-5-(1H-1,2,3-triazol-1-yl)-N-(2-(trifluoromethyl)benzyl)pyrazine-2-carboxamide, and LC/MS=398 [M+1].

Using the above-described chemistries and appropriately-substituted precursors, compounds of the invention listed in Table III were prepared.

TABLE III

| Exp No. | Structure | IUPAC Name | Exact Mass [M + H]+ |
|---|---|---|---|
| Ex-268 | 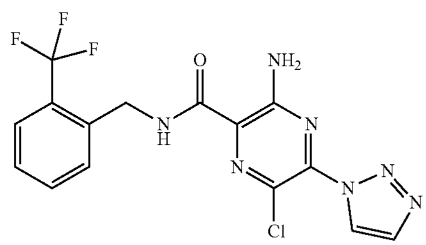 [SMILES: Nc1nc(-n2ccnn2)c(Cl)nc1C(=O)NCc1ccccc1C(F)(F)F] | 3-amino-6-chloro-5-(1H-1,2,3-triazol-1-yl)-N-[2-(trifluoromethyl)benzyl]pyrazine-2-carboxamide | 398 |
| Ex-269 | 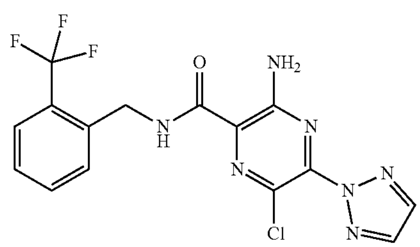 [SMILES: Nc1nc(-n2nccn2)c(Cl)nc1C(=O)NCc1ccccc1C(F)(F)F] | 3-amino-6-chloro-5-(2H-1,2,3-triazol-2-yl)-N-[2-(trifluoromethyl)benzyl]pyrazine-2-carboxamide | 398 |
| Ex-270 | 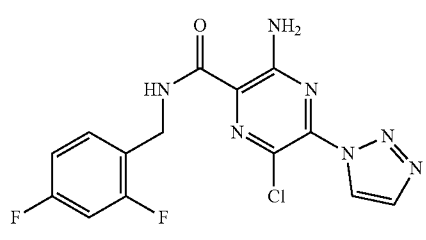 [SMILES: Nc1nc(-n2ccnn2)c(Cl)nc1C(=O)NCc1ccc(F)cc1F] | 3-amino-6-chloro-N-(2,4-difluorobenzyl)-5-(1H-1,2,3-triazol-1-yl)pyrazine-2-carboxamide | 366 |
| Ex-271 | 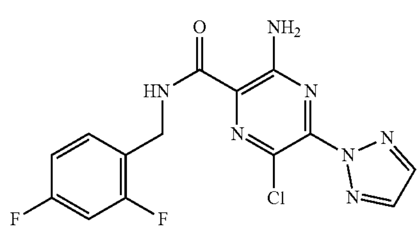 | 3-amino-6-chloro-N-(2,4-difluorobenzyl)-5-(2H-1,2,3-triazol-2-yl)pyrazine-2-carboxamide | 366 |

TABLE III-continued

| Exp No. | IUPAC Name | Exact Mass [M + H]+ |
|---|---|---|
| Ex-272 | 3-amino-6-chloro-N-(quinolin-8-ylmethyl)-5-(1H-1,2,3-triazol-1-yl)pyrazine-2-carboxamide | 381 |
| Ex-273 | 3-amino-6-chloro-N-(quinolin-8-ylmethyl)-5-(2H-1,2,3-triazol-2-yl)pyrazine-2-carboxamide | 381 |
| Ex-274 | 3-amino-N-(2,6-difluorobenzyl)-6-methyl-5-(2H-1,2,3-triazol-2-yl)pyrazine-2-carboxamide | 346 |
| Ex-275 | 3-amino-6-methyl-N-(quinolin-8-ylmethyl)-5-(2H-1,2,3-triazol-2-yl)pyrazine-2-carboxamide | 361 |
| Ex-276 | ethyl 3-amino-6-methyl-5-(2H-1,2,3-triazol-2-yl)pyrazine-2-carboxylate | 249 |
| Ex-277 | 3-amino-6-methyl-N-[(3-methylpyridin-2-yl)methyl]-5-(2H-1,2,3-triazol-2-yl)pyrazine-2-carboxamide | 325 |
| Ex-278 | 3-amino-6-methyl-N-[(3-methylpyridin-2-yl)methyl]-5-(1H-1,2,3-triazol-1-yl)pyrazine-2-carboxamide | 325 |

TABLE III-continued

| Exp No. | Structure | IUPAC Name | Exact Mass [M + H]+ |
|---|---|---|---|
| Ex-279 | 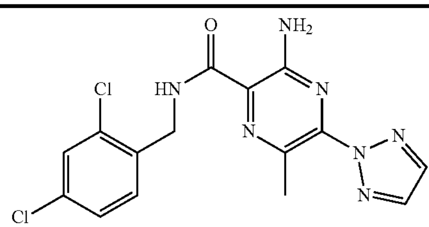 | 3-amino-N-(2,4-dichlorobenzyl)-6-methyl-5-(2H-1,2,3-triazol-2-yl)pyrazine-2-carboxamide | 378 |
| Ex-280 | 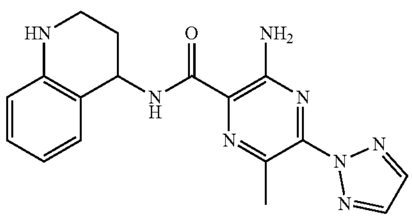 [SMILES: Cc1nc(C(=O)NC2CCNc3ccccc32)c(N)nc1-n1nccn1] | 3-amino-6-methyl-N-(1,2,3,4-tetrahydroquinolin-4-yl)-5-(2H-1,2,3-triazol-2-yl)pyrazine-2-carboxamide | 351 |
| Ex-281 | 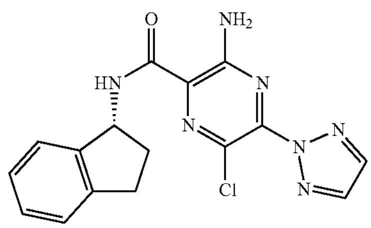 [SMILES: Nc1nc(-n2nccn2)c(Cl)nc1C(=O)N[C@@H]1CCc2ccccc21] | 3-amino-6-chloro-N-[(1R)-2,3-dihydro-1H-inden-1-yl]-5-(2H-1,2,3-triazol-2-yl)pyrazine-2-carboxamide | 356 |
| Ex-282 | 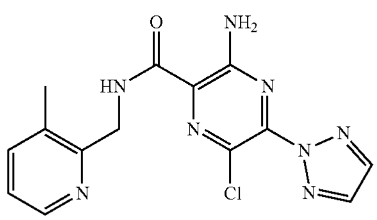 [SMILES: Cc1cccnc1CNC(=O)c1nc(Cl)c(-n2nccn2)nc1N] | 3-amino-6-chloro-N-[(3-methylpyridin-2-yl)methyl]-5-(2H-1,2,3-triazol-2-yl)pyrazine-2-carboxamide | 345 |
| Ex-283 | 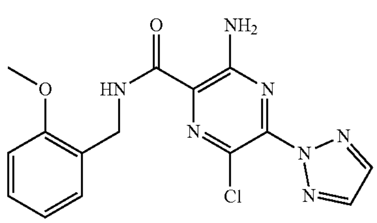 [SMILES: COc1ccccc1CNC(=O)c1nc(Cl)c(-n2nccn2)nc1N] | 3-amino-6-chloro-N-(2-methoxybenzyl)-5-(2H-1,2,3-triazol-2-yl)pyrazine-2-carboxamide | 360 |
| Ex-284 | 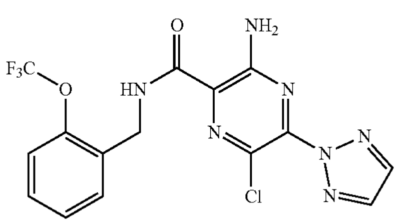 [SMILES: Nc1nc(-n2nccn2)c(Cl)nc1C(=O)NCc1ccccc1OC(F)(F)F] | 3-amino-6-chloro-5-(2H-1,2,3-triazol-2-yl)-N-[2-(trifluoromethoxy)benzoyl]pyrazine-2-carboxamide | 414 |
| Ex-285 | 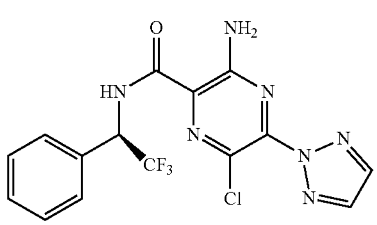 [SMILES: Nc1nc(-n2nccn2)c(Cl)nc1C(=O)N[C@H](c1ccccc1)C(F)(F)F] | 3-amino-6-chloro-5-(2H-1,2,3-triazol-2-yl)-N-[(1R)-2,2,2-trifluoro-1-phenylethyl]pyrazine-2-carboxamide | 398 |

TABLE III-continued

| Exp No. | Structure | IUPAC Name | Exact Mass [M + H]+ |
|---|---|---|---|
| Ex-286 | 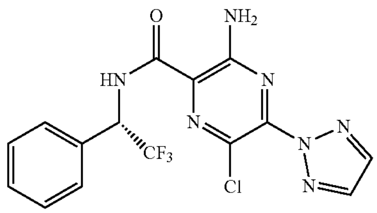 [SMILES: Nc1nc(-n2nccn2)c(Cl)nc1C(=O)N[C@@H](c1ccccc1)C(F)(F)F] | 3-amino-6-chloro-5-(2H-1,2,3-triazol-2-yl)-N-[(1S)-2,2,2-trifluoro-1-phenylethyl]pyrazine-2-carboxamide | 398 |
| Ex-287 | 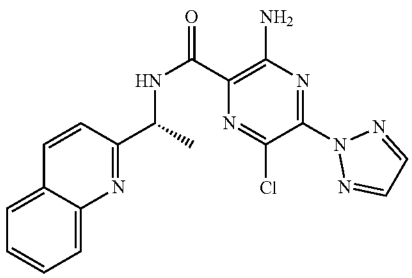 [SMILES: C[C@@H](NC(=O)c1nc(Cl)c(-n2nccn2)nc1N)c1ccc2ccccc2n1] | 3-amino-6-chloro-N-[(1R)-1-quinolin-2-ylethyl]-5-(2H-1,2,3-triazol-2-yl)pyrazine-2-carboxamide | 395 |
| Ex-288 | 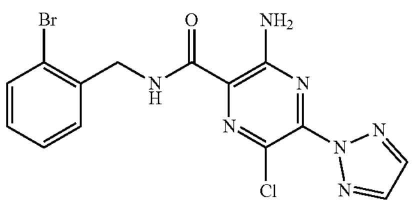 [SMILES: Nc1nc(-n2nccn2)c(Cl)nc1C(=O)NCc1ccccc1Br] | 3-amino-N-(2-bromobenzyl)-6-chloro-5-(2H-1,2,3-triazol-2-yl)pyrazine-2-carboxamide | 408 |
| Ex-289 | 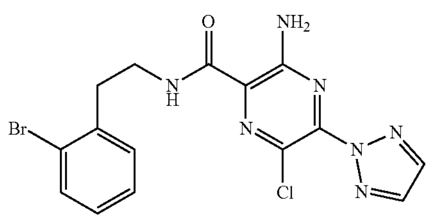 [SMILES: Nc1nc(-n2nccn2)c(Cl)nc1C(=O)NCCc1ccccc1Br] | 3-amino-N-[2-(2-bromophenyl)ethyl]-6-chloro-5-(2H-1,2,3-triazol-2-yl)pyrazine-2-carboxamide | 422 |
| Ex-290 | 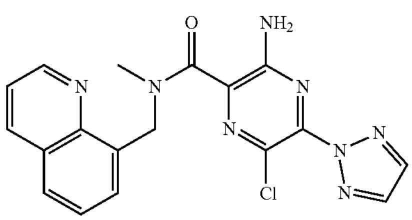 [SMILES: CN(Cc1cccc2cccnc12)C(=O)c1nc(Cl)c(-n2nccn2)nc1N] | 3-amino-6-chloro-N-methyl-N-(quinolin-8-ylmethyl)-5-(2H-1,2,3-triazol-2-yl)pyrazine-2-carboxamide | 395 |
| Ex-291 | 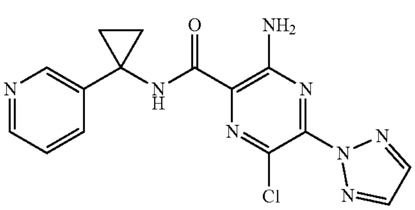 [SMILES: Nc1nc(-n2nccn2)c(Cl)nc1C(=O)NC1(c2cccnc2)CC1] | 3-amino-6-chloro-N-(1-pyridin-3-ylcyclopropyl)-5-(2H-1,2,3-triazol-2-yl)pyrazine-2-carboxamide | 357 |
| Ex-292 | 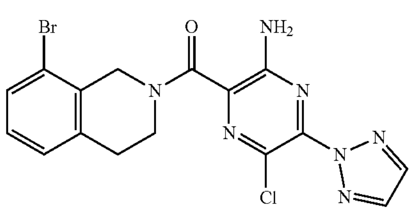 [SMILES: Nc1nc(-n2nccn2)c(Cl)nc1C(=O)N1CCc2cccc(Br)c2C1] | 3-[(8-bromo-3,4-dihydroisoquinolin-2(1H)-yl)carbonyl]-5-chloro-6-(2H-1,2,3-triazol-2-yl)pyrazin-2-amine | 434 |

TABLE III-continued

| Exp No. | IUPAC Name | Exact Mass [M + H]+ |
|---|---|---|
| Ex-293 | 3-amino-6-chloro-N-(1,2,3,4-tetrahydroquinolin-4-yl)-5-(2H-1,2,3-triazol-2-yl)pyrazine-2-carboxamide | 371 |
| Ex-294 | 3-amino-6-chloro-N-[2-(3,4-dimethoxyphenyl)ethyl]-5-(2H-1,2,3-triazol-2-yl)pyrazine-2-carboxamide | 404 |
| Ex-295 | 3-amino-6-chloro-N-(pyrazolo[1,5-a]pyridin-3-ylmethyl)-5-(2H-1,2,3-triazol-2-yl)pyrazine-2-carboxamide | 370 |
| Ex-296 | 3-amino-6-chloro-N-(isoquinolin-5-ylmethyl)-5-(2H-1,2,3-triazol-2-yl)pyrazine-2-carboxamide | 381 |
| Ex-297 | 3-amino-6-chloro-N-(isoquinolin-8-ylmethyl)-5-(2H-1,2,3-triazol-2-yl)pyrazine-2-carboxamide | 381 |
| Ex-298 | 3-amino-N-(1,3-benzothiazol-2-ylmethyl)-6-chloro-5-(2H-1,2,3-triazol-2-yl)pyrazine-2-carboxamide | 387 |
| Ex-299 | 3-amino-N-(1,3-benzoxazol-2-ylmethyl)-6-chloro-5-(2H-1,2,3-triazol-2-yl)pyrazine-2-carboxamide | 371 |

TABLE III-continued

| Exp No. | Structure | IUPAC Name | Exact Mass [M + H]+ |
|---|---|---|---|
| Ex-300 | 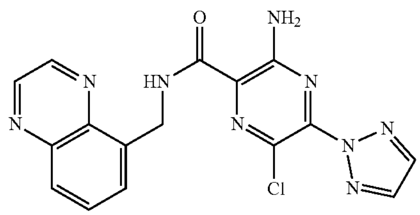 [SMILES: Nc1nc(-n2nccn2)c(Cl)nc1C(=O)NCc1cccc2nccnc12] | 3-amino-6-chloro-N-(quinoxalin-5-ylmethyl)-5-(2H-1,2,3-triazol-2-yl)pyrazine-2-carboxamide | 382 |
| Ex-301 | 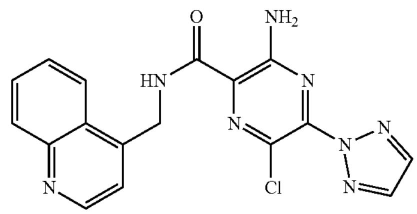 [SMILES: Nc1nc(-n2nccn2)c(Cl)nc1C(=O)NCc1ccnc2ccccc12] | 3-amino-6-chloro-N-(quinolin-4-ylmethyl)-5-(2H-1,2,3-triazol-2-yl)pyrazine-2-carboxamide | 381 |
| Ex-302 | 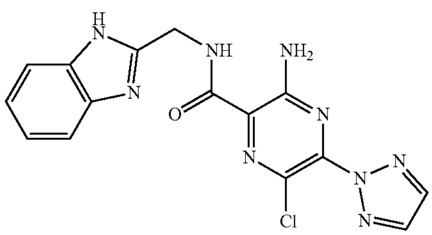 [SMILES: Nc1nc(-n2nccn2)c(Cl)nc1C(=O)NCc1nc2ccccc2[nH]1] | 3-amino-N-(1H-benzimidazol-2-ylmethyl)-6-chloro-5-(2H-1,2,3-triazol-2-yl)pyrazine-2-carboxamide | 370 |
| Ex-303 | 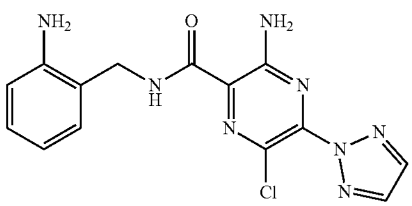 [SMILES: Nc1ccccc1CNC(=O)c1nc(Cl)c(-n2nccn2)nc1N] | 3-amino-N-(2-aminobenzyl)-6-chloro-5-(2H-1,2,3-triazol-2-yl)pyrazine-2-carboxamide | 345 |
| Ex-304 | 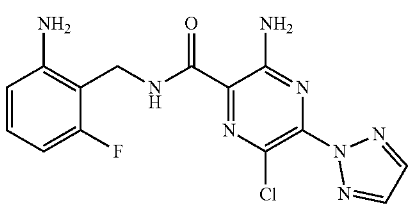 [SMILES: Nc1cccc(F)c1CNC(=O)c1nc(Cl)c(-n2nccn2)nc1N] | 3-amino-N-(2-amino-6-fluorobenzyl)-6-chloro-5-(2H-1,2,3-triazol-2-yl)pyrazine-2-carboxamide | 363 |
| Ex-305 | 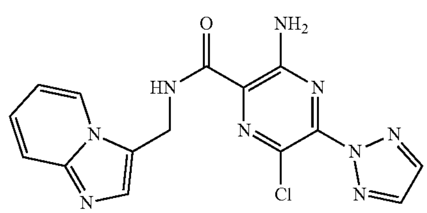 [SMILES: Nc1nc(-n2nccn2)c(Cl)nc1C(=O)NCc1cnc2ccccn12] | 3-amino-6-chloro-N-(imidazo[1,2-a]pyridin-3-ylmethyl)-5-(2H-1,2,3-triazol-2-yl)pyrazine-2-carboxamide | 370 |
| Ex-306 | 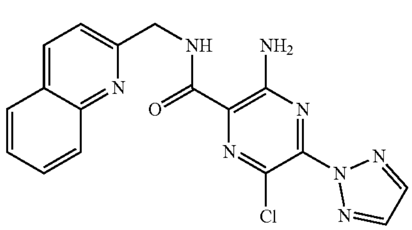 [SMILES: Nc1nc(-n2nccn2)c(Cl)nc1C(=O)NCc1ccc2ccccc2n1] | 3-amino-6-chloro-N-(quinolin-2-ylmethyl)-5-(2H-1,2,3-triazol-2-yl)pyrazine-2-carboxamide | 381 |

US 10,472,347 B2

TABLE III-continued

| Exp No. | IUPAC Name | Exact Mass [M + H]+ |
|---|---|---|
| Ex-307 | 3-amino-6-chloro-N-(isoquinolin-3-ylmethyl)-5-(2H-1,2,3-triazol-2-yl)pyrazine-2-carboxamide | 381 |
| Ex-308 | 3-amino-6-chloro-N-(1H-indol-2-ylmethyl)-5-(2H-1,2,3-triazol-2-yl)pyrazine-2-carboxamide | 369 |
| Ex-309 | 3-amino-6-chloro-N-(quinolin-5-ylmethyl)-5-(2H-1,2,3-triazol-2-yl)pyrazine-2-carboxamide | 381 |
| Ex-310 | 3-amino-6-chloro-N-(imidazo[2,1-b][1,3]thiazol-6-ylmethyl)-5-(2H-1,2,3-triazol-2-yl)pyrazine-2-carboxamide | 376 |
| Ex-311 | 3-amino-6-chloro-N-(2-pyrazin-2-ylethyl)-5-(2H-1,2,3-triazol-2-yl)pyrazine-2-carboxamide | 346 |
| Ex-312 | 3-amino-6-chloro-N-[(1R)-2-hydroxy-1-phenylethyl]-5-(2H-1,2,3-triazol-2-yl)pyrazine-2-carboxamide | 360 |
| Ex-313 | 3-amino-6-chloro-N-[(1S)-2-hydroxy-1-phenylethyl]-5-(2H-1,2,3-triazol-2-yl)pyrazine-2-carboxamide | 360 |

TABLE III-continued

| Exp No. | Structure | IUPAC Name | Exact Mass [M + H]+ |
|---|---|---|---|
| Ex-314 | 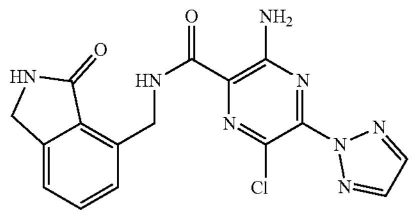 [SMILES: Nc1nc(-n2nccn2)c(Cl)nc1C(=O)NCc1cccc2c1C(=O)NC2] | 3-amino-6-chloro-N-[(3-oxo-2,3-dihydro-1H-isoindol-4-yl)methyl]-5-(2H-1,2,3-triazol-2-yl)pyrazine-2-carboxamide | 385 |
| Ex-315 | 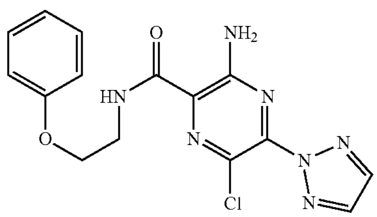 [SMILES: Nc1nc(-n2nccn2)c(Cl)nc1C(=O)NCCOc1ccccc1] | 3-amino-6-chloro-N-(2-phenoxyethyl)-5-(2H-1,2,3-triazol-2-yl)pyrazine-2-carboxamide | 360 |
| Ex-316 | 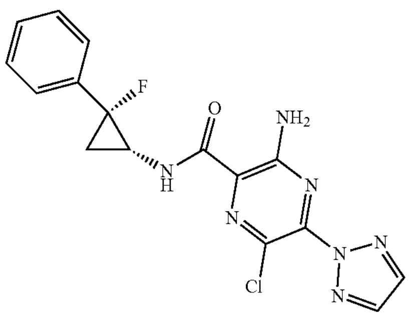 [SMILES: Nc1nc(-n2nccn2)c(Cl)nc1C(=O)N[C@@H]1C[C@@]1(F)c1ccccc1] | 3-amino-6-chloro-N-[(1R,2R)-2-fluoro-2-phenylcyclopropyl]-5-(2H-1,2,3-triazol-2-yl)pyrazine-2-carboxamide | 374 |
| Ex-317 | 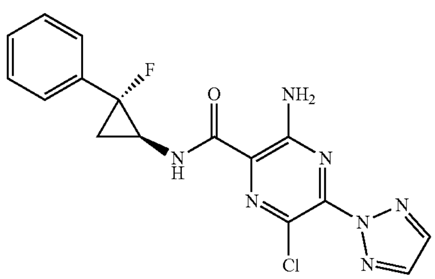 [SMILES: Nc1nc(-n2nccn2)c(Cl)nc1C(=O)N[C@H]1C[C@@]1(F)c1ccccc1] | 3-amino-6-chloro-N-[(1S,2R)-2-fluoro-2-phenylcyclopropyl]-5-(2H-1,2,3-triazol-2-yl)pyrazine-2-carboxamide | 374 |
| Ex-318 | 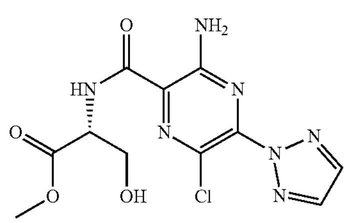 [SMILES: COC(=O)[C@@H](CO)NC(=O)c1nc(Cl)c(-n2nccn2)nc1N] | methyl N-{[3-amino-6-chloro-5-(2H-1,2,3-triazol-2-yl)pyrazin-2-yl]carbonyl}-D-serinate | 342 |
| Ex-319 | 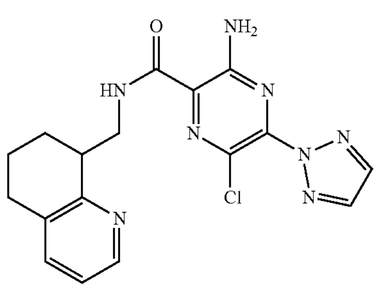 [SMILES: Nc1nc(-n2nccn2)c(Cl)nc1C(=O)NCC1CCCc2cccnc21] | 3-amino-6-chloro-N-(5,6,7,8-tetrahydroquinolin-8-ylmethyl)-5-(2H-1,2,3-triazol-2-yl)pyrazine-2-carboxamide | 385 |

TABLE III-continued

| Exp No. | Structure | IUPAC Name | Exact Mass [M + H]+ |
|---|---|---|---|
| Ex-320 | 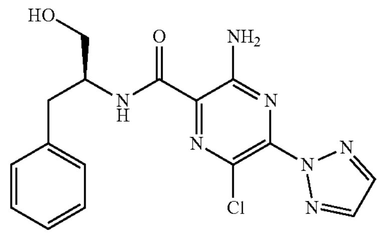 [SMILES: Nc1nc(-n2nccn2)c(Cl)nc1C(=O)N[C@H](CO)Cc1ccccc1] | 3-amino-N-[(1S)-1-benzyl-2-hydroxyethyl]-6-chloro-5-(2H-1,2,3-triazol-2-yl)pyrazine-2-carboxamide | 374 |
| Ex-321 | 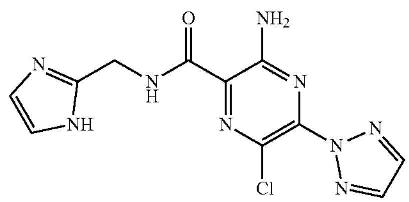 [SMILES: Nc1nc(-n2nccn2)c(Cl)nc1C(=O)NCc1ncc[nH]1] | 3-amino-6-chloro-N-(1H-imidazol-2-ylmethyl)-5-(2H-1,2,3-triazol-2-yl)pyrazine-2-carboxamide | 320 |
| Ex-322 | 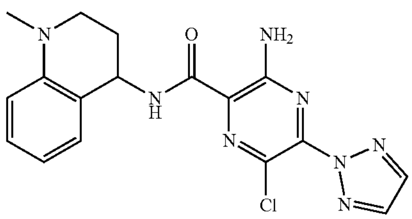 [SMILES: CN1CCC(NC(=O)c2nc(Cl)c(-n3nccn3)nc2N)c2ccccc21] | 3-amino-6-chloro-N-(1-methyl-1,2,3,4-tetrahydroquinolin-4-yl)-5-(2H-1,2,3-triazol-2-yl)pyrazine-2-carboxamide | 385 |
| Ex-323 | 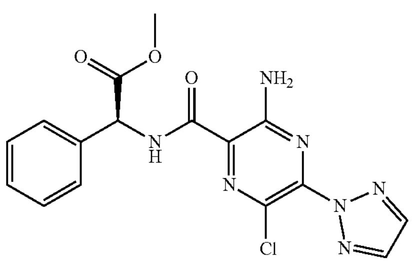 [SMILES: COC(=O)[C@@H](NC(=O)c1nc(Cl)c(-n2nccn2)nc1N)c1ccccc1] | methyl (2S)-({[3-amino-6-chloro-5-(2H-1,2,3-triazol-2-yl)pyrazin-2-yl]carbonyl}amino)(phenyl)ethanoate | 388 |
| Ex-324 | 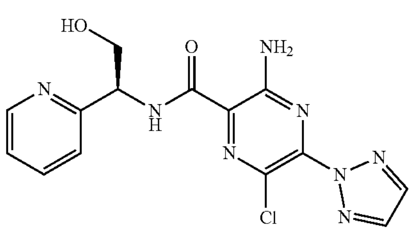 [SMILES: Nc1nc(-n2nccn2)c(Cl)nc1C(=O)N[C@H](CO)c1ccccn1] | 3-amino-6-chloro-N-[(1S)-2-hydroxy-1-pyridin-2-ylethyl]-5-(2H-1,2,3-triazol-2-yl)pyrazine-2-carboxamide | 361 |
| Ex-325 | 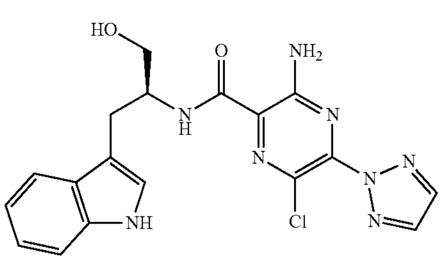 [SMILES: Nc1nc(-n2nccn2)c(Cl)nc1C(=O)N[C@H](CO)Cc1c[nH]c2ccccc12] | 3-amino-6-chloro-N-[(1S)-2-hydroxy-1-(1H-indol-3-ylmethyl)ethyl]-5-(2H-1,2,3-triazol-2-yl)pyrazine-2-carboxamide | 413 |

TABLE III-continued

| Exp No. | IUPAC Name | Exact Mass [M + H]+ |
|---|---|---|
| Ex-326 | 3-amino-6-chloro-N-[(6-methylpyridin-2-yl)methyl]-5-(2H-1,2,3-triazol-2-yl)pyrazine-2-carboxamide | 345 |
| Ex-327 | 3-amino-6-chloro-5-(1H-1,2,4-triazol-1-yl)-N-[2-(trifluoromethyl)benzyl]pyrazine-2-carboxamide | 398 |
| Ex-328 | 3-amino-6-chloro-N-(2,4-difluorobenzyl)-5-(1H-1,2,4-triazol-1-yl)pyrazine-2-carboxamide | 366 |
| Ex-329 | 3-amino-6-chloro-5-(1H-pyrazol-1-yl)-N-[2-(trifluoromethyl)benzyl]pyrazine-2-carboxamide | 397 |
| Ex-330 | 3-amino-6-chloro-N-(4-fluorobenzyl)-5-(1H-pyrazol-1-yl)pyrazine-2-carboxamide | 347 |
| Ex-331 | 3-amino-6-chloro-N-(2,4-difluorobenzyl)-5-(1H-pyrazol-1-yl)pyrazine-2-carboxamide | 365 |
| Ex-332 | 3-amino-6-chloro-5-(1H-pyrazol-1-yl)-N-(quinolin-8-ylmethyl)pyrazine-2-carboxamide | 380 |

TABLE III-continued

| Exp No. | IUPAC Name | Exact Mass [M + H]+ |
|---|---|---|
| Ex-333 | 3-amino-6-chloro-N-[(1R)-2,3-dihydro-1H-inden-1-yl]-5-(1H-pyrazol-1-yl)pyrazine-2-carboxamide | 355 |
| Ex-334 | 3-amino-6-chloro-N-[(3-methylpyridin-2-yl)methyl]-5-(1H-pyrazol-1-yl)pyrazine-2-carboxamide | 344 |
| Ex-335 | 3-amino-6-chloro-5-(4-methyl-1H-pyrazol-1-yl)-N-[2-(trifluoromethyl)benzyl]pyrazine-2-carboxamide | 411 |
| Ex-336 | 3-amino-6-chloro-N-[(1R)-2,3-dihydro-1H-inden-1-yl]-5-(4-methyl-1H-pyrazol-1-yl)pyrazine-2-carboxamide | 369 |
| Ex-337 | 3-amino-6-chloro-5-(4-methyl-1H-pyrazol-1-yl)-N-[(3-methylpyridin-2-yl)methyl]pyrazine-2-carboxamide | 358 |
| Ex-338 | 3-amino-6-chloro-5-(3-methyl-1H-pyrazol-1-yl)-N-[2-(trifluoromethyl)benzyl]pyrazine-2-carboxamide | 411 |
| Ex-339 | 3-amino-6-chloro-N-[(1R)-2,3-dihydro-1H-inden-1-yl]-5-(3-methyl-1H-pyrazol-1-yl)pyrazine-2-carboxamide | 369 |

TABLE III-continued

| Exp No. | Structure | IUPAC Name | Exact Mass [M + H]+ |
|---|---|---|---|
| Ex-340 | 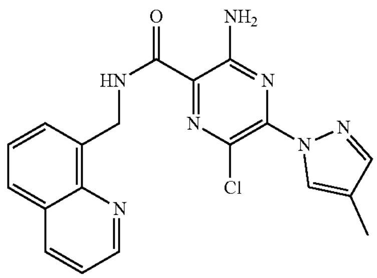 [SMILES: Cc1cnn(-c2nc(N)c(C(=O)NCc3cccc4cccnc34)nc2Cl)c1] | 3-amino-6-chloro-5-(4-methyl-1H-pyrazol-1-yl)-N-(quinolin-8-ylmethyl)pyrazine-2-carboxamide | 394 |
| Ex-341 | 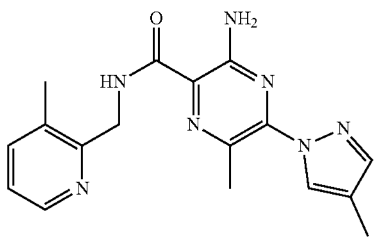 [SMILES: Cc1cnn(-c2nc(N)c(C(=O)NCc3ncccc3C)nc2C)c1] | 3-amino-6-methyl-5-(4-methyl-1H-pyrazol-1-yl)-N-[(3-methylpyridin-2-yl)methyl]pyrazine-2-carboxamide | 338 |
| Ex-342 | 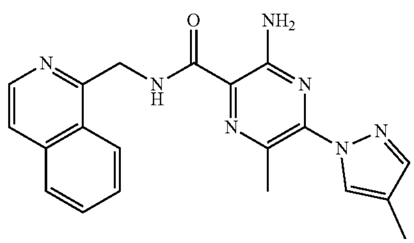 [SMILES: Cc1cnn(-c2nc(N)c(C(=O)NCc3nccc4ccccc34)nc2C)c1] | 3-amino-N-(isoquinolin-1-ylmethyl)-6-methyl-5-(4-methyl-1H-pyrazol-1-yl)pyrazine-2-carboxamide | 374 |
| Ex-343 | 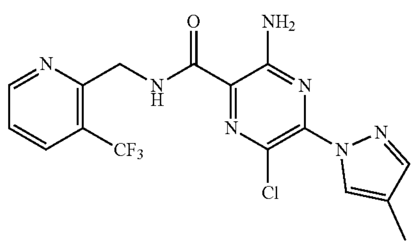 [SMILES: Cc1cnn(-c2nc(N)c(C(=O)NCc3ncccc3C(F)(F)F)nc2Cl)c1] | 3-amino-6-chloro-5-(4-methyl-1H-pyrazol-1-yl)-N-{[3-(trifluoromethyl)pyridin-2-yl]methyl}pyrazine-2-carboxamide | 412 |
| Ex-344 | 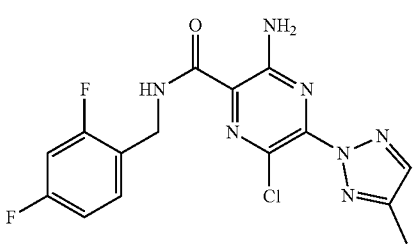 [SMILES: Cc1cnn(-c2nc(N)c(C(=O)NCc3ccc(F)cc3F)nc2Cl)n1] | 3-amino-6-chloro-N-(2,4-difluorobenzyl)-5-(4-methyl-2H-1,2,3-triazol-2-yl)pyrazine-2-carboxamide | 380 |
| Ex-345 | 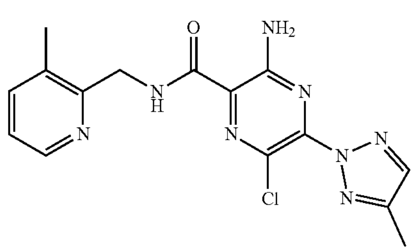 [SMILES: Cc1cnn(-c2nc(N)c(C(=O)NCc3ncccc3C)nc2Cl)n1] | 3-amino-6-chloro-N-[(3-methylpyridin-2-yl)methyl]-5-(4-methyl-2H-1,2,3-triazol-2-yl)pyrazine-2-carboxamide | 359 |

TABLE III-continued

| Exp No. | Structure | IUPAC Name | Exact Mass [M + H]+ |
|---|---|---|---|
| Ex-346 | 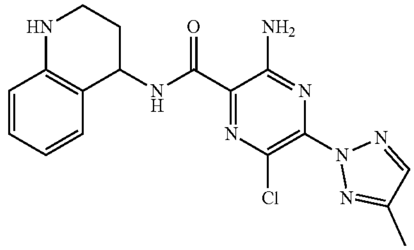 [SMILES: Cc1cnn(-c2nc(N)c(C(=O)NC3CCNc4ccccc43)nc2Cl)n1] | 3-amino-6-chloro-5-(4-methyl-2H-1,2,3-triazol-2-yl)-N-(1,2,3,4-tetrahydroquinolin-4-yl)pyrazine-2-carboxamide | 385 |
| Ex-347 | 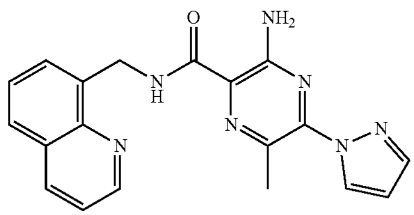 [SMILES: Cc1nc(C(=O)NCc2cccc3cccnc23)c(N)nc1-n1cccn1] | 3-amino-6-methyl-5-(1H-pyrazol-1-yl)-N-(quinolin-8-ylmethyl)pyrazine-2-carboxamide | 360 |
| Ex-348 | 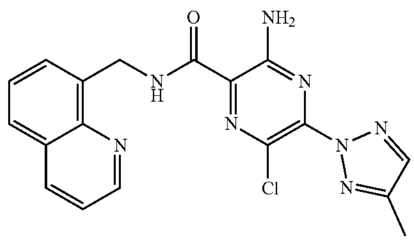 [SMILES: Cc1cnn(-c2nc(N)c(C(=O)NCc3cccc4cccnc34)nc2Cl)n1] | 3-amino-6-chloro-5-(4-methyl-2H-1,2,3-triazol-2-yl)-N-(quinolin-8-ylmethyl)pyrazine-2-carboxamide | 395 |
| Ex-349 | 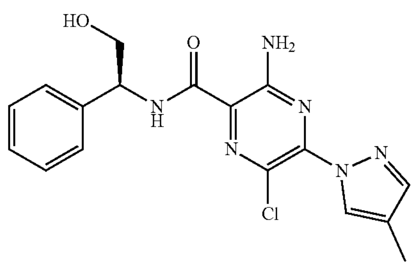 [SMILES: Cc1cnn(-c2nc(N)c(C(=O)N[C@H](CO)c3ccccc3)nc2Cl)c1] | 3-amino-6-chloro-N-[(1S)-2-hydroxy-1-phenylethyl]-5-(4-methyl-1H-pyrazol-1-yl)pyrazine-2-carboxamide | 373 |
| Ex-350 | 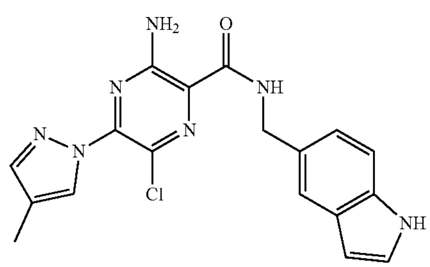 [SMILES: Cc1cnn(-c2nc(N)c(C(=O)NCc3ccc4[nH]ccc4c3)nc2Cl)c1] | 3-amino-6-chloro-N-(1H-indol-5-ylmethyl)-5-(4-methyl-1H-pyrazol-1-yl)pyrazine-2-carboxamide | 382 |
| Ex-351 | 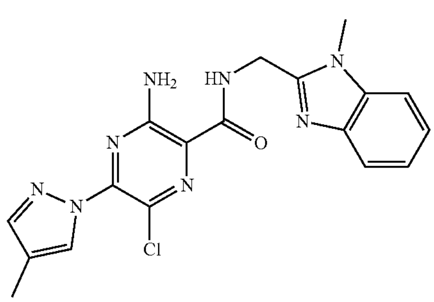 [SMILES: Cc1cnn(-c2nc(N)c(C(=O)NCc3nc4ccccc4n3C)nc2Cl)c1] | 3-amino-6-chloro-N-[(1-methyl-1H-benzimidazol-2-yl)methyl]-5-(4-methyl-1H-pyrazol-1-yl)pyrazine-2-carboxamide | 397 |

TABLE III-continued

| Exp No. | Structure | IUPAC Name | Exact Mass [M + H]+ |
|---|---|---|---|
| Ex-352 | 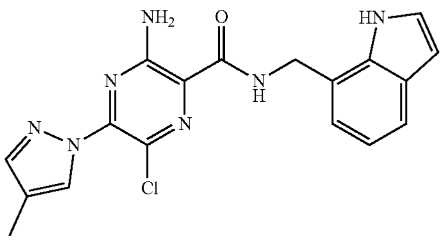 [SMILES: Cc1cnn(-c2nc(N)c(C(=O)NCc3cccc4cc[nH]c34)nc2Cl)c1] | 3-amino-6-chloro-N-(1H-indol-7-ylmethyl)-5-(4-methyl-1H-pyrazol-1-yl)pyrazine-2-carboxamide | 382 |
| Ex-353 | 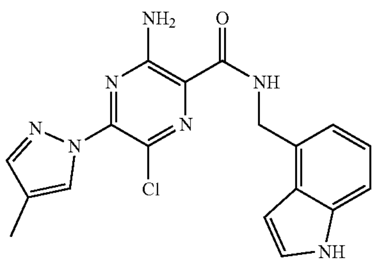 [SMILES: Cc1cnn(-c2nc(N)c(C(=O)NCc3cccc4[nH]ccc34)nc2Cl)c1] | 3-amino-6-chloro-N-(1H-indol-4-ylmethyl)-5-(4-methyl-1H-pyrazol-1-yl)pyrazine-2-carboxamide | 382 |
| Ex-354 | 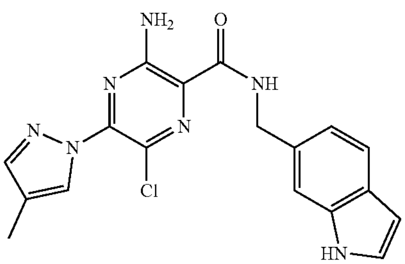 [SMILES: Cc1cnn(-c2nc(N)c(C(=O)NCc3ccc4cc[nH]c4c3)nc2Cl)c1] | 3-amino-6-chloro-N-(1H-indol-6-ylmethyl)-5-(4-methyl-1H-pyrazol-1-yl)pyrazine-2-carboxamide | 382 |
| Ex-355 | 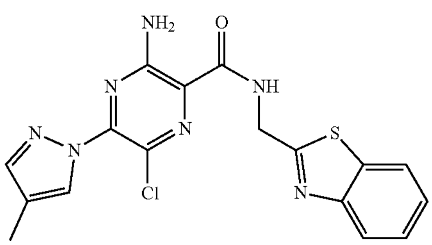 [SMILES: Cc1cnn(-c2nc(N)c(C(=O)NCc3nc4ccccc4s3)nc2Cl)c1] | 3-amino-N-(1,3-benzothiazol-2-ylmethyl)-6-chloro-5-(4-methyl-1H-pyrazol-1-yl)pyrazine-2-carboxamide | 400 |
| Ex-356 | 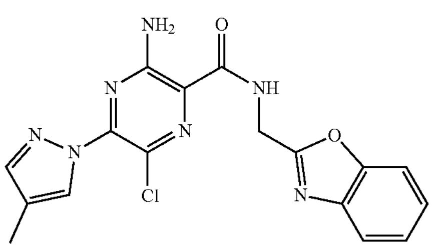 [SMILES: Cc1cnn(-c2nc(N)c(C(=O)NCc3nc4ccccc4o3)nc2Cl)c1] | 3-amino-N-(1,3-benzoxazol-2-ylmethyl)-6-chloro-5-(4-methyl-1H-pyrazol-1-yl)pyrazine-2-carboxamide | 384 |
| Ex-357 | 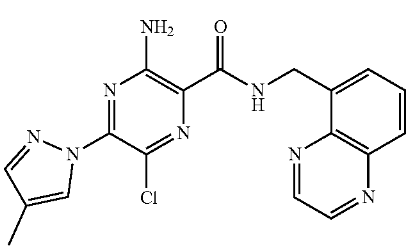 [SMILES: Cc1cnn(-c2nc(N)c(C(=O)NCc3cccc4nccnc34)nc2Cl)c1] | 3-amino-6-chloro-5-(4-methyl-1H-pyrazol-1-yl)-N-(quinoxalin-5-ylmethyl)pyrazine-2-carboxamide | 395 |

TABLE III-continued

| Exp No. | Structure | IUPAC Name | Exact Mass [M + H]+ |
|---|---|---|---|
| Ex-358 | 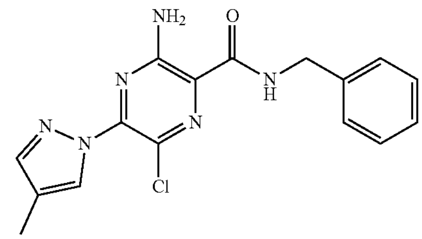 [SMILES: Cc1cnn(-c2nc(N)c(C(=O)NCc3ccccc3)nc2Cl)c1] | 3-amino-N-benzyl-6-chloro-5-(4-methyl-1H-pyrazol-1-yl)pyrazine-2-carboxamide | 343 |
| Ex-359 | 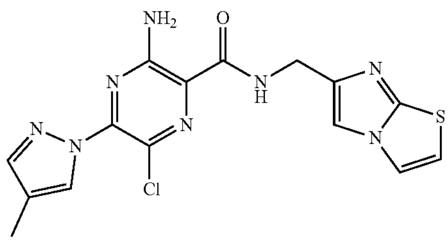 [SMILES: Cc1cnn(-c2nc(N)c(C(=O)NCc3cn4ccsc4n3)nc2Cl)c1] | 3-amino-6-chloro-N-(imidazo[2,1-b][1,3]thiazol-6-ylmethyl)-5-(4-methyl-1H-pyrazol-1-yl)pyrazine-2-carboxamide | 389 |
| Ex-360 | 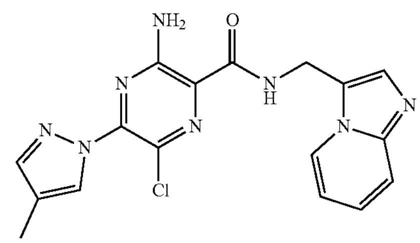 [SMILES: Cc1cnn(-c2nc(N)c(C(=O)NCc3cnc4ccccn34)nc2Cl)c1] | 3-amino-6-chloro-N-(imidazo[1,2-a]pyridin-3-ylmethyl)-5-(4-methyl-1H-pyrazol-1-yl)pyrazine-2-carboxamide | 383 |
| Ex-361 | 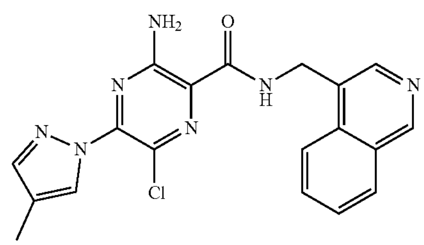 [SMILES: Cc1cnn(-c2nc(N)c(C(=O)NCc3cncc4ccccc34)nc2Cl)c1] | 3-amino-6-chloro-N-(isoquinolin-4-ylmethyl)-5-(4-methyl-1H-pyrazol-1-yl)pyrazine-2-carboxamide | 394 |
| Ex-362 | 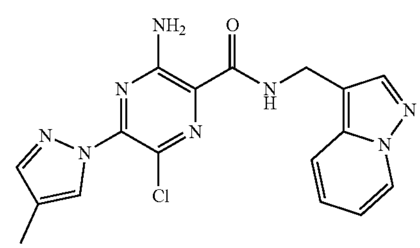 [SMILES: Cc1cnn(-c2nc(N)c(C(=O)NCc3cnn4ccccc34)nc2Cl)c1] | 3-amino-6-chloro-5-(4-methyl-1H-pyrazol-1-yl)-N-(pyrazolo[1,5-a]pyridin-3-ylmethyl)pyrazine-2-carboxamide | 383 |
| Ex-363 | 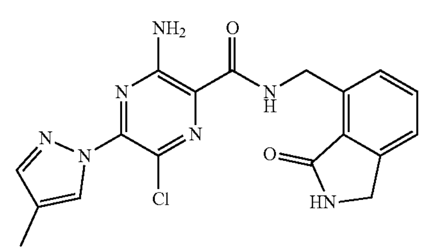 [SMILES: Cc1cnn(-c2nc(N)c(C(=O)NCc3cccc4c3C(=O)NC4)nc2Cl)c1] | 3-amino-6-chloro-5-(4-methyl-1H-pyrazol-1-yl)-N-[(3-oxo-2,3-dihydro-1H-isoindol-4-yl)methyl]pyrazine-2-carboxamide | 398 |

TABLE III-continued

| Exp No. | Structure | IUPAC Name | Exact Mass [M + H]+ |
|---|---|---|---|
| Ex-364 | 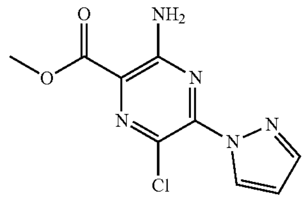 [SMILES: COC(=O)c1nc(Cl)c(-n2cccn2)nc1N] | methyl 3-amino-6-chloro-5-(1H-pyrazol-1-yl)pyrazine-2-carboxylate | 254 |

Preparation of 3-amino-6-methyl-N-((3-methylpyridin-2-yl)methyl)-5-(4-(trifluoromethyl) oxazol-2-yl) pyrazine-2-carboxamide (Ex-364)

The compound of Ex-364 was prepared in accordance with Scheme ES-6.

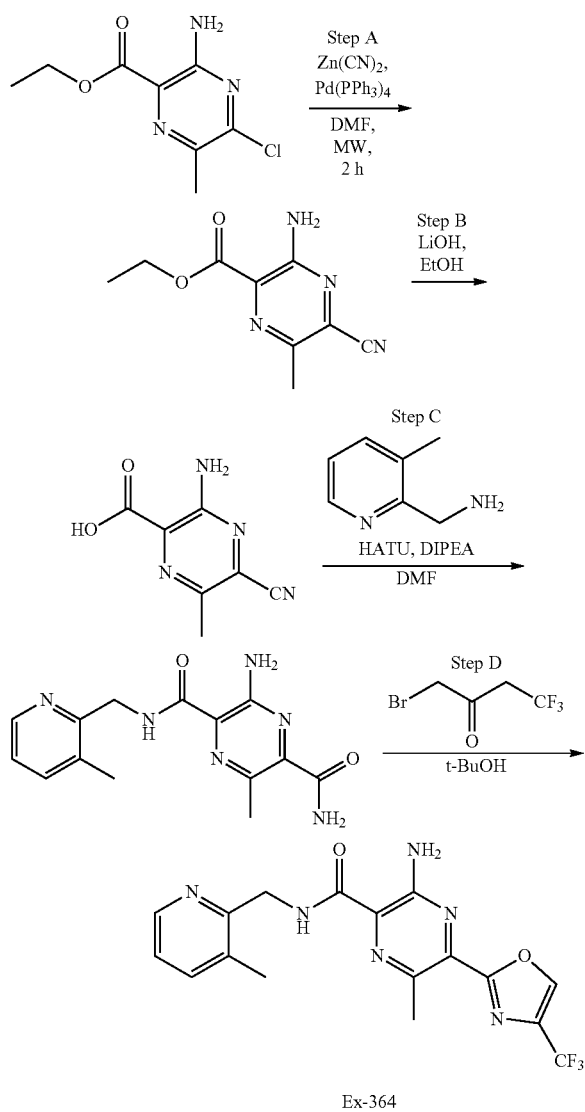

Ex-364

Step A: Ethyl 3-amino-5-cyano-6-methylpyrazine-2-carboxylate

A 20 mL sealed tube was charged with ethyl 3-amino-5-chloro-6-methylpyrazine-2-carboxylate (900 mg, 4.17 mmol), zinc cyanide (1.47 g, 12.52 mmol) and [1,1'-bis(diphenylphosphino)ferrocene]dichloropalladium(II) (916 mg, 1.25 mmol) in DMF (10.0 mL). The resulting mixture was heated in a microwave reactor to 140° C. for 2 hours. The mixture was cooled to ambient. Water (30 mL) was added and the mixture was extracted with EtOAc (3×50 mL). The combined organic fractions were washed with brine (70 mL), dried ($Na_2SO_4$), filtered, and the solvent was evaporated under reduced pressure. The residue was purified by Prep-TLC (hexane:EtOAc=1:1) to give ethyl 3-amino-5-cyano-6-methylpyrazine-2-carboxylate as a solid. LC/MS=207 [M+1].

Step B: 3-Amino-5-cyano-6-methylpyrazine-2-carboxylic acid

To a stirred mixture of ethyl 3-amino-5-cyano-6-methylpyrazine-2-carboxylate (330 mg, 1.55 mmol) in water (0.5 mL) and EtOH (5.0 mL) at room temperature was added lithium hydroxide (74 mg, 3.1 mmol). The mixture was then stirred for 30 minutes, at which point no more starting material was present (LCMS). The mixture was acidified with 1M HCl solution to adjust pH to 5. The mixture was filtered and concentrated under reduced pressure. The residue was further dried in a vacuum oven overnight to afford 3-amino-5-cyano-6-methylpyrazine-2-carboxylic acid as a solid. LC/MS=179 [M+1].

Step C: 3-Amino-6-methyl-N2-((3-methylpyridin-2-yl)methyl)pyrazine-2,5-dicarboxamide The title compound was prepared following similar procedures described in example 1. LC/MS=301 [M+1]. $^1$H-NMR ($CD_3OD$-d4, 400 MHz) δ 8.39 (d, 1H), 7.66-7.64 (m, 1H), 7.28-7.25 (m, 1H), 4.70 (s, 2H), 2.70 (s, 3H), 2.43 (s, 3H).

Step D: 3-Amino-6-methyl-N-((3-methylpyridin-2-yl)methyl)-5-(4-(trifluoromethyl)oxazol-2-yl)pyrazine-2-carboxamide A solution of 3-amino-6-methyl-N2-((3-methylpyridin-2-yl)methyl)pyrazine-2,5-dicarboxamide (15 mg, 0.05 mmol) and bromo-trifluoroacetone in t-BuOH (5 ml was heated at 100° C. for 20 hours. The mixture was cooled and the solvent was evaporated under reduced pressure. The residue was purified by prep-HPLC using MeCN/0.05% TFA in H2O=5%~95% to give 3-amino-6-methyl-N-((3-methyl-pyridin-2-yl)methyl)-5-(4-(trifluoromethyl)oxazol-2-yl)pyrazine-2-carboxamide as a solid. LC/MS=393 [M+1]. ¹H-NMR (CD₃OD-d₄, 400 MHz) δ 8.56-8.54 (m, 2H), 8.21-8.19 (m, 1H), 7.72-7.69 (m, 1H), 5.01 (s, 2H), 2.73 (s, 3H), 2.62 (s, 3H).

Preparation of 3-amino-5-(4,5-dimethyloxazol-2-yl)-6-methyl-N-((3-methylpyridin-2-yl)methyl)pyrazine-2-carboxamide (Ex-365)

The compound of Ex-365 was prepared in accordance with Scheme ES-7.

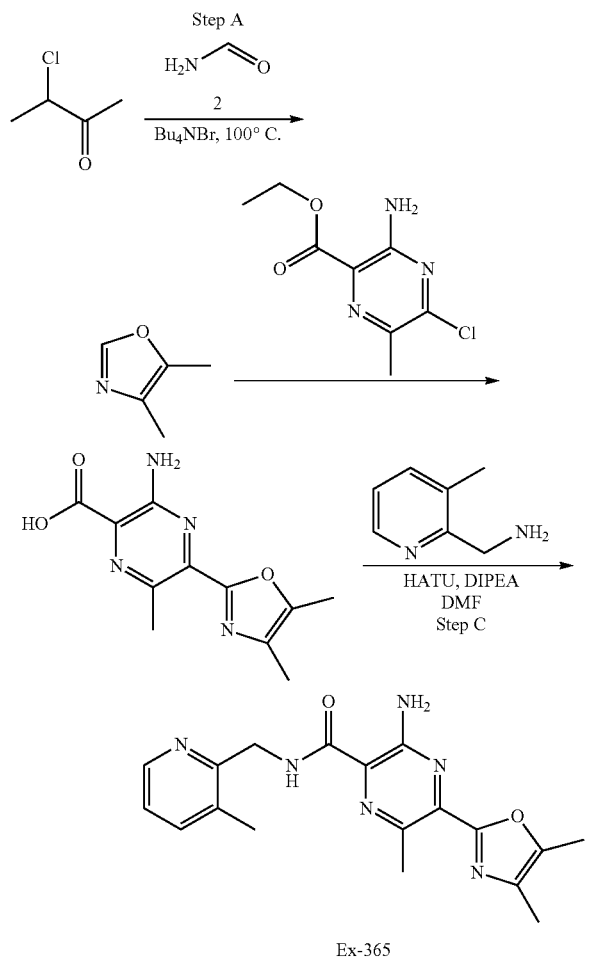

Ex-365

Step A: 4,5-Dimethyloxazole

A mixture of 3-chlorobutan-2-one (5 g, 46.9 mmol), tetrabutylammoniumbromide (303 mg, 0.94 mmol) and formamide (15 ml, 376 mmol) was heated at 100° C. for 6 hours. The product was distilled from the mixture under atmospheric pressure to give 4,5-dimethyloxazole as an oil. ¹H-NMR (CDCl₃, 400 MHz) δ7.66 (s, 1H), 2.23 (s, 3H), 2.07 (s, 3H).

Step B: 3-Amino-5-(4,5-dimethyloxazol-2-yl)-6-methylpyrazine-2-carboxylic acid

To a stirred solution of 4,5-dimethyloxazole (116 mg, 1.20 mmol) in THF (3.0 mL) at −78° C., butyllithium (0.9 mL, 1.44 mmol) was added dropwise. The solution was stirred at this temperature for 10 min followed by dropwise addition of zinc (II) chloride (380 mg, 2.79 mmol) solution in THF (5.0 mL). The mixture was stirred for 15 min at −78° C. Cooling bath was removed and reaction mixture was warmed to room temperature. Ethyl 3-amino-5-chloro-6-methylpyrazine-2-carboxylate (215 mg, 0.99 mmol) and Pd(PPh₃)₄ (115 mg, 0.1 mmol) were added to this reaction mixture. The mixture was stirred at 80° C. for 16 hours and water (20 mL) was added. The mixture was extracted using EtOAc (20 mL×3). The organic layers were combined, washed with brine (20 mL), dried (Na₂SO₄) and concentrated. The residue was purified by silica gel column, eluting with hexane/EtOAc=3/1-1/1 to give 3-amino-5-(4,5-dimethyloxazol-2-yl)-6-methylpyrazine-2-carboxylic acid as a solid. LC/MS=249 [M+1].

Step C: 3-Amino-5-(4,5-dimethyloxazol-2-yl)-6-methyl-N-((3-methylpyridin-2-yl)methyl)pyrazine-2-carboxamide (Ex-365)

Compound Ex-365 was prepared following similar procedures described for the preparation of example compounds in Schemes ES-1 through ES-7, and was characterized using LC/MS=353 [M+1] and proton NMR: ¹H-NMR (CDCl₃, 400 MHz) δ 9.50 (br, 1H), 8.65-8.64 (m, 1H), 8.03 (d, 1H), 7.61-7.58 (m, 1H), 4.93-4.92 (m, 2H), 2.83 (s, 3H), 2.74 (s, 3H), 2.41 (s, 3H), 2.24 (s, 3H).

Preparation of Example Compounds Ex-366 Ex-367, Ex-368, and Ex-369

Example compounds Ex-366 Ex-367, Ex-368, and Ex-369 were prepared from compound Ex-340 in accordance with Scheme ES-8.

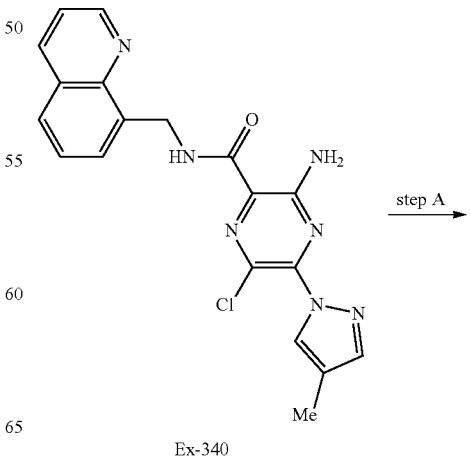

Ex-340

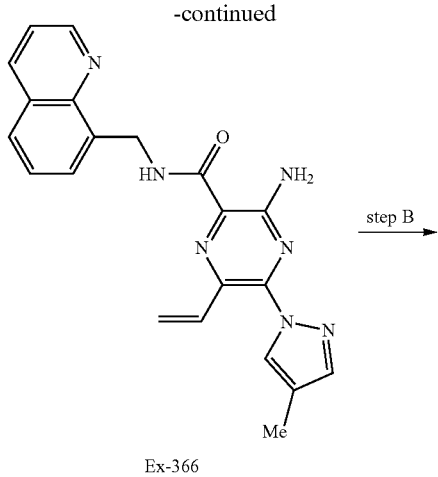

Ex-366

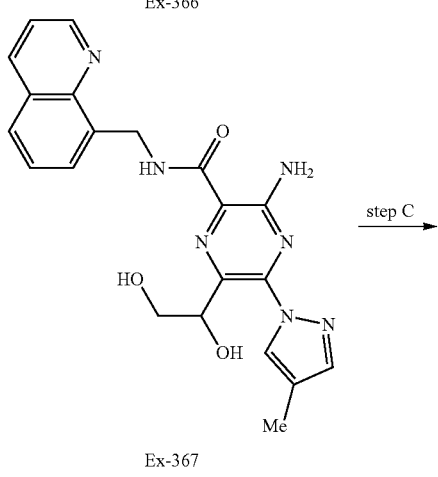

Ex-367

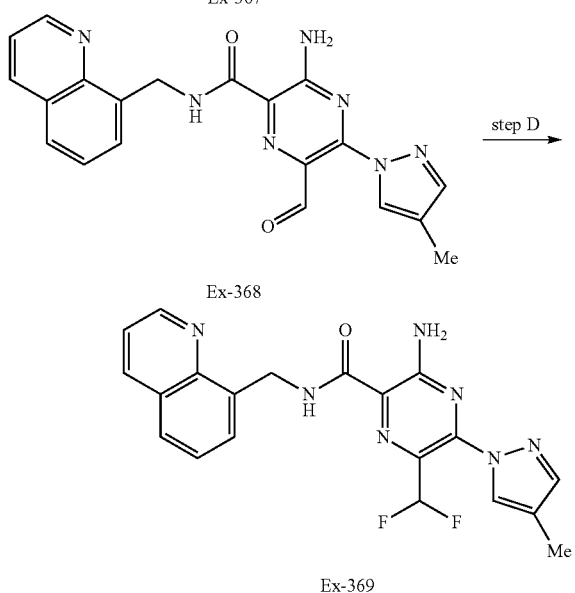

Ex-368

Ex-369

Step A: 3-amino-5-(4-methyl-1H-pyrazol-1-yl)-N-(quinolin-8-ylmethyl)-6-vinylpyrazine-2-carboxamide (Ex-366)

A microwave reaction vial was charged with 3-amino-6-chloro-5-(4-methyl-1H-pyrazol-1-yl)-N-(quinolin-8-ylmethyl)pyrazine-2-carboxamide (Ex-340, prepared above, 0.520 g, 1.32 mmol), potassium vinyl trifluoroborate (0.212 g, 1.58 mmol), [1,1'-bis(diphenylphosphino)ferrocene]dichloropalladium(II) (0.145 g, 0.20 mmol) and potassium carbonate (0.547 g, 3.96 mmol) and capped, exchanged air with $N_2$ by 3 times of cycle of vacuum-refilling with nitrogen. Degassed MeCN/water was added, followed by heating to 140° C. for 30 minutes in a microwaver reactor. After cooling down, the crude mixture was concentrated. The crude concentrate was taken up in EtOAc, washed with brine, dried over anhydrous sodium sulfate, concentrated, and purified by flash chromatography on a silica-gel column with ISCO and EtOAc/Hexane (0-60%) as eluant to give the title compound as a solid. LC/MS=386 [M+1].

Step B: 3-amino-6-(1,2-dihydroxyethyl)-5-(4-methyl-1H-pyrazol-1-yl)-N-(quinolin-8-ylmethyl)pyrazine-2-carboxamide (Ex-367)

4-Methylmorpholine-N-oxide (0.137 g, 1.168 mmol) and osmium tetraoxide (0.024 g, 0.093 mmol) were added in a solution of Ex-366, prepared in the previous step (0.18 g, 0.467 mmol) in acetone/acetonitrile/water, followed by stirring at RT for 1.5 days. Then, additional 0.2 equivalent of osmium tetraoxide (0.024 g, 0.093 mmol) and t-butanol (3.0 ml) were added to the reaction mixture and stirred at room temperature (RT) for 24 hours. The mixture was filtered, concentrated and purified by HPLC Gilson with acetonitrile/water with 0.01% TFA as eluant to give Ex-367 as a solid. LC/MS=420 [M+1].

Step C: 3-amino-6-formyl-5-(4-methyl-1H-pyrazol-1-yl)-N-(quinolin-8-ylmethyl)pyrazine-2-carboxamide (Ex-368)

Sodium periodate (0.043 g, 0.200 mmol) and water (2.50 ml) were added to a solution of Ex-367 prepared in the previous step (0.070 g, 0.167 mmol) in acetone (5.0 ml) at RT, followed by stirring for 3 hours. Then, additional sodium periodate (0.043 g, 0.200 mmol) was added to the reaction mixture, followed by stirring for an additional 3 hours. The mixture was diluted with water and extracted with EtOAc/$CH_2Cl_2$. The organic phase was dried over MgSO4, filtered, concentrated and purified by a flash chromatography on a silica gel column with ISCO and 0-80% EtOAc/hexane as eluant to give Ex-368 as a solid. LC/MS=388 [M+1].

Step D: 3-amino-6-(difluoromethyl)-5-(4-methyl-1H-pyrazol-1-yl)-N-(quinolin-8-ylmethyl)pyrazine-2-carboxamide (Ex-369)

A solution of DAST (0.041 ml, 0.310 mmol) in $CH_2Cl_2$ (3.0 ml) was dropped to a solution of Ex-368 prepared in the previous step (0.048 g, 0.124 mmol) in $CH_2Cl_2$ (5 mL) at −78° C., followed by stirring for 4 hours after which the reaction mixture was allowed to rise to RT. The solvent was removed by evaporation and the residue purified by preparative HPLC reverse phase (C-18), eluting with acetonitrile/water+0.1% TFA, to give Ex-369 as a solid. LC/MS=410 [M+1].

Preparation of Example Compound Ex-370

Example Compound Ex-370, 3-amino-6-(hydroxymethyl)-N-(quinolin-8-ylmethyl)-5-(2H-1,2,3-triazol-2-yl)pyrazine-2-carboxamide, was prepared in accordance with Scheme ES-9:

SCHEME ES-9

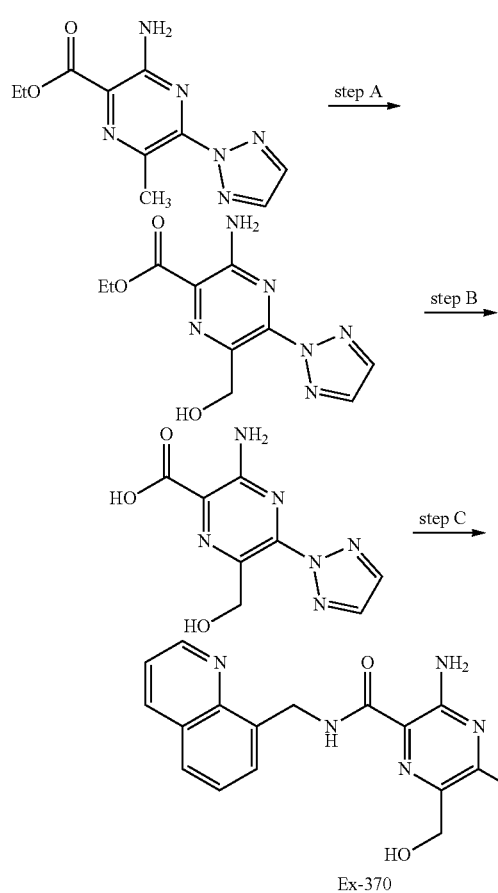

Step A: Ethyl 3-amino-6-(hydroxymethyl)-5-(2H-1,2,3-triazol-2-yl)pyrazine-2-carboxylate Into a reaction vessel was placed a mixture of ethyl 3-amino-6-methyl-5-(2H-1,2,3-triazol-2-yl)pyrazine-2-carboxylate (0.248 g, 1.00 mmol), N-bromosuccinimide (0.214 g, 1.20 mmol) and benzoyl peroxide (0.290 g, 1.20 mmol) in CCl4 (20 ml). The mixture was heated at 85° C. for 3 hours. After cooling to ambient temperature, the mixture was concentrated and taken up in CH3CN (10 ml) and mixed with potassium acetate (0.15 g, 1.50 mmol) and the mixture stirred at ambient temperature for 24 hours. The solvent was removed and the residue was taken up in MeOH (10.0 ml) and mixed with Na₂CO₃ (0.42 g, 4.0 mmol) and H₂O (0.25 ml), followed by stirring at RT for 4 hours. The reaction mixture was concentrated and purified by by preparative HPLC reverse phase (C-18), eluting with acetonitrile/water+0.1% TFA, to give the title compound as a solid. LC/MS=265 [M+1].

Step B: 3-amino-6-(hydroxymethyl)-5-(2H-1,2,3-triazol-2-yl)pyrazine-2-carboxylic acid A mixture of ethyl 3-amino-6-(hydroxymethyl)-5-(2H-1,2,3-triazol-2-yl)pyrazine-2-carboxylate (0.15 g, 0.568 mmol), and lithium hydroxide hydrate (0.119 g, 2.84 mmol) in THF (5.0 ml) and water (2.0 ml) was stirred at RT for 3 hours. The solvent was removed and the residue was taken up in DMF and purified by preparative HPLC reverse phase (C-18), eluting with acetonitrile/water+0.1% TFA, to give the title compound as a solid. LC/MS=237 [M+1].

Step C: 3-amino-6-(hydroxymethyl)-N-(quinolin-8-ylmethyl)-5-(2H-1,2,3-triazol-2-yl)pyrazine-2-carboxamide Hunig's base (0.251 ml, 1.440 mmol) was added to a solution of 3-amino-6-(hydroxymethyl)-5-(2H-1,2,3-triazol-2-yl)pyrazine-2-carboxylic acid (0.068 g, 0.288 mmol), and quinolin-8-ylmethanamine dihydrochloride (0.073 g, 0.317 mmol) and HATU (0.120 g, 0.317 mmol) in DMF (2.0 ml) at 0° C. in an ice-bath. The mixture was stirred at 0° C. for 30 min and at RT for 30 minutes. A saturated aqueous solution of NaHCO₃ (50 ml) was added to the mixture and extracted with CH₂Cl₂ (2×50 mL). The combined organic phase was dried over MgSO₄, filtered, concentrated, purified by flash chromatography on a silica gel column with 0-60% EtOAc/hexane as eluant to give the title compound as a solid. LC/MS=377 [M+1].

Preparation of Example Compound Ex-371

Example Compound Ex-371, 3-amino-6-cyano-5-(1H-pyrazol-1-yl)-N-(quinolin-8-ylmethyl)pyrazine-2-carboxamide, was prepared in accordance with Scheme ES-10:

SCHEME ES-10

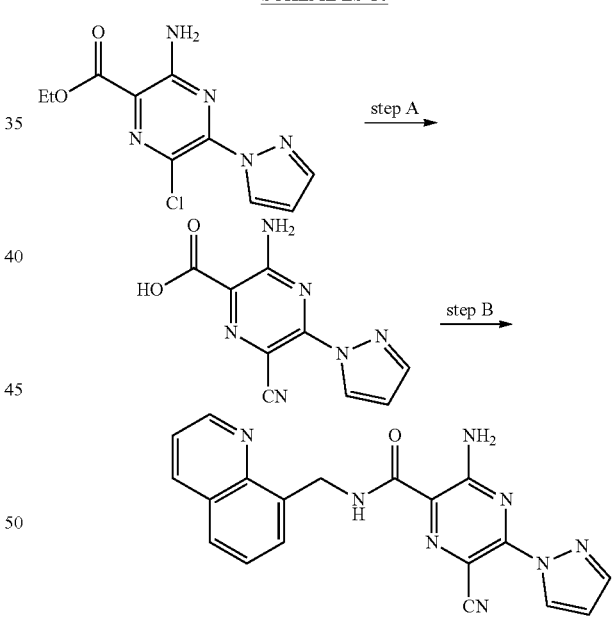

Step A: 3-Amino-6-cyano-5-(1H-pyrazol-1-yl)pyrazine-2-carboxylic acid

A microwave vial was charged with ethyl 3-amino-6-chloro-5-(1H-pyrazol-1-yl)pyrazine-2-carboxylate (1.02 g, 4.00 mmol), potassium ferrocyanide (1.473 g, 4.00 mmol) and copper (I) iodide (0.762 g, 4.00 mmol), capped, degassed and filled with nitrogen. To the reaction mixture was added NMP (8.0 ml) and the mixture was stirred at 150° C. for 8 hours. After cooling, the mixture was diluted with ethyl acetate and treated with 1 N HCl aqueous solution. The organic layer was separated and the aqueous was extracted with ethyl acetate (2×100 ml). The combined organic layers were dried over MgSO4, filtered and concentrated, purified by preparative HPLC reverse phase (C-18), eluting with acetonitrile/water+0.1% TFA, to give the title compound as a solid. LC/MS=231 [M+1].

Step B: 3-amino-6-cyano-5-(1H-pyrazol-1-yl)-N-(quinolin-8-ylmethyl)pyrazine-2-carboxamide Hunig's base (0.218 ml, 1.250 mmol) was added into a solution of 3-amino-6-cyano-5-(1H-pyrazol-1-yl)pyrazine-2-carboxylic acid (0.058 g, 0.25 mmol), and quinolin-8-ylmethanamine dihydrochloride (0.064 g, 0.275 mmol) and HATU (0.105 g, 0275 mmol) in DMF (2 ml), followed by stirring at RT for 3 hours. The mixture was purified by preparative HPLC reverse phase (C-18), eluting with acetonitrile/water+0.1% TFA to give the title compound as a solid. LC/MS=371 [M+1].

Preparation of Example Compound Ex-372

Example Compound Ex-372, 3-amino-6-cyano-5-(oxazol-2-yl)-N-((3-(trifluoromethyl)pyridin-2-yl)methyl)pyrazine-2-carboxamide was prepared in accordance with Scheme ES-11:

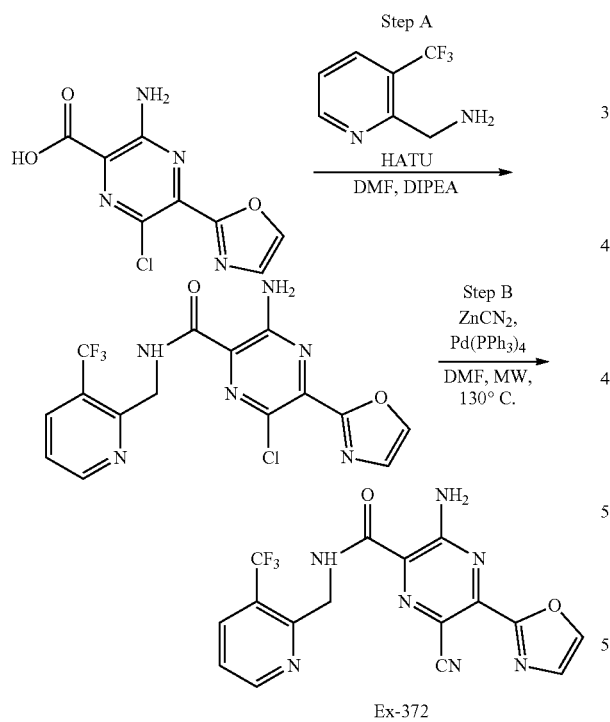

Step A: 3-Amino-6-chloro-5-(oxazol-2-yl)-N-((3-(trifluoromethyl)pyridin-2-yl)methyl)pyrazine-2-carboxamide A solution of compound 3-amino-6-chloro-5-(oxazol-2-yl)pyrazine-2-carboxylic acid (42 mg, 0.18 mmol), HATU (74 mg, 0.26 mmol) and DIPEA (67 mg, 0.53 mmol) in DMF (5 mL) was stirred at room temperature for 0.5 hour. After ½ hour, (3-(Trifluoromethyl)pyridin-2-yl)methanamine (56 mg, 0.26 mmol) was added to the mixture, and the reaction mixture was stirred at room temperature for additional 10 hours. At the end of 10 hours the reaction mixture was diluted with ethyl acetate (50 mL) and washed with water (50 mL×2). The organic layer was separated and dried over anhydrous Na2SO4, then concentrated to give crude product, which was purified by preparative TLC (eluting with 1:2 hexane/ethyl acetate) to give 3-amino-6-chloro-5-(oxazol-2-yl)-N-((3-(trifluoromethyl)pyridin-2-yl)methyl)pyrazine-2-carboxamide as a solid. LC/MS=399 [M+1].

Step B: 3-Amino-6-cyano-5-(oxazol-2-yl)-N-((3-(trifluoromethyl)pyridin-2-yl)methyl)pyrazine-2-carboxamide A solution of zinc cyanide (24 mg, 0.20 mmol), amino-6-chloro-5-(oxazol-2-yl)-N-((3-(trifluoromethyl)pyridin-2-yl)methyl)pyrazine-2-carboxamide (27 mg, 0.068 mmol) and Pd(PPh3)4 (24 mg, 0.02 mmol) in DMF (2 ml) in a sealed tube was heated in a microwave reactor to 130° C. for 2 hours under nitrogen. After filtration, the filtrate was purified by preparative HPLC to give 3-amino-6-cyano-5-(oxazol-2-yl)-N-((3-(trifluoromethyl)pyridin-2-yl)methyl)pyrazine-2-carboxamide (Ex-373) as a solid. LC/MS=390 [M+1]. $^1$H NMR (DMSO-d6, 400 MHz) δ 9.37 (t, 1H), 8.83 (d, 1H), 8.65 (s, 2H), 8.49 (s, 1H), 8.20 (d, 1H), 7.66 (s, 1H), 7.56 (dd, 1H), 4.78 (d, 2H).

Preparation of Example Compound Ex-373

Example Compound Ex-373, 1-(3-amino-6-methyl-5-(oxazol-2-yl)pyrazin-2-yl)-3-(4,6-dimethylpyridin-2-yl)propan-1-one was prepared in accordance with Scheme ES-12:

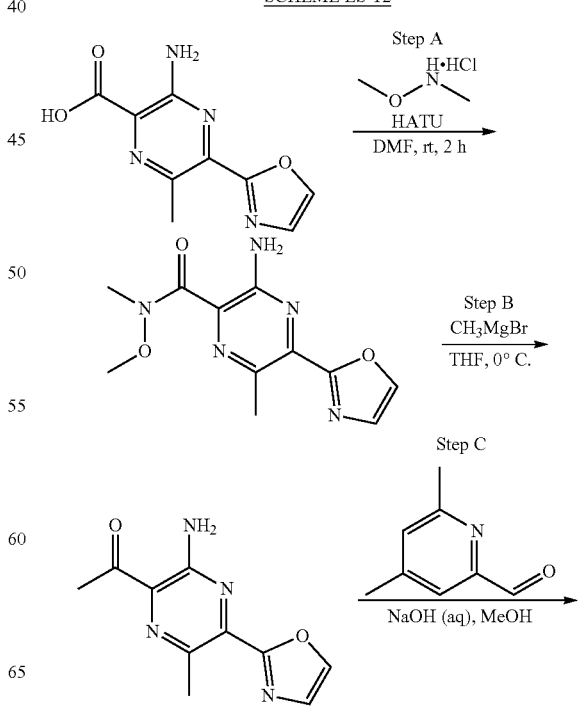

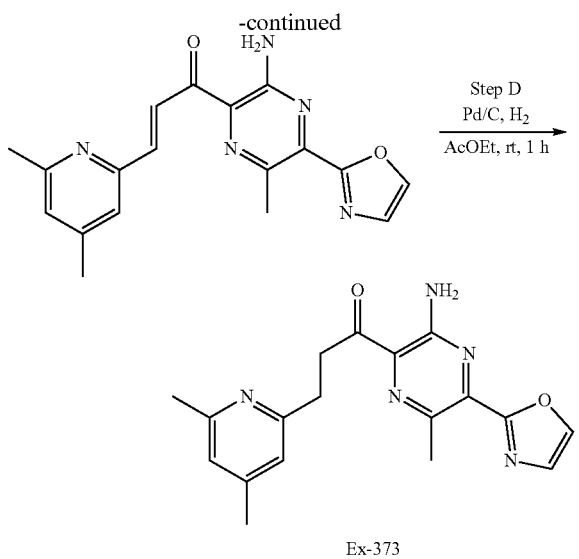

Step A: 3-Amino-N-methoxy-N,6-dimethyl-5-(oxazol-2-yl)pyrazine-2-carboxamide A solution of compound 3-amino-6-chloro-5-(oxazol-2-yl)pyrazine-2-carboxylic acid (440 mg, 2 mmol), HATU (1.13 g, 3 mmol) and DIPEA (774 mg, 6 mmol) in DMF 5 mL was stirred at room temperature for 0.5 hours, followed by addition of N,O-dimethylhydroxylamine hydrochloride (388 mg, 4 mmol) to the reaction mixture, and then reaction mixture was then stirred at room temperature for additional 12 hours. The reaction mixture was diluted with ethyl acetate (200 mL) and washed with water (100 mL). The organic layer was dried over anhydrous $Na_2SO_4$, concentrated to give a crude product which was purified by chromatography on silica gel eluting with (1:1 hexane/ethyl acetate) to give 3-amino-N-methoxy-N,6-dimethyl-5-(oxazol-2-yl)pyrazine-2-carboxamide. LC/MS=264 [M+1].

Step B: 1-(3-Amino-6-methyl-5-(oxazol-2-yl)pyrazin-2-yl)ethanone

A solution of compound 3-amino-N-methoxy-N,6-dimethyl-5-(oxazol-2-yl)pyrazine-2-carboxamide (380 mg, 1.44 mmol) in dry THF (5 mL) was added $CH_3MgBr$ (2.0 mL, 6 mmol) at 0° C. in 1 minute. After the addition completed, the mixture was stirred at room temperature for 1 hour, then the reaction mixture was quenched with saturated ammonium chloride solution (20 mL), diluted with ethyl acetate (100 mL) and washed with water (100 mL×1). The organic layer was dried over anhydrous $Na_2SO_4$, and concentrated to give crude product which was purified by chromatography on silica gel eluting with (hexane/ethyl acetate: 1:1) to give 1-(3-amino-6-methyl-5-(oxazol-2-yl)pyrazin-2-yl)ethanone. LC/MS=219 [M+1].

Step C: 1-(3-Amino-6-methyl-5-(oxazol-2-yl)pyrazin-2-yl)-3-(4,6-dimethylpyridin-2-yl)prop-2-en-1-one To a solution of 4,6-dimethylpicolinaldehyde (130 mg, 0.97 mmol) in MeOH 5 mL was added NaOH (78 mg, 1.94 mmol) in $H_2O$ (0.5 mL) at 0° C., followed by dropwise addition of 1-(3-Amino-6-methyl-5-(oxazol-2-yl)pyrazin-2-yl)ethanone (106 mg, 0.48 mmol) in MeOH (2 mL) at 0° C. After the addition completed, the mixture was stirred at room temperature for 12 hours. LC-MS showed that the reaction completed. The reaction mixture was diluted with ethyl acetate (100 mL) and washed with water (50 mL×2). The organic layer was dried over anhydrous $Na_2SO_4$, concentrated to give 1-(3-amino-6-methyl-5-(oxazol-2-yl)pyrazin-2-yl)-3-(4,6-dimethylpyridin-2-yl)prop-2-en-1-one as a solid. LC/MS=336 [M+1].

Step D: 1-(3-Amino-6-methyl-5-(oxazol-2-yl)pyrazin-2-yl)-3-(4,6-dimethylpyridin-2-yl)propan-1-one (Ex-373)

To a solution of 1-(3-amino-6-methyl-5-(oxazol-2-yl)pyrazin-2-yl)-3-(4,6-dimethylpyridin-2-yl)prop-2-en-1-one (150 mg, 0.447 mmol) in ethyl acetate (60 mL) was added Pd/C (10%, 100 mg), and then the reaction mixture was stirred at room temperature under $H_2$ for 1 hour, following which the reaction mixture was filtered and the filtrate concentrated to give crude product. The crude residue was purified by preparative HPLC to give 1-(3-amino-6-methyl-5-(oxazol-2-yl)pyrazin-2-yl)-3-(4,6-dimethylpyridin-2-yl)propan-1-one as a solid. LC/MS=338 [M+1]. $^1$H NMR (DMSO-d6, 400 MHz) d δ: 8.38 (s, 1H), 7.65 (s, 2H), 7.58 (s, 1H), 6.90 (d, 1H), 6.85 (d, 1H), 3.54 (t, 2H), 3.00 (t, 2H), 2.75 (s, 3H), 2.24 (s, 3H), 2.19 (s, 3H).

Preparation of Example Compound Ex-374

Example Compound Ex-374, 3-amino-6-methyl-N#5-methylpyrimidin-4-yl)methyl)-5-(oxazol-2-yl)pyrazine-2-carboxamide was prepared in accordance with Scheme ES-13:

SCHEME ES-13

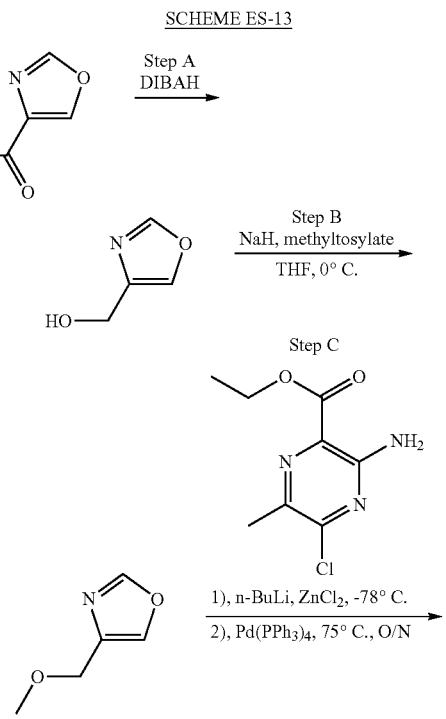

163

-continued

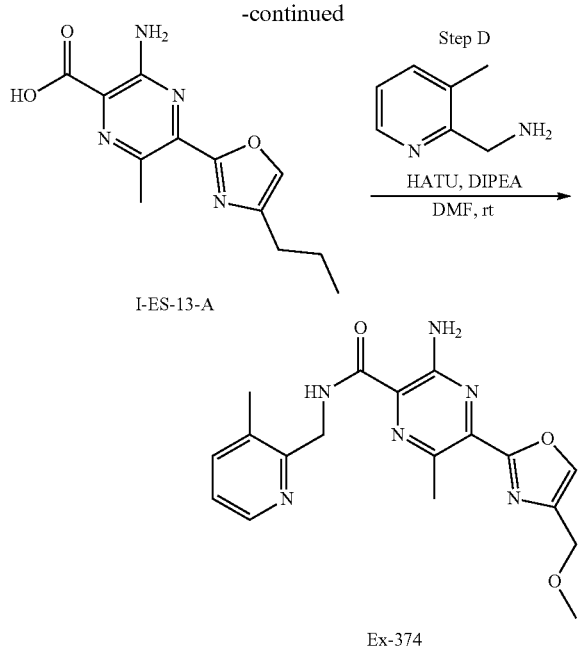

I-ES-13-A

Ex-374

Step A: Oxazol-4-ylmethanol

A flame-dried three-neck flask (100 mL) was charged with methyl oxazole-4-carboxylate (2.0 g, 14 mmol) and ethyl ether (15 mL). DIBAL-H (30 mL, 30 mmol) was added dropwise at −78° C. under nitrogen. Once the addition was completed, the reaction mixture was allowed to warm to rt and stirred for 1 hour. The reaction mixture was quenched with Na$_2$SO$_4$-10H$_2$O (5 g). After stirred for 10 hours, the suspension was filtered, the filtrate was evaporated under reduced pressure, the residue was purified by prep-HPLC to give oxazol-4-ylmethanol as an oil. LC/MS=100 [M+1].

Step B: 4-(Methoxymethyl)oxazole

A flame-fried three-neck flask (100 mL) was charged with oxazol-4-ylmethanol (1.0 mmol) and ethyl ether (15 mL). NaH (50 mg, 1.2 mmol) was added portions at 0° C. under nitrogen. After stirred for 30 minutes, methyl tosylate (250 mg, 1.2 mmol) was added. The suspension was stirred overnight at room temperature. The reaction mixture was filtered and the filtrate was concentrated in vacuo. The residue was purified by prep-HPLC to give 4-(methoxymethyl)oxazoleas. LC/MS=114 [M+1].

Step C: 3-Amino-5-(4-(methoxymethyl)oxazol-2-yl)-6-methylpyrazine-2-carboxylic acid A flame-fried three-neck flask (100 mL) was charged with 4-(methoxymethyl)oxazole (1.6 mmol) and THF (15 mL). The mixture was degassed and back-filled with nitrogen. The mixture was cooled to −78° C., and then n-BuLi (1.2 mL, 1.8 mmol) was added dropwise. After stirred for 15 minutes, dry ZnCl$_2$ (512 mg, 3.77 mmol) in dry THF (5 mL) was added at −78° C. After stirred for 30 minutes, the mixture was warmed to room temperature. Ethyl 3-amino-5-chloro-6-methylpyrazine-2-carboxylate (311 mg, 1.45 mmol) and Pd(PPh$_3$)$_4$ (334 mg, 0.29 mmol) was added at room temperature. The resulting mixture was heated to 70° C. overnight. The reaction mixture was filtered. The filtrate was concentrated in vacuo. The residue was purified prep-HPLC to give 3-amino-5-(4-(methoxymethyl)oxazol-2-yl)-6-methylpyrazine-2-carboxylic acid as an oil. LC/MS=265 [M+1].

Step D: 3-Amino-5-(4-(methoxymethyl)oxazol-2-yl)-6-methyl-N-((3-methylpyridin-2-yl)methyl)pyrazine-2-carboxamide (Ex-374)

Example compound Ex-374 was prepared from intermediate I-ES-12-A and 2-methylamino-3-methyl-piperidine using the procedures of Schemes ES-1 through ES-5. Ex-374 was characterized by LC/MS and proton NMR. LC/MS=369 [M+1]. $^1$H NMR (MeOD-d4, 400 MHz) d δ: 8.45-8.30 (d, 1H), 8.26-8.23 (d, 1H), 8.00 (s, 1H), 7.74-7.70 (m, 1H), 4.77 (s, 2H), 4.39 (s, 2H), 3.22-3.20 (m, 5H), 2.72 (s, 3H), 2.50 (s, 3H).

Preparation of Example Compounds Ex-375 A

Example Compound 3-amino-6-methyl-5-(5-methyloxazol-2-yl)-N-((3-methylpyridin-2-yl)methyl)pyrazine-2-carboxamide (Ex-375) was prepared in accordance with Scheme ES-14:

SCHEME ES-14

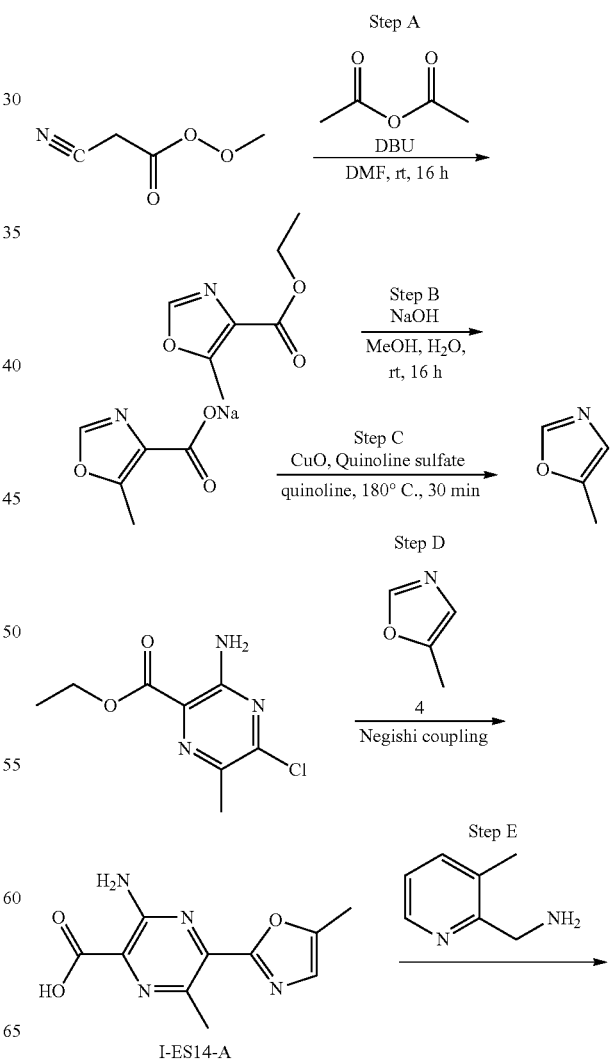

I-ES14-A

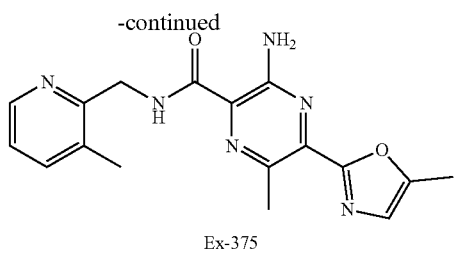

Ex-375

Step A: Ethyl 2-amino-2-cyanoacetate

A mixture of methyl 2-cyanoethaneperoxoate (3.0 g, 26 mmol) and 1,8-diazabicyclo[5.4.0]undec-7-ene (7.9 ml, 52 mmol) in DMF (13 ml) was stirred at room temperature for 30 minutes. Acetic anhydride (5.32 g, 52.1 mmol) was added and the mixture was stirred at room temperature for additional 18 hours. The organic solvent was evaporated under reduced pressure, and the residue was poured into 150 mL of water. Water layer was extracted with ethyl acetate (150 mL×3). The organic layers were combined and dried over $Na_2SO_4$, filtered, and the organic solvent was evaporated from the resulting solution under reduced pressure. The product was distilled from the residue at 120° C. with oil pump to give ethyl 5-methyloxazole-4-carboxylate as an oil. LC/MS=157 [M+1].

Step B: Sodium 5-methyloxazole-4-carboxylate

A mixture of ethyl 5-methyloxazole-4-carboxylate (2.3 g, 14.8 mmol) and NaOH (0.59 g, 14.8 mmol) in MeOH (10 ml) and water (0.5 ml) was stirred at room temperature for 18 hours. The mixture was concentrated under reduced pressure and the residue thus obtained was washed with diethyl ether (30 mL), and dried in vacuum to give sodium 5-methyloxazole-4-carboxylate as a solid. LC/MS=128 [M+1].

Step C: 5-Methyloxazole

A mixture of sodium 5-methyloxazole-4-carboxylate (2.4 g, 16.1 mmol), $Cu_2O$ (0.230 g, 1.6 mmol) and quinolone sulphate (2.2 g, 9.7 mmol) in quinoline (2 ml) was stirred at 200° C. for 1 hour. The product was distilled at 150° C. to give 5-methyloxazole as a liquid. $^1$HNMR ($CDCl_3$, 400 MHz) δ 7.75 (s, 1H), 6.75 (s, 1H).

Step D: 3-Amino-6-methyl-5-(5-methyloxazol-2-yl) pyrazine-2-carboxylic acid

To a pre-dried 100 mL 3-neck flask was added a mixture of 5-methyloxazole (200 mg, 2.407 mmol) in THF (20 ml). The mixture was stirred at −78° C. for 15 min and then n-BuLi (1.16 ml, 2.89 mmol) was added dropwise. The mixture was stirred at −78° C. for 1 hours. $ZnCl_2$ (656 mg, 4.81 mmol) in THF (6 ml) was added and the mixture was stirred at −78° C. for 10 min. The mixture was warmed to room temperature and stirred for 1 hour followed by addition of Xphos second generation pre-catalyst (23 mg, 0.29 mmol) and ethyl 3-amino-5-chloro-6-methylpyrazine-2-carboxylate (42 mg, 1.9 mmol). The mixture was stirred at 85° C. under $N_2$ for 20 hours. The organic solvent was evaporated under reduced pressure. Aqueous 1M HCl (120 mL) was added and the water layer was extracted with dichloromethane (120 mL×5). The organic layers were combined, dried over $Na_2SO_4$, filtered and concentrated under reduced pressure. The residue was purified with Biotage Isolera One (acetonitrile/water (0.05% TFA)) to give 3-amino-6-methyl-5-(5-methyloxazol-2-yl)pyrazine-2-carboxylic acid as a solid. LC/MS=235 [M+1].

Step E: 3-Amino-6-methyl-5-(5-methyloxazol-2-yl)-N-((3-methylpyridin-2-yl)methyl)pyrazine-2-carboxamide (Ex-375)

Example compound Ex-375 was prepared from intermediate I-ES14-A and 2-methylamine-3-methyl-piperidine using the same procedure followed for the preparation of Example compound Ex-374. Ex-375 was characterized by LC/MS and proton NMR: LC/MS=339 [M+1]. The product was characterized by proton NMR: $^1$HMR ($CDCl_3$, 400 MHz) δ 9.37 (s, 1H), 8.48 (d, 1H), 7.56 (d, 1H), 7.24-7.21 (m, 1H), 7.00 (s, 1H), 4.74 (d, 2H), 2.86 (s, 3H), 2.47 (s, 3H), 2.43 (s, 3H).

Preparation of Example Compounds Ex-376 A, Ex-376 B, Ex-376 C and Ex-376 D

Example Compounds Ex-376A to Ex 376D, various isomers of 3-Amino-N-(5-fluoro-6,7-dihydro-5H-cyclopenta[b]pyridin-7-yl)-6-methyl-5-(oxazol-2-yl)pyrazine-2-carboxamide, were prepared in accordance with Scheme ES-15:

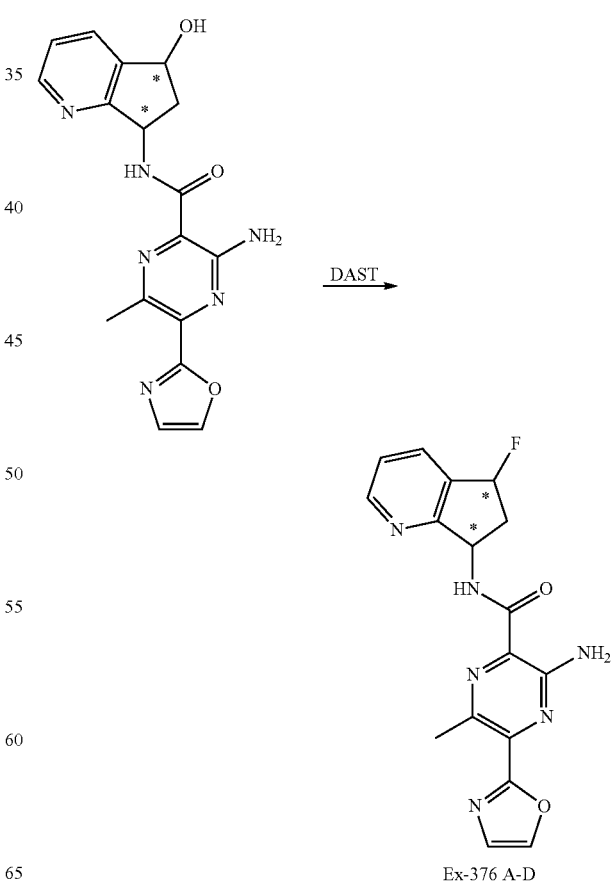

SCHEME ES-15

Ex-376 A-D

Preparation of 3-amino-N-(5-fluoro-6,7-dihydro-5H-cyclopenta[b]pyridin-7-yl)-6-methyl-5-(oxazol-2-yl)pyrazine-2-carboxamide 3-Amino-N-(5-hydroxy-6,7-dihydro-5H-cyclopenta[b]pyridin-7-yl)-6-methyl-5-(oxazol-2-yl)pyrazine-2-carboxamide was prepared from intermediate I-ES-14-A, prepared in accordance with Scheme ES-14, and 7-amino-6,7-dihydro-5H-cyclopenta[b]pyridin-5-ol following the procedure in Step E, above.

The 3-Amino-N-(5-hydroxy-6,7-dihydro-5H-cyclopenta[b]pyridin-7-yl)-6-methyl-5-(oxazol-2-yl)pyrazine-2-carboxamide thus prepared (230 mg, 0.65 mmol) was dissolved in anhydrous DCM (15 ml) and the solution cooled to −10° C. DAST (0.11 ml, 0.85 mmol) was added. Mixture was stirred at −10° C. for 20 minutes. Saturated $NH_4Cl$ solution was added to quench the reaction. Product was extracted with ethyl acetate (3×50 mL). The organic layers were combined, and dried over anhydrous sodium sulfate. The solution was filtered and concentrated, and the crude residue was purified by column chromatography on a 50 g-prepacked silica gel column, eluting with 10~70% gradient EtOAc/hexane to give two pairs of diastereomers.

The fast eluting pair of diastereomers was further separated by chiral SFC (AS-H column, 15% methanol (0.1% DEA)/$CO_2$) to afford isomer Ex-376A (faster eluting): LCMS: 355 [M+1], and isomer Ex-376B (slower eluting): LCMS: 355 [M+1].

The slow eluting pair of diastereomers was further separated by chiral SFC (OJ-H column, 20% methanol/$CO_2$) to afford isomer Ex-376C (faster eluting): LCMS: 355 [M+1], and isomer Ex-376D (slower eluting): LCMS: 355 [M+1].

Preparation of Example Compounds Ex-377 and Ex-378

Example Compounds Ex-377, 3-Amino-N-(6-fluoro-6,7-dihydro-5H-cyclopenta[b]pyridin-7-yl)-6-methyl-5-(oxazol-2-yl)pyrazine-2-carboxamide and Ex-378, 3-amino-N-(7H-cyclopenta[b]pyridin-7-yl)-6-methyl-5-(oxazol-2-yl)pyrazine-2-carboxamide were prepared in accordance with Scheme ES-16:

SCHEME ES-16

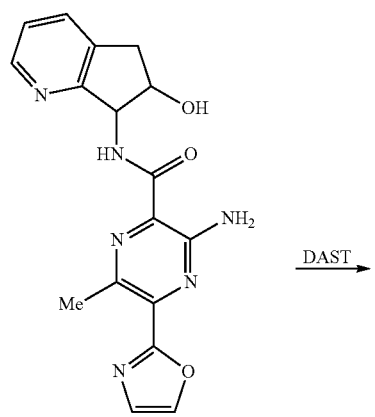

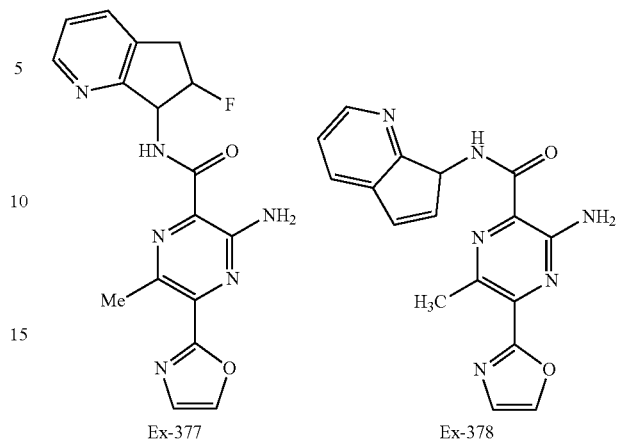

Ex-377    Ex-378

Accordingly, 3-Amino-N-(5-hydroxy-6,7-dihydro-5H-cyclopenta[b]pyridin-7-yl)-6-methyl-5-(oxazol-2-yl)pyrazine-2-carboxamide, prepared in accordance with the procedure described in Scheme ES-15. DAST (0.030 ml, 0.227 mmol) was added dropwise into a solution of 3-amino-N-(6-hydroxy-6,7-dihydro-5H-cyclopenta[b]pyridin-7-yl)-6-methyl-5-(oxazol-2-yl)pyrazine-2-carboxamide (0.040 g, 0.114 mmol) in $CH_2Cl_2$ (4.0 ml) at −78° C., followed by stirring for 1 h, then warming to ambient temperature with continued stirring for 2 additional hours at ambient temperature. The reaction mixture was treated with saturated aqueous $NaHCO_3$ solution (2 ml). The organic layer was separated and the aqueous layer extracted with $CH_2Cl_2$. Combined organic phase was dried over MgSO4, filtered, concentrated and purified on a silica-gel column with ISCO and 0-15% MeOH/CH2Cl2 to give the fluorinated product, Ex-377, as a solid (LC/MS=355 [M+1]), and a elemination product, Ex-378, as a solid (LC/MS=335 [M+1]).

Using the processes of Schemes ES-1 to ES-16, and appropriate carboxylate and amine precursor compounds, the compounds of Table IV were prepared. Where indicated in the table, enantiomeric forms present were separated via chiral HPLC. Absolute stereochemistry was not determined in all instances. Where identified in Table IV, absolute stereochemistry was determined using using super critical $CO_2$-chromatography (SCF chromatography). Isomers separated are labelled in Table 1 as "First", "Second", etc. as their order of elution from the column. The following conditions were employed (noted in Table IV as "Cond. 9" or "Cond. 10" in the column identifying the example:

Conditions 9: SCF/$CO_2$ with 15% methanol (1% DEA) running AS-H column;

Conditions 10: SCF/$CO_2$ with 20% methanol running OJ-H column.

TABLE IV

| Ex No. | Structure | IUPAC Name | [M + H]+ |
|---|---|---|---|
| Ex-379 | 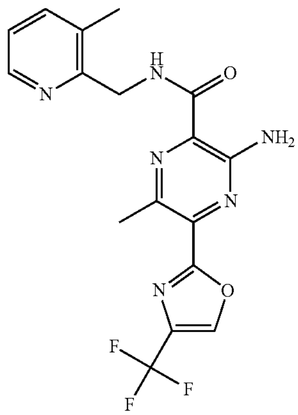 [SMILES: Cc1cccnc1CNC(=O)c1nc(C)c(-c2nc(C(F)(F)F)co2)nc1N] | 3-amino-6-methyl-N-[(3-methylpyridin-2-yl)methyl]-5-[4-(trifluoromethyl)-1,3-oxazol-2-yl]pyrazine-2-carboxamide | 393 |
| Ex-380 | 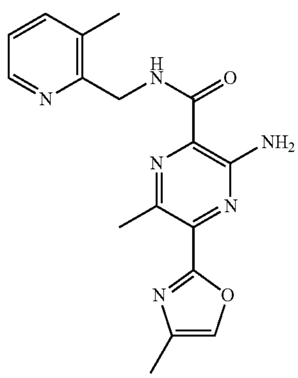 [SMILES: Cc1coc(-c2nc(N)c(C(=O)NCc3ncccc3C)nc2C)n1] | 3-amino-6-methyl-5-(4-methyl-1,3-oxazol-2-yl)-N-[(3-methylpyridin-2-yl)methyl]pyrazine-2-carboxamide | 339 |
| Ex-381 | 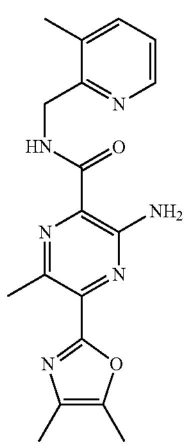 [SMILES: Cc1cccnc1CNC(=O)c1nc(C)c(-c2nc(C)c(C)o2)nc1N] | 3-amino-5-(4,5-dimethyl-1,3-oxazol-2-yl)-6-methyl-N-[(3-methylpyridin-2-yl)methyl]pyrazine-2-carboxamide | 353 |

TABLE IV-continued

| Ex No. | Structure | IUPAC Name | [M + H]+ |
| --- | --- | --- | --- |
| Ex-382 | 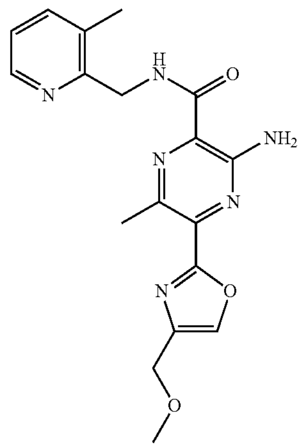 [SMILES: COCc1coc(-c2nc(N)c(C(=O)NCc3ncccc3C)nc2C)n1] | 3-amino-5-[4-(methoxymethyl)-1,3-oxazol-2-yl]-6-methyl-N-[(3-methylpyridin-2-yl)methyl]pyrazine-2-carboxamide | 369 |
| Ex-383 | 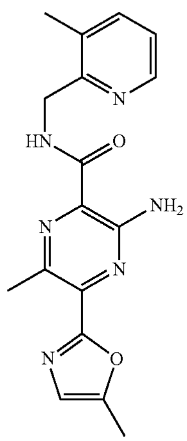 [SMILES: Cc1cnc(-c2nc(N)c(C(=O)NCc3ncccc3C)nc2C)o1] | 3-amino-6-methyl-5-(5-methyl-1,3-oxazol-2-yl)-N-[(3-methylpyridin-2-yl)methyl]pyrazine-2-carboxamide | 339 |
| Ex-384 | 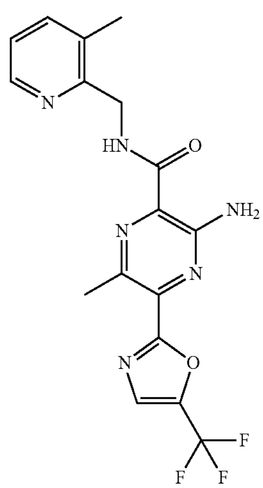 [SMILES: Cc1cccnc1CNC(=O)c1nc(C)c(-c2ncc(C(F)(F)F)o2)nc1N] | 3-amino-6-methyl-N-[(3-methylpyridin-2-yl)methyl]-5-[5-(trifluoromethyl)-1,3-oxazol-2-yl]pyrazine-2-carboxamide | 393 |
| Ex-385 | 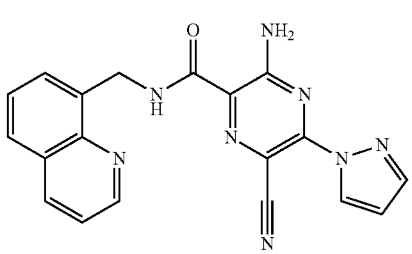 [SMILES: N#Cc1nc(C(=O)NCc2cccc3cccnc23)c(N)nc1-n1cccn1] | 3-amino-6-cyano-5-(1H-pyrazol-1-yl)-N-(quinolin-8-ylmethyl)pyrazine-2-carboxamide | 371 |

TABLE IV-continued

| Ex No. | Structure | IUPAC Name | [M + H]+ |
|---|---|---|---|
| Ex-386 | 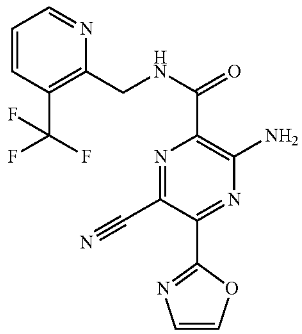 [SMILES: N#Cc1nc(C(=O)NCc2ncccc2C(F)(F)F)c(N)nc1-c1ncco1] | 3-amino-6-cyano-5-(1,3-oxazol-2-yl)-N-{[3-(trifluoromethyl)pyridin-2-yl]methyl}pyrazine-2-carboxamide | 390 |
| Ex-387 | 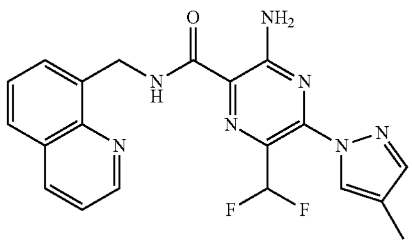 [SMILES: Cc1cnn(-c2nc(N)c(C(=O)NCc3cccc4cccnc34)nc2C(F)F)c1] | 3-amino-6-(difluoromethyl)-5-(4-methyl-1H-pyrazol-1-yl)-N-(quinolin-8-ylmethyl)pyrazine-2-carboxamide | 410 |
| Ex-388 | 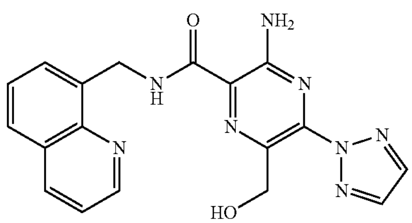 [SMILES: Nc1nc(-n2nccn2)c(CO)nc1C(=O)NCc1cccc2cccnc12] | 3-amino-6-(hydroxymethyl)-N-(quinolin-8-ylmethyl)-5-(2H-1,2,3-triazol-2-yl)pyrazine-2-carboxamide | 377 |
| Ex-389A Cond. 9 First | 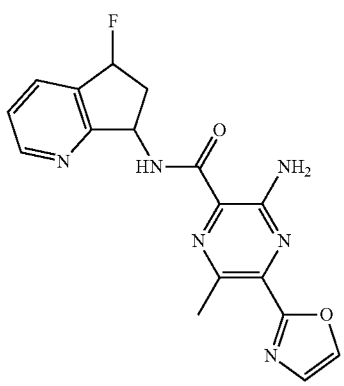 [SMILES: Cc1nc(C(=O)NC2CC(F)c3cccnc32)c(N)nc1-c1ncco1] | 3-amino-N-(5-fluoro-6,7-dihydro-5H-cyclopenta[b]pyridin-7-yl)-6-methyl-5-(1,3-oxazol-2-yl)pyrazine-2-carboxamide | 355 |
| Ex-389B Cond. 9 Second | 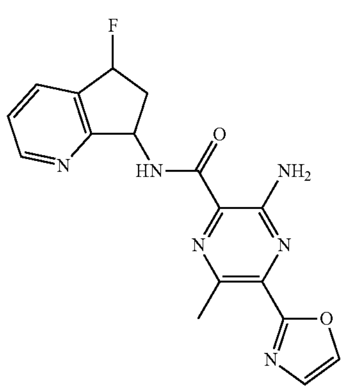 [SMILES: Cc1nc(C(=O)NC2CC(F)c3cccnc32)c(N)nc1-c1ncco1] | 3-amino-N-(5-fluoro-6,7-dihydro-5H-cyclopenta[b]pyridin-7-yl)-6-methyl-5-(1,3-oxazol-2-yl)pyrazine-2-carboxamide | 355 |

TABLE IV-continued

| Ex No. | Structure | IUPAC Name | [M + H]+ |
|---|---|---|---|
| Ex-389C Cond. 10 First | 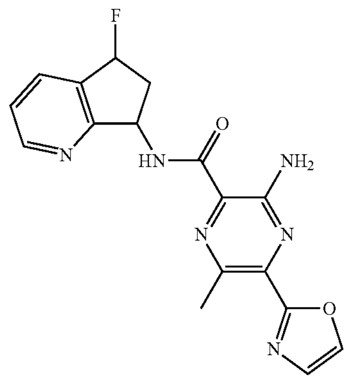 [SMILES: Cc1nc(C(=O)NC2CC(F)c3cccnc32)c(N)nc1-c1ncco1] | 3-amino-N-(5-fluoro-6,7-dihydro-5H-cyclopenta[b]pyridin-7-yl)-6-methyl-5-(1,3-oxazol-2-yl)pyrazine-2-carboxamide | 355 |
| Ex-389D Cond. 10 Second | 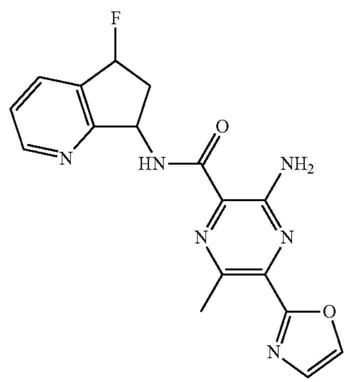 [SMILES: Cc1nc(C(=O)NC2CC(F)c3cccnc32)c(N)nc1-c1ncco1] | 3-amino-N-(5-fluoro-6,7-dihydro-5H-cyclopenta[b]pyridin-7-yl)-6-methyl-5-(1,3-oxazol-2-yl)pyrazine-2-carboxamide | 355 |
| Ex-393 | 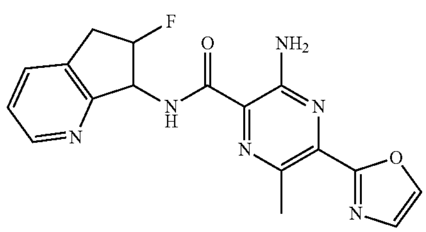 [SMILES: Cc1nc(C(=O)NC2c3ncccc3CC2F)c(N)nc1-c1ncco1] | 3-amino-N-(5-fluoro-6,7-dihydro-5H-cyclopenta[b]pyridin-7-yl)-6-methyl-5-(1,3-oxazol-2-yl)pyrazine-2-carboxamide | 355 |

In the following section are presented examples showing the preparation of suitable intermediate compounds which are useful in preparing compounds of the invention. It will be appreciated that the following description is not an exhaustive listing or the sole means for providing suitable intermediates. It will be appreciated that in addition to the methods presented herein, suitable intermediates may also be provided by adapting known means or may be commercially available.

3-Amino-6-methyl-5-(oxazol-2-yl)pyrazine-2-carboxylic acid (Intermediate A-1)

Scheme 1

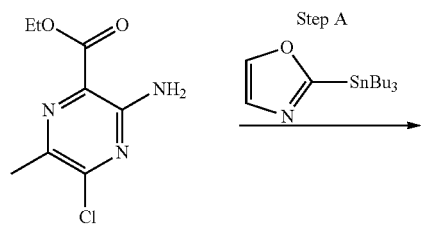

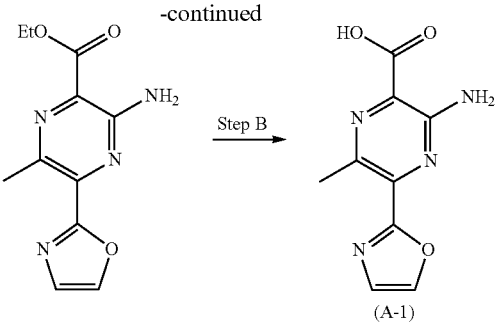

Step A: Ethyl 3-amino-6-methyl-5-(oxazol-2-yl)pyrazine-2-carboxylate

A microwave vial was charged with ethyl 3-amino-5-chloro-6-methylpyrazine-2-carboxylate (0.33 g, 1.5 mmol), tetrakis (0.18 g, 0.15 mmol), 2-(tributylstannyl)oxazole (0.49 ml, 2.2 mmol), capped, evacuated and flushed with nitrogen three times. While stirring, dioxane (8 ml) was added and sparged three additional times. The mixture was heated to 120° C. for 18 hours. Concentrated and purified by column chromatography on silica gel (40 g prepacked), eluting with gradient DCM/EtOAc to give ethyl 3-amino-6-methyl-5-(oxazol-2-yl)pyrazine-2-carboxylate as a solid. MS: 249 (M+1). The product was characterized by proton NMR: $^1$H-NMR (DMSO-d6, 400 MHz) δ 8.39 (s, 1H), 7.57 (s, 1H), 7.35 (s, 2H), 4.36 (t, 3H), 2.72 (s, 3H), 1.32 (t, 3H).

Step B: 3-Amino-6-methyl-5-(oxazol-2-yl)pyrazine-2-carboxylic acid

Ethyl 3-amino-6-methyl-5-(oxazol-2-yl)pyrazine-2-carboxylate (200 mg, 0.81 mmol) was suspended in a mixed solvent of water (2.7 mL), tetrahydrofuran (2.7 mL), and methanol (2.7 mL). Lithium hydroxide (82 mg, 3.40 mmol) was added. The mixture was then stirred for 30 minutes, at which point no more starting material was present. The mixture was acidified with 1M HCl solution. The precipitate was collected by filtration and dried in a vacuum oven overnight to afford 3-amino-6-methyl-5-(oxazol-2-yl)pyrazine-2-carboxylic acid. LC/MS=221 (M+1).

3-Amino-6-chloro-5-(oxazol-2-yl)pyrazine-2-carboxylic acid (Intermediate A-2)

Using the same procedure for intermediate A-1, 3-amino-6-chloro-5-(oxazol-2-yl)pyrazine-2-carboxylic acid (intermediate A-2) was prepared from methyl 3-amino-5,6-dichloro-pyrazine-2-carboxylate

3-Amino-6-methyl-5-(oxazol-5-yl)pyrazine-2-carboxylic acid (intermediate B-1)

Step A: Ethyl 3-amino-6-methyl-5-(oxazol-5-yl)pyrazine-2-carboxylate

Ethyl 3-amino-5-chloro-6-methylpyrazine-2-carboxylate (0.40 g, 1.86 mmol), 5-(4,4,5,5-tetramethyl-1,3,2-dioxaborolan-2-yl)oxazole (0.40 g, 2.04 mmol), bis(triphenylphosphine) palladium(II) dichloride (0.14 g, 0.20 mmol) and potassium carbonate (0.77 g, 5.56 mmol) were placed in a flask (100 mL) and exchanged air with nitrogen by vacuum-refilling for 3 times. Then, acetonitrile (20 ml) and water (5 ml) were added to the flask. The mixture was stirred at RT for 4 h, concentrated, taken up with EtOAc, washed with water (20 mL). The organic phase was separated and the aqueous was extracted with ethyl acetate (2×50 mL). The combined organic phase was washed with brine (50 mL), dried over MgSO$_4$, filtered and concentrated and purified by column chromatography on silica gel column with ISCO and 0-65% ethylacetate/hexane as eluant to give the title compound. LC/MS=249 (M+1).

Step B: 3-amino-6-methyl-5-(oxazol-5-yl)pyrazine-2-carboxylic acid

A mixture of ethyl-3-amino-6-methyl-5-(oxazol-5-yl)pyrazine-2-carboxylate (0.32 g, 1.29 mmol) and lithium hydroxide (0.15 g, 6.45 mmol) in THF (4 ml) and water (1 ml) was stirred at RT for 2 hours. The solvents were removed by rotary evaporator. The residue was diluted with water (15 mL) and acidified with 1.0 M HCl aqueous solution (6.5 mL) to precipitate the product. The solid was collected by filtration, washed with water (5 mL), dried in the oven to give the title compound. LC/MS=221 (M+1).

3-Amino-6-methyl-5-(2H-1,2,3-triazol-2-yl)pyrazine-2-carboxylic acid (C-1) and 3-amino-6-methyl-5-(1H-1,2,3-triazol-1-yl)pyrazine-2-carboxylic acid (D-1)

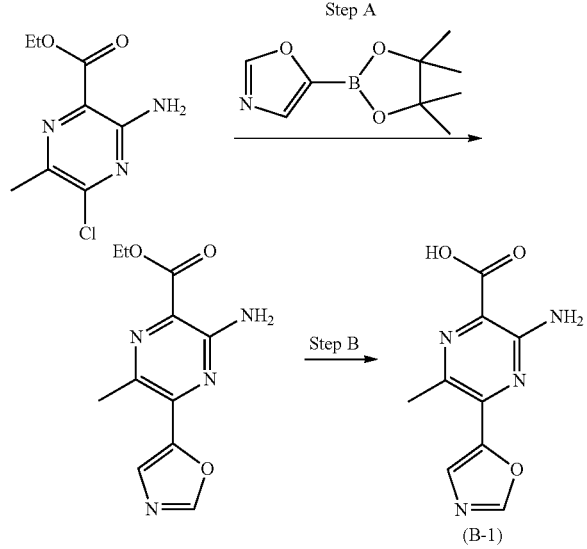

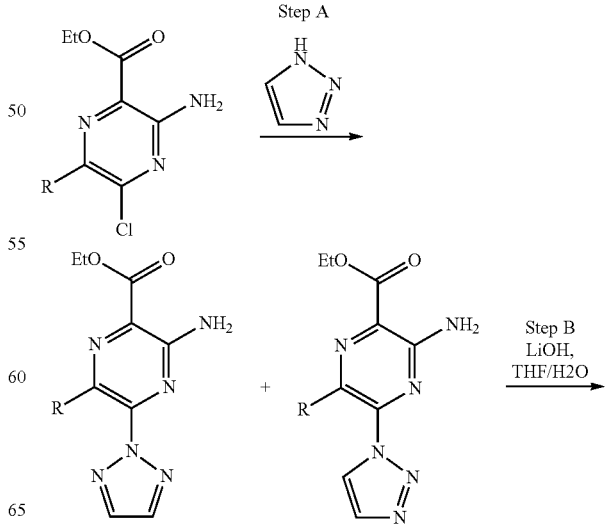

-continued

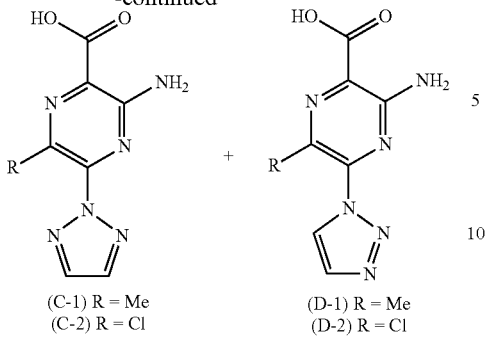

(C-1) R = Me
(C-2) R = Cl (D-1) R = Me
(D-2) R = Cl

Step A: Ethyl 3-amino-6-methyl-5-(2H-1,2,3-triazol-2-yl)pyrazine-2-carboxylate, and ethyl 3-amino-6-methyl-5-(1H-1,2,3-triazol-1-yl)pyrazine-2-carboxylate Ethyl 3-amino-5-chloro-6-methylpyrazine-2-carboxylate (2.2 g, 10 mmol) and 1,2,3-triazole (1.0 g, 15 mmol) were dissolved in dry DMF (20 mL) and the solution was cooled in an ice-water bath. KOH powder was added to the solution, ice-water bath was then removed. The resulting mixture was stirred at RT overnight, then poured into 100 ml of water. The mixture was stirred at room temperature for 30 min. Precipitate was collected by filtration and washed with water. The aqueous layer was extracted with EtOH/CH$_2$Cl$_2$ (3:1, 3×50 mL), then dried over MgSO$_4$, filtered, and concentrated. The combined product was dried in a vacuum oven to give products (mixture of two isomers). LCMS: 249 (M+1).

Step B: 3-Amino-6-methyl-5-(2H-1,2,3-triazol-2-yl)pyrazine-2-carboxylic acid and 3-amino-6-methyl-5-(1H-1,2,3-triazol-1-yl)pyrazine-2-carboxylic acid The ester mixture of methyl 3-amino-6-methyl-5-(2H-1,2,3-triazol-2-yl)pyrazine-2-carboxylate and methyl-3-amino-6-methyl-5-(2H-1,2,3-triazol-2-yl)pyrazine-2-carboxylate (1.8 g, 3.6 mmol) in a mixed solvent of THF (20 mL) and water (5 mL) was stirred with LiOH (170 mg, 7.3 mmol) at room temperature for 2 hours. Water (25 mL) was added. HCl solution (1N, 7.3 mL) was used to acidified the solution. The precipitate was collected by filtration and washed with water, then dried in oven overnight to give the products (mixture of two isomers). LCMS: 221 (M+1).

3-Amino-6-chloro-5-(2H-1,2,3-triazol-2-yl)pyrazine-2-carboxylic acid (C-2) and 3-amino-6-chloro-5-(1H-1,2,3-triazol-1-yl)pyrazine-2-carboxylic acid (D-2)

Using the same procedure for intermediates C-1 and D-1, 3-amino-6-chloro-5-(2H-1,2,3-triazol-2-yl)pyrazine-2-carboxylic acid (C-2) and 3-amino-6-chloro-5-(1H-1,2,3-triazol-1-yl)pyrazine-2-carboxylic acid (D-2) were prepared from methyl-3-amino-5,6-dichloro-pyrazine-2-carboxylate.

Using the same procedure, intermediates E-G were similarly obtained with pyrazole, methyl pyrazole, or 1,2,4-triazole.

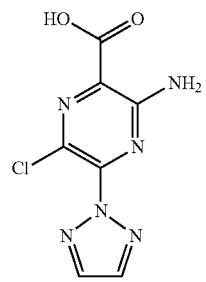

(C-2)

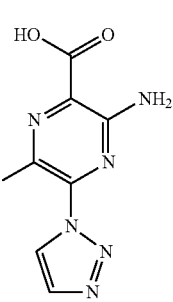

(D-2)

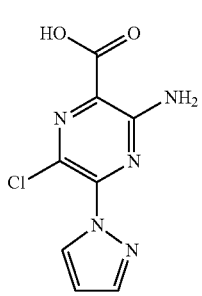

(E)

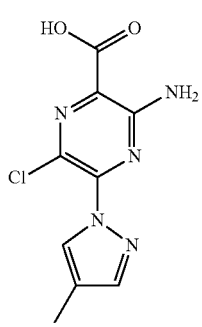

(F)

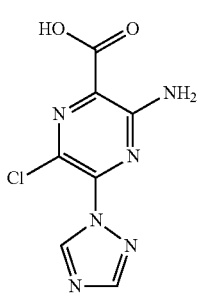

(G)

Syntheses of Amine Intermediates

The amine intermediates (AI) that are not commercially available were synthesized using the following procedures.

AI-1. (4-Cyclopropyl-1-methyl-1H-pyrazol-3-yl)methanamine

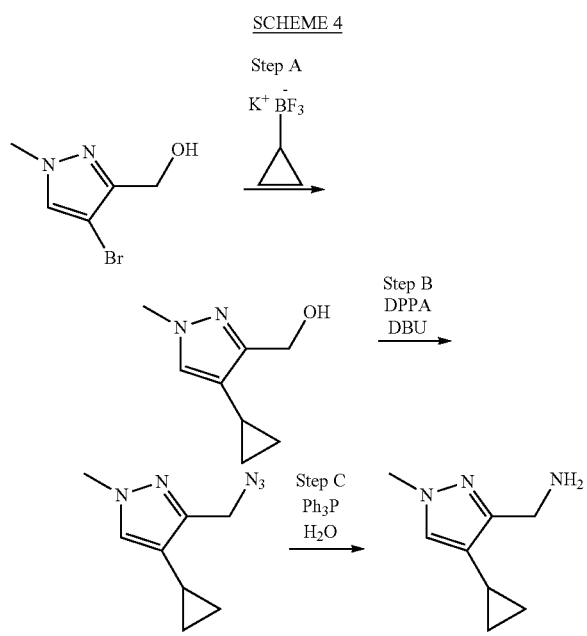

Step A: (4-Cyclopropyl-1-methyl-1H-pyrazol-3-yl)methanol (4-Bromo-1-methyl-1H-pyrazol-3-yl)methanol (900 mg, 4.71 mmol), potassium cyclopropyltrifluoroborate (1400 mg, 9.4 mmol), K$_2$CO$_3$ (3900 mg, 28 mmol), and 2nd generation XPhos precatalyst (370 mg, 0.47 mmol) were mixed in a microwave reaction vial. The vial was capped, and air was removed by vacuum then back filled with nitrogen (×3). Toluene (16 ml) and water (4 ml) were introduced with a syringe. Air was removed and back filled with nitrogen (×3). Mixture was heated to 70° C. for 15 hours. The mixture was diluted with EtOAc, and washed with water and brine. After dried over anhydrous sodium sulfate, the organic layer was concentrated, and the crude was purified by column chromatography on a 50 g prepacked silica gel column, eluting with 0~100% gradient EtOAc/hexane to give the product as an oil. MS: 153 [M+1]

Step B: 3-(Azidomethyl)-4-cyclopropyl-1-methyl-1H-pyrazole

Diphenylphosphoryl azide (180 mg, 0.66 mmol) and DBU (0.1 ml, 0.66 mmol) were added to a solution of (4-cyclopropyl-1-methyl-1H-pyrazol-3-yl)methanol (100 mg, 0.66 mmol) in DCM (1 ml). Mixture was stirred at 50° C. for 5 h, then at room temperature overnight. Mixture was diluted with DCM, washed with saturated sodium bicarbonate, then 5% HCl solution. The organic layer was dried over anhydrous sodium sulfate. After filtered and concentrated, the crude was purified by column chromatography on a 20 g prepacked silica gel column, eluting with gradient 0~40% EtOAc/hexane to give the product as an oil, after concentrated.

Step C: (4-Cyclopropyl-1-methyl-1H-pyrazol-3-yl)methanamine 3-(Azidomethyl)-4-cyclopropyl-1-methyl-1H-pyrazole (95 mg, 0.54 mmol) in THF (1.5 ml) was mixed Ph$_3$P (170 mg, 0.64 mmol). After 30 minutes, water (0.3 ml, 16 mmol) was added. Mixture was stirred at room temperature overnight. Mixture was concentrated to dryness. The crude mixture was used in the next step without further treatment.

AI-2. (3-cyclopropyl-5-fluoropyridin-2-yl)methanamine hydrochloride

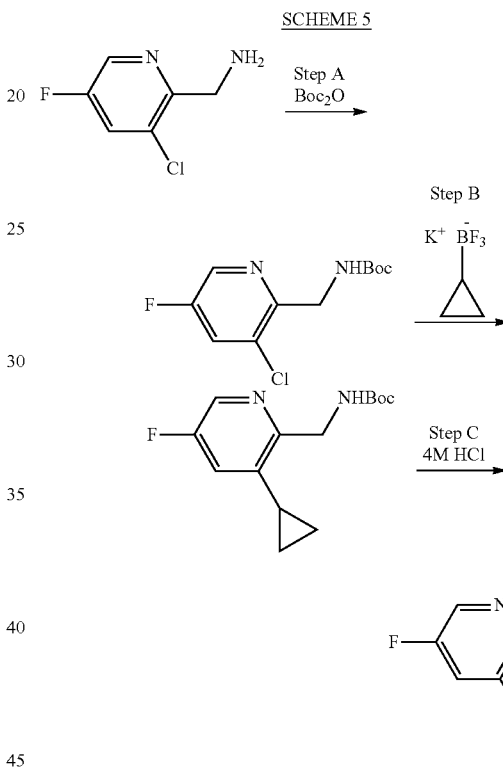

Step A: tert-Butyl ((3-chloro-5-fluoropyridin-2-yl)methyl)carbamate (3-Chloro-5-fluoropyridin-2-yl)methanamine (1000 mg, 6.2 mmol), (Boc)$_2$C (1.7 ml, 7.5 mmol), and Hunig's base (1.3 ml, 7.5 mmol) were mixed in CH$_2$Cl$_2$ (15 ml), and stirred at room temperature for 15 hours. Mixture was diluted with CH$_2$Cl$_2$, and washed with water. The organic layer was separated, dried over anhydrous sodium sulfate, and concentrated. The residue was purified by column chromatography on a 50 g prepacked silica gel column, eluting with 0~50% gradient EtOAc/hexane to give the product as an oil.

Step B: tert-Butyl ((3-cyclopropyl-5-fluoropyridin-2-yl)methyl)carbamate tert-Butyl ((3-chloro-5-fluoropyridin-2-yl)methyl)carbamate (200 mg, 0.77 mmol), potassium cyclopropyltrifluoroborate (180 mg, 1.2 mmol), K$_2$CO$_3$ (530 mg, 3.8 mmol), and 2nd generation XPhos precatalyst (60 mg, 0.077 mmol) were mixed in a microwave reaction vial. The vial was capped, and air was removed by vacuum then back filled with nitrogen (×3). Toluene (3.0 ml) and water (0.7 ml) were introduced with a syringe. Air was removed and back filled with nitrogen (×3). Mixture was heated to 70° C. for 15 hours. Mixture was diluted with ethyl acetate, and washed with water and brine. After dried over anhydrous sodium sulfate, the solution was concentrated, the crude was purified by column chromatography on a 50 g prepacked silica gel column, eluting with 0-50% gradient EtOAc/hexane to give the product as an oil. LCMS: 267 [M+1]

Step C:
(3-cyclopropyl-5-fluoropyridin-2-yl)methanamine hydrochloride tert-Butyl ((3-cyclopropyl-5-fluoropyridin-2-yl)methyl)carbamate (170 mg, 0.64 mmol) in a solution of 4M HCl in dioxane (5 ml, 20.00 mmol) was stirred at 25° C. for 5 hours. Mixture was then concentrated to dryness to give the product as HCl salt. Product was used in the next step without further treatment.

AI-3. 6,7-Dihydro-5H-cyclopenta[b]pyridin-7-amine, 2HCl

SCHEME 6

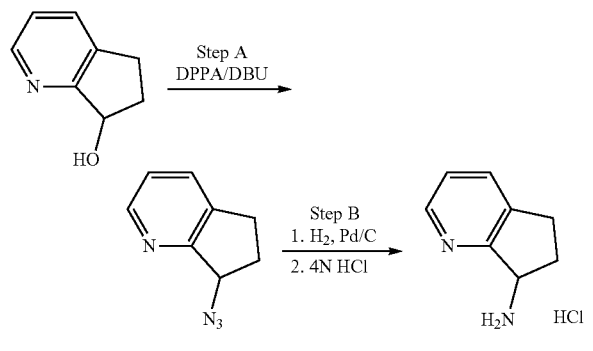

Step A: 7-Azido-6,7-dihydro-5H-cyclopenta[b]pyridine

Diphenylphosphoryl azide (2400 mg, 8.9 mmol) and DBU (1.3 ml, 8.9 mmol) were added to a solution of 6,7-dihydro-5H-cyclopenta[b]pyridin-7-ol (1000 mg, 7.4 mmol) in toluene (12 ml). Mixture was stirred at room temperature for 3 days. Mixture was diluted with EtOAc, and washed with water and brine. The organic layer was dried over anhydrous sodium sulfate, and concentrated. The crude was purified by column chromatography on a 50 g-prepacked silica gel column, eluting with 0~30% EtOAc/hexane to give the product as a colorless oil.

Step B: 6,7-Dihydro-5H-cyclopenta[b]pyridin-7-amine, 2HCl

7-Aazido-6,7-dihydro-5H-cyclopenta[b]pyridine (500 mg, 3.12 mmol) in MeOH (30 ml) was mixed with HCl (4M in dioxane, 3 ml, 12 mmol) and 10% Pd—C (170 mg). Mixture was degassed, then stirred under balloon hydrogen at room temperature overnight. Mixture was filtered, and the solution was concentrated to dryness to give the HCl salt of the product as a solid.

AI-4. 6,7-Dihydro-5H-cyclopenta[b]pyridin-7-amine, 2HCl

SCHEME 7

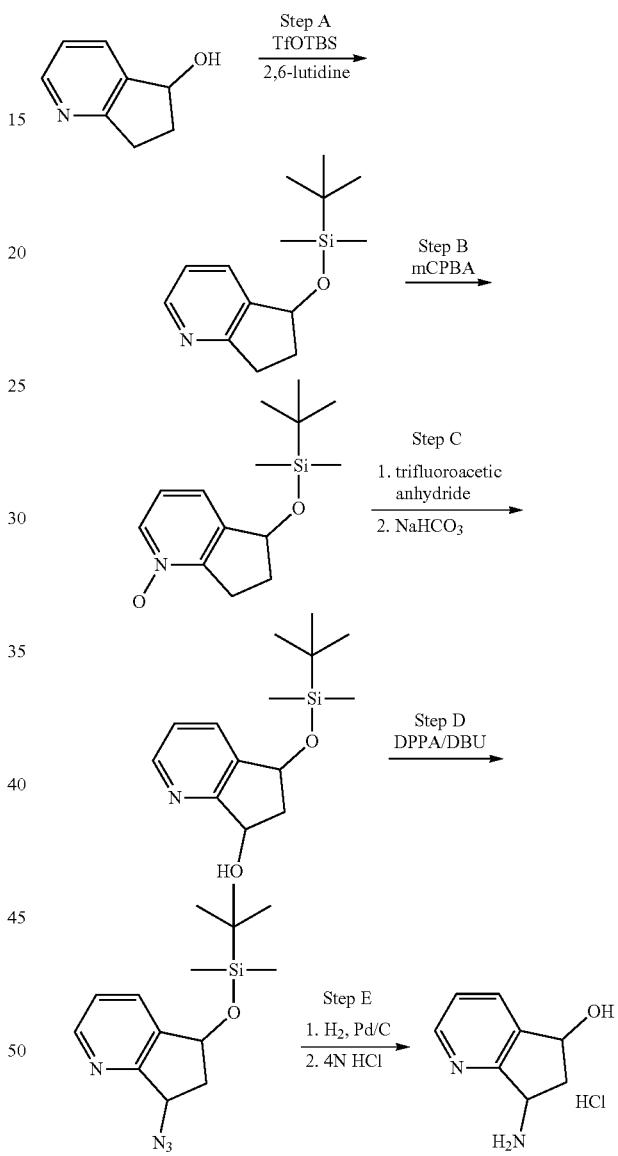

Step A: 5-((tert-Butyldimethylsilyl)oxy)-6,7-dihydro-5H-cyclopenta[b]pyridine 6,7-Dihydro-5H-cyclopenta[b]pyridin-5-ol (2800 mg, 21 mmol) in THF (70 ml) was cooled in an ice-water bath. 2,6-lutidine (3.2 ml, 27.0 mmol), then tert-butyldimethylsilyl trifluoromethanesulfonate (5.3 ml, 23 mmol) was then added dropwise. Mixture was stirred overnight while the temperature slowly warm to room temperature. THF was removed by rotavapor. The residue was diluted with ethyl acetate, and washed with water twice to remove most lutidine, then washed with brine. After dried over anhydrous sodium sulfate, and concentrated, the crude was purified by flash chromatography on a 100 g-size prepacked silica gel column, eluting with gradient 0~30% EtOAc/hexane to give the product as a colorless oil.

Step B: 5-((tert-butyldimethylsilyl)oxy)-6,7-dihydro-5H-cyclopenta[b]pyridine 1-oxide 5-((tert-Butyldimethylsilyl)oxy)-6,7-dihydro-5H-cyclopenta[b]pyridine (4400 mg, 18 mmol) in DCM (50 ml) was mixed with mCPBA (75%, 4100 mg, 18 mmol), then stirred overnight at room temperature. Mixture was diluted with DCM, washed with saturated sodium bicarbonate. After dried over anhydrous sodium sulfate, and concentrated, the crude was purified by column chromatography on 100 g prepacked silica gel column, eluting first with 10~65% EtOAc/isohexane, then 0~8% MeOH/DCM to give the product as a solid after concentrated and dried in vacuum oven overnight. LCMS: 266 [M+1]

Step C: 5-((tert-Butyldimethylsilyl)oxy)-6,7-dihydro-5H-cyclopenta[b]pyridin-7-ol 5-((tert-Butyldimethylsilyl)oxy)-6,7-dihydro-5H-cyclopenta[b]pyridine 1-oxide (4.5 g, 17 mmol) in DCM (80 ml) was cooled in an ice-water bath. TFAA (7.2 ml, 51 mmol) in DCM (15 ml) was added dropwise, then stirred overnight while the temperature slowly warm up to room temperature. Toluene was added, mixture was then concentrated to remove most TFAA and TFA. Residue was diluted with 5 mL of MeOH and 5 mL of water. Saturated sodium bicarbonate solution was added to adjust pH to 8. Product was extracted with DCM (3×100 mL). The combined DCM solution was dried over anhydrous sodium sulfate. After filtered and concentrated, the crude was purified by column chromatography on a 50 g-prepacked silica gel column, eluting with 0~5% MeOH/DCM to give the product as a solid after concentrated and dried in vacuum ocen overnight. LC/MS: 266 [M+1]

Step D: 7-Azido-5-((tert-butyldimethylsilyl)oxy)-6,7-dihydro-5H-cyclopenta[b]pyridine 5-((tert-Butyldimethylsilyl)oxy)-6,7-dihydro-5H-cyclopenta[b]pyridin-7-ol (4.7 g, 18 mmol) in toluene (30 ml) was cooled in an ice-water bath. DBU (3.2 ml, 21 mmol), then diphenylphosphoryl azide (5.8 g, 21 mmol) was added. Mixture was stirred in an ice-water bath for 2 hours, then was heated at 50° C. for 2 days. Reaction mixture was diluted with ethyl acetate, washed with water. After dried over anhydrous sodium sulfate, the solution was concentrated, and the crude was purified by column chromatography on a 100 g-prepacked silica gel column, eluting with 0~20% gradient EtOAc/hexane to give a racemic mixture of the product. LCMS: 291 [M+1]

Step E: 7-amino-6,7-dihydro-5H-cyclopenta[b]pyridin-5-ol hydrochloride

7-Aazido-5-((tert-butyldimethylsilyl)oxy)-6,7-dihydro-5H-cyclopenta[b]pyridine (2.5 g, 8.6 mmol) in MeOH (50 ml) was mixed with Pd—C, 10% (0.46 g, 0.43 mmol). Mixture was stirred at room temperature under balloon hydrogen for 1 hour. Mixture was filtered. The solution was treated with 4M HCl in dioxane (5.5 ml, 22 mmol) over-night. Mixture was concentrated, and dried in vacuum oven at 50° C. for 2 days to give the product as an HCl salt. LCMS: 151 [M+1]

AI-5. 7-Amino-6,7-dihydro-5H-cyclopenta[b]pyridin-6-ol hydrochloride

SCHEME 8

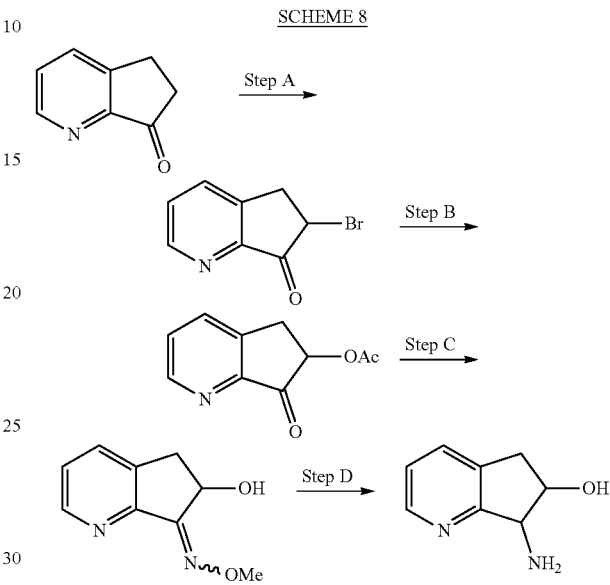

Step A: 6-bromo-5H-cyclopenta[b]pyridin-7(6H)-one

Br$_2$ (0.35 ml, 6.76 mmol) was added dropwise to a solution of 5H-cyclopenta[b]pyridin-7(6H)-one (1.00 g, 7.51 mmol) in HBr (3.0 ml, 55.20 mmol) and AcOH (7 ml) at 10° C., followed by stirring at RT for 1 h. The precipitate was filtered and washed with acetic acid. The solid was taken up with EtOAc/CH2Cl2 (1:2) and the resulting solution was neutralized with saturated NaHCO3 aq. Solution. The organic phase was separated and the aqueous was extracted with CH2Cl2/EtOAc (2:1). The combined organic phase was washed with brine, separated, dried over MgSO4, filtered and concentrated and dried in vacuum to give title compound as a solid. LC/MS=213 [M+1].

Step B: 7-oxo-6,7-dihydro-5H-cyclopenta[b]pyridin-6-yl acetate

A mixture of potassium acetate (0.42 g, 4.24 mmol) and 6-bromo-5H-cyclopenta[b]pyridin-7(6H)-one (0.45 g, 2.12 mmol) in CH3CN (15 ml) was stirred at RT for 24 h. The solvent was removed and the residue was taken up in CH2Cl2 and washed with water. The organic phase was separated and the aqueous was extracted with CH2Cl2. The combined organic phase was dried over MgSO4, filtered, concentrated and purified on a silica-gel column with 0-30% EtOAc/CH2Cl2 to give the title compound as an oil. LC/MS=192 [M+1].

Step C: (E)/(Z)-6-hydroxy-5H-cyclopenta[b]pyridin-7(6H)-one O-methyl oxime

A mixture of 7-oxo-6,7-dihydro-5H-cyclopenta[b]pyridin-6-yl acetate (0.25 g, 1.31 mmol), O-methyl oxime hydrochloride (0.22 g, 2.62 mmol) and Hunig's base (0.46 ml, 2.62 mmol) in EtOH (10 ml) was stirred at RT for 5 h. The mixture was concentrated to give crude intermediate (Z)-7-(methoxyimino)-6,7-dihydro-5H-cyclopenta[b]pyridin-6-yl acetate. The residue was taken up in MeOH (10.0 ml). Then, Na₂CO₃ (0.55 g, 5.23 mmol) and H₂O (0.25 ml) was added, followed by stirring at RT for 4 h. Removed solvent and the residue was taken up in CH2Cl2, washed with brine. The organic phase was dried over MgSO4, filtered, concentrated and purified on a silica-gel column with 0-70% EtOAc/CH2Cl2 to give the title compound as a solid. LC/MS=179 [M+1].

Step D: 7-amino-6,7-dihydro-5H-cyclopenta[b]pyridin-6-ol hydrochloride

BH₃.THF (2.19 ml, 2.19 mmol) in THF was added dropwise into a solution of (E)/(Z)-6-hydroxy-5H-cyclopenta[b]pyridin-7(6H)-one O-methyl oxime (0.13 g, 0.73 mmol) in THF (5 ml) at RT, followed by refluxing for 3 h. After cooling down, water (0.5 mL) was carefully added, followed by addition of 20% KOH aq. (2 ml) and heating at 70° C. for 4 h. Then, the reaction mixture was cooled down to 0° C., to it was added BOC-anhydride (0.34 ml, 1.46 mmol), followed by stirring at RT for 3 h, diluted with DCM, washed with brine. The organic phase was separated and the aqueous was extracted with DCM. The combined organic phase was dried over MgSO4, filtered, concentrated and purified on a silica-gel column with 0-80% EtOAc/DCM to give tert-butyl (6-hydroxy-6,7-dihydro-5H-cyclopenta[b]pyridin-7-yl)carbamate. This intermediate was then dissolved in DCM and treated with 1 mL of 4N HCl in dioxane, followed by stirring at RT for 3 h. Remove solvent and dried in vacuum to give the title compound as a solid. LC/MS=151 [M+1].

AI-9. Isoquinolin-8-ylmethanamine

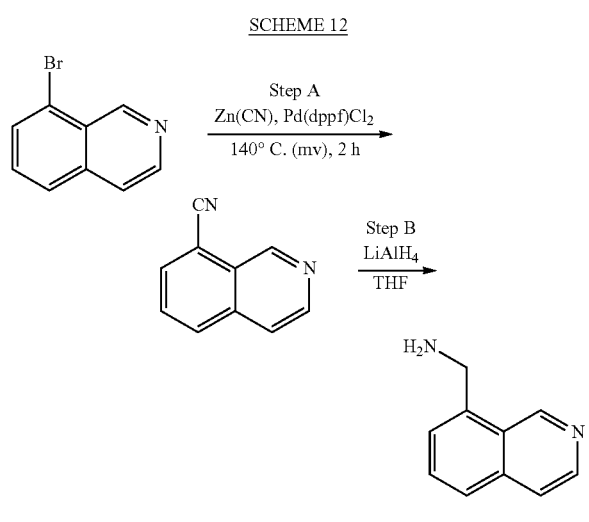

SCHEME 12

Step A: Isoquinoline-8-carbonitrile

A mixture of 8-bromoisoquinoline (440 mg, 2.14 mmol), Zn(CN)₂ (500 mg, 4.27 mmol) and Pd(dppa)Cl₂ (784 mg, 1.07 mmol) and DMF (5 mL) in a capped microwave reaction vial was heated at 140° C. for 5 hours. The reaction mixture was filtered through Celite, washed with water (20 mL), and extracted with EtOAc (3×20 mL). The combined organic layers were washed with brine (10 mL), dried over Na₂SO₄, and concentrated to give a residue which was purified with column chromatography on a silica gel with EtOAc/hexane (2/1) to give isoquinoline-8-carbonitrile as a solid. LC/MS=155 [M+1].

Step B: Isoquinolin-8-ylmethanamine

A solution of isoquinoline-8-carbonitrile (210 mg, 1.36 mmol) in anhydrous THF (10 mL) was added dropwise to a slurry of LiAlH₄ (103 mg, 2.72 mmol) in anhydrous THF (5 mL) at 0° C. under nitrogen atmosphere. Upon completion of the addition, the cooling bath was removed and the mixture was stirred at ambient temperature for 2 hours. The reaction was quenched with Na₂SO₄.10H₂O (0.5 g), and then filtered. The filtrate was concentrated to give isoquinolin-8-ylmethanamine as an oil, which was used in the next step without further purification. LC/MS=159 [M+1].

AI-10.
(4-(Trifluoromethyl)pyridin-2-yl)methanamine

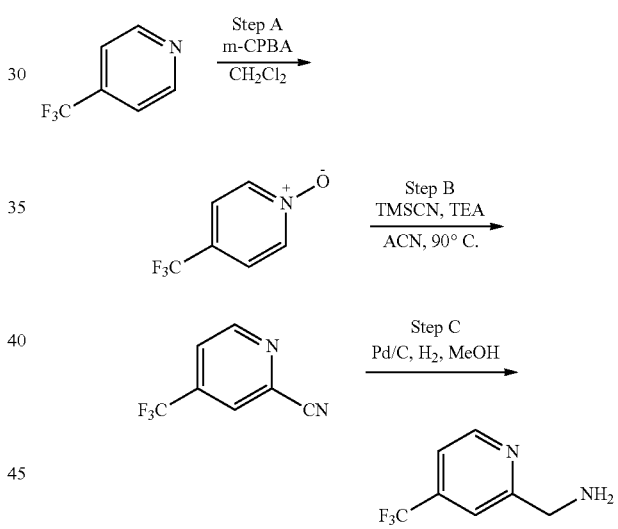

Step A: 4-(Trifluoromethyl)pyridine 1-oxide

To the solution of 4-(trifluoromethyl)pyridine (1.0 g, 6.8 mmol) in dichloromethane (50 mL) was added 3-chlorobenzoperoxoic acid (3.5 g, 20.4 mmol). The mixture was stirred at room temperature for overnight. The mixture was basified with 2N NaOH until pH to 8. The mixture was washed with saturated aqueous Na₂CO₃ solution (40 mL) followed by extraction with DCM (3×40 mL). The combined organic layers were dried over Na₂SO₄ and then concentrated to give 4-(trifluoromethyl)pyridine 1-oxide a solid. LC/MS=164 [M+1].

Step B: 4-(Trifluoromethyl)picolinonitrile

A solution of 4-(trifluoromethyl)pyridine 1-oxide (970 mg, 5.91 mmol), TMSCN (1.5 g, 14.78 mmol), and TEA (3.3 mL, 23.64 mmol) in acetonitrile (15 mL) was stirred at 90° C. for overnight. After cooling to room temperature, the reaction mixture was concentrated to give a crude product which was purified using prep-HPLC eluting with a gradient of 5/95 to 95/5 acetonitrile/water (containing 0.05% NH₄HCO₃) to afford 4-(trifluoromethyl)picolinonitrile as a solid. LC/MS=173 [M+1].

Step C: (4-(Trifluoromethyl)pyridin-2-yl)methanamine

A mixture of 4-(trifluoromethyl)picolinonitrile (840 mg, 4.88 mmol) and 10% Pd/C (168 mg, 0.16 mmol) was stirred under hydrogen (balloon) in MeOH (10 mL) at ambient temperature for overnight. The reaction mixture was filtered through Celite and concentrated to afford (4-(trifluoromethyl)pyridin-2-yl)methanamine as an oil. LC/MS=177 [M+1].

AI-11. 3-Cyclopropylpyrazin-2-yl)methanamine

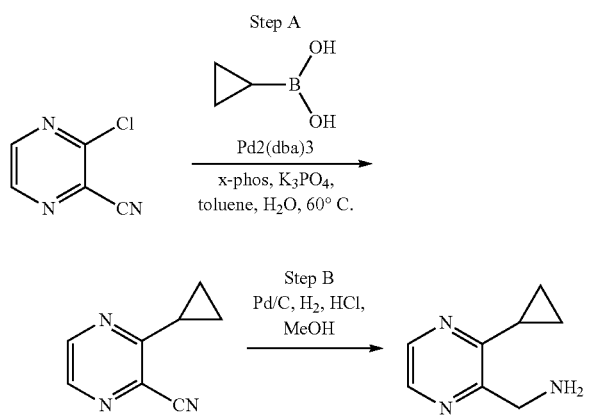

Step A: 3-cyclopropylpyrazine-2-carbonitrile

A mixture of 3-chloropyrazine-2-carbonitrile (556 mg, 4 mmol), cyclopropylboronic acid (688 mg, 8 mmol), Pd₂(dba)₃ (732 mg, 0.8 mmol), X-Phos (763 mg, 1.6 mmol) and K₃PO₄.H₂O (3.2 g, 12 mmol) in toluene (10 mL) was heated in a sealed tube at 60° C. for overnight. After cooling to room temperature, the reaction mixture was filtered and concentrated to give a crude product which was purified by column chromatography on a silica gel with EtOAc/hexane (1/1) to give 3-cyclopropylpyrazine-2-carbonitrile as a solid. LC/MS=146 [M+1].

Step B: 3-Cyclopropylpyrazin-2-yl)methanamine

A mixture of 3-cyclopropylpyrazine-2-carbonitrile (280 mg, 1.93 mmol) and 10% Pd/C (84 mg, 0.08 mmol) was stirred under hydrogen in HCl/MeOH (0.1 mL/5 mL) at ambient temperature for overnight. The reaction mixture was filtered through a Celitepad and concentrated to afford the HCl salt of (3-cyclopropylpyrazin-2-yl)methanamine as an oil. LC/MS=150 [M+1].

AI-12. (5-Methylpyrimidin-2-yl)methanamine

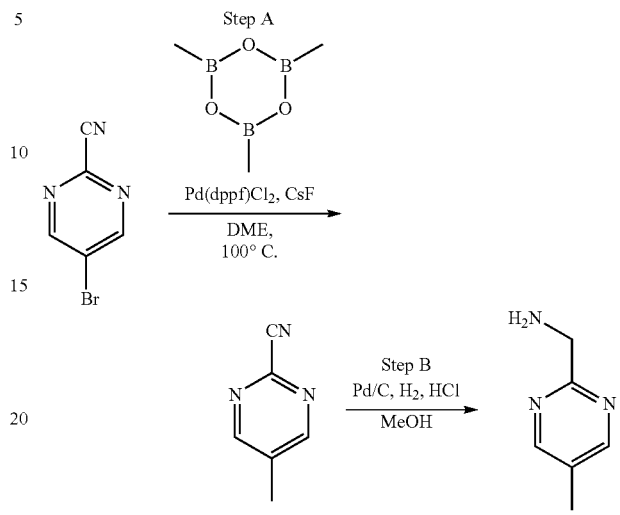

Step A: 5-Methylpyrimidine-2-carbonitrile

A mixture of 5-bromopyrimidine-2-carbonitrile (800 mg, 4.37 mmol), 2,4,6-trimethyl-1,3,5,2,4,6-trioxatriborinane (1.1 g, 8.74 mmol), Pd(dppf)Cl₂ (639 mg, 0.87 mmol) and CsF (763 mg, 8.74 mmol) and K₃PO₄.H₂O (3.2 g, 12 mmol) in toluene (10 mL) was heated in a sealed tube at 60° C. for overnight. After cooling to room temperature, the reaction mixture was filtered and concentrated to give a crude product which was purified by column chromatography on a silica gel with ethyl acetate/hexane (1/1) to give 3-cyclopropylpyrazine-2-carbonitrile as a solid. LC/MS=146 [M+1].

Step B: (5-Methylpyrimidin-2-yl)methanamine

A mixture of 5-methylpyrimidine-2-carbonitrile (280 mg, 2.35 mmol) and 10% Pd/C (84 mg, 0.08 mmol) was stirred under hydrogen (balloon) in HCl/MeOH (0.1 mL/5 mL) at ambient temperature for overnight. The reaction mixture was filtered through Celite and concentrated to afford the HCl salt of (5-methylpyrimidin-2-yl)methanamine as an oil. LC/MS=124 [M+1].

AI-13. (5-Cyclopropylpyrimidin-2-yl)methanamine

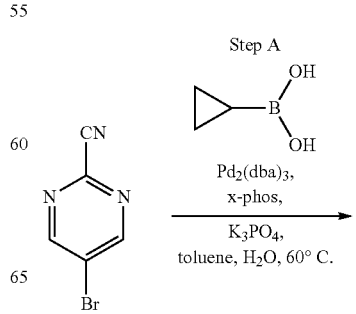

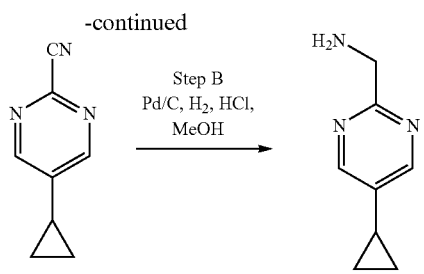

Step A: 5-Cyclopropylpyrimidine-2-carbonitrile

A mixture of 5-bromopyrimidine-2-carbonitrile (640 mg, 3.5 mmol), cyclopropylboronic acid (601 mg, 7 mmol), Pd$_2$(dba)$_3$ (640 mg, 0.7 mmol), X-Phos (668 mg, 1.4 mmol) and K$_3$PO$_4$·H$_2$O (2.79 g, 10.5 mmol) in toluene (10 mL) was heated in a sealed tube at 60° C. for overnight. After cooling to room temperature, the reaction mixture was filtered and concentrated to give a crude product which was by column chromatography on a silica gel with ethyl acetate/hexane (1/1) to give 5-cyclopropylpyrimidine-2-carbonitrile as a solid. LC/MS=146 [M+1].

Step B: (5-Cyclopropylpyrimidin-2-yl)methanamine

A mixture of 5-cyclopropylpyrimidine-2-carbonitrile (240 mg, 1.66 mmol) and 10% Pd/C (84 mg, 0.08 mmol) was stirred under hydrogen (balloon) in HCl/MeOH (0.1 mL/5 mL) at ambient temperature for overnight. After cooling to room temperature, the reaction mixture was filtered through Celite and concentrated to afford the HCl salt of (5-cyclopropylpyrimidin-2-yl)methanamine as an oil. LC/MS=150 [M+1].

(3,6-Dimethylpyridin-2-yl)methanamine

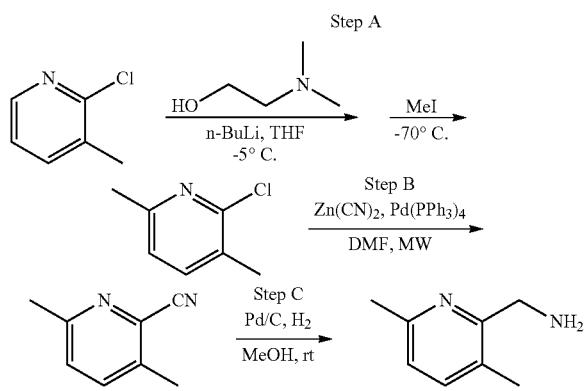

Step A: 2-Chloro-3,6-dimethylpyridine

To a solution of 2-(dimethylamino)ethanol (2.15 g, 24 mmol) in THF (15 mL) at −5° C. was added n-BuLi (2.5 M, 25 mmol) slowly and the resulting mixture was stirred for 30 minutes at −5° C., then cooled to −75° C. followed by slow addition of 2-chloro-3-methylpyridine (1.0 g, 8 mmol) solution in THF (5 mL). The reaction was stirred for 1.5 hours while maintaining the temperature lower than −70° C. A solution of MeI (2 mL, 32 mmol) in THF (60 mL) was slowly added to the above mixture. Upon completion of the addition, the cooling bath was removed and the reaction was warmed to 0° C. The reaction was carefully quenched using water (60 mL) and extracted with Et$_2$O (3×50 mL). The organic layers were combined, washed using water (30 mL) and brine (30 mL), dried over MgSO$_4$ and concentrated to give 1.0 g (88% yield) colorless oil which was used in the next step without further purification. LC/MS=142 [M+1]

Step B: 3,6-Dimethylpicolinonitrile

A mixture of 2-chloro-3,6-dimethylpyridine (320 mg, 2.3 mmol), Pd(PPh$_3$)$_4$ (810 mg, 6.80 mmol), and Zn(CN)$_2$ (820 mg, 6.80 mmol) in DMF (2 ml) was heated by microwave reactor at 130° C. for 2 hours. The reaction mixture was cooled to room temperature and water (5 mL) was added. The resulting mixture was extracted using ethyl acetate (3×10 mL). The organic fractions were combined, washed with brine (5 mL), dried over Na$_2$SO$_4$, filtered and concentrated in vacuo. The residue was purified by prep-TLC (hexane/EtOAc=30:1) to afford 3,6-dimethylpicolinonitrile (200 mg, 66% yield) as a colorless oil. LC/MS=133 [M+1]

Step C: (3,6-Dimethylpyridin-2-yl)methanamine

A mixture of 3,6-dimethylpicolinonitrile (120 mg, 0.91 mmol), EtOH (8 ml), HCl (0.2 mL) and 10% Pd/C (12 mg, 0.011 mmol) was stirred at room temperature for 2 hours under H$_2$ atmosphere (at 1 atm). The mixture was filtered through a thin layer of silica gel and the solvent was evaporated under reduced pressure to afford 3,6-dimethylpyridin-2-yl)methanamineas (140 mg, 89% yield) as a white solid. LC/MS=137 [M+1]

The following amine intermediates (AI) were prepared using similar procedures as described for AI-8 to AI-14, from the corresponding arylnitriles, heteroarylnitriles, or aryl/heteroaryl bromide/chloride

| Number | Amine Intermediate |
|---|---|
| AI-15 | |
| AI-16 | |
| AI-17 | |
| AI-18 | |

-continued
| Number | Amine Intermediate |
|---|---|
| AI-19 | 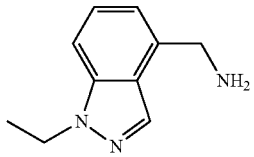 |
| AI-20 | 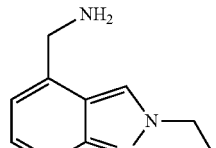 |
| AI-21 | 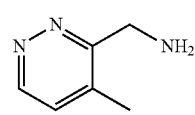 |
| AI-22 | 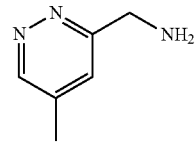 |
| AI-23 | 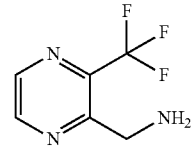 [SMILES: NCc1nccnc1C(F)(F)F] |
| AI-24 | 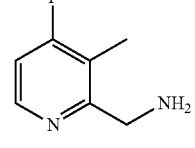 |
| AI-25 | 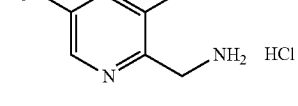 |
| AI-26 | 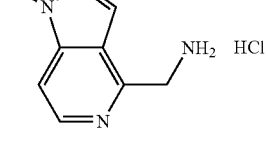 |
| AI-27 | 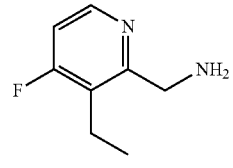 |
-continued
| Number | Amine Intermediate |
|---|---|
| AI-28 | 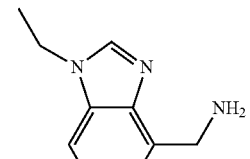 |
| AI-29 | 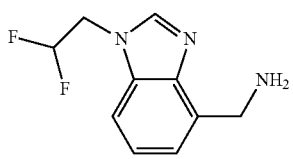 [SMILES: NCc1cccc2c1ncn2CC(F)F] |
| AI-30 | 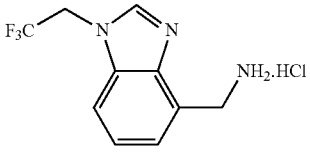 |
| AI-31 | 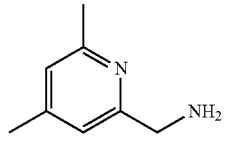 |
| AI-32 | 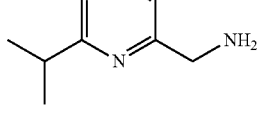 |
| AI-34 | 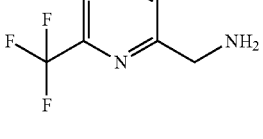 |
| AI-35 | 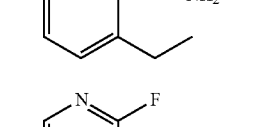 |
| AI-36 | 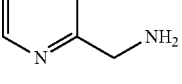 |
| AI-37 | 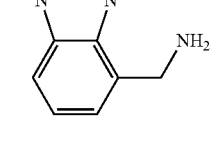 |
| AI-38 | 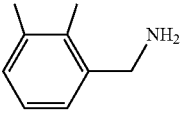 |

| Number | Amine Intermediate |
|---|---|
| AI-39 | ![structure] |
| AI-40 | ![structure] |
| AI-41 | ![structure] |
| AI-42 | ![structure] |
| AI-43 | ![structure] |
| AI-44 | ![structure] |
| AI-45 | ![structure] |
| AI-46 | ![structure] |
| AI-47 | ![structure] |

| Number | Amine Intermediate |
|---|---|
| AI-48 | ![structure] |
| AI-49 | ![structure] |

(6-(Methoxymethyl)pyridin-2-yl)methanamine

SCHEME 13

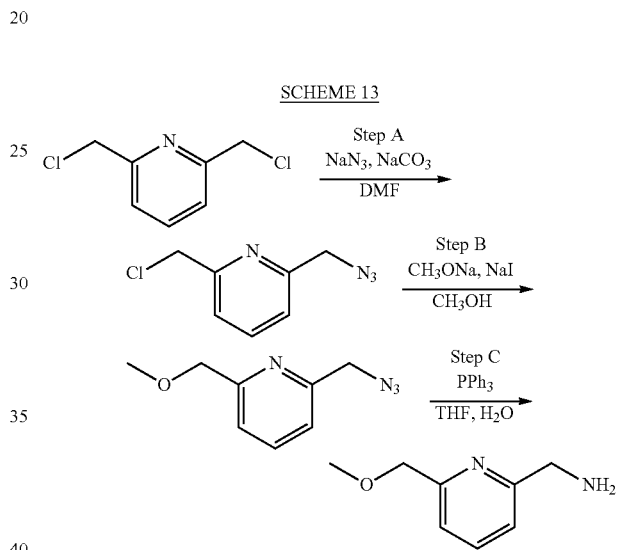

Step A: 2-(Azidomethyl)-6-(chloromethyl)pyridine

A 50 ml flask was charged with 2,6-bis(chloromethyl)pyridine (500 mg, 2.86 mmol), sodium azide (186 mg, 2.86 mmol) and sodium carbonate (606 mg, 5.71 mmol) in DMF (5.0 ml). The resulting mixture was heated at 50° C. under $N_2$ for overnight. The mixture was filtered and the filtrate was washed with brine (30 mL), dried (MgSO4), filtered and concentrated. The resulting 2-(azidomethyl)-6-(chloromethyl)pyridine as an oil which was used for the next step without further purification. LC/MS=183 (M+1).

Step B: 2-(Azidomethyl)-6-(methoxymethyl)pyridine

To a solution of 2-(azidomethyl)-6-(chloromethyl)pyridine (420 mg, 2.13 mmol) in MeOH (5.0 ml), sodium methanolate (249 mg, 4.6 mmol) and NaI (35 mg, 0.23 mmol) were added. The reaction mixture was heated at 50° C. under Ar for 2 h. The mixture was quenched with water (10 mL) after cooling. The MeOH was removed under reduce pressure and the aqueous mixture was extracted with EtOAc (3×10 mL). The EtOAc phases were combined and washed with brine, dried (MgSO$_4$), filtered and concentrated. The crude product was purified by prep-TLC to give 2-(azidomethyl)-6-(methoxymethyl)pyridine as a solid LC/MS=179 (M+1).

Step C: (6-(Methoxymethyl)pyridin-2-yl)methanamine

To a solution of 2-(azidomethyl)-6-(methoxymethyl)pyridine (200 mg, 1.12 mmol) in THF (3 ml) and H$_2$O (0.3 ml), triphenylphosphine (591 mg, 2.25 mmol) was added. The reaction mixture was stirred at room temperature for overnight. The mixture was concentrated in vacuo and the residue was purified by prep-TLC to afford (6-(methoxymethyl)pyridin-2-yl)methanamine as an oil. LC/MS=153 (M+1).

4-Chloro-6,7-dihydro-5H-cyclopenta[b]pyridin-7-amine

SCHEME 14

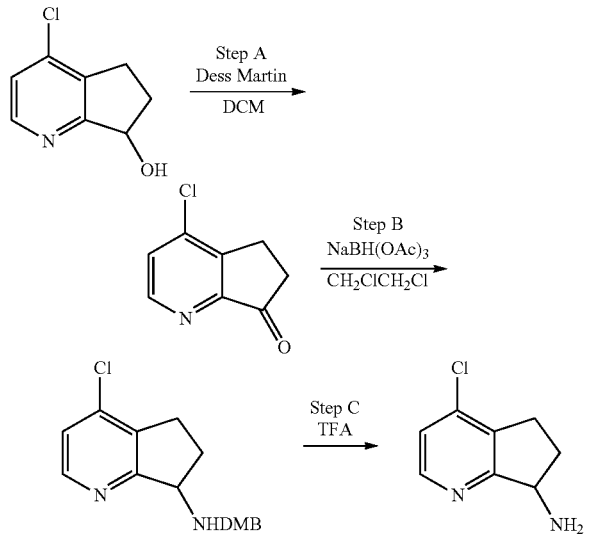

Step A: 4-Chloro-5H-cyclopenta[b]pyridin-7(6H)-one

To a solution of 4-chloro-6,7-dihydro-5H-cyclopenta[b]pyridin-7-ol (900 mg, 5.31 mmol) in anhydrous CH$_2$Cl$_2$ (10 ml), Dess-Martin periodinane (4501 mg, 10.61 mmol) was added. The reaction mixture was stirred at room temperature under N$_2$ atmosphere overnight. The mixture was quenched with NaHCO$_3$ (aq.), extracted with DCM. And the DCM phase was washed with brine, dried over Na$_2$SO$_4$, filtered and concentrated to give crude product. The crude product was purified by silica column chromatography, eluting with hexane:ethyl acetate=3:1 to give 4-chloro-5H-cyclopenta[b]pyridin-7(6H)-one as a solid. LC/MS=168 [M+1].

Step B: 4-Chloro-N-(2,4-dimethoxybenzyl)-6,7-dihydro-5H-cyclopenta[b]pyridin-7-amine To a stirred solution of 4-chloro-5H-cyclopenta[b]pyridin-7(6H)-one (200 mg, 1.193 mmol) and 2,4-dimethoxybenzylamine (399 mg, 2.387 mmol) in ClCH$_2$CH$_2$Cl (10 ml), sodium triacetoxyborohydride (1012 mg, 4.77 mmol) was added. The reaction mixture was stirred at room temperature overnight. The mixture was quenched with aq. NaHCO$_3$ extracted with DCM. The DCM phases was washed with brine, dried over Na$_2$SO$_4$, filtrated and concentrated. The crude was purified by Prep-TLC to give 4-chloro-N-(2,4-dimethoxybenzyl)-6,7-dihydro-5H-cyclopenta[b]pyridin-7-amine as a solid. LC/MS=319 [M+1].

Step C: 4-Chloro-6,7-dihydro-5H-cyclopenta[b]pyridin-7-amine

A 4-chloro-N-(2,4-dimethoxybenzyl)-6,7-dihydro-5H-cyclopenta[b]pyridin-7-amine (150 mg, 0.471 mmol) was dissolved in TFA (3 ml), the reaction mixture was stirred in 50° C. oil bath overnight. The mixture was concentrated, and the residue was dissolved in DCM (30 ml), washed with NaHCO$_3$ aq, dried over Na$_2$SO$_4$, filtrated and concentrated to give 4-chloro-6,7-dihydro-5H-cyclopenta[b]pyridin-7-amine as a solid. LC/MS=169 [M+1].

(1-(2,2-Difluoroethyl)-1H-imidazol-2-yl)methanamine

SCHEME 15

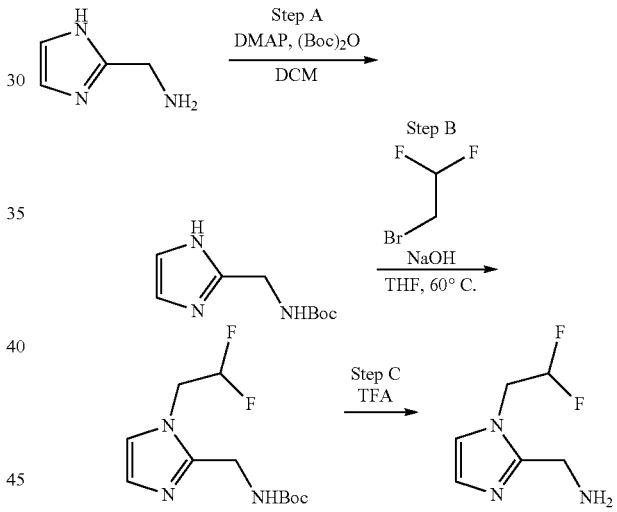

Step A: tert-Butyl (1H-imidazol-2-yl)methylcarbamate

A solution of (1H-imidazol-2-yl)methanamine (300 mg, 3.1 mmol), (Boc)$_2$O (2020 mg, 9.3 mmol), Et$_3$N (937 mg, 9.3 mmol) and DMAP (76 mg, 0.62 mmol) in DCM (20 mL) was stirred at 60° C. for overnight. The solution was washed with water (3×20 mL) and the organic layer was concentrated to afford tert-butyl (1H-imidazol-2-yl)methylcarbamate as a solid. LC/MS=198 [M+1].

Step B: tert-Butyl (1-(2,2-difluoroethyl)-1H-imidazol-2-yl)methylcarbamate

A solution of tert-butyl (1H-imidazol-2-yl)methylcarbamate (220 mg, 1.12 mmol), 2-bromo-1,1-difluoroethane (487 mg, 3.36 mmol), NaOH (134 mg, 3.36 mmol) and NaI (84 mg, 0.56 mmol) in THF (20 mL) was stirred at 60° C. for overnight. The solution was purified by prep-HPLC with MeCN/H$_2$O to afford tert-butyl (1-(2,2-difluoroethyl)-1H-imidazol-2-yl)methylcarbamate as a solid. LC/MS=262 [M+1].

Step C: (1-(2,2-Difluoroethyl)-1H-imidazol-2-yl)methanamine

A solution of tert-butyl (1-(2,2-difluoroethyl)-1H-imidazol-2-yl)methylcarbamate (160 mg, 0.61 mmol) in TFA/DCM (2 ml/20 ml) was stirred at 0° C. for 4 hours. The solution was washed with aqueous saturated NaHCO$_3$ (3×20 mL) and the organic layer was concentrated to afford (1-(2,2-difluoroethyl)-1H-imidazol-2-yl)methanamine as a solid. LC/MS=162 [M+1].

(1-Isopropyl-1H-1,2,4-triazol-5-yl)methanamine

SCHEME 16

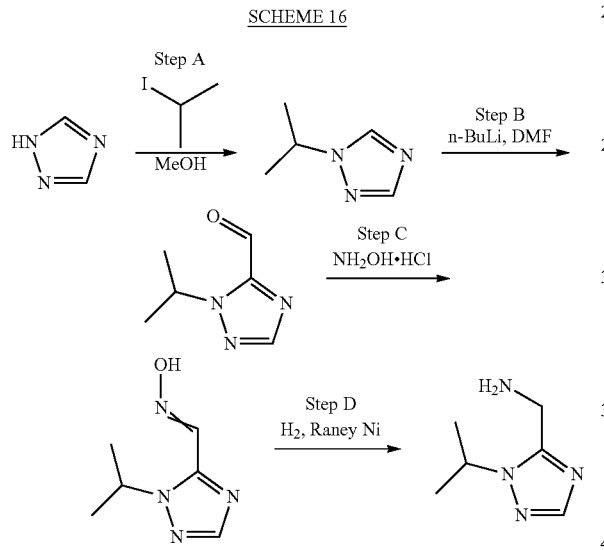

Step A: 1-Isopropyl-1H-1,2,4-triazole

A mixture of 1H-1,2,4-triazole (1 g, 14.48 mmol), 2-iodopropane (3.69 g, 21.72 mmol) and K$_2$CO$_3$ (3.00 g, 21.72 mmol) in MeOH (15 ml) was microwaved at 60° C. for 2 hours. The mixture was filtrated. The filtrate was evaporated under reduced pressure and purified by column chromatography on a silica gel with (DCM/MeOH: 50/1) to give 1-isopropyl-1H-1,2,4-triazole as a colorless oil. LC/MS=112 [M+1].

Step B: 1-Isopropyl-1H-1,2,4-triazole-5-carbaldehyde

To a 25 mL 3-neck flask was added a mixture of 1-isopropyl-1H-1,2,4-triazole (600 mg, 5.40 mmol) in dry THF (3 ml). The mixture was stirred at 0° C. for 10 minutes. n-BuLi (2.59 ml, 6.48 mmol) was added. After addition, the mixture was stirred at 0° C. for 45 minutes. Anhydrous DMF (0.35 ml, 4.53 mmol) was added at 0° C. The mixture was warmed to room temperature and stirred for 16 hours. The reaction was quenched with sat. NH$_4$Cl (20 mL). Aqueous layer was extracted with ethyl acetate (20 mL×3). The organic layers were combined and dried over Na$_2$SO$_4$. After filtration, the organic solvent was evaporated under reduced pressure to give 1-isopropyl-1H-1,2,4-triazole-5-carbaldehyde as an oil without further purification. LC/MS=158 [M+H$_2$O+H].

Step C: 1-Isopropyl-1H-1,2,4-triazole-5-carbaldehyde oxime

To a 50 mL round bottom flask, a mixture of 1-isopropyl-1H-1,2,4-triazole-5-carbaldehyde (800 mg, 5.75 mmol), hydroxylamine hydrochloride (799 mg, 11.50 mmol) and pyridine (1.4 g, 17.70 mmol) in MeOH (15 ml) was added. The mixture was stirred at 80° C. for 6 hours. The resulting mixture was cooled to room temperature. The organic solvent was evaporated under reduced pressure and the residue was purified with prep-TLC (DCM/MeOH: 50/1) to give 1-isopropyl-1H-1,2,4-triazole-5-carbaldehyde oxime as an oil. LC/MS=155 [M+1].

Step D: (1-Isopropyl-1H-1,2,4-triazol-5-yl)methanamine

To a 25 mL round bottom flask, a mixture of (E)-1-isopropyl-1H-1,2,4-triazole-5-carbaldehyde oxime (10 mg, 0.065 mmol) and Raney nickel (20 mg, 0.341 mmol) in MeOH (10 ml) was added. The mixture was stirred at room temperature for 18 hours. After filtration, the organic solvent was evaporated under reduced pressure to give (1-isopropyl-1H-1,2,4-triazol-5-yl)methanamine as an oil without further purification. LC/MS=141 [M+1].

2-Chloro-6,7-dihydro-5H-cyclopenta[b]pyridin-7-amine

SCHEME 17

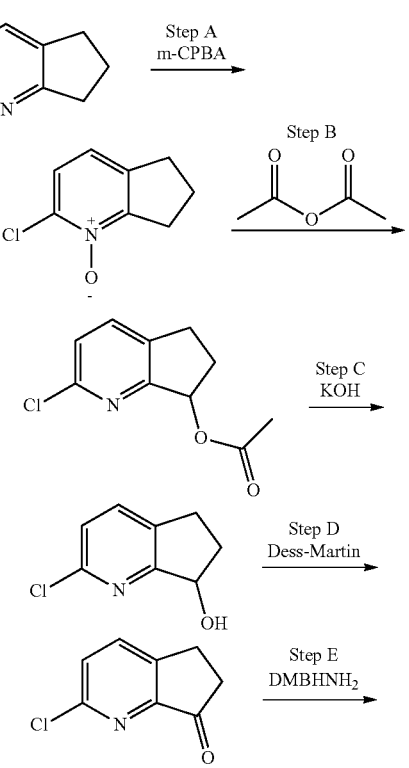

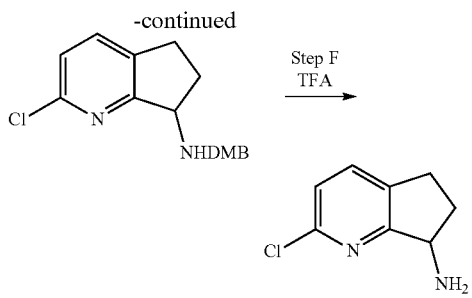

Step A: 2-Chloro-6,7-dihydro-5H-cyclopenta[b]pyridine 1-oxide

A solution of 70 percent 3-chlorobenzoperoxoic acid (1.41 g, 5.73 mmol) in CH$_2$Cl$_2$ (15 ml) was added dropwise to a stirring solution of 2-chloro-6,7-dihydro-5H-cyclopenta[b]pyridine (800 mg, 5.21 mmol) in CH$_2$Cl$_2$ (8 ml) and the resulting solution was allowed to stir at room temperature for overnight. The reaction mixture was quenched with saturated NaHCO$_3$ solution and the CH$_2$Cl$_2$ layer was separated. The aqueous phase was then extracted with CH$_2$Cl$_2$ (3×50 mL). The organic layer was combined, washed with brine (20 mL), dried over anhydrous Na$_2$SO$_4$ and concentrated under reduced pressure, the residue was purified by prep-TLC (eluting with hexane/ethyl acetate 1:1) to afford 2-chloro-6,7-dihydro-5H-cyclopenta[b]pyridine 1-oxide as a solid. LC/MS=170 [M+1].

Step B: 2-Chloro-6,7-dihydro-5H-cyclopenta[b]pyridin-7-yl acetate

In a round bottom flask equipped with a condenser, 2-chloro-6,7-dihydro-5H-cyclopenta[b]pyridine 1-oxide (200 mg, 1.18 mmol) was dissolved in acetic anhydride (5 ml) and heated at 110° C. for overnight. LCMS showed SM has been consumed. The reaction mixture was allowed to cool and the solvent was removed under reduced pressure. The resulting residue was dissolved up in CH$_2$Cl$_2$ (70 mL), and washed successively with saturated aqueous solution of NaHCO$_3$ (2×60 mL) and brine (100 mL). After drying over anhydrous Na$_2$SO$_4$, the solution was removed under reduce pressure and purified by prep-TLC eluting with ethyl acetate/hexane (1:5) to give 2-chloro-6,7-dihydro-5H-cyclopenta[b]pyridin-7-yl acetate as a oil. LC/MS=212 [M+1].

Step C: 2-Chloro-6,7-dihydro-5H-cyclopenta[b]pyridin-7-ol

To a stirred solution of 2-chloro-6,7-dihydro-5H-cyclopenta[b]pyridin-7-yl acetate (190 mg, 0.90 mmol) in EtOH (2 ml), a solution of KOH (55 mg, 0.99 mmol) in EtOH (5 ml) was added. The resulting mixture was stirred at room temperature for 3 hours and then the solvent was removed under reduced pressure to yield a dark solid, which was treated with 30 mL of water and extracted with dichloromethane (3×20 mL). The combined organic fractions were washed with brine (saturated, 50 mL), dried (Na$_2$SO$_4$), filtered and the solvent was evaporated under reduced pressure. The residue was purified by prep TLC eluting with hexane/ethyl acetate (5:1) to give 2-chloro-6,7-dihydro-5H-cyclopenta[b]pyridin-7-ol as a oil. LC/MS=170 [M+1].

Step D: 2-Chloro-5,6-dihydro-7H-cyclopenta[b]pyridin-7-one

Dess-Martin periodinane (725 mg, 1.710 mmol) was added to a solution of 2-chloro-6,7-dihydro-5H-cyclopenta[b]pyridin-7-ol (145 mg, 0.86 mmol) in DCM (5 mL). The solution was stirred at room temperature for 2 hours, then was washed with 1N NaOH, dried over sodium sulfate, decanted and concentrated to give 2-chloro-5H-cyclopenta[b]pyridin-7(6H)-one as a solid. LC/MS=168 [M+1].

Step E: 2-Chloro-N-(2,4-dimethoxybenzyl)-6,7-dihydro-5H-cyclopenta[b]pyridin-7-amine A solution of 2-chloro-5H-cyclopenta[b]pyridin-7(6H)-one (125 mg, 0.75 mmol) and (2,4-dimethoxyphenyl)methanamine (187 mg, 1.12 mmol) in DMF (5 ml) was stirred at room temperature for 30 min. Sodium triacetoxyborohydride (632 mg, 2.98 mmol) was added and the mixture was stirred at room temperature for overnight. The solution was diluted with ethyl acetate (80 mL), washed with brine (saturated, 2×50 mL), dried (Na$_2$SO$_4$), filtered and concentrated under reduced pressure. The residue was purified by prep-TLC eluting with hexane/ethyl acetate (1:2) to give 2-chloro-N-(2,4-dimethoxybenzyl)-6,7-dihydro-5H-cyclopenta[b]pyridin-7-amine as an oil. LC/MS=319 [M+1].

Step F: 2-Chloro-6,7-dihydro-5H-cyclopenta[b]pyridin-7-amine

A solution of 2-chloro-N-(2,4-dimethoxybenzyl)-6,7-dihydro-5H-cyclopenta[b]pyridin-7-amine (160 mg, 0.50 mmol) in TFA (5 mL) was stirred at 50° C. for 2 hr. The solvent was removed under reduced pressure, and the residue was neutralized by aqueous sodium hydrogen carbonate, extracted with dichloromethane (3×30 mL), dried over Na$_2$SO$_4$, and concentrated to give 2-chloro-6,7-dihydro-5H-cyclopenta[b]pyridin-7-amine as an oil. LC/MS=169 [M+1].

(3-Ethylpyrazin-2-yl)methanamine

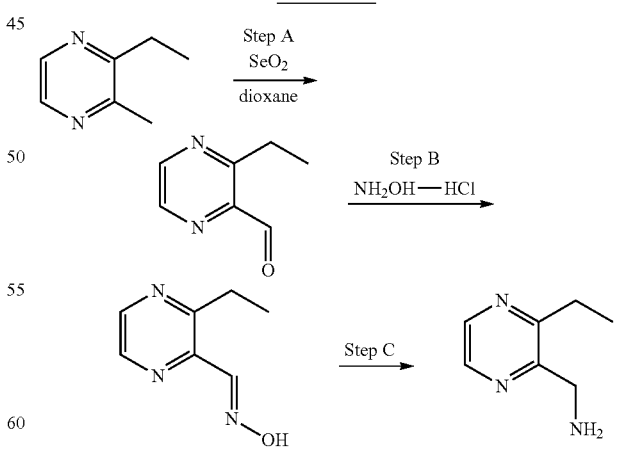

Step A: 3-Ethylpyrazine-2-carbaldehyde

A mixture of 2-methyl-3-ethylpyrazine (1.0 g, 8.19 mmol), selenium dioxide (1.8 g, 16.38 mmol), and diatomaceous earth (1.8 g) in dioxane (20 ml) was refluxed for overnight. The mixture was allowed to cool to room temperature. The solid material was removed by filtration through diatomaceous earth. The solvent was evaporated under reduced pressure. The crude product was washed with water (3×10 ml), extracted with ethyl acetate (3×20 ml), dried with Na$_2$SO$_4$ and concentrated. The crude product was used directly for the next step reaction without purification. LC/MS=137 [M+1].

Step B: 3-Ethylpyrazine-2-carbaldehyde oxime

A mixture of 3-ethylpyrazine-2-carbaldehyde (111 mg, 0.816 mmol), hydroxylamine hydrochloride (2.5 ml, 50%) and water (5 ml) was stirred at room temperature for 2 hours. The resulting mixture was washed with water (3×10 ml), extracted with ethyl acetate (3×20 ml), dried with Na$_2$SO$_4$ and evaporated. The crude product was purified by prep-HPLC to give 3-ethylpyrazine-2-carbaldehyde oxime as a solid. LC/MS=152 [M+1].

Step C: (3-Ethylpyrazin-2-yl)methanamine

3-Ethylpyrazine-2-carbaldehyde oxime (103 mg, 0.69 mmol) and 10% palladium on barium sulfate (10 mg, 1 mmol) were mixed with ethanol (10 ml) and attached to a hydrogenation apparatus. The mixture was charged with hydrogen. The mixture was stirred at room temperature for 2 hours. The resulting mixture was filtered and the filtrate was concentrated. The crude product was used for the next step directly without purification. LC/MS=138 [M+1].

(4-(Difluoromethyl)-1-methyl-1H-pyrazol-3-yl) methanamine

SCHEME 19

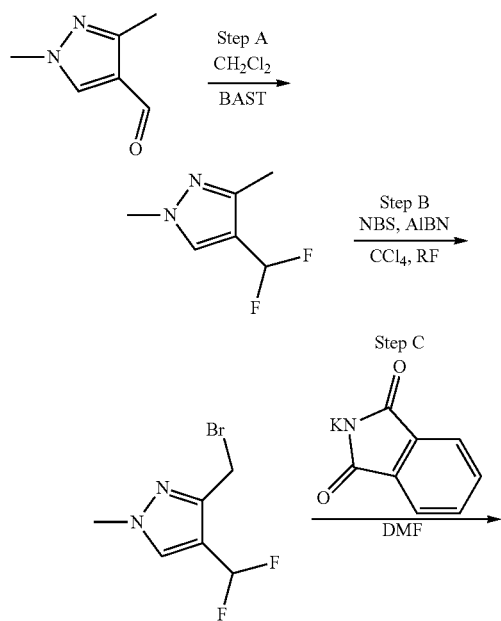

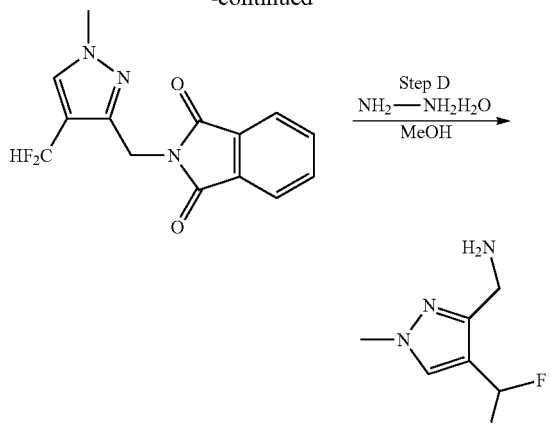

Step A: 4-(Difluoromethyl)-1,3-dimethyl-1H-pyrazole

Bis(2-methoxyethyl)aminosulfurtrifluoride (3.71 ml, 20.14 mmol) was added to a stirred solution of 1,3-dimethyl-1H-pyrazole-4-carbaldehyde (500 mg, 4.03 mmol) in DCM (6 ml) at 0° C. Then the mixture was stirred at room temperature for overnight. The reaction was quenched by NaHCO$_3$ solution (20 ml), extracted with dichloromethane (3×10 mL). The combined organic fractions were washed with brine (3×10 ml), dried with Na$_2$SO$_4$, filtered and concentrated under reduced pressure. The residue was purified by preparative HPLC reverse phase (C-8), eluting with (MeCN/H$_2$O=2/1), to give 4-(difluoromethyl)-1,3-dimethyl-1H-pyrazole as an oil. LC/MS=147 [M+1].

Step B: 3-(Bromomethyl)-4-(difluoromethyl)-1-methyl-1H-pyrazole

To a solution of 4-(difluoromethyl)-1,3-dimethyl-1H-pyrazole (300 mg, 2.053 mmol) in CCl$_4$ (3 ml) was added NBS (475 mg, 2.67 mmol) and AIBN (34 mg, 0.207 mmol). The mixture was refluxed for 3 hours. The reaction was cooled to room temperature and filtered. The filtrate was concentrated under reduced pressure to give crude product as a solid. The crude product was used for the next step reaction directly without purification. LC/MS=225 [M+1].

Step C: ((4-(Difluoromethyl)-1-methyl-1H-pyrazol-3-yl)methyl)isoindoline-1,3-dione A mixture of 3-(bromomethyl)-4-(difluoromethyl)-1-methyl-1H-pyrazole (290 mg, 1.289 mmol) and potassium 1,3-dioxoisoindolin-2-ide (477 mg, 2.58 mmol) in DMF (2 ml) was stirred at 80° C. for 1 hour. The mixture was cooled to room temperature and water (20 ml) was added. The mixture was extracted with ethyl acetate (3×10 ml). The combined organic fractions were washed with brine (10 ml), dried with Na$_2$SO$_4$, filtered and concentrated under reduced pressure. The residue was purified by column chromatography on a silica gel with (hexane/ethyl acetate=2/1) to give 2-((4-(difluoromethyl)-1-methyl-1H-pyrazol-3-yl)methyl)isoindoline-1,3-dione as a solid. LC/MS=292 [M+1].

Step D: (4-(Difluoromethyl)-1-methyl-1H-pyrazol-3-yl)methanamine

A mixture of 2-((4-(difluoromethyl)-1-methyl-1H-pyrazol-3-yl)methyl)isoindoline-1,3-dione (89 mg, 0.30 mmol)

and hydrazine hydrate (42 mg, 0.82 mmol) in methanol (2 ml) was stirred at room temperature for overnight. DCM (2 ml) was added and filtered. The filtrate was concentrated and used in the next step directly without further purification. LC/MS=162 [M+1].

(1-Methyl-4-(trifluoromethyl)-1H-imidazol-2-yl)methanamine

SCHEME 20

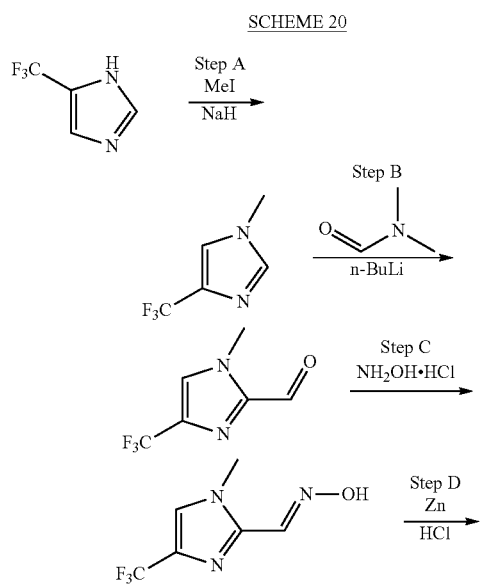

Step A: 1-Methyl-4-(trifluoromethyl)-1H-imidazole

A solution of 5-(trifluoromethyl)-1H-imidazole (1 g, 6.67 mmol) in 5 ml dry THF, NaH (399 mg, 9.99 mmol) of 60% was added under $N_2$ protection. The solution was stirred at room temperature for 1 hour. Then methyl iodide (1.42 g, 9.99 mmol) was added. The mixture solution was stirred at room temperature for 3 hours. The solvent was evaporated, and water (20 mL) was added to the mixture. The mixture was extracted with DCM (3×20 mL). The organic phase was dried by $Na_2SO_4$ and evaporated. The crude product was purified by chromatographic column with hexane/ethyl acetate=1:1 to give 1-methyl-4-(trifluoromethyl)-1H-imidazole. LC/MS=165 [M+1].

Step B: 1-Methyl-4-(trifluoromethyl)-1H-imidazole-2-carbaldehyde n-Butyllithium (1.6 M in hexane, 2 ml, 3.2 mmol) was added dropwise to a solution (10 ml) of 1-methyl-4-(trifluoromethyl)-1H-imidazole (440 mg, 2.94 mmol) in THF at −78° C. under argon atmosphere. The mixture was stirred for 30 minutes, and then a tetrahydrofuran solution (2 ml) of dimethylformamide (236 mg, 3.22) was added dropwise. The mixture was stirred at 0° C. for 2 hours, and then the reaction solution was added to ice water (10 mL), followed by extraction with ethyl acetate (3×10 mL). The organic layer was washed with saturated saline (10 mL) and then dried over anhydrous magnesium sulfate and concentrated to give a crude product was obtained by evaporating the solvent. LC/MS=179 [M+1].

Step C: 1-Methyl-4-(trifluoromethyl)-1H-imidazole-2-carbaldehyde oxime

A mixture of 1-methyl-4-(trifluoromethyl)-1H-imidazole-2-carb aldehyde (400 mg, 2.25 mmol), hydroxylamine hydrochloride (232 mg, 3.37 mmol), pyridine (266 mg, 3.37 mmol), and ethanol (20 ml) was refluxed overnight. The mixture was concentrated in vacuo and the residue was washed with dichloromethane (50 ml). The organic layer was concentrated to afford the product as a white solid without further purification. LC/MS=194 [M+1].

Step D: (1-Methyl-4-(trifluoromethyl)-1H-imidazol-2-yl)methanamine

A mixture of (E)-1-methyl-4-(trifluoromethyl)-1H-imidazole-2-carbaldehyde oxime (143 mg 0.74 mmol), hydrochloric acid (6 M, 4 ml) and zinc (721 mg, 11.1 mmol) in EtOH (50 ml) was stirred at 80° C. for 1 hour. The mixture was filtered and the filtrate was concentrated in vacuo to give the crude product which was used in the next step without further purification. LC/MS=180 [M+1].

(1-Ethyl-1H-1,2,4-triazol-5-yl)methanamine

SCHEME 21

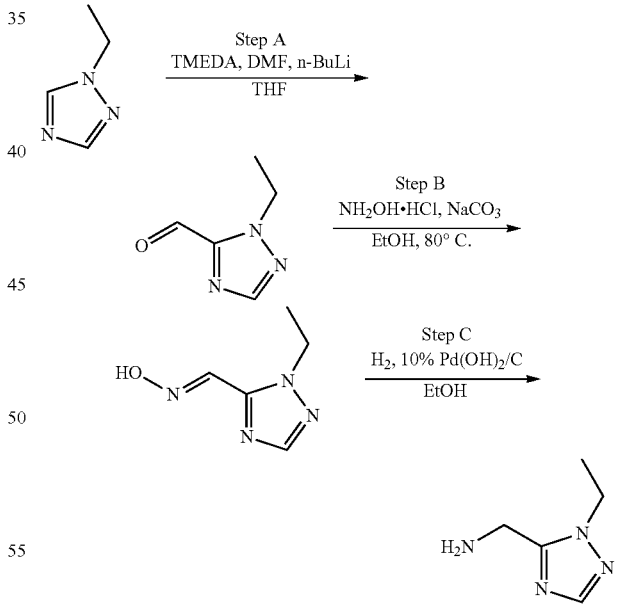

Step A: 1-Methyl-4-(trifluoromethyl)-1H-imidazole-2-carbaldehyde n-Butyllithium (0.8 ml, 2.5 M in hexane, 2.0 mmol) was dropped into a stirred solution of 1-ethyl-1H-1,2,4-triazole (200 mg, 2.06 mmol), TMEDA (0.3 ml) and THF (4 ml) at −78° C. in an argon atmosphere. The mixture was stirred at −78° C. for 2 hours. DMF (0.3 ml) was added to the mixture at −78° C. The mixture was warmed to room temperature and stirred for overnight. The mixture was poured into NH₄Cl (aq.) solution (10 ml) and extracted with DCM (15 ml×2). The organic layer was washed with saturated saline (10 ml) and dried over MgSO₄. The solvent was concentrated to give the crude product of 1-ethyl-1H-1,2,4-triazole-5-carbaldehyde as an oil. LC/MS=144 [M+18+1].

Step B:
(E)-1-Ethyl-1H-1,2,4-triazole-5-carbaldehyde oxime

A mixture of 1-methyl-4-(trifluoromethyl)-1H-imidazole-2-carbaldehyde (160 mg, 1.28 mmol), hydroxylamine hydrochloride (177 mg, 2.56 mmol) and NaHCO₃ (188 mg, 2.56 mmol) in ethanol (10 ml) was heated to reflux overnight. The mixture was concentrated in vacuo and the residue was washed with dichloromethane (50 ml). The organic layer was concentrated to afford the product as a solid. LC/MS=141 [M+1].

Step C: (1-Ethyl-1H-1,2,4-triazol-5-yl)methanamine

A mixture of (E)-1-ethyl-1H-1,2,4-triazole-5-carbaldehydeoxime (140 mg 1 mmol), hydrochloric acid (6 M, 4 ml) and Pd(OH)₂/C (70 mg) in EtOH (30 ml) was charged into a 50 ml round bottom flask. The system was evacuated and refilled with hydrogen for 3 times. The mixture was stirred at room temperature overnight. The mixture was filtered and the filtrate was concentrated to give the crude product as an oil. LC/MS=127 [M+1].

(5-Methylpyrimidin-4-yl)methanamine

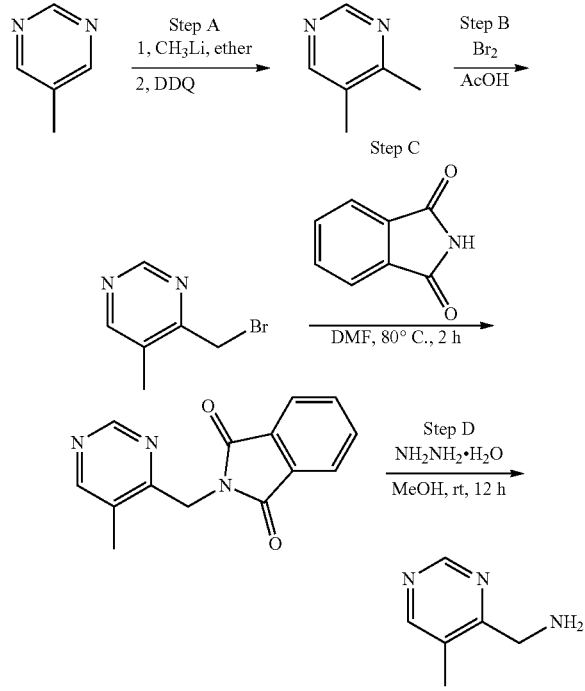

SCHEME 22

Step A: 4,5-Dimethylpyrimidine

A flame-fried three-neck flask (100 mL) was charged with methyllithium (1.78 mL, 5.3 mmol) and ethyl ether (15 mL). The solution of 5-methylpyrimidine (500 mg, 5.3 mmol) in ethyl ether (15 mL) was added dropwise at −30° C. under nitrogen. Once the addition was completed, the reaction mixture was allowed to warm to rt and stirred for 1 hour, then the solution of DDQ (1.2 g, 5.3 mmol) in tetrahydron (5 mL) was added dropwise. The mixture was stirred at rt for 1 hour. The reaction mixture was washed with sodium hydroxide aqueous (10 mL). The organic fractions were dried over sodium sulfate, filtered and the solvent was evaporated under reduced pressure to give 4,5-dimethylpyrimidineas an oil. The product was used immediately in the next step. LC/MS=109 [M+1].

Step B: 4-(Bromomethyl)-5-methylpyrimidine

A solution of 4,5-dimethylpyrimidine (572 mg, 5.3 mmol), and bromine (763 mg, 4.77 mmol) in acetic acid (10 mL) was sealed in tube, and the reaction mixture was heated to 50° C. for 2 hours. The reaction mixture was diluted with ethyl ether (100 mL) and neutralized with saturated sodium carbonate solution (200 mL). The organic layer were dried over sodium sulfate, filtered and the solvent was evaporated under reduced pressure to give 4-(bromomethyl)-5-methylpyrimidine as an oil. The product was used immediately in the next step. LC/MS=187 [M+1].

Step C: 2-((5-Methylpyrimidin-4-yl)methyl)isoindoline-1,3-dione

A solution of 4-(bromomethyl)-5-methylpyrimidine (100 mg, 0.537 mmol) and potassium 1,3-dioxoisoindolin-2-ide (198 mg, 1.07 mmol) in DMF (5 mL) was heated to 80° C. for 2 hours. The reaction mixture was filtered and the filtrate was purified by prep-HPLC to give 2-((5-methylpyrimidin-4-yl)methyl)isoindoline-1,3-dione as a solid. LC/MS=254 [M+1].

Step D: (5-Methylpyrimidin-4-yl)methanamine 2-((5-Methylpyrimidin-4-yl)methyl)isoindoline-1,3-dione (150 mg, 0.592 mmol) in methanol (3 mL) was stirred with hydrazine monohydrate (111 mg, 1.776 mmol) at rt for 12 hours. The reaction mixture was filtered and the filtrate was concentrated in vacuo. The residue was purified by prep-HPLC to give (5-methylpyrimidin-4-yl)methanamine. LC/MS=124 [M+1].

A2a Activity of Compounds of the Invention

Binding affinities of compounds of the invention for the human A2a receptor were determined in a competition binding assay using Scintillation Proximity technology. Thus, 0.3 of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 100 μg of wheat germ agglutin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. Ki values were determined using the Cheng-Prusoff equation.

Summary of Materials and Methods Used in A2a Activity Determination

Materials

HEK293 cells expressing the human, rat, dog or monkey adenosine 2a receptor (Purchased from Perkin-Elmer # RBHA2AM400UA).

The Tritiated compound was prepared in-house by MRL Radiochemistry according to published methods.

Wheat germ agglutinin-coated yttrium silicate SPA beads (GE Healthcare #RPNQ0023). Dilute to 25 mg/ml in assay buffer.

Assay Buffer was prepared in house: Dulbecco's calcium and magnesium free phosphate buffered saline+10 mM $MgCl_2$ Adenosine deaminase from calf intestine, 10 mg/2 ml (Roche #10 102 105 001).

DMSO

A2a antagonist standard (9-chloro-1-(2-furanyl)-[1,2,4]triazolo1,5-c]quinazolin-5-amine from Tocris Bioscience)

Compound Dilution

Make eight 1:3 serial dilutions in 100% DMSO from a 3 mM compound stock

Transfer 50 nl of compound into a 384-well OptiPlate (Perkin Elmer).

Typically, final concentrations of compound used in the assay ranged from 3000 nM to 0.152 nM.

Radioisotope

Dilute a solution of the Tritiated compound to 1.25 nM in assay buffer. This is a 2.5× solution. The final concentration in the assay is 0.5 nM. Calculate the concentration by counting two 5 μl aliquots.

Membrane Preparation

Use 0.25 ug of membrane/well. Dilute membranes to 9.7 μg/ml in assay buffer. Treat with 20 ug/ml adenosine deaminase (ADA) for 15 minutes at room temperature to degrade endogenous adenosine.

Membrane-Bead Mixture

Use 100 μg/well wheat germ agglutinin-coated yttrium silicate SPA beads.

Mix ADA-treated membranes and SPA beads together for 30 min prior to assay.

Assay Assembly

To the Perkin-Elmer Optiplate-384 containing the compound titration add 20 μl of 2.5× solution of the Tritiated compound and 30 μl of the membrane-bead mixture. Incubate for one hour at room temperature with agitation.

Include total binding (assay buffer+1% DMSO) and non-specific binding (CGS15943, 1 μM) wells.

Counting

Allow the beads to settle for one hour.

Count in TopCount.

Calculations

A curve fitting program (i.e., Prism, Activity Base, Chemcart) is used to determine the EC50. The Ki value is calculated using the Cheng-Prusoff equation.

$$Ki = EC50/(1+(\text{radioligand concentration}/Kd))$$

Using the foregoing assay method, the following results were obtained using various of the compounds of the invention described herein. Each example compound tested is reported in the following format: Example number: A2a EC50 reported in nM. Thus, for example, the compound Ex-1 was determined to have an EC50 using the above-described assay, of 4.0 nM, and is accordingly reported as "Ex-1: A2a=4.0":

Ex-1A: A2a=4.0; Ex-1B: A2a=2.9; Ex-3: A2a=3.4; Ex-4: A2a=4.6; Ex-5: A2a=4.7; Ex-6: A2a=5.9; Ex-7: A2a=1.4; Ex-8: A2a=2.2; Ex-9: A2a=2.1; Ex-10: A2a=1.2;

Table I compounds A2a Ki (nM)

Ex-5: A2a Ki=0.1994; Ex-6: A2a Ki=0.2244; Ex-7A: A2a Ki=5.183; Ex-7B: A2a Ki=0.3873; Ex-9: A2a Ki=0.6396; Ex-10: A2a Ki=0.5734; Ex-11: A2a Ki=0.1247; Ex-12: A2a Ki=9.825; Ex-13: A2a Ki=6.059; Ex-14: A2a Ki=2.119; Ex-15: A2a Ki=1.255; Ex-16: A2a Ki=5.143; Ex-17: A2a Ki=17.3; Ex-18: A2a Ki=0.1514; Ex-19: A2a Ki=2.763; Ex-20: A2a Ki=0.3655; Ex-21: A2a Ki=0.9344; Ex-22: A2a Ki=0.9189; Ex-23: A2a Ki=0.2927; Ex-24: A2a Ki=78.48; Ex-25: A2a Ki=16.15; Ex-26: A2a Ki=1.712; Ex-27: A2a Ki=119.5; Ex-28: A2a Ki=14.48; Ex-29: A2a Ki=0.3361; Ex-30: A2a Ki=0.3139; Ex-31: 2a Ki=0.7366; Ex-32: A2a Ki=1.505; Ex-33: A2a Ki=2.801; Ex-34: A2a Ki=846.6; Ex-35: A2a Ki=0.3959; Ex-36: A2a Ki=0.4639; Ex-37: A2a Ki=7.773; Ex-38: A2a Ki=2.268; Ex-39: A2a Ki=33.86; Ex-40: A2a Ki=14.59; Ex-41: A2a Ki=0.5931; Ex-42: A2a Ki=0.6718; Ex-43: A2a Ki=0.1155; Ex-44: A2a Ki=0.5328; Ex-45: A2a Ki=0.7352; Ex-46: A2a Ki=5.59; Ex-47: A2a Ki=1.802; Ex-48: A2a Ki=1.007; Ex-49: A2a Ki=1.265; Ex-50: A2a Ki=1.247; Ex-51: A2a Ki=0.7168; Ex-52: A2a Ki=4.876; Ex-53: A2a Ki=26.1; Ex-54: A2a Ki=1.77; Ex-55: A2a Ki=3.892; Ex-56: A2a Ki=21.52; Ex-57: A2a Ki=1.032; Ex-58: A2a Ki=4.559; Ex-59: A2a Ki=14.82; Ex-60: A2a Ki=9.202; Ex-61: A2a Ki=2.463; Ex-62: A2a Ki=0.6221; Ex-63: A2a Ki=2.517; Ex-64: A2a Ki=1.495; Ex-65: A2a Ki=4.192; Ex-66: A2a Ki=24.38; Ex-67: A2a Ki=64.09; Ex-68: A2a Ki=27.29; Ex-69: A2a Ki=56.46; Ex-70: A2a Ki=41.03; Ex-71: A2a Ki=23.84; Ex-72: A2a Ki=0.2868; Ex-73: A2a Ki=4.639; Ex-74: A2a Ki=2.271; Ex-75: A2a Ki=40.37; Ex-76: A2a Ki=50.14; Ex-77: A2a Ki=0.8283; Ex-78: A2a Ki=5.724; Ex-79: A2a Ki=0.3395; Ex-80: A2a Ki=1.588; Ex-81: A2a Ki=2.802; Ex-82A: A2a Ki=2.48; Ex-82B: A2a Ki=43.5; Ex-83: A2a Ki=3.178; Ex-84A: A2a Ki=279.9; Ex-84B: A2a Ki=245.4; Ex-85: A2a Ki=0.7; Ex-87: A2a Ki=0.4708; Ex-88: A2a Ki=6.155; Ex-89: A2a Ki=0.7461; Ex-90: A2a Ki=4.95; Ex-91: A2a Ki=2.931; Ex-92: A2a Ki=11.43; Ex-93: A2a Ki=3.996; Ex-94A: A2a Ki=8.7; Ex-94B: A2a Ki=137.6; Ex-95: A2a Ki=0.2765; Ex-96: A2a Ki=12.85; Ex-97: A2a Ki=35.23; Ex-98: A2a Ki=2.929; Ex-99: A2a Ki=208.2; Ex-100: A2a Ki=110.2; Ex-101: A2a Ki=12.88; Ex-102: A2a Ki=11.89; Ex-103: A2a Ki=0.3534; Ex-106: A2a Ki=251.6; Ex-107: A2a Ki=1.152; Ex-108: A2a Ki=6.581; Ex-109: A2a Ki=14.98; Ex-110: A2a Ki=1.324; Ex-111: A2a Ki=82.2; Ex-112: A2a Ki=14.54; Ex-113: A2a Ki=30.22; Ex-114: A2a Ki=5.76; Ex-115: A2a Ki=8.745; Ex-116: A2a Ki=21.35; Ex-117: A2a Ki=104.2; Ex-118: A2a Ki=31.68; Ex-119: A2a Ki=6.239; Ex-120: A2a Ki=5.808; Ex-121: A2a Ki=3.178; Ex-122: A2a Ki=2.913; Ex-123: A2a Ki=17.41; Ex-124: A2a Ki=1.77; Ex-125: A2a Ki=18.81; Ex-126: A2a Ki=83; Ex-127: A2a Ki=0.279; Ex-128: A2a Ki=12.49; Ex-129: A2a Ki=0.1983; Ex-130: A2a Ki=3.411; Ex-131: A2a Ki=10.33; Ex-132: A2a Ki=0.3574; Ex-133: A2a Ki=2.591; Ex-134: A2a Ki=3.394; Ex-135: A2a Ki=0.1686; Ex-136: A2a Ki=0.2665; Ex-137: A2a Ki=0.3068; Ex-138: A2a Ki=0.5878; Ex-139: A2a Ki=3.034; Ex-140: A2a Ki=0.2251; Ex-141: A2a Ki=0.3905; Ex-142: A2a Ki=0.7041; Ex-143: A2a Ki=1.72; Ex-144: A2a Ki=0.3817; Ex-145: A2a Ki=4.219; Ex-146: A2a Ki=5.573; Ex-147: A2a Ki=0.6007; Ex-148: A2a

Ki=15.82; Ex-149: A2a Ki=0.8552; Ex-150: A2a Ki=3.589; Ex-151: A2a Ki=4.581; Ex-153: A2a Ki=0.1413; Ex-154: A2a Ki=0.1248; Ex-155: A2a Ki=13.92; Ex-156: A2a Ki=68.93; Ex-157: A2a Ki=0.6009; Ex-158: A2a Ki=1.967; Ex-159: A2a Ki=1.201; Ex-160: A2a Ki=264; Ex-161: A2a Ki=0.2934; Ex-162: A2a Ki=0.3331; Ex-163: A2a Ki=0.1966; Ex-164: A2a Ki=1.286; Ex-165A: A2a Ki=13.12; Ex-165B: A2a Ki=2.12; Ex-165C: A2a Ki=7.639; Ex-165D: A2a Ki=9.338; Ex-166: A2a Ki=0.5993; Ex-167: A2a Ki=0.1583; Ex-169: A2a Ki=0.3747; Ex-170: A2a Ki=0.4818; Ex-171: A2a Ki=1.034; Ex-172: A2a Ki=3.053; Ex-173: A2a Ki=0.1908; Ex-174: A2a Ki=2.964; Ex-175: A2a Ki=6.313; Ex-178: A2a Ki=0.2169; Ex-179: A2a Ki=0.1002; Ex-180: A2a Ki=0.1678; Ex-181: A2a Ki=1.303; Ex-182: A2a Ki=2.701; Ex-183: A2a Ki=6.721; Ex-184: A2a Ki=0.208; Ex-185: A2a Ki=4.254; Ex-186: A2a Ki=0.1809; Ex-187: A2a Ki=0.4489; Ex-188: A2a Ki=0.2902; Ex-189: A2a Ki=1.026; Ex-190: A2a Ki=12.27; Ex-191A: A2a Ki=1.329; Ex-191B: A2a Ki=2.563; Ex-193: A2a Ki=0.4352; Ex-194: A2a Ki=1.648; Ex-195: A2a Ki=1.714; Ex-196: A2a Ki=2.527; Ex-197: A2a Ki=6.372; Ex-198: A2a Ki=8.772; Ex-199: A2a Ki=9.424; Ex-200: A2a Ki=14.7; Ex-201: A2a Ki=0.6331; Ex-202: A2a Ki=2.22; Ex-203: A2a Ki=3.481; Ex-204: A2a Ki=1504; Ex-205: A2a Ki=385; Ex-206: A2a Ki=3.718; Ex-207: A2a Ki=2.922; Ex-208: A2a Ki=0.9819; Ex-209: A2a Ki=2.971; Ex-210: A2a Ki=1.419; Ex-211: A2a Ki=7.366; Ex-212: A2a Ki=98.95; Ex-213: A2a Ki=0.4199; Ex-214: A2a Ki=0.689; Ex-215: A2a Ki=1.444; Ex-216: A2a Ki=0.1228; Ex-217: A2a Ki=1.402; Ex-218: A2a Ki=0.3088; Ex-219: A2a Ki=36.48; Ex-222: A2a Ki=9.219; Ex-223: A2a Ki=2.977; Ex-224: A2a Ki=0.2012; Ex-225: A2a Ki=0.178; Ex-226A: A2a Ki=38.24; Ex-226B: A2a Ki=0.1741; Ex-228: A2a Ki=1.739; Ex-229: A2a Ki=0.3578; Ex-230A: A2a Ki=3.74; Ex-230B: A2a Ki=0.7618; Ex-231A: A2a Ki=29.18; Ex-231B: A2a Ki=10.47; Ex-233A: A2a Ki=1.154; Ex-233B: A2a Ki=0.5717; Ex-235: A2a Ki=0.2432; Ex-236: A2a Ki=1.609; Ex-237: A2a Ki=1.77; Ex-238A: A2a Ki=5.508; Ex-238B: A2a Ki=0.9399; Ex-240A: A2a Ki=40.45; Ex-240B: A2a Ki=1.725; Ex-242: A2a Ki=1.092; Ex-243: A2a Ki=15.09; Ex-244A: A2a Ki=0.2195; Ex-244B: A2a Ki=1.28; Ex-245A: A2a Ki=6.692; Ex-245B: A2a Ki=4.394;
Table II Compounds
Ex-249: A2a Ki=3.451; Ex-250: A2a Ki=2.4; Ex-251: A2a Ki=1.104; Ex-252: A2a Ki=1.809; Ex-253: A2a Ki=8.569; Ex-254: A2a Ki=1.473; Ex-255: A2a Ki=0.1997; Ex-256: A2a Ki=0.1956; Ex-257: A2a Ki=1.944; Ex-258: A2a Ki=2.898; Ex-259: A2a Ki=403.1; Ex-260: A2a Ki=786.3; Ex-261: A2a Ki=1418; Ex-262: A2a Ki=339.7; Ex-263: A2a Ki=3.746; Ex-264A: A2a Ki=99; Ex-264B: A2a Ki=2.4;
Table III Compounds
Ex-268: A2a Ki=359.1; Ex-269: A2a Ki=4.3; Ex-270: A2a Ki=6469.7; Ex-271: A2a Ki=6.19; Ex-272: A2a Ki=269.01; Ex-273: A2a Ki=2.23; Ex-274: A2a Ki=2; Ex-275: A2a Ki=2.1; Ex-276: A2a Ki=407.9; Ex-277: A2a Ki=3.3; Ex-278: A2a Ki=191.3; Ex-279: A2a Ki=59.3; Ex-280: A2a Ki=148.2; Ex-281: A2a Ki=5.7; Ex-282: A2a Ki=1.4; Ex-283: A2a Ki=2.4; Ex-284: A2a Ki=6.5; Ex-285: A2a Ki=10000; Ex-286: A2a Ki=123.7; Ex-287: A2a Ki=131; Ex-288: A2a Ki=1.9; Ex-289: A2a Ki=34.8; Ex-290: A2a Ki=317.6; Ex-291: A2a Ki=10000; Ex-292: A2a Ki=54.8; Ex-293: A2a Ki=106.8; Ex-294: A2a Ki=68.8; Ex-295: A2a Ki=13.6; Ex-296: A2a Ki=35.6; Ex-297: A2a Ki=1.65; Ex-298: A2a Ki=32.9; Ex-299: A2a Ki=33.6; Ex-300: A2a Ki=44.4; Ex-301: A2a Ki=182.5; Ex-302: A2a Ki=28.3; Ex-303: A2a Ki=14.4; Ex-304: A2a Ki=3.6; Ex-305: A2a Ki=49.5; Ex-306: A2a Ki=48.6; Ex-307: A2a Ki=21.6; Ex-308: A2a Ki=34.5; Ex-309: A2a Ki=179.6; Ex-310: A2a Ki=15.65; Ex-311: A2a Ki=1161.5; Ex-312: A2a Ki=606.9; Ex-313: A2a Ki=22.8; Ex-314: A2a Ki=3.7; Ex-315: A2a Ki=194.7; Ex-316: A2a Ki=66.9; Ex-317: A2a Ki=2196.9; Ex-318: A2a Ki=316.7; Ex-319: A2a Ki=77.9; Ex-320: A2a Ki=149.2; Ex-321: A2a Ki=70.2; Ex-322: A2a Ki=61.9; Ex-323: A2a Ki=65.3; Ex-324: A2a Ki=54; Ex-325: A2a Ki=337; Ex-326: A2a Ki=6.1; Ex-327: A2a Ki=55.7; Ex-328: A2a Ki=626.9; Ex-329: A2a Ki=8.6; Ex-330: A2a Ki=61.5; Ex-331: A2a Ki=75.4; Ex-332: A2a Ki=4.1; Ex-333: A2a Ki=57.9; Ex-334: A2a Ki=13.7; Ex-335: A2a Ki=114.4; Ex-336: A2a Ki=134.8; Ex-337: A2a Ki=11.2; Ex-338: A2a Ki=132.9; Ex-339: A2a Ki=117.4; Ex-340: A2a Ki=12.8; Ex-341: A2a Ki=104.6; Ex-342: A2a Ki=122.1; Ex-343: A2a Ki=35.9; Ex-344: A2a Ki=31; Ex-345: A2a Ki=6; Ex-346: A2a Ki=397.4; Ex-347: A2a Ki=46.39; Ex-348: A2a Ki=10.07; Ex-349: A2a Ki=179.67; Ex-350: A2a Ki=629.7; Ex-351: A2a Ki=314.9; Ex-352: A2a Ki=51.1; Ex-353: A2a Ki=49; Ex-354: A2a Ki=389.6; Ex-355: A2a Ki=543.4; Ex-356: A2a Ki=4.3; Ex-357: A2a Ki=69.4; Ex-358: A2a Ki=73.3; Ex-359: A2a Ki=90; Ex-360: A2a Ki=615.2; Ex-361: A2a Ki=63.2; Ex-362: A2a Ki=142.9; Ex-363: A2a Ki=0.5; Ex-394: A2a Ki=1911.
Table IV Compounds
Ex-379: A2a Ki=1486; Ex-380: A2a Ki=0.3836; Ex-381: A2a Ki=80.5; Ex-382: A2a Ki=38.4; Ex-383: A2a Ki=6.4; Ex-384: A2a Ki=63.7; Ex-385: A2a Ki=0.6; Ex-386: A2a Ki=0.3; Ex-387: A2a Ki=2.8; Ex-388: A2a Ki=2.5; Ex-389A: A2a Ki=12.27; Ex-389B: A2a Ki=1.117; Ex-389C: A2a Ki=0.3169; Ex-389D: A2a Ki=2.209; Ex-393: A2a Ki=3.621.

The invention claimed is:
1. A compound, or a pharmaceutically acceptable salt thereof, having the structure of Formula A:

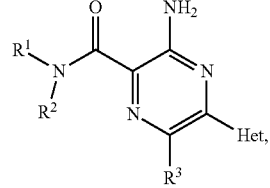

Formula A wherein:
"Het" is a moiety of the formula:

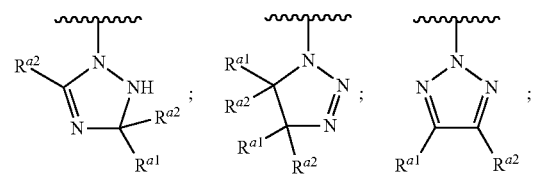

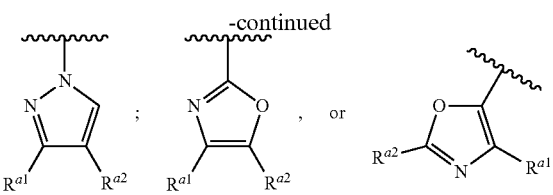

wherein "$R^{a1}$" and "$R^{a2}$" are, independently for each occurrence: (a) —H; or (b) lower alkyl which is optionally substituted with one or more moieties which are: (i) halogen; or (ii) lower alkoxy;

(A) one of $R^1$ or $R^2$ is lower alkyl or H and the other is:
(a) a linear, branched, mono-cyclic, or hi-cyclic-alkyl moiety of up to 10 carbon atoms, which is optionally substituted with one or more substituents which are independently:
  (i) halogen;
  (ii) —$NR^{1g}R^{2g}$, wherein $R^{1g}$ and $R^{2g}$ are, independently: (ai) —H; or (bi) lower alkyl;
  (iii) —CN;
  (iv) —OH;
  (v) mono- or poly-cyclic heteroaryl comprising at least two carbon atoms and up to 3 heteroatoms which are, independently, N, O, or S and which is optionally substituted with:
    (ai) lower alkyl, which moiety is optionally substituted with one or more moieties which are independently;
    (aii) halogen;
    (bii) lower alkoxy; or
    (cii) —OH
    (bi) —$NR^{1g}R^{2g}$, wherein $R^{1g}$ and $R^{2g}$ are, independently: (aii) —H; or (bii) lower alkyl;
    (ci) lower-alkoxy, which is optionally substituted in its alkyl portion with a halogen;
    (di) halogen;
    (ei) —OH;
    (fi) heteroaryl;
    (gi) heterocycloalkyl which is optionally substituted with one or more halogen atoms;
    and wherein, if said heteroaryl comprises a single nitrogen heteroatom in the ring, optionally said ring nitrogen is present in the N-oxide oxidized form;
  (vi) heteroarylone which is optionally substituted with one or more moieties which are, independently, a lower alkyl, which lower alkyl substituent is optionally fluorine substituted;
  (vii) heteroarylaryl fused moiety, which is optionally substituted with one or more lower alkyl moieties, which lower alkyl moieties are optionally substituted with fluorine;
  (viii) aryl, which is optionally substituted with one or more moieties which are independently:
    (ai) lower alkyl which is optionally substituted with a halogen;
    (bi) halogen;
    (ci) —OH;
    (di) lower alkoxy which is optionally halogen substituted; or
    (ei) —$N(R^{a8})_2$, wherein "$R^{a8}$" is independently —H or lower alkyl;
  (ix) arylheteroaryl fused moiety, which is optionally substituted with one or more moieties which are lower alkyl;
  (x) cycloalkylheteroaryl fused moiety;
  (xi) linear, branched, or cyclic alkyl of up to 6 carbon atoms which is optionally substituted with one or more moieties which are independently: (ai) —CN; (bi) lower alkoxy; or (ci) halogen;
  (xii) a moiety of the formula "—C(O)—$R^{a12}$", wherein "$R^{a12}$" is a moiety which is: (ai) lower alkyl; (bi) lower alkoxy; (ci) heteroaryl; or (di) aryl, and wherein said "$R^{a12}$" moiety is optionally substituted with one or more halogen moieties;
  (xiii) a moiety of the formula "—O—$R^{a13}$", wherein "$R^{a13}$" is lower alkyl or aryl;
  (xiv) —OH;
  (xv) heteroaryl-heterocycloalkyl fused moiety;
(b) heteroarylcycloalkyl fused moiety which is optionally substituted with:
  (i) —OH; or (ii) halogen;
(c) heterocycloalkyl, which is optionally substituted with one or more moieties which are independently:
  (i) —F; or (ii) heteroaryl;
(d) a compound of the Formula:

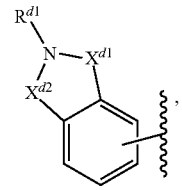

wherein "$R^{d1}$" is —H or lower alkyl, and wherein one of "$X^{d1}$" or "$X^{d2}$" is —$CH_2$— and the other is —C(=O)—;
(e) arylheterocycloalkyl fused moiety;
(f) heterocycloalkylaryl fused moiety which is optionally substituted with —OH or halogen;
(g) heteroarylheterocycloalkyl fused moiety which is optionally substituted with —OH or halogen;
(h) arylcycloalkyl fused moiety, which is optionally substituted with one or more moieties which are, independently:
  (i) —OH;
  (ii) —CN;
  (iii) halogen; or
  (iv) lower alkoxy;
(B) $R^1$ and $R^2$ taken together are a moiety of the formula —$[(CR^{B1}R^{B2})_2)_n]$—, wherein, "n" is an integer of 3 to 6, and "$R^{B1}$" and "$R^{B2}$" are independently for each occurrence: (a) lower alkyl; (b) hydrogen; (c) aryl; or (d) halogen, thereby forming with the nitrogen to which they are bonded a heterocycloalkyl moiety; or
(C) $R^1$ and $R^2$ taken together form an arylheterocycloalkyl fused moiety; and "$R^3$" is: selected from —CN, halogen, and lower alkyl, wherein said lower alkyl is unsubstituted or substituted with one or more moieties independently selected from OH and halogen.

2. A compound, or a pharmaceutically acceptable salt thereof, having the structure of Formula A-1:

Formula A-1

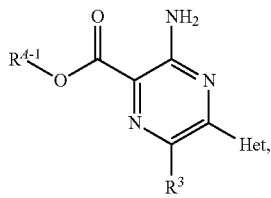

wherein:
R$^{A-1}$ is lower alkyl;
"Het" is a moiety of the formula:

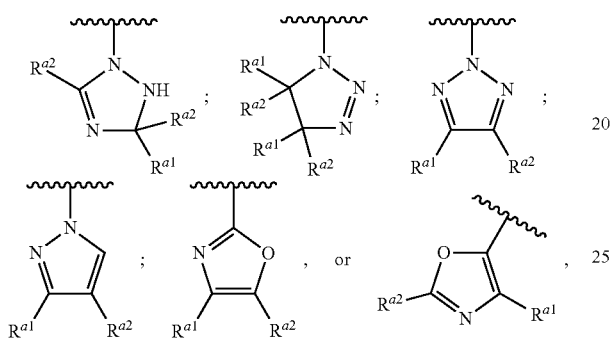

wherein "R$^{a1}$" and "R$^{a2}$" are, independently for each occurrence: (a) —H; or (b) lower alkyl which is optionally substituted with one or more moieties which are: (i) halogen: or (ii) lower alkoxy; and
"R$^3$" is: (a) —CN; (b) halogen; (c) lower alkyl which is optionally substituted with one or more moieties which are: (i) —OH; or (ii) halogen.

3. A compound of claim 1, or a pharmaceutically acceptable salt thereof, wherein "Het" is:

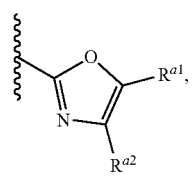

wherein "R$^{a1}$" and "R$^{a2}$" are, independently for each occurrence: (a) —H; or (b) lower alkyl which is optionally substituted with one or more moieties which are: (i) halogen; or (ii) lower alkoxy.

4. A compound of claim 1, or a pharmaceutically acceptable salt thereof, wherein "Het" is:

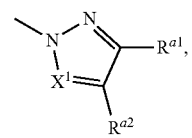

wherein "R$^{a1}$" and "R$^{a2}$" are, independently for each occurrence: (a) —H; or (b) lower alkyl which is optionally substituted with one or more moieties which are: (i) halogen; or (ii) lower alkoxy, and X$^1$ is [—CH=] or [—N=].

5. A compound of claim 3 having the Formula:

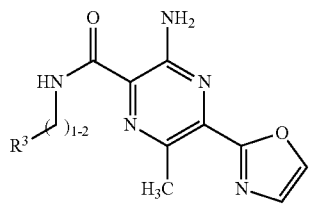

wherein —R$^3$ is:

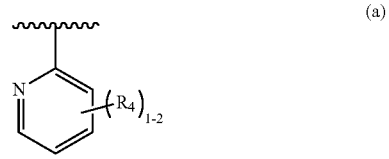

wherein
R$^4$ is (i) linear, branched or cyclic alkyl of up to four carbon atoms, wherein said alkyl is optionally substituted with one or more fluorine atoms; (ii) halogen; (iii) —O—R$^{4a}$, wherein R$^{4a}$ is linear, branched or cyclic alkyl of up to four carbon atoms; or (iv) —N(R$^{4b}$)$_2$ wherein R$^{4b}$ is independently for each occurrence linear, branched or cyclic alkyl of up to four carbon atoms;

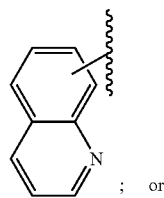

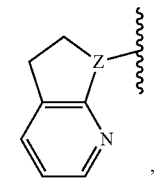

wherein Z is —CH$_2$.N—, or is —CH—,
or a pharmaceutically acceptable salt thereof.

6. The following compounds of claim 2:
methyl 3-amino-6-chloro-5-(1H-pyrazol-1-yl)pyrazine-2-carboxylate;
ethyl 3-amino-6-methyl-5-(2H-1,2,3-triazol-2-yl)pyrazine-2-carboxylate,
or a pharmaceutically acceptable salt thereof.

7. The following compounds of claim 3, or a pharmaceutically acceptable salt thereof:
3-amino-6-methyl-N-[(3-methylpyridin-2-yl)methyl]-5-(1,3-oxazol-2-yl)pyrazine-2-carboxamide;
3-amino-N-[(3-cyclopropylpyridin-2-yl)methyl]-6-methyl-5-(1,3-oxazol-2-yl)pyrazine-2-carboxamide.

8. The following compounds of claim 3, or a pharmaceutically (R)-3-amino-N-(6,7-dihydro-5H-cyclopenta[b]pyridin-7-yl)-6-methyl-5-(1,3-oxazol-2-yl)pyrazine-2-carboxamide;
3-amino-N-[(3-methoxypyridin-2-yl)methyl]-6-methyl-5-(1,3-oxazol-2-yl)pyrazine-2-carboxamide;
(S)-3-amino-N-(6,7-dihydro-5H-cyclopenta[b]pyridin-7-yl)-6-methyl-5-(1,3-oxazol-2-yl)pyrazine-2-carboxamide.

9. The following compounds of claim 3, or a pharmaceutically acceptable salt thereof:
3-amino-N-[(3-fluoropyridin-2-yl)methyl]-6-methyl-5-(1,3-oxazol-2-yl)pyrazine-2-carboxamide;
3-amino-N-{[6-(dimethylamino)pyridin-2-yl]methyl}-6-methyl-5-(1,3-oxazol-2-yl)pyrazine-2-carboxamide;
3-amino-N-[(6-methoxypyridin-2-yl)methyl]-6-methyl-5-(1,3-oxazol-2-yl)pyrazine-2-carboxamide.

10. The following compounds of claim 3, or a pharmaceutically acceptable salt thereof:
3-amino-N-(isoquinolin-8-ylmethyl)-6-methyl-5-(1,3-oxazol-2-yl)pyrazine-2-carboxamide;
3-(3,4-dihydroquinolin-1 (2H)-ylcarbonyl)-5-methyl-6-(1,3-oxazol-2-yl)pyrazin-2-amine;
3-amino-6-methyl-5-(1,3-oxazol-2-yl)-N-(2-pyridin-2-ylethyl)pyrazine-2-carboxamide.

11. A compound of claim 1 which is:
3-amino-6-methyl-N-[(3-methylpyridin-2-yl)methyl]-5-(1,3-oxazol-2-yl)pyrazine-2-carboxamide;
3-amino-N-[(3-cyclopropylpyridin-2-yl)methyl]-6-methyl-5-(1,3-oxazol-2-yl)pyrazine-2-carboxamide;
3-amino-N-(6,7-dihydro-5H-cyclopenta[b]pyridin-7-yl)-6-methyl-5-(1,3-oxazol-2-yl)pyrazine-2-carboxamide;
3-amino-N-(6,7-dihydro-5H-cyclopenta[b]pyridin-7-yl)-6-methyl-5-(1,3-oxazol-2-yl)pyrazine-2-carboxamide;
3-amino-6-methyl-5-(1,3-oxazol-2-yl)-N-(quinolin-8-ylmethyl)pyrazine-2-carboxamide;
3-amino-6-methyl-N-[(6-methylpyridin-2-yl)methyl]-5-(1,3-oxazol-2-yl)pyrazine-2-carboxamide;
3-amino-N-(2,6-difluorobenzyl)-6-methyl-5-(1,3-oxazol-2-yl)pyrazine-2-carboxamide;
3-amino-N-(isoxazol-5-ylmethyl)-6-methyl-5-(1,3-oxazol-2-yl)pyrazine-2-carboxamide;
3-amino-6-methyl-5-(1,3-oxazol-2-yl)-N-(1,3-oxazol-2-ylmethyl)pyrazine-2-carboxamide;
3-amino-6-methyl-N-[(4-methyl-1H-imidazol-2-yl)methyl]-5-(1,3-oxazol-2-yl)pyrazine-2-carboxamide;
3-amino-6-methyl-N-[(1-methyl-1H-imidazol-2-yl)methyl]-5-(1,3-oxazol-2-yl)pyrazine-2-carboxamide;
3-amino-N-(1H-imidazol-2-ylmethyl)-6-methyl-5-(1,3-oxazol-2-yl)pyrazine-2-carboxamide;
3-amino-6-methyl-5-(1,3-oxazol-2-yl)-N-(1,3-thiazol-5-ylmethyl)pyrazine-2-carboxamide;
3-amino-6-methyl-5-(1,3-oxazol-2-yl)-N-{[3-(trifluoromethyl)pyridin-2-yl]methyl}pyrazine-2-carboxamide;
3-amino-6-methyl-5-(1,3-oxazol-2-yl)-N-(pyrimidin-2-ylmethyl)pyrazine-2-carboxamide;
3-amino-N-[(3-fluoropyridin-2-yl)methyl]-6-methyl-5-(1,3-oxazol-2-yl)pyrazine-2-carboxamide;
3-amino-N-{[6-(dimethylamino)pyridin-2-yl]methyl}-6-methyl-5-(1,3-oxazol-2-yl)pyrazine-2-carboxamide;
3-amino-N-[(6-methoxypyridin-2-yl)methyl]-6-methyl-5-(1,3-oxazol-2-yl)pyrazine-2-carboxamide;
3-amino-N-(isoquinolin-8-ylmethyl)-6-methyl-5-(1,3-oxazol-2-yl)pyrazine-2-carboxamide;
3-(3,4-dihydroquinolin-1(2H)-ylcarbonyl)-5-methyl-6-(1,3-oxazol-2-yl)pyrazin-2-amine;
3-amino-6-methyl-5-(1,3-oxazol-2-yl)-N-(2-pyridin-2-ylethyl)pyrazine-2-carboxamide;
3-amino-6-methyl-N-[(1-methyl-1H-pyrazol-3-yl)methyl]-5-(1,3-oxazol-2-yl)pyrazine-2-carboxamide;
3-amino-6-methyl-5-(1,3-oxazol-2-yl)-N-(pyridin-4-ylmethyl)pyrazine-2-carboxamide;
3-amino-6-methyl-5-(1,3-oxazol-2-yl)-N-(pyridin-3-ylmethyl)pyrazine-2-carboxamide;
3-amino-N-(isoquinolin-3-ylmethyl)-6-methyl-5-(1,3-oxazol-2-yl)pyrazine-2-carboxamide;
3-amino-N-(2-fluorobenzyl)-6-methyl-5-(1,3-oxazol-2-yl)pyrazine-2-carboxamide;
3-amino-N-(3-fluorobenzyl)-6-methyl-5-(1,3-oxazol-2-yl)pyrazine-2-carboxamide;
3-amino-N-(4-fluorobenzyl)-6-methyl-5-(1,3-oxazol-2-yl)pyrazine-2-carboxamide;
3-amino-6-methyl-5-(1,3-oxazol-2-yl)-N-(quinolin-2-ylmethyl)pyrazine-2-carboxamide;
3-[(3,3-difluoropiperidin-1-yl)carbonyl]-5-methyl-6-(1,3-oxazol-2-yl)pyrazin-2-amine;
3-amino-N-[(4,6-dimethylpyridin-2-yl)methyl]-6-methyl-5-(1,3-oxazol-2-yl)pyrazine-2-carboxamide;
3-amino-N-{[1-(2,2-difluoroethyl)-1H-benzimidazol-4-yl]methyl}-6-methyl-5-(1,3-oxazol-2-yl)pyrazine-2-carboxamide;
3-amino-6-methyl-5-(1,3-oxazol-2-yl)-N-[(1,4,5-trimethyl-1H-imidazol-2-yl)methyl]pyrazine-2-carboxamide;
3-amino-6-methyl-N-{[5-methyl-1-(1-methylethyl)-1H-imidazol-4-yl]methyl}-5-(1,3-oxazol-2-yl)pyrazine-2-carboxamide;
3-amino-6-methyl-5-(1,3-oxazol-2-yl)-N-(1,3-oxazol-5-ylmethyl)pyrazine-2-carboxamide;
3-amino-N-(isothiazol-5-ylmethyl)-6-methyl-5-(1,3-oxazol-2-yl)pyrazine-2-carboxamide;
3-amino-N-[(3,6-dimethylpyridin-2-yl)methyl]-6-methyl-5-(1,3-oxazol-2-yl)pyrazine-2-carboxamide;
3-amino-6-methyl-5-(1,3-oxazol-2-yl)-N-{[4-(trifluoromethyl)pyridin-2-yl]methyl}pyrazine-2-carboxamide;
3-amino-N-[(3-methoxypyridin-2-yl)methyl]-6-methyl-5-(1,3-oxazol-2-yl)pyrazine-2-carboxamide;
3-amino-N-{[1-(2,2-difluoroethyl)-1H-imidazol-2-yl]methyl}-6-methyl-5-(1,3-oxazol-2-yl)pyrazine-2-carboxamide;
3-amino-N-[(4-chloropyridin-2-yl)methyl]-6-methyl-5-(1,3-oxazol-2-yl)pyrazine-2-carboxamide;
3-amino-N-[(3-chloropyridin-4-yl)methyl]-6-methyl-5-(1,3-oxazol-2-yl)pyrazine-2-carboxamide;
3-amino-N-[(3-chloro-5-fluoropyridin-2-y)methyl]-6-methyl-5-(1,3-oxazol-2-yl)pyrazine-2-carboxamide;
3-amino-6-methyl-N-[(4-methylpyridazin-3-yl)methyl]-5-(1,3-oxazol-2-yl)pyrazine-2-carboxamide;
3-amino-N-[(5-chloropyridin-2-yl)methyl]-6-methyl-5-(1,3-oxazol-2-yl)pyrazine-2-carboxamide;
3-amino-6-methyl-N-[(1-methyl-2-oxo-1,2-dihydropyridin-3-yl)methyl]-5-(1,3-oxazol-2-yl)pyrazine-2-carboxamide;
3-amino-6-methyl-5-(1,3-oxazol-2-yl)-N-(pyridin-2-ylmethyl)pyrazine-2-carboxamide;
3-amino-6-methyl-5-(1,3-oxazol-2-yl)-N-[(1-oxidopyridin-2-yl)methyl]pyrazine-2-carboxamide;
3-amino-N-[(6-fluoropyridin-3-yl)methyl]-6-methyl-5-(1,3-oxazol-2-yl)pyrazine-2-carboxamide;
3-amino-N-{[6-chloro-4-(trifluoromethyl)pyridin-2-yl]methyl}-6-methyl-5-(1,3-oxazol-2-yl)pyrazine-2-carboxamide;

3-amino-N-{[5-methoxy-6-(trifluoromethyl)pyridin-2-yl]
methyl}-6-methyl-5-(1,3-oxazol-2-yl)pyrazine-2-carboxamide;
3-amino-6-methyl-N-[(5-methylpyridazin-3-yl)methyl]-
5-(1,3-oxazol-2-yl)pyrazine-2-carboxamide;
3-amino-N-[(5-fluoropyridin-2-yl)methyl]-6-methyl-5-
(1,3-oxazol-2-yl)pyrazine-2-carboxamide;
3-amino-6-methyl-N-{[3-methyl-4-(2,2,2-trifluoroeth-
oxy)pyridin-2-yl]methyl}-5-(1,3-oxazol-2-yl)pyra-
zine-2-carboxamide;
3-amino-6-methyl-5-(1,3-oxazol-2-yl)-N-{[5-(trifluo-
romethyl)pyridin-2-yl]methyl}pyrazine-2-carboxam-
ide;
3-amino-6-methyl-N-(2-methyl-2-pyridin-4-ylpropyl)-5-
(1,3-oxazol-2-yl)pyrazine-2-carboxamide;
3-amino-N-[(4-fluoropyridin-2-yl)methyl]-6-methyl-5-
(1,3-oxazol-2-yl)pyrazine-2-carboxamide;
3-amino-N-[(3,5-difluoropyridin-2-yl)methyl]-6-methyl-
5-(1,3-oxazol-2-yl)pyrazine-2-carboxamide;
3-amino-N-{[4,6-bis(difluoromethyl)pyridin-2-yl]
methyl}-6-methyl-5-(1,3-oxazol-2-yl)pyrazine-2-car-
boxamide;
3-amino-N-[(2-hydroxypyridin-3-yl)methyl]-6-methyl-5-
(1,3-oxazol-2-yl)pyrazine-2-carboxamide;
3-amino-N-[(2-chloropyridin-3-yl)methyl]-6-methyl-5-
(1,3-oxazol-2-yl)pyrazine-2-carboxamide;
3-amino-6-methyl-5-(1,3-oxazol-2-yl)-N-(1-pyrimidin-2-
ylpiperidin-4-yl)pyrazine-2-carboxamide;
3-amino-6-methyl-N-[(3-methylpyridin-4-yl)methyl]-5-
(1,3-oxazol-2-yl)pyrazine-2-carboxamide;
3-amino-N-(2-azetidin-1-yl-2-oxoethyl)-6-methyl-5-(1,
3-oxazol-2-yl)pyrazine-2-carboxamide;
3-amino-6-methyl-5-(1,3-oxazol-2-yl)-N-(pyrimidin-5-
ylmethyl)pyrazine-2-carboxamide;
3-amino-N-[(2,6-dimethylpyridin-3-yl)methyl]-6-
methyl-5-(1,3-oxazol-2-yl)pyrazine-2-carboxamide;
3-amino-N-[(2,4-dimethyl-1,3-thiazol-5-yl)methyl]-6-
methyl-5-(1,3-oxazol-2-yl)pyrazine-2-carboxamide;
3-amino-N-[(3-chloropyridin-2-yl)methyl]-6-methyl-5-
(1,3-oxazol-2-yl)pyrazine-2-carboxamide;
3-amino-N-[(2-fluoro-5-methylpyridin-3-yl)methyl]-6-
methyl-5-(1,3-oxazol-2-yl)pyrazine-2-carboxamide;
3-amino-N-[(5-chloro-3-fluoropyridin-2-yl)methyl]-6-
methyl-5-(1,3-oxazol-2-yl)pyrazine-2-carboxamide;
3-amino-N-{[2,6-bis(difluoromethyl)pyridin-4-yl]
methyl}-6-methyl-5-(1,3-oxazol-2-yl)pyrazine-2-car-
boxamide;
3-amino-6-methyl-5-(1,3-oxazol-2-yl)-N-(pyrimidin-4-
ylmethyl)pyrazine-2-carboxamide;
3-amino-N-[(1,4-dimethyl-1H-pyrazol-3-yl)methyl]-6-
methyl-5-(1,3-oxazol-2-yl)pyrazine-2-carboxamide;
3-amino-N-[(1,5-dimethyl-1H-pyrazol-4-yl)methyl]-6-
methyl-5-(1,3-oxazol-2-yl)pyrazine-2-carboxamide;
3-amino-N-[(1-ethyl-1H-imidazol-2-yl)methyl]-6-
methyl-5-(1,3-oxazol-2-yl)pyrazine-2-carboxamide;
3-amino-N-[(6-methoxy-3-methylpyridin-2-yl)methyl]-
6-methyl-5-(1,3-oxazol-2-yl)pyrazine-2-carboxamide;
3-amino-N-[(4,6-dimethylpyrimidin-2-yl)methyl]-6-
methyl-5-(1,3-oxazol-2-yl)pyrazine-2-carboxamide;
3-amino-6-methyl-5-(1,3-oxazol-2-yl)-N-(1-pyridin-2-
ylethyl)pyrazine-2-carboxamide;
3-amino-N-(4,4-difluorocyclohexyl)-6-methyl-5-(1,3-ox-
azol-2-yl)pyrazine-2-carboxamide;
3-amino-6-methyl-5-(1,3-oxazol-2-yl)-N-(5,6,7,8-tetra-
hydroisoquinolin-5-yl)pyrazine-2-carboxamide;
3-amino-6-methyl-N-([6-(1-methylethyl)pyridin-2-yl]
methyl)-5-(1,3-oxazol-2-yl)pyrazine-2-carboxamide;

3-amino-6-methyl-5-(1,3-oxazol-2-yl)-N-(1-pyridin-2-
ylethyl)pyrazine-2-carboxamide;
3-amino-6-methyl-N-{[1-(1-methylethyl)-1H-imidazol-
2-yl]methyl}-5-(1,3-oxazol-2-yl)pyrazine-2-carbox-
amide;
3-amino-6-methyl-N-[(3-methyl-2,2'-bipyridin-6-yl)
methyl]-5-(1,3-oxazol-2-yl)pyrazine-2-carboxamide;
3-amino-6-methyl-N-{[3-methyl-6-(1-methylethyl)pyri-
din-2-yl]methyl}-5-(1,3-oxazol-2-yl)pyrazine-2-car-
boxamide;
3-amino-N-{[6-(2-ethoxyethyl)-3-methylpyridin-2-yl]
methyl}-6-methyl-5-(1,3-oxazol-2-yl)pyrazine-2-car-
boxamide;
3-amino-N-{[1-(2,2-difluoroethyl)-2-oxo-1,2-dihydro-
pyridin-3-yl]methyl}-6-methyl-5-(1,3-oxazol-2-yl)
pyrazine-2-carboxamide;
3-amino-6-methyl-N-{[1-methyl-4-(trifluoromethyl)-1H-
imidazol-2-yl]methyl}-5-(1,3-oxazol-2-yl)pyrazine-2-
carboxamide;
3-amino-N-[(1-cyanocyclobutyl)methyl]-6-methyl-5-(1,
3-oxazol-2-yl)pyrazine-2-carboxamide;
3-amino-6-methyl-5-(1,3-oxazol-2-yl)-N-(1-pyridin-2-
ylpropyl)pyrazine-2-carboxamide;
3-amino-N-(1H-indol-7-ylmethyl)-6-methyl-5-(1,3-ox-
azol-2-yl)pyrazine-2-carboxamide;
3-amino-N-(imidazo-[1,2-a]pyridin-3-yl-methyl)-6-
methyl-5-(1,3-oxazol-2-yl)-pyrazine-2-carboxamide;
3-amino-6-methyl-N-[(2-methylimidazo[1,2-a]pyridin-3-
yl)methyl]-5-(1,3-oxazol-2-yl)pyrazine-2-carboxam-
ide;
3-amino-6-methyl-5-(1,3-oxazol-2-yl)-N-(5,6,7,8-tetra-
hydro-1,8-naphthyridin-2-ylmethyl)pyrazine-2-car-
boxamide;
3-amino-6-methyl-5-(1,3-oxazol-2-yl)-N-[(1-oxidopyri-
din-3-yl)methyl]pyrazine-2-carboxamide;
3-amino-N-{[1-(cyclopropylmethyl)-5-methyl-1H-imi-
dazol-4-yl]methyl}-6-methyl-5-(1,3-oxazol-2-yl)pyra-
zine-2-carboxamide;
3-amino-6-methyl-5-(1,3-oxazol-2-yl)-N-[cis-4-(trifluo-
romethyl)cyclohexyl]pyrazine-2-carboxamide;
3-amino-6-methyl-N-[(6-methylimidazo[1,2-a]pyridin-2-
yl)methyl]-5-(1,3-oxazol-2-yl)pyrazine-2-carboxam-
ide;
3-amino-6-methyl-5-(1,3-oxazol-2-yl)-N-(1,4,5,6-tetra-
hydrocyclopenta[c]pyrazol-3-ylmethyl)pyrazine-2-car-
boxamide;
3-amino-6-methyl-5-(1,3-oxazol-2-yl)-N-(5,6,7,8-tetra-
hydroisoquinolin-5-yl)pyrazine-2-carboxamide;
3-amino-6-methyl-5-(1,3-oxazol-2-yl)-N-(1-pyrindin-2-
ylpropyl)pyrazine-2-carboxamide;
3-amino-N,6-dimethyl-5-(1,3-oxazol-2-yl)-N-(1-pyridin-
2-ylethyl)pyrazine-2-carboxamide;
3-amino-N-[(5-fluoro-3-methylpyridin-2-yl)methyl]-6-
methyl-5-(1,3-oxazol-2-yl)pyrazine-2-carboxamide;
3-amino-6-methyl-5-(1,3-oxazol-2-yl)-N-{[4-(trifluo-
romethyl)pyrimidin-2-yl]methyl}pyrazine-2-carbox-
amide;
3-amino-N-[(5-fluoropyrimidin-2-yl)methyl]-6-methyl-
5-(1,3-oxazol-2-yl)pyrazine-2-carboxamide;
3-amino-N-[(4-methoxypyrimidin-2-yl)methyl]-6-
methyl-5-(1,3-oxazol-2-yl)pyrazine-2-carboxamide;
3-amino-6-methyl-N-[(7-methylimidazo[1,2-a]pyridin-2-
yl)methyl]-5-(1,3-oxazol-2-yl)pyrazine-2-carboxam-
ide;
3-amino-N-[2-(4-fluorophenyl)-2-oxoethyl]-6-methyl-5-
(1,3-oxazol-2-yl)pyrazine-2-carboxamide;

3-amino-N-[3-(3,3-difluoropyrrolidin-1-yl)propyl]-6-methyl-5-(1,3-oxazol-2-yl)pyrazine-2-carboxamide;
3-amino-N-{[1-(cyclopropylmethyl)-1H-imidazol-4-yl]methyl}-6-methyl-5-(1,3-oxazol-2-yl)pyrazine-2-carboxamide;
3-amino-N-(3,3-difluorocyclopentyl)-6-methyl-5-(1,3-oxazol-2-yl)pyrazine-2-carboxamide;
3-amino-6-methyl-5-(1,3-oxazol-2-yl)-N-[1-(2,2,2-trifluoroethyl)piperidin-3-yl]pyrazine-2-carboxamide;
3-amino-6-methyl-5-(1,3-oxazol-2-yl)-N-piperidin-3-ylpyrazine-2-carboxamide;
3-amino-6-methyl-5-(1,3-oxazol-2-yl)-N-[trans-4-(trifluoromethyl)cyclohexyl]pyrazine-2-carboxamide;
3-amino-N-([6-(1-hydroxy-1-methylethyl)pyridin-2-yl]methyl)-6-methyl-5-(1,3-oxazol-2-yl)pyrazine-2-carboxamide;
3-amino-N-[(1,4-dimethyl-1H-imidazol-2-yl)methyl]-6-methyl-5-(1,3-oxazol-2-yl)pyrazine-2-carboxamide;
3-amino-6-methyl-5-(1,3-oxazol-2-yl)-N-{[6-(trifluoromethyl)pyridin-2-yl]methyl}pyrazine-2-carboxamide;
3-amino-N-{[6-(methoxymethyl)pyridin-2-yl]methyl}-6-methyl-5-(1,3-oxazol-2-yl)pyrazine-2-carboxamide;
3-amino-N-(2-methoxyethyl)-6-methyl-5-(1,3-oxazol-2-yl)pyrazine-2-carboxamide;
3-amino-N-[(2-methoxypyridin-3-yl)methyl]-6-methyl-5-(1,3-oxazol-2-yl)pyrazine-2-carboxamide;
3-(5,8-dihydro-1,7-naphthyridin-7(6H)-ylcarbonyl)-5-methyl-6-(1,3-oxazol-2-yl)pyrazin-2-amine;
3-amino-6-methyl-5-(1,3-oxazol-2-yl)-N-{[5-(trifluoromethyl)pyrimidin-2-yl]methyl}pyrazine-2-carboxamide;
3-amino-N-[(1-cyclobutyl-1H-imidazol-2-yl)methyl]-6-methyl-5-(1,3-oxazol-2-yl)pyrazine-2-carboxamide;
3-amino-N-(cyclopropylmethyl)-6-methyl-5-(1,3-oxazol-2-yl)pyrazine-2-carboxamide;
3-amino-N-(5-fluoro-2-hydroxybenzyl)-6-methyl-5-(1,3-oxazol-2-yl)pyrazine-2-carboxamide;
3-amino-N-[(1S,2S)-2-hydroxy-2,3-dihydro-1H-inden-1-yl]-6-methyl-5-(1,3-oxazol-2-yl)pyrazine-2-carboxamide;
5-methyl-6-(1,3-oxazol-2-yl)-3-[(2-phenylazetidin-1-yl)carbonyl]pyrazin-2-amine;
3-amino-6-methyl-5-(1,3-oxazol-2-yl)-N-(thiophen-2-ylmethyl)pyrazine-2-carboxamide;
3-amino-6-methyl-N-[4-(1-methylethyl)benzyl]-5-(1,3-oxazol-2-yl)pyrazine-2-carboxamide;
3-amino-N-(4-cyclopropylbenzyl)-6-methyl-5-(1,3-oxazol-2-yl)pyrazine-2-carboxamide;
3-amino-N-(2-fluoro-3-methylbenzyl)-6-methyl-5-(1,3-oxazol-2-yl)pyrazine-2-carboxamide;
3-amino-6-methyl-5-(1,3-oxazol-2-yl)-N-(2,4,6-trimethylbenzyl)pyrazine-2-carboxamide;
3-amino-N-(4-fluoro-3-methylbenzyl)-6-methyl-5-(1,3-oxazol-2-yl)pyrazine-2-carboxamide;
3-amino-N-[(1S)-2,3-dihydro-1H-inden-1-yl]-6-methyl-5-(1,3-oxazol-2-yl)pyrazine-2-carboxamide;
3-amino-N-(4-ethylbenzyl)-6-methyl-5-(1,3-oxazol-2-yl)pyrazine-2-carboxamide;
3-amino-N-[(1R)-2,3-dihydro-1H-inden-1-yl]-6-methyl-5-(1,3-oxazol-2-yl)pyrazine-2-carboxamide;
3-amino-6-methyl-N-[(1-methyl-1H-pyrrol-2-yl)methyl]-5-(1,3-oxazol-2-yl)pyrazine-2-carboxamide;
3-amino-N-[(1,5-dimethyl-1H-pyrrol-2-yl)methyl]-6-methyl-5-(1,3-oxazol-2-yl)pyrazine-2-carboxamide;
3-amino-N-(3-methoxybenzyl)-6-methyl-5-(1,3-oxazol-2-yl)pyrazine-2-carboxamide;
3-amino-N-(2-methoxybenzyl)-6-methyl-5-(1,3-oxazol-2-yl)pyrazine-2-carboxamide;
3-amino-N-[(4R)-3,4-dihydro-2H-chromen-4-yl]-6-methyl-5-(1,3-oxazol-2-yl)pyrazine-2-carboxamide;
3-amino-N-[(4S)-3,4-dihydro-2H-chromen-4-yl]-6-methyl-5-(1,3-oxazol-2-yl)pyrazine-2-carboxamide;
3-amino-N-[(3R)-2,3-dihydro-1-benzofuran-3-yl]-6-methyl-5-(1,3-oxazol-2-yl)pyrazine-2-carboxamide;
3-amino-N-(4-methoxybenzyl)-6-methyl-5-(1,3-oxazol-2-yl)pyrazine-2-carboxamide;
3-amino-N-(1,3-benzothiazol-2-ylmethyl)-6-methyl-5-(1,3-oxazol-2-yl)pyrazine-2-carboxamide 3-amino-6-methyl-5-(1,3-oxazol-2-yl)-N-[(2-thiophen-2-yl-1,3-thiazol-4-yl)methyl]pyrazine-2-carboxamide;
3-(5,7-dihydro-6H-pyrrolo[3,4-d]pyrimidin-6-ylcarbonyl)-5-methyl-6-(1,3-oxazol-2-yl)pyrazin-2-amine;
3-(5,7-dihydro-6H-pyrrolo[3,4-d]pyrimidin-6-ylcarbonyl)-5-methyl-6-(1,3-oxazol-2-yl)pyrazin-2-amine;
3-amino-N-(2-hydroxybenzyl)-6-methyl-5-(1,3-oxazol-2-yl)pyrazine-2-carboxamide;
3-amino-N-(2-hydroxy-5-methylbenzyl)-6-methyl-5-(1,3-oxazol-2-yl)pyrazine-2-carboxamide;
3-amino-N-(4-hydroxybenzyl)-6-methyl-5-(1,3-oxazol-2-yl)pyrazine-2-carboxamide;
3-amino-N-[(1R,2S)-2-hydroxy-2,3-dihydro-1H-inden-1I-yl]-6-methyl-5-(1,3-oxazol-2-yl)pyrazine-2-carboxamide;
3-amino-N-[(3S)-2,3-dihydro-1-benzofuran-3-yl]-6-methyl-5-(1,3-oxazol-2-yl)pyrazine-2-carboxamide;
3-amino-N-(3-hydroxybenzyl)-6-methyl-5-(1,3-oxazol-2-yl)pyrazine-2-carboxamide;
3-amino-N-[(1R,2R)-2-hydroxy-2,3-dihydro-1H-inden-1-yl]-6-methyl-5-(1,3-oxazol-2-yl)pyrazine-2-carboxamide;
3-amino-N-(6,7-dihydro-5H-pyrrolo[2,1-c][1,2,4]triazol-3-ylmethyl)-6-methyl-5-(1,3-oxazol-2-yl)pyrazine-2-carboxamide;
3-amino-N-(1,4,5,6,7,8-hexahydrocyclohepta[c]pyrazol-3-ylmethyl)-6-methyl-5-(1,3-oxazol-2-yl)pyrazine-2-carboxamide;
3-amino-N-[(4-fluoro-3-methylpyridin-2-yl)methyl]-6-methyl-5-(1,3-oxazol-2-yl)pyrazine-2-carboxamide;
3-amino-N-[(3-ethyl-4-fluoropyridin-2-yl)methyl]-6-methyl-5-(1,3-oxazol-2-yl)pyrazine-2-carboxamide;
3-amino-N-(1H-benzimidazol-2-ylmethyl)-6-methyl-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-[(1H-ethyl-1H-1,2,4-triazol-5-yl)methyl]-6-methyl-5-(1,3-oxazol-2-yl)pyrazine-2-carboxamide;
3-amino-N-[(3-ethoxypyridin-2-yl)methyl]-6-methyl-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-[(3-cyclopropyl-5-fluoropyridin-2-yl)methyl]-6-methyl-5-(1,3-oxazol-2-yl)pyrazine-2-carboxamide;
3-amino-N-[(4-cyclopropyl-1-methyl-1H-pyrazol-3-yl)methyl]-6-methyl-5-(1,3-oxazol-2-yl)pyrazine-2-carboxamide;
3-amino-N-[(1R,2S)-2-(methoxymethyl)cyclopentyl]-6-methyl-5-(1,3-oxazol-2-yl)pyrazine-2-carboxamide;
3-amino-N-[(3-fluoropyrazin-2-yl)methyl]-6-methyl-5-(1,3-oxazol-2-yl)pyrazine-2-carboxamide;
3-amino-N-(2-ethoxy-6-fluorobenzyl)-6-methyl-5-(1,3-oxazol-2-yl)pyrazine-2-carboxamide;

3-amino-6-methyl-N-[(1-methyl-1,4,5,6-tetrahydrocyclopenta[c]pyrazol-3-yl)methyl]-5-(1,3-oxazol-2-yl)pyrazine-2-carboxamide;
3-amino-6-methyl-N-[(5-methylpyrimidin-4-yl)methyl]-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-(4-hydroxycycloheptyl)-6-methyl-5-(1,3-oxazol-2-yl)pyrazine-2-carboxamide;
3-amino-N-(isoquinolin-11-ylmethyl)-6-methyl-5-(1,3-oxazol-2-yl)pyrazine-2-carboxamide;
3-amino-N-[(3-ethylpyridin-2-yl)methyl]-6-methyl-5-(1,3-oxazol-2-yl)pyrazine-2-carboxamide;
3-amino-N-[(3-cyclopropyl-4-fluoropyridin-2-yl)methyl]-6-methyl-5-(1,3-oxazol-2-yl)pyrazine-2-carboxamide;
3-amino-6-methyl-5-(1,3-oxazol-2-yl)-N-{[1-(2,2,2-trifluoroethyl)-1H-benzimidazol-4-yl]methyl}pyrazine-2-carboxamide;
3-amino-N-{[3-cyclopropyl-5-(trifluoromethyl)pyridin-2-yl]methyl}-6-methyl-5-(1,3-oxazol-2-yl)pyrazine-2-carboxamide;
3-amino-6-methyl-N-{[3-methyl-5-trifluoromethyl)pyridin-2-yl]methyl}-5-(1,3-oxazol-2-yl)pyrazine-2-carboxamide;
3-amino-N-[(3-cyclopropyl-pyrazin-2-yl)methyl]-6-methyl-5-(1,3-oxazol-2-yl)pyrazine-2-carboxamide;
3-amino-6-methyl-N-[(5-methylpyrimidin-2-yl)methyl]-5-(1,3-oxazol-2-yl)pyrazine-2-carboxamide;
3-amino-N-(2-fluoro-6-methoxybenzyl)-6-methyl-5-(1,3-oxazol-2-yl)pyrazine-2-carboxamide;
3-amino-N-[(3-ethylpyrazin-2-yl)methyl]-6-methyl-5-(1,3-oxazol-2-yl)pyrazine-2-carboxamide;
3-amino-6-methyl-N-{[1-(1-methylethyl)-1H-1,2,4-triazol-5-yl]methyl}-5-(1,3-oxazol-2-yl)pyrazine-2-carboxamide;
3-amino-6-methyl-N-{[1-(1-methylethyl)-1H-benzimidazol-4-yl]methyl}-5-(1,3-oxazol-2-yl)pyrazine-2-carboxamide;
3-amino-6-methyl-N-[2-(2-methyl-6,7-dihydro[1,3]oxazolo[5,4-c]pyridin-5(4H)-yl)ethyl]-5-(1,3-oxazol-2-yl)pyrazine-2-carboxamide;
3-amino-N-(2,2-difluorocyclopentyl)-6-methyl-5-(1,3-oxazol-2-yl)pyrazine-2-carboxamide;
3-amino-N-(2,2-difluorocyclopentyl)-6-methyl-5-(1,3-oxazol-2-yl)pyrazine-2-carboxamide;
3-amino-N-[(1-ethyl-1H-benzimidazol-4-yl)methyl]-6-methyl-5-(1,3-oxazol-2-yl)pyrazine-2-carboxamide;
3-amino-N-{[4-(difluoromethyl)-1-methyl-1H-pyrazol-3-yl]methyl}-6-methyl-5-(1,3-oxazol-2-yl)pyrazine-2-carboxamide;
3-amino-6-methyl-N-[(3-methylpyrazin-2-yl)methyl]-5-(1,3-oxazol-2-yl)pyrazine-2-carboxamide;
3-amino-N-{[3-ethyl-5-(trifluoromethyl)pyridin-2-yl]methyl}-6-methyl-5-(1,3-oxazol-2-yl)pyrazine-2-carboxamide;
3-amino-N-[(5-cyclopropylpyrimidin-2-yl)methyl]-6-methyl-5-(1,3-oxazol-2-yl)pyrazine-2-carboxamide;
3-amino-6-methyl-N-[(3-methyl-3H-imidazo[4,5-c]pyridin-4-yl)methyl]-5-(1,3-oxazol-2-yl)pyrazine-2-carboxamide;
3-amino-N-[(5-ethylpyrimidin-2-yl)methyl]-6-methyl-5-(1,3-oxazol-2-yl)pyrazine-2-carboxamide;
3-amino-N-[(1S)-5-fluoro-2,3-dihydro-1H-inden-1-yl]-6-methyl-5-(1,3-oxazol-2-yl)pyrazine-2-carboxamide;
3-amino-N-[(1S)-6-fluoro-2,3-dihydro-1H-inden-1-yl]-6-methyl-5-(1,3-oxazol-2-yl)pyrazine-2-carboxamide;
3-amino-N-[(1R,2R)-2-hydroxycyclopentyl]-6-methyl-5-(1,3-oxazol-2-yl)pyrazine-2-carboxamide;
3-amino-N-[(1S,2R)-2-fluorocyclopentyl]-6-methyl-5-(1,3-oxazol-2-yl)pyrazine-2-carboxamide;
3-amino-N-[(1R,2R)-2-(dimethylamino)cyclopentyl]-6-methyl-5-(1,3-oxazol-2-yl)pyrazine-2-carboxamide;
3-amino-N-[(1R,2R)-2-hydroxycyclopentyl]-N,6-dimethyl-5-(1,3-oxazol-2-yl)pyrazine-2-carboxamide;
3-amino-N-[(1R,2R)-2-fluorocyclopentyl]-6-methyl-5-(1,3-oxazol-2-yl)pyrazine-2-carboxamide;
3-amino-N-[(1S,2R,5R)-2-hydroxy-5-methylcyclopentyl]-6-methyl-5-(1,3-oxazol-2-yl)pyrazine-2-carboxamide;
3-amino-6-methyl-5-(1,3-oxazol-2-yl)-N-[(1R,2R)-2-prop-2-yn-1-ylcyclopentyl]pyrazine-2-carboxamide;
3-amino-N-[(1S,2R)-2-ethynylcyclopentyl]-6-methyl-5-(1,3-oxazol-2-yl)pyrazine-2-carboxamide;
3-amino-N-(2-fluorocyclopentyl)-6-methyl-5-(1,3-oxazol-2-yl)pyrazine-2-carboxamide;
3-amino-N-[(1S,2S)-2-hydroxycyclopentyl]-6-methyl-5-(1,3-oxazol-2-yl)pyrazine-2-carboxamide;
3-amino-N-[(1R,2S)-2-hydroxycyclopentyl]-6-methyl-5-(1,3-oxazol-2-yl)pyrazine-2-carboxamide;
3-amino-N-[(1R,2R,4S)-bicyclo[2.2.1]hept-2-yl]-6-methyl-5-(1,3-oxazol-2-yl)pyrazine-2-carboxamide;
3-amino-6-methyl-N-[(1-methyl-1H-pyrrolo[3,2-c]pyridin-4-yl)methyl]-5-(1,3-oxazol-2-yl)pyrazine-2-carboxamide;
3-amino-6-methyl-5-(1,3-oxazol-2-yl)-N-{[3-(trifluoromethyl)pyrazin-2-yl]methyl}pyrazine-2-carboxamide;
3-amino-N-[(2-ethyl-2H-indazol-7-yl)methyl]-6-methyl-5-(1,3-oxazol-2-yl)pyrazine-2-carboxamide;
3-amino-N-{[1-(2,2-difluoroethyl)-1H-indol-4-yl]methyl}-6-methyl-5-(1,3-oxazol-2-yl)pyrazine-2-carboxamide;
3-amino-6-methyl-N-[(1-methyl-1H-benzimidazol-4-yl)methyl]-5-(1,3-oxazol-2-yl)pyrazine-2-carboxamide;
3-amino-6-methyl-N-[(1-methyl-1H-benzimidazol-7-yl)methyl]-5-(1,3-oxazol-2-yl)pyrazine-2-carboxamide;
3-amino-N-[(1S)-5-chloro-2,3-dihydro-1H-inden-1-yl]-6-methyl-5-(1,3-oxazol-2-yl)pyrazine-2-carboxamide;
3-amino-N-(5-hydroxy-6,7-dihydro-5H-cyclopenta[b]pyridin-7-yl)-6-methyl-5-(1,3-oxazol-2-yl)pyrazine-2-carboxamide;
3-amino-N-{[3-(fluoromethyl)pyridin-2-yl]methyl}-6-methyl-5-(1,3-oxazol-2-yl)pyrazine-2-carboxamide;
3-amino-N-{[3-(hydroxymethyl)pyridin-2-yl]methyl}-6-methyl-5-(1,3-oxazol-2-yl)pyrazine-2-carboxamide;
3-amino-6-methyl-N-[1-(3-methylpyridin-2-yl)ethyl]-5-(1,3-oxazol-2-yl)pyrazine-2-carboxamide;
3-amino-6-methyl-N-[1-(3-methylpyridin-2-yl)ethyl]-5-(1,3-oxazol-2-yl)pyrazine-2-carboxamide;
3-amino-N-{[1-(2,2-difluoroethyl)-1H-indazol-4-yl]methyl}-6-methyl-5-(1,3-oxazol-2-yl)pyrazine-2-carboxamide;
3-amino-N-{[1-(cyclopropylmethyl)-1H-benzimidazol-4-yl]methyl}-6-methyl-5-(1,3-oxazol-2-yl)pyrazine-2-carboxamide;
3-amino-6-methyl-5-(1,3-oxazol-2-yl)-N-(5,6,7,8-tetrahydroquinolin-8-yl)pyrazine-2-carboxamide;
3-amino-N-(5-methoxy-2,3-dihydro-1H-inden-1-yl)-6-methyl-5-(1,3-oxazol-2-yl)pyrazine-2-carboxamide;
3-amino-N-(5-methoxy-2,3-dihydro-1H-inden-1-yl)-6-methyl-5-(1,3-oxazol-2-yl)pyrazine-2-carboxamide;
3-amino-6-methyl-5-(1,3-oxazol-2-yl)-N-(1,2,3,4-tetrahydronaphthalen-2-yl)pyrazine-2-carboxamide;

3-amino-6-methyl-5-(1,3-oxazol-2-yl)-N-(1,2,3,4-tetrahydronaphthalen-2-yl)pyrazine-2-carboxamide;
3-amino-N-(2,3-dihydro-1H-inden-2-yl)-6-methyl-5-(1,3-oxazol-2-yl)pyrazine-2-carboxamide;
3-amino-N-{[6-(1-hydroxy-1-methylethyl)-3-methyl-pyridin-2-yl]methyl}-6-methyl-5-(1,3-oxazol-2-yl)pyrazine-2-carboxamide;
3-amino-N-{[6-(1-hydroxy-1-methylethyl)-3-methoxy-pyridin-2-yl]methyl}-6-methyl-5-(1,3-oxazol-2-yl)pyrazine-2-carboxamide;
3-amino-N-(6-hydroxy-6,7-dihydro-5H-cyclopenta[b]pyridin-7-yl)-6-methyl-5-(1,3-oxazol-2-yl)pyrazine-2-carboxamide;
3-amino-N-(6-hydroxy-6,7-dihydro-5H-cyclopenta[b]pyridin-7-yl)-6-methyl-5-(1,3-oxazol-2-yl)pyrazine-2-carboxamide;
3-amino-N-(5-hydroxy-6,7-dihydro-5H-cyclopenta[b]pyridin-7-yl)-6-methyl-5-(1,3-oxazol-2-yl)pyrazine-2-carboxamide;
3-amino-N-(5-hydroxy-6,7-dihydro-5H-cyclopenta[b]pyridin-7-yl)-6-methyl-5-(1,3-oxazol-2-yl)pyrazine-2-carboxamide;
3-amino-N-[(1-ethyl-1H-indazol-4-yl)methyl]-6-methyl-5-(1,3-oxazol-2-yl)pyrazine-2-carboxamide;
3-amino-N-[(2-ethyl-2H-indazol-4-yl)methyl]-6-methyl-5-(1,3-oxazol-2-yl)pyrazine-2-carboxamide;
3-amino-N-(4-chloro-6,7-dihydro-5H-cyclopenta[b]pyridin-7-yl)-6-methyl-5-(1,3-oxazol-2-yl)pyrazine-2-carboxamide;
3-amino-N-(2-chloro-6,7-dihydro-5H-cyclopenta[b]pyridin-7-yl)-6-methyl-5-(1,3-oxazol-2-yl)pyrazine-2-carboxamide;
3-amino-6-methyl-5-(1,3-oxazol-2-yl)-N-(5,6,7,8-tetrahydroquinolin-8-yl)pyrazine-2-carboxamide;
3-amino-N-(4-chloro-6,7-dihydro-5H-cyclopenta[b]pyridin-7-yl)-6-methyl-5-(1,3-oxazol-2-yl)pyrazine-2-carboxamide;
3-amino-N-(2-chloro-6,7-dihydro-5H-cyclopenta[b]pyridin-7-yl)-6-methyl-5-(1,3-oxazol-2-yl)pyrazine-2-carboxamide;
3-amino-6-methyl-5-(1,3-oxazol-5-yl)-N-{[3-(trifluoromethyl)-pyridin-2-yl]-methyl)}pyrazine-2-carboxamide;
3-amino-6-chloro-5-(1,3-oxazol-5-yl)-N-(quinolin-8-ylmethyl)pyrazine-2-carboxamide;
3-amino-N-(2,6-difluorobenzyl)-6-methyl-5-(1,3-oxazol-5-yl)pyrazine-2-carboxamide;
3-amino-6-methyl-N-[(3-methylpyridin-2-yl)methyl]-5-(1,3-oxazol-5-yl)pyrazine-2-carboxamide;
3-amino-N-(2,4-difluorobenzyl)-6-methyl-5-(1,3-oxazol-5-yl)pyrazine-2-carboxamide;
3-amino-N-(2-methoxybenzyl)-6-methyl-5-(1,3-oxazol-5-yl)pyrazine-2-carboxamide;
3-amino-N-(2,6-dichlorobenzyl)-6-methyl-5-(1,3-oxazol-5-yl)pyrazine-2-carboxamide;
3-amino-N-(2-chloro-6-methylbenzyl)-6-methyl-5-(1,3-oxazol-5-yl)pyrazine-2-carboxamide;
3-amino-6-methyl-5-(1,3-oxazol-5-yl)-N-{[3-(trifluoromethyl)pyridin-2-yl]methyl}pyrazine-2-carboxamide;
3-amino-N-(2,4-dichloro-6-methylbenzyl)-6-methyl-5-(1,3-oxazol-5-yl)pyrazine-2-carboxamide;
3-amino-6-methyl-N-(1-methyl-1-pyridin-2-ylethyl)-5-(1,3-oxazol-5-yl)pyrazine-2-carboxamide;
3-amino-N-[1-(3,4-difluorophenyl)-1-methylethyl]-6-methyl-5-(1,3-oxazol-5-yl)pyrazine-2-carboxamide;
3-amino-6-methyl-N-(1-methyl-1-pyridin-4-ylethyl)-5-(1,3-oxazol-5-yl)pyrazine-2-carboxamide;
3-amino-N-(2,2-difluoropropyl)-6-methyl-5-(1,3-oxazol-5-yl)pyrazine-2-carboxamide;
3-amino-6-methyl-N-[(6-methylpyridin-2-yl)methyl]-5-(1,3-oxazol-5-yl)pyrazine-2-carboxamide;
3-amino-N-(6,7-dihydro-5H-cyclopenta[b]pyridin-7-yl)-6-methyl-5-(1,3-oxazol-5-yl)pyrazine-2-carboxamide;
3-amino-N-(6,7-dihydro-5H-cyclopenta[b]pyridin-7-yl)-6-methyl-5-(1,3-oxazol-5-yl)pyrazine-2-carboxamide;
3-amino-6-chloro-5-(1H-1,2,3-triazol-1-yl)-N-[2-(trifluoromethyl)benzyl]pyrazine-2-carboxamide;
3-amino-6-chloro-5-(2H-1,2,3-triazol-2-yl)-N-[2-(trifluoromethyl)benzyl]pyrazine-2-carboxamide;
3-amino-6-chloro-N-(2,4-difluorobenzyl)-5-(1H-1,2,3-triazol-1-yl)pyrazine-2-carboxamide;
3-amino-6-chloro-N-(2,4-difluorobenzyl)-5-(2H-1,2,3-triazol-2-yl)pyrazine-2-carboxamide;
3-amino-6-chloro-N-(quinolin-8-ylmethyl)-5-(1H-1,2,3-triazol-1-yl)pyrazine-2-carboxamide;
3-amino-6-chloro-N-(quinolin-8-ylmethyl)-5-(2H-1,2,3-triazol-2-yl)pyrazine-2-carboxamide;
3-amino-N-(2,6-difluorobenzyl)-6-methyl-5-(2H-1,2,3-triazol-2-yl)pyrazine-2-carboxamide;
3-amino-6-methyl-N-(quinolin-8-ylmethyl)-5-(2H-1,2,3-triazol-2-yl)pyrazine-2-carboxamide;
3-amino-6-methyl-N-[(3-methylpyridin-2-yl)methyl]-5-(2H-1,2,3-triazol-2-yl)pyrazine-2-carboxamide;
3-amino-6-methyl-N-[(3-methylpyridin-2-yl)methyl]-5-(1H-1,2,3-triazol-1-yl)pyrazine-2-carboxamide;
3-amino-N-(2,4-dichlorobenzyl)-6-methyl-5-(2H-1,2,3-triazol-2-yl)pyrazine-2-carboxamide;
3-amino-6-methyl-N-(1,2,3,4-tetrahydroquinolin-4-yl)-5-(2H-1,2,3-triazol-2-yl)pyrazine-2-carboxamide;
3-amino-6-chloro-N-[(1R)-2,3-dihydro-1H-inden-1-yl]-5-(2H-1,2,3-triazol-2-yl)pyrazine-2-carboxamide;
3-amino-6-chloro-N-[(3-methylpyridin-2-yl)methyl]-5-(2H-1,2,3-triazol-2-yl)pyrazine-2-carboxamide;
3-amino-6-chloro-N-(2-methoxybenzyl)-5-(2H-1,2,3-triazol-2-yl)pyrazine-2-carboxamide;
3-amino-6-chloro-5-(2H-1,2,3-triazol-2-yl)-N-[2-(trifluoromethoxy)benzyl]pyrazine-2-carboxamide;
3-amino-6-chloro-5-(2H-1,2,3-triazol-2-yl)-N-[(1R)-2,2,2-trifluoro-1-phenylethyl]pyrazine-2-carboxamide;
3-amino-6-chloro-5-(2H-1,2,3-triazol-2-yl)-N-[(1S)-2,2,2-trifluoro-1-phenylethyl]pyrazine-2-carboxamide;
3-amino-6-chloro-N-[(1R)-1-quinolin-2-ylethyl]-5-(2H-1,2,3-triazol-2-yl)pyrazine-2-carboxamide;
3-amino-N-(2-bromobenzyl)-6-chloro-5-(2H-1,2,3-triazol-2-yl)pyrazine-2-carboxamide;
3-amino-N-[2-(2-bromophenyl)ethyl]-6-chloro-5-(2H-1,2,3-triazol-2-yl)pyrazine-2-carboxamide;
3-amino-6-chloro-N-methyl-N-(quinolin-8-ylmethyl)-5-(2H-1,2,3-triazol-2-yl)pyrazine-2-carboxamide;
3-amino-6-chloro-N-(1-pyridin-3-ylcyclopropyl)-5-(2H-1,2,3-triazol-2-yl)pyrazine-2-carboxamide;
3-[(8-bromo-3,4-dihydroisoquinolin-2(1H)-yl)carbonyl]-5-chloro-6-(2H-1,2,3-triazol-2-yl)pyrazin-2-amine;
3-amino-6-chloro-N-(1,2,3,4-tetrahydroquinolin-4-yl)-5-(2H-1,2,3-triazol-2-yl)pyrazine-2-carboxamide;
3-amino-6-chloro-N-[2-(3,4-dimethoxyphenyl)ethyl]-5-(2H-1,2,3-triazol-2-yl)pyrazine-2-carboxamide;
3-amino-6-chloro-N-pyrazolo[1,5-a]pyridin-3-ylmethyl)-5-(2H-1,2,3-triazol-2-yl)pyrazine-2-carboxamide;
3-amino-6-chloro-N-(isoquinolin-5-ylmethyl)-5-(2H-1,2,3-triazol-2-yl)pyrazine-2-carboxamide;

3-amino-6-chloro-N-isoquinolin-8-ylmethyl)-5-(2H-1,2,3-triazol-2-yl)pyrazine-2-carboxamide;
3-amino-N-(1,3-benzothiazol-2-ylmethyl)-6-chloro-5-(2H-1,2,3-triazol-2-yl)pyrazine-2-carboxamide;
3-amino-N-(1,3-benzoxazol-2-ylmethyl)-6-chloro-5-(2H-1,2,3-triazol-2-yl)pyrazine-2-carboxamide;
3-amino-6-chloro-N-(quinoxalin-5-ylmethyl)-5-(2H-1,2,3-triazol-2-yl)pyrazine-2-carboxamide;
3-amino-6-chloro-N-quinolin-4-ylmethyl)-5-(2H-1,2,3-triazol-2-yl)pyrazine-2-carboxamide;
3-amino-N-(1H-benzimidazol-2-ylmethyl)-6-chloro-5-(2H-1,2,3-triazol-2-yl)pyrazine-2-carboxamide;
3-amino-N-(2-aminobenzyl)-6-chloro-5-(2H-1,2,3-triazol-2-yl)pyrazine-2-carboxamide;
3-amino-N-(2-amino-6-fluorobenzyl)-6-chloro-5-(2H-1,2,3-triazol-2-yl)pyrazine-2-carboxamide;
3-amino-6-chloro-N-(imidazo[1,2-a]pyridin-3-ylmethyl)-5-(2H-1,2,3-triazol-2-yl)pyrazine-2-carboxamide;
3-amino-6-chloro-N-(quinolin-2-ylmethyl)-5-(2H-1,2,3-triazol-2-yl)pyrazine-2-carboxamide;
3-amino-6-chloro-N-(isoquinolin-3-ylmethyl)-5-2H-1,2,3-triazol-2-yl)pyrazine-2-carboxamide;
3-amino-6-chloro-N-(1H-indol-2-ylmethyl)-5-(2H-1,2,3-triazol-2-yl)pyrazine-2-carboxamide;
3-amino-6-chloro-N-(quinolin-5-ylmethyl)-5-(2H-1,2,3-triazol-2-yl)pyrazine-2-carboxamide;
3-amino-6-chloro-N-imidazo[2,1-b][1,3]thiazol-6-ylmethyl)-5-(2H-1,2,3-triazol-2-yl)pyrazine-2-carboxamide;
3-amino-6-chloro-N-(2-pyrazin-2-ylethyl)-5-(2H-1,2,3-triazol-2-yl)pyrazine-2-carboxamide;
3-amino-6-chloro-N-[(1R)-2-hydroxy-1-phenylethyl]-5-(2H-1,2,3-triazol-2-yl)pyrazine-2-carboxamide;
3-amino-6-chloro-N-[(1S)-2-hydroxy-1-phenylethyl]-5-(2H-1,2,3-triazol-2-yl)pyrazine-2-carboxamide;
3-amino-6-chloro-N-[(3-oxo-2,3-dihydro-1H-isoindol-4-yl)methyl]-5-(2H-1,2,3-triazol-2-yl)pyrazine-2-carboxamide;
3-amino-6-chloro-N-(2-phenoxyethyl)-5-(2H-1,2,3-triazol-2-yl)pyrazine-2-carboxamide;
3-amino-6-chloro-N-[(1R,2R)-2-fluoro-2-phenylcyclopropyl]-5-(2H-1,2,3-triazol-2-yl)pyrazine-2-carboxamide;
3-amino-6-chloro-N-[(1S,2R)-2-fluoro-2-phenylcyclopropyl]-5-(2H-1,2,3-triazol-2-yl)pyrazine-2-carboxamide;
methyl N-{[3-amino-6-chloro-5-(2H-1,2,3-triazol-2-yl)pyrazin-2-yl]carbonyl}-D-serinate;
3-amino-6-chloro-N-(5,6,7,8-tetrahydroquinolin-8-ylmethyl)-5-(2H-1,2,3-triazol-2-yl)pyrazine-2-carboxamide;
3-amino-N-[(1 S)-1-benzyl-2-hydroxyethyl]-6-chloro-5-(2H-1,2,3-triazol-2-yl)pyrazine-2-carboxamide;
3-amino-6-chloro-N-(1H-imidazol-2-ylmethyl)-5-(2H-1,2,3-triazol-2-yl)pyrazine-2-carboxamide;
3-amino-6-chloro-N-(1-methyl-1,2,3,4-tetrahydroquinolin-4-yl)-5-(2H-1,2,3-triazol-2-yl)pyrazine-2-carboxamide;
methyl (2S)-({[3-amino-6-chloro-5-(2H-1,2,3-triazol-2-yl)pyrazin-2-yl]carbonyl}amino)(phenyl)ethanoate;
3-amino-6-chloro-N-[(1S)-2-hydroxy-1-pyridin-2-ylethyl]-5-(2H-1,2,3-triazol-2-yl)pyrazine-2-carboxamide;
3-amino-6-chloro-N-[(1S)-2-hydroxy-1-(1H-indol-3-ylmethyl)ethyl]-5-(2H-1,2,3-triazol-2-yl)pyrazine-2-carboxamide;
3-amino-6-chloro-N-[(6-methylpyridin-2-yl)methyl]-5-(2H-1,2,3-triazol-2-yl)pyrazine-2-carboxamide;
3-amino-6-chloro-5-(1H-1,2,4-triazol-1-yl)-N-[2-(trifluoromethyl)benzyl]pyrazine-2-carboxamide;
3-amino-6-chloro-N-2,4-difluorobenzyl)-5-(1H-1,2,4-triazol-1-yl)pyrazine-2-carboxamide
3-amino-6-chloro-5-(1H-pyrazol-1-yl)-N-[2-(trifluoromethyl)benzyl]pyrazine-2-carboxamide;
3-amino-6-chloro-N-(4-fluorobenzyl)-5-(1H-pyrazol-1-yl)pyrazine-2-carboxamide;
3-amino-6-chloro-N-(2,4-difluorobenzyl)-5-(1H-pyrazol-1-yl)pyrazine-2-carboxamide;
3-amino-6-chloro-5-(1H-pyrazol-1-yl)-N-(quinolin-8-ylmethyl)pyrazine-2-carboxamide;
3-amino-6-chloro-N-[(1R)-2,3-dihydro-1H-inden-1-yl]-5-(1H-pyrazol-1-yl)pyrazine-2-carboxamide;
3-amino-6-chloro-N-[(3-methylpyridin-2-yl)methyl]-5-(1H-pyrazol-1-yl)pyrazine-2-carboxamide;
3-amino-6-chloro-5-(4-methyl-1H-pyrazol-1-yl)-N-[2-(trifluoromethyl)benzyl]pyrazine-2-carboxamide;
3-amino-6-chloro-N-[(1R)-2,3-dihydro-1H-inden-1-yl]-5-(4-methyl-1H-pyrazol-1-yl)pyrazine-2-carboxamide;
3-amino-6-chloro-5-(4-methyl-1H-pyrazol-1-yl)-N-[(3-methylpyridin-2-yl)methyl]pyrazine-2-carboxamide;
3-amino-6-chloro-5-(3-methyl-1H-pyrazol-1-yl)-N-[2-(trifluoromethyl)benzyl]pyrazine-2-carboxamide;
3-amino-6-chloro-N-[(1R)-2,3-dihydro-1H-inden-1-yl]-5-(3-methyl-11H-pyrazol-1-yl)pyrazine-2-carboxamide;
3-amino-6-chloro-5-(4-methyl-1H-pyrazol-1-yl)-N-(quinolin-8-ylmethyl)pyrazine-2-carboxamide;
3-amino-6-methyl-5-(4-methyl-1H-pyrazol-1-yl)-N-[(3-methylpyridin-2-yl)methyl]pyrazine-2-carboxamide;
3-amino-N-(isoquinolin-1-ylmethyl)-6-methyl-5-(4-methyl-1H-pyrazol-1-yl)pyrazine-2-carboxamide;
3-amino-6-chloro-5-(4-methyl-1H-pyrazol-11-yl)-N-{[3-(trifluoromethyl)pyridin-2-yl]methyl}pyrazine-2-carboxamide;
3-amino-6-chloro-N-2,4-difluorobenzyl)-5-(4-methyl-2H-1,2,3-triazol-2-yl)pyrazine-2-carboxamide;
3-amino-6-chloro-N-[(3-methylpyridin-2-yl)methyl]-5-(4-methyl-2H-1,2,3-triazol-2-yl)pyrazine-2-carboxamide;
3-amino-6-chloro-5-(4-methyl-2H-1,2,3-triazol-2-yl)-N-(1,2,3,4-tetrahydroquinolin-4-yl)pyrazine-2-carboxamide;
3-amino-6-methyl-5-(1H-pyrazol-1-yl)-N-(quinolin-8-ylmethyl)pyrazine-2-carboxamide;
3-amino-6-chloro-5-(4-methyl-2H-1,2,3-triazol-2-yl)-N-(quinolin-8-ylmethyl)pyrazine-2-carboxamide;
3-amino-6-chloro-N-[(1S)-2-hydroxy-1-phenylethyl]-5-(4-methyl-1H-pyrazol-1-yl)pyrazine-2-carboxamide;
3-amino-6-chloro-N-(1H-indol-5-ylmethyl)-54(4-methyl-1H-pyrazol-1-yl)pyrazine-2-carboxamide;
3-amino-6-chloro-N-[(1-methyl-1H-benzimidazol-2-yl)methyl]-5-(4-methyl-1H-pyrazol-1-yl)pyrazine-2-carboxamide;
3-amino-6-chloro-N-(1H-indol-7-ylmethyl)-54(4-methyl-1H-pyrazol-1-yl)pyrazine-2-carboxamide;
3-amino-6-chloro-N-(1H-indol-4-ylmethyl)-5-(4-methyl-1H-pyrazol-1-yl)pyrazine-2-carboxamide;
3-amino-6-chloro-N-(1H-indol-6-ylmethyl)-54(4-methyl-1H-pyrazol-1-yl)pyrazine-2-carboxamide;
3-amino-N-(1,3-benzothiazol-2-ylmethyl)-6-chloro-5-(4-methyl-1H-pyrazol-1-yl)pyrazine-2-carboxamide;
3-amino-N-(1,3-benzoxazol-2-ylmethyl)-6-chloro-5-(4-methyl-11H-pyrazol-1-yl)pyrazine-2-carboxamide;

3-amino-6-chloro-5-(4-methyl-1H-pyrazol-1-yl)-N-(quinoxalin-5-ylmethyl)pyrazine-2-carboxamide;
3-amino-N-benzyl-6-chloro-5-(4-methyl-1H-pyrazol-1-yl)pyrazine-2-carboxamide;
3-amino-6-chloro-N-(imidazo[2,1-b][1,3]thiazol-6-ylmethyl)-5-(4-methyl-1H-pyrazol-1-yl)pyrazine-2-carboxamide;
3-amino-6-chloro-N-(imidazo[1,2-a]pyridin-3-ylmethyl)-5-(4-methyl-1H-pyrazol-1-yl)pyrazine-2-carboxamide;
3-amino-6-chloro-N-(isoquinolin-4-ylmethyl)-5-(4-methyl-1H-pyrazol-1-yl)pyrazine-2-carboxamide
3-amino-6-chloro-5-(4-methyl-1H-pyrazol-1-yl)-N-(pyrazolo[1,5-a]pyridin-3-ylmethyl)pyrazine-2-carboxamide;
3-amino-6-chloro-5-(4-methyl-1H-pyrazol-1-yl)-N-[(3-oxo-2,3-dihydro-1H-isoindol-4-yl)methyl]pyrazine-2-carboxamide;
3-amino-6-methyl-N-((3-methylpyridin-2-yl)methyl)-5-(4-(trifluoromethyl) oxazol-2-yl) pyrazine-2-carboxamide;
3-amino-5-(4,5-dimethyloxazol-2-yl)-6-methyl-N-((3-methylpyridin-2-yl)methyl)pyrazine-2-carboxamide;
3-amino-5-(4-methyl-1H-pyrazol-1-yl)-N-(quinolin-8-ylmethyl)-6-vinylpyrazine-2-carboxamide;
3-amino-6-(1,2-dihydroxyethyl)-5-(4-methyl-1H-pyrazol-1-yl)-N-(quinolin-8-ylmethyl)pyrazine-2-carboxamide;
3-amino-6-formyl-5-(4-methyl-1H-pyrazol-1-yl)-N-(quinolin-8-ylmethyl)pyrazine-2-carboxamide
3-amino-6-(difluoromethyl)-5-(4-methyl-1H-pyrazol-1-yl)-N-(quinolin-8-ylmethyl)pyrazine-2-carboxamide;
3-amino-6-(hydroxymethyl)-N-(quinolin-8-ylmethyl)-5-(2H-1,2,3-triazol-2-yl)pyrazine-2-carboxamide;
3-amino-6-cyano-5-(1H-pyrazol-1-yl)-N-(quinolin-8-ylmethyl)pyrazine-2-carboxamide;
3-amino-6-cyano-5-(oxazol-2-yl)-N-((3-(trifluoromethyl)pyridin-2-yl)methyl)pyrazine-2-carboxamide;
1-(3-amino-6-methyl-5-(oxazol-2-yl)pyrazin-2-yl)-3-(4,6-dimethylpyridin-2-yl)propan-1-one;
3-amino-6-methyl-N-((5-methylpyrimidin-4-yl)methyl)-5-(oxazol-2-yl)pyrazine-2-carboxamide;
3-amino-6-methyl-5-(5-methyloxazol-2-yl)-N-((3-methylpyridin-2-yl)methyl)pyrazine-2-carboxamide;
3-amino-N-((5R,7S)-5-fluoro-6,7-dihydro-5H-cyclopenta[b]pyridin-7-yl)-6-methyl-5-(oxazol-2-yl)pyrazine-2-carboxamide;
3-amino-N-((5R,7R)-5-fluoro-6,7-dihydro-5H-cyclopenta[b]pyridin-7-yl)-6-methyl-5-(oxazol-2-yl)pyrazine-2-carboxamide;
3-amino-N-((5 S,7S)-5-fluoro-6,7-dihydro-5H-cyclopenta[b]pyridin-7-yl)-6-methyl-5-(oxazol-2-yl)pyrazine-2-carboxamide;
3-amino-N-((5 S,7R)-5-fluoro-6,7-dihydro-5H-cyclopenta[b]pyridin-7-yl)-6-methyl-5-(oxazol-2-yl)pyrazine-2-carboxamide;
3-Amino-N-(6-fluoro-6,7-dihydro-5H-cyclopenta[b]pyridin-7-yl)-6-methyl-5-(oxazol-2-yl)pyrazine-2-carboxamide;
3-amino-N-(7H-cyclopenta[b]pyridin-7-yl)-6-methyl-5-(oxazol-2-yl)pyrazine-2-carboxamide;
3-amino-6-methyl-N-[(3-methylpyridin-2-yl)methyl]-5-[4-(trifluoromethyl)-1,3-oxazol-2-yl]pyrazine-2-carboxamide;
3-amino-6-methyl-5-(4-methyl-1,3-oxazol-2-yl)-N-[(3-methylpyridin-2-yl)methyl]pyrazine-2-carboxamide;
3-amino-5-(4,5-dimethyl-1,3-oxazol-2-yl)-6-methyl-N-[(3-methylpyridin-2-yl)methyl]pyrazine-2-carboxamide;
3-amino-5-[4-(methoxymethyl)-1,3-oxazol-2-yl]-6-methyl-N-[(3-methylpyridin-2-yl)methyl]pyrazine-2-carboxamide;
3-amino-6-methyl-5-(5-methyl-1,3-oxazol-2-yl)-N-[(3-methylpyridin-2-yl)methyl]pyrazine-2-carboxamide;
3-amino-6-methyl-N-[(3-methylpyridin-2-yl)methyl]-5-[5-(trifluoromethyl)-1,3-oxazol-2-yl]pyrazine-2-carboxamide;
3-amino-6-cyano-5-(1H-pyrazol-1-yl)-N-(quinolin-8-ylmethyl)pyrazine-2-carboxamide;
3-amino-6-cyano-5-(1,3-oxazol-2-yl)-N-{[3-(trifluoromethyl)pyridin-2-yl]methyl}pyrazine-2-carboxamide;
3-amino-6-(difluoromethyl)-5-(4-methyl-1H-pyrazol-1-yl)-N-(quinolin-8-ylmethyl)pyrazine-2-carboxamide;
3-amino-6-(hydroxymethyl)-N-(quinolin-8-ylmethyl)-5-(2H-1,2,3-triazol-2-yl)pyrazine-2-carboxamide;
3-amino-N-(5-fluoro-6,7-dihydro-5H-cyclopenta[b]pyrindin-7-yl)-6-methyl-5-(1,3-oxazol-2-yl)pyrazine-2-carboxamide;
3-amino-N-(5-fluoro-6,7-dihydro-5H-cyclopenta[b]pyridin-7-yl)-6-methyl-5-(1,3-oxazol-2-yl)pyrazine-2-carboxamide;
3-amino-N-(5-fluoro-6,7-dihydro-5H-cyclopenta[b]pyrindin-7-yl)-6-methyl-5-(1,3-oxazol-2-yl)pyrazine-2-carboxamide;
3-amino-N-(5-fluoro-6,7-dihydro-5H-cyclopenta[b]pyridin-7-yl)-6-methyl-5-(1,3-oxazol-2-yl)pyrazine-2-carboxamide; or
3-amino-N-(6-fluoro-6,7-dihydro-5H-cyclopenta[b]pyrindin-7-yl)-6-methyl-5-(1,3-oxazol-2-yl)pyrazine-2-carboxamide,
or a pharmaceutically acceptable salt of any thereof.

12. A compound which is:
3-amino-6-methyl-N-[(3-methylpyridin-2-yl)methyl]-5-(1,3-oxazol-2-yl)pyrazine-2-carboxamide;
3-amino-6-methyl-5-(1,3-oxazol-2-yl)-N-{[3-(trifluoromethyl)pyridin-2-yl]methyl}pyrazine-2-carboxamide;
3-amino-6-methyl-5-(1,3-oxazol-2-yl)-N-(pyrimidin-2-ylmethyl)pyrazine-2-carboxamide;
3-amino-N-[(3-cyclopropylpyridin-2-yl)methyl]-6-methyl-5-(1,3-oxazol-2-yl)pyrazine-2-carboxamide;
3-amino-6-methyl-N-[(4-methylpyridazin-3-yl)methyl]-5-(1,3-oxazol-2-yl)pyrazine-2-carboxamide;
3-amino-6-methyl-N-{[1-(1-methylethyl)-1H-imidazol-2-yl]methyl}-5-(1,3-oxazol-2-yl)pyrazine-2-carboxamide;
3-amino-N-(6,7-dihydro-5H-cyclopenta[b]pyridin-7-yl)-6-methyl-5-(1,3-oxazol-2-yl)pyrazine-2-carboxamide;
3-amino-N-[(3-ethyl-4-fluoropyridin-2-yl)methyl]-6-methyl-5-(1,3-oxazol-2-yl)pyrazine-2-carboxamide;
3-amino-N-[(1-ethyl-1H-1,2,4-triazol-5-yl)methyl]-6-methyl-5-(1,3-oxazol-2-yl)pyrazine-2-carboxamide;
3-amino-N-[(3-ethylpyridin-2-yl)methyl]-6-methyl-5-(1,3-oxazol-2-yl)pyrazine-2-carboxamide;
3-amino-N-[(3-cyclopropyl-4-fluoropyridin-2-yl)methyl]-6-methyl-5-(1,3-oxazol-2-yl)pyrazine-2-carboxamide;
3-amino-N-[(3-cyclopropylpyrazin-2-yl)methyl]-6-methyl-5-(1,3-oxazol-2-yl)pyrazine-2-carboxamide;
3-amino-6-methyl-N-{[1-(1-methylethyl)-1H-1,2,4-triazol-5-yl]methyl}-5-(1,3-oxazol-2-yl)pyrazine-2-carboxamide;

3-amino-N-[(1-ethyl-1H-benzimidazol-4-yl)methyl]-6-methyl-5-(1,3-oxazol-2-yl)pyrazine-2-carboxamide;

3-amino-6-methyl-N-[(3-methylpyrazin-2-yl)methyl]-5-(1,3-oxazol-2-yl)pyrazine-2-carboxamide;

3-amino-6-cyano-5-(1,3-oxazol-2-yl)-N-{[3-(trifluoromethyl)pyridin-2-yl]methyl}pyrazine-2-carboxamide;

3-amino-N-{[3-(fluoromethyl)pyridin-2-yl]methyl}-6-methyl-5-(1,3-oxazol-2-yl)pyrazine-2-carboxamide;

3-amino-N-{[3-(hydroxymethyl)pyridin-2-yl]methyl}-6-methyl-5-(1,3-oxazol-2-yl)pyrazine-2-carboxamide;

3-amino-6-methyl-N-[1-(3-methylpyridin-2-yl)ethyl]-5-(1,3-oxazol-2-yl)pyrazine-2-carboxamide; or 3-amino-N-(6-hydroxy-6,7-dihydro-5H-cyclopenta[b]pyridin-7-yl)-6-methyl-5-(1,3-oxazol-2-yl)pyrazine-2-carboxamide, or a pharmaceutically acceptable salt of any thereof.

13. A pharmaceutical composition comprising a compound of claim 1, or a pharmaceutically acceptable salt thereof, and at least one excipient.

14. A pharmaceutical composition comprising a compound of claim 2, or a pharmaceutically acceptable salt thereof, and at least one excipient.

15. A pharmaceutical composition comprising a compound of claim 3, or a pharmaceutically acceptable salt thereof, and at least one excipient.

16. A pharmaceutical composition comprising a compound of claim 11, or a pharmaceutically acceptable salt thereof, and at least one excipient.

17. A pharmaceutical composition comprising a compound of claim 4, or a pharmaceutically acceptable salt thereof, and at least one excipient.

18. A pharmaceutical composition comprising a compound of claim 12, or a pharmaceutically acceptable salt thereof, and at least one excipient.

19. A method of treating central nervous system (CNS) disorders comprising administering to a patient in need thereof a therapeutically effective amount of a pharmaceutical composition of claim 16.

* * * * *